(12) United States Patent
Chriss

(10) Patent No.: US 7,307,509 B2
(45) Date of Patent: Dec. 11, 2007

(54) ASSISTIVE COMMUNICATION DEVICE

(75) Inventor: Terry M Chriss, Haddam, CT (US)

(73) Assignee: Custom Lab Software Systems, Inc., Essex, CT (US)

( * ) Notice: Subject to any disclaimer, the term of this patent is extended or adjusted under 35 U.S.C. 154(b) by 104 days.

(21) Appl. No.: 11/262,880

(22) Filed: Oct. 31, 2005

(65) Prior Publication Data

US 2006/0105301 A1    May 18, 2006

Related U.S. Application Data

(60) Provisional application No. 60/624,395, filed on Nov. 2, 2004, now abandoned.

(51) Int. Cl.
*G08B 13/02* (2006.01)
(52) U.S. Cl. .................. 340/286.07; 340/539.12; 340/573.1; 340/825.19; 600/300; 600/301; 128/903; 128/904
(58) Field of Classification Search ........... 340/286.07, 340/539.12, 539.19, 573.1, 825.19; 434/112; 600/300, 301; 128/903, 904
See application file for complete search history.

(56) References Cited

U.S. PATENT DOCUMENTS

| | | | |
|---|---|---|---|
| 3,651,512 A | 3/1972 | Summers | |
| 4,761,633 A | 8/1988 | Leff et al. | |
| 5,416,695 A | 5/1995 | Stutman et al. | |
| 5,564,429 A | 10/1996 | Bomn et al. | |
| 5,838,223 A | 11/1998 | Gallant et al. | |
| 6,362,725 B1 | 3/2002 | Ulrich et al. | |
| 6,923,652 B2 | 8/2005 | Kerns et al. | |
| 2002/0044043 A1 | 4/2002 | Chaco et al. | |
| 2002/0093427 A1 | 7/2002 | Roth et al. | |
| 2002/0186136 A1 | 12/2002 | Schuman | |
| 2003/0052788 A1 | 3/2003 | Chung | |
| 2003/0062989 A1 | 4/2003 | Tsunezumi | |

*Primary Examiner*—Hung Nguyen
(74) *Attorney, Agent, or Firm*—Ropes & Gray LLP; Jeffrey H. Ingerman

(57) ABSTRACT

An assistive communication device of the type on which a user can compose a message to be spoken by the device, using an input device to select items on a display to construct the message, can operate in a mode suitable for visually impaired and/or inexperienced users by aurally stepping through the available choices, explaining to the user the consequences of selecting each choice. The order in which choices are presented in these modes may differ from a mode in which they would be presented to an experienced or fully-sighted user. Even for an experienced user, the order in which choices are highlighted on the display may differ according the user's usage history. The device may be connected to external communications, including a telephone line, a data network for electronic mail, or a caregiver alert device. The caregiver alert device may be portable, or may be a caregivers' station console.

26 Claims, 119 Drawing Sheets

FIG. 3

| SCAN | ERASE | HELP |
|---|---|---|
| SPEAK | SPELL | MORE |
| TELEPHONE | E-MAIL | RE-START |
| I NEED ||||
| MY MEDICINE | MY FAMILY |
| BATHROOM | TO SLEEP |
| ICE | A BIBLE |

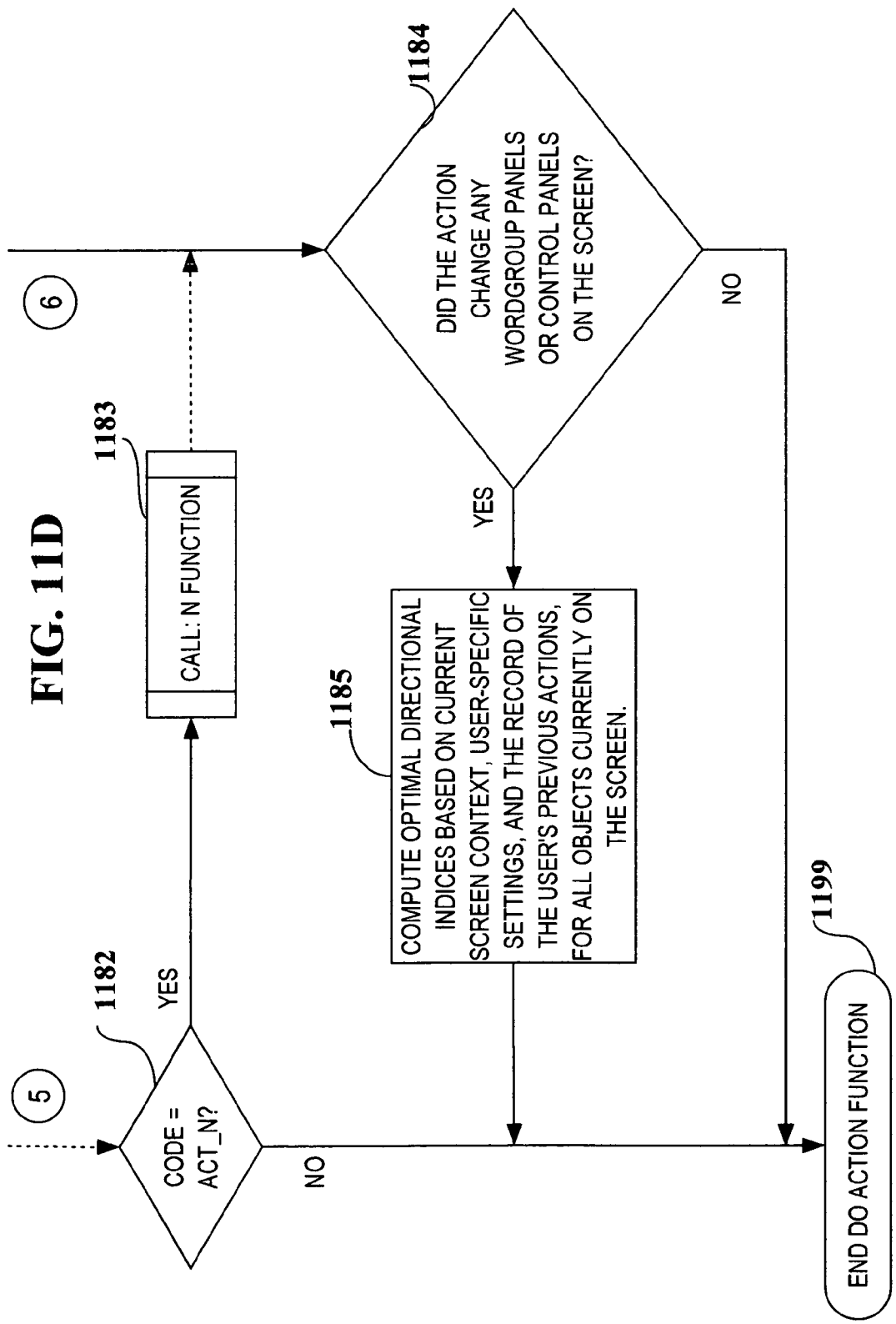

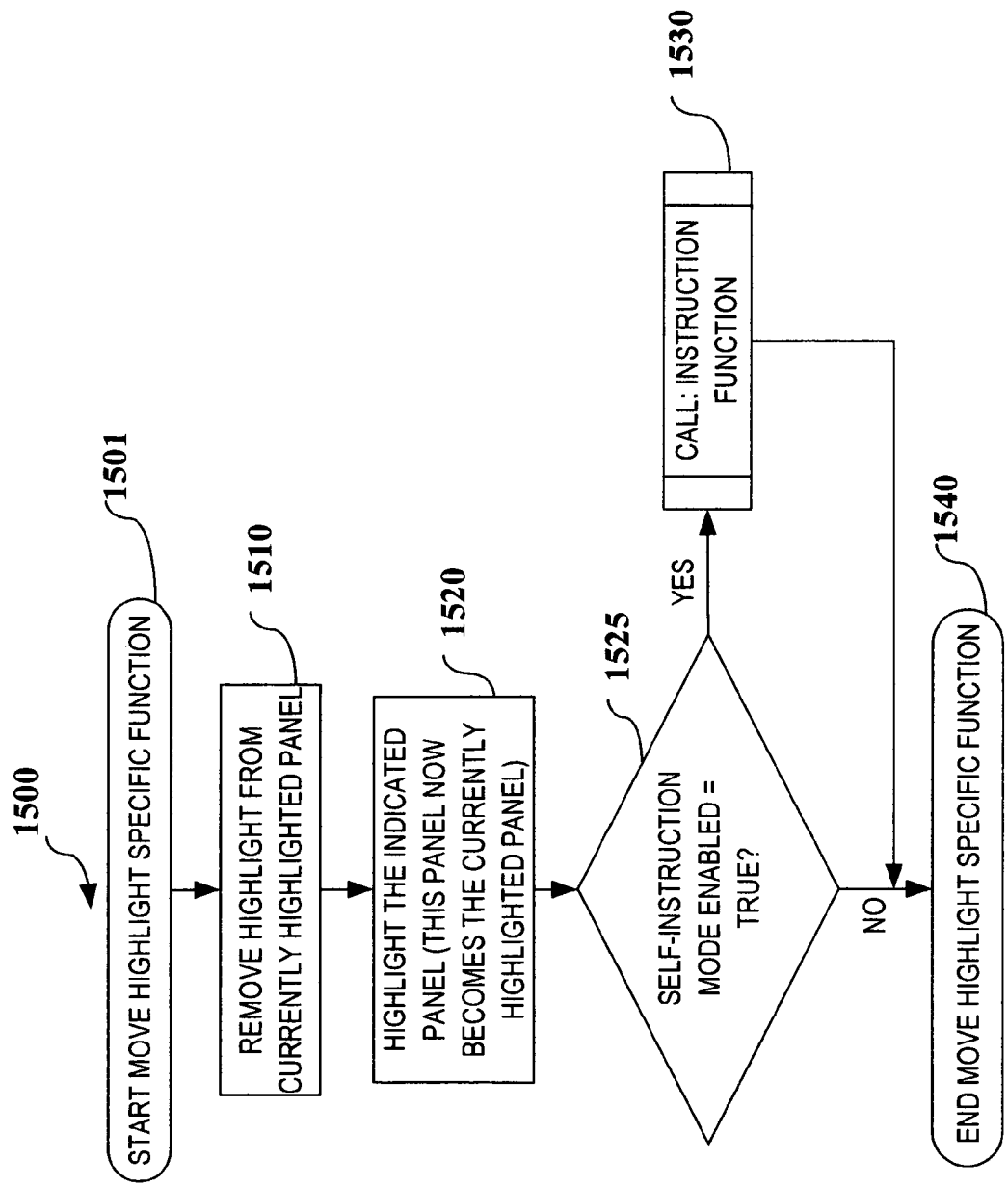

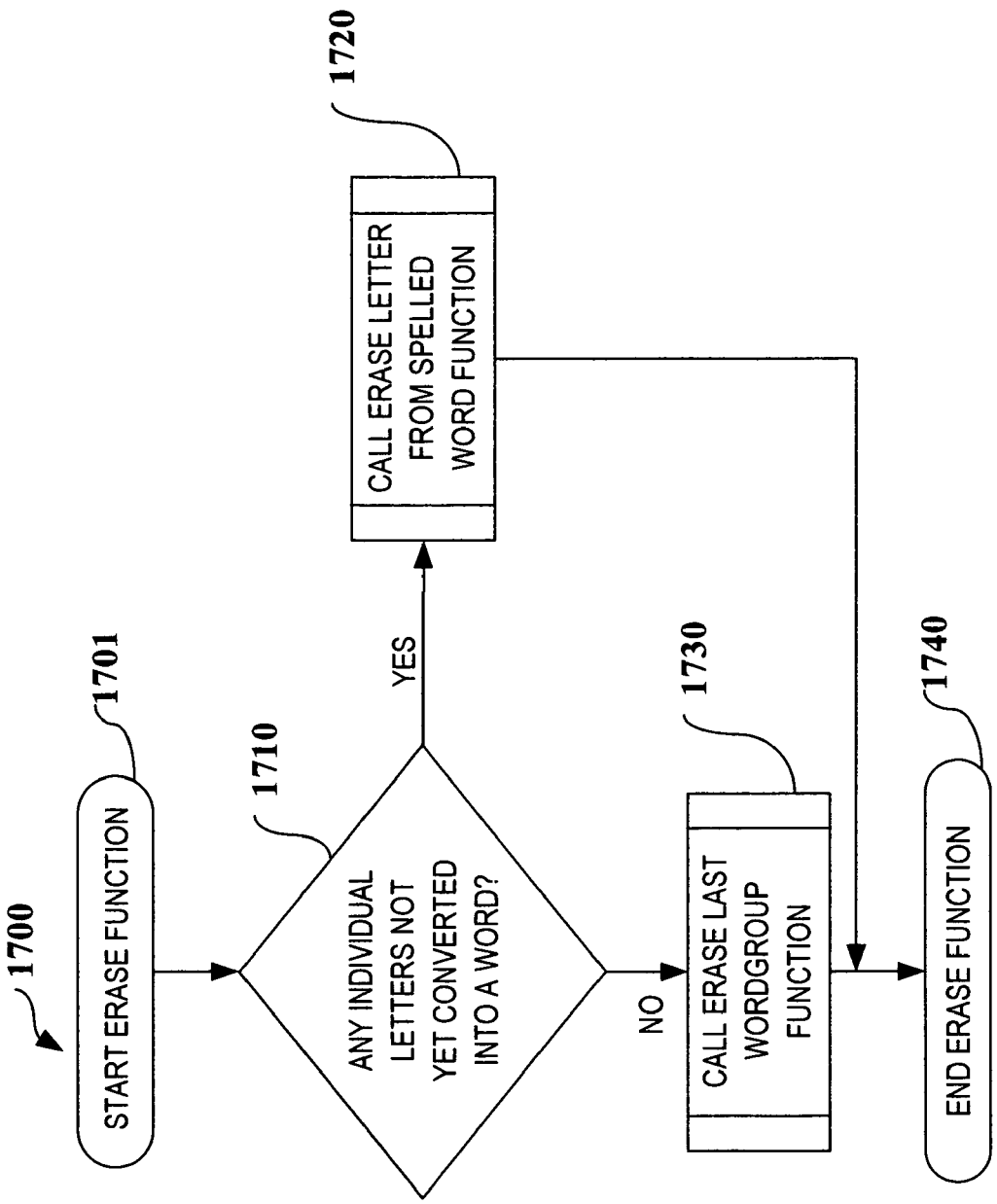

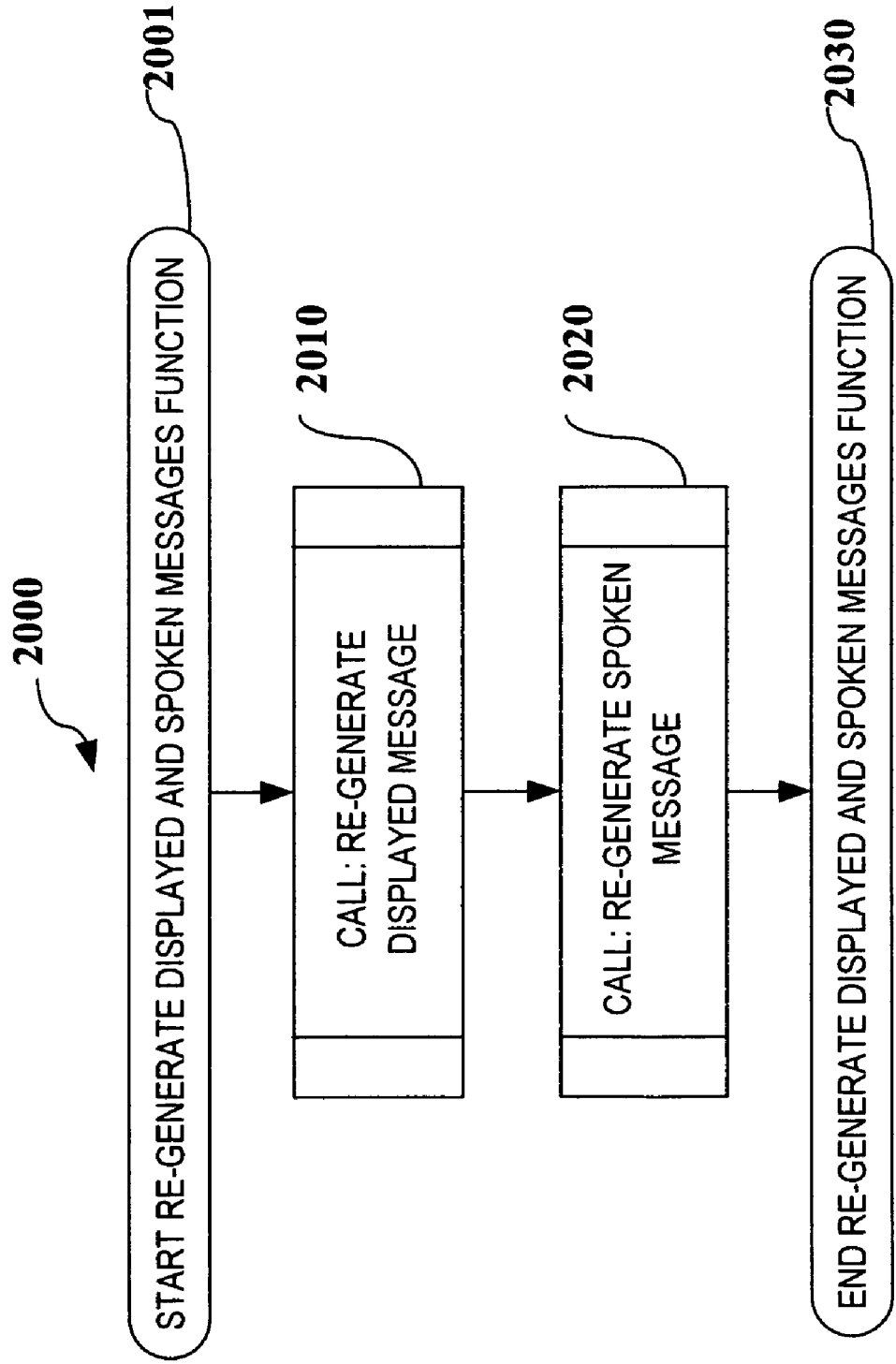

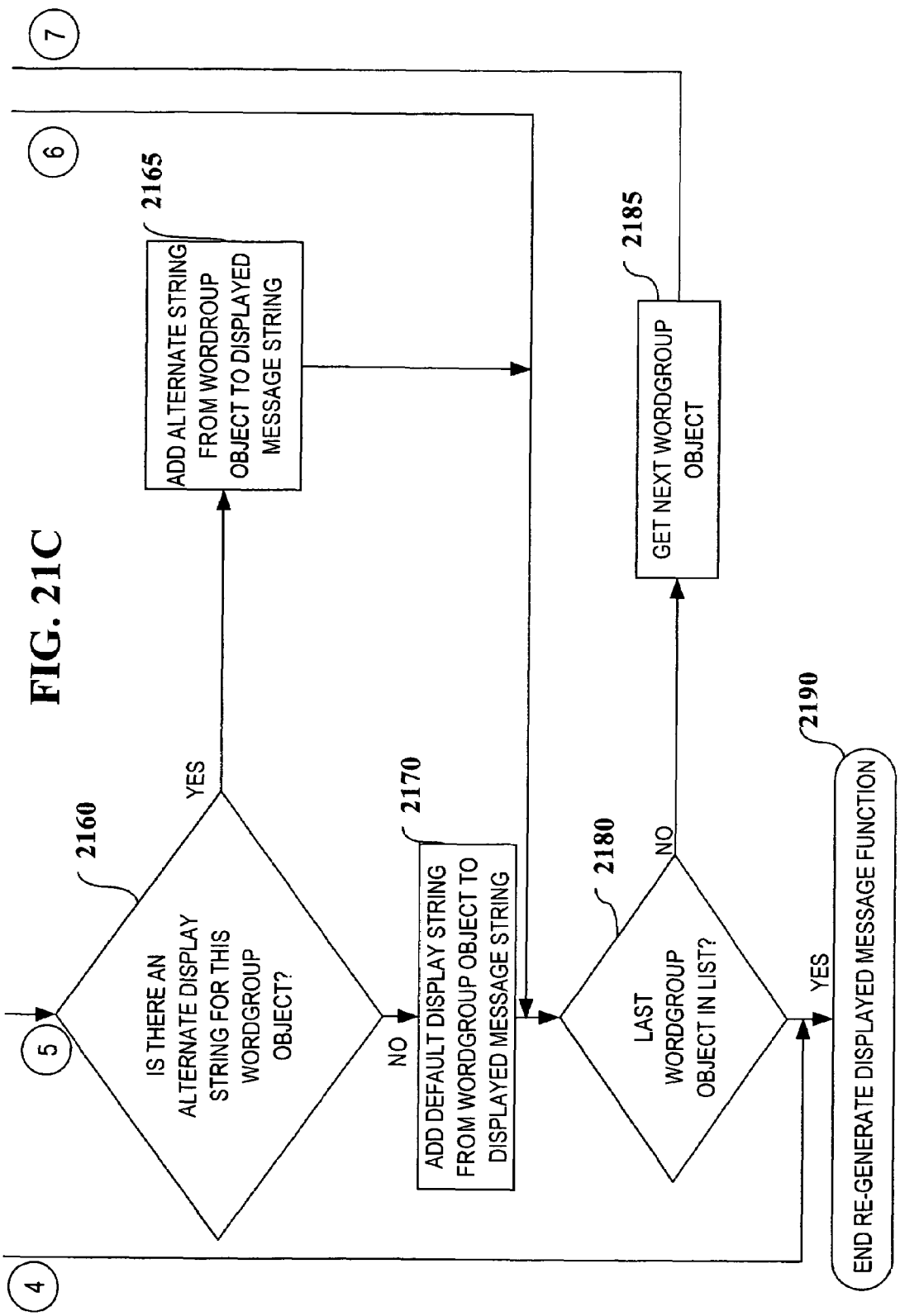

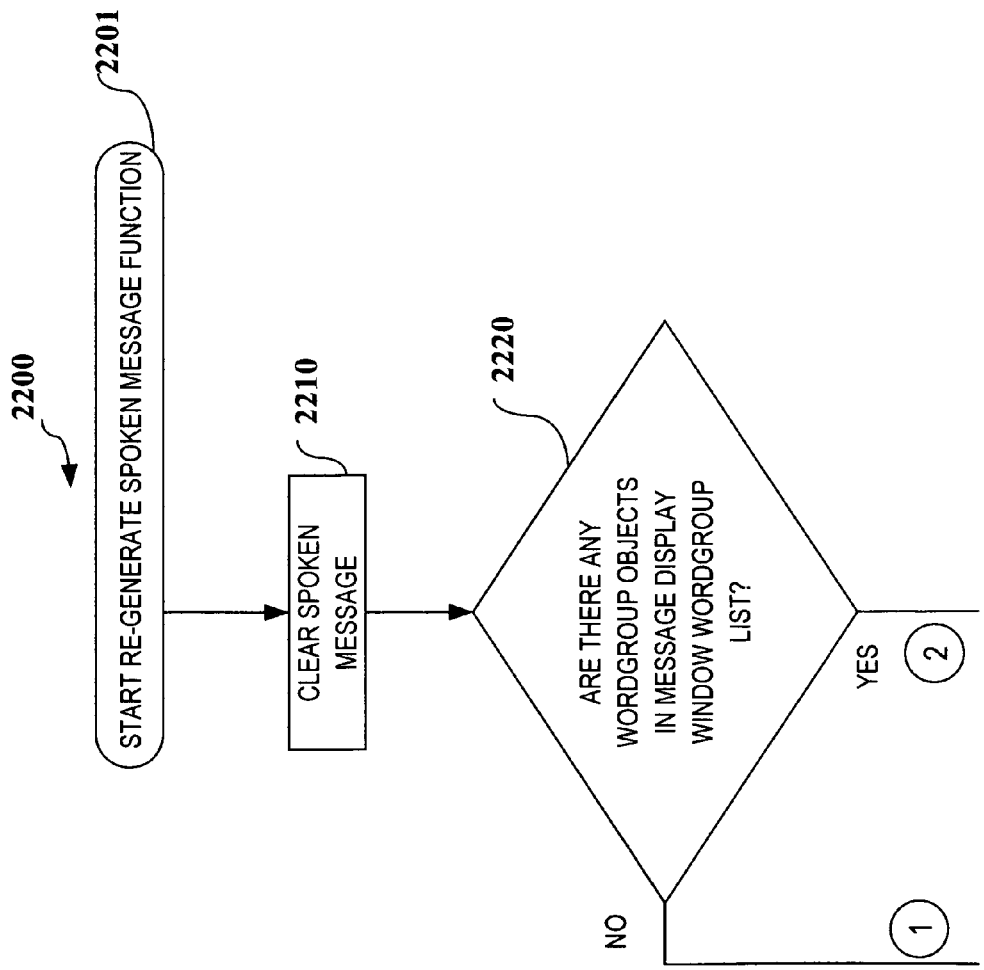

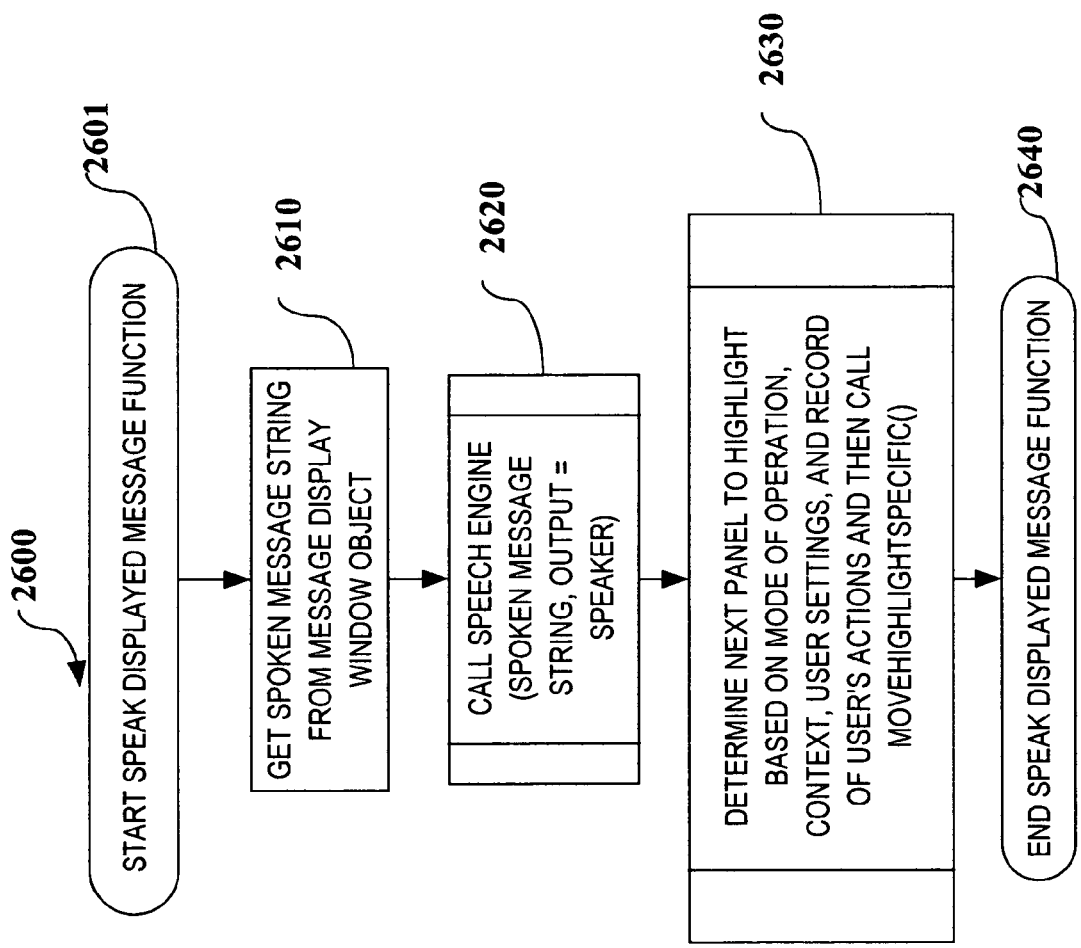

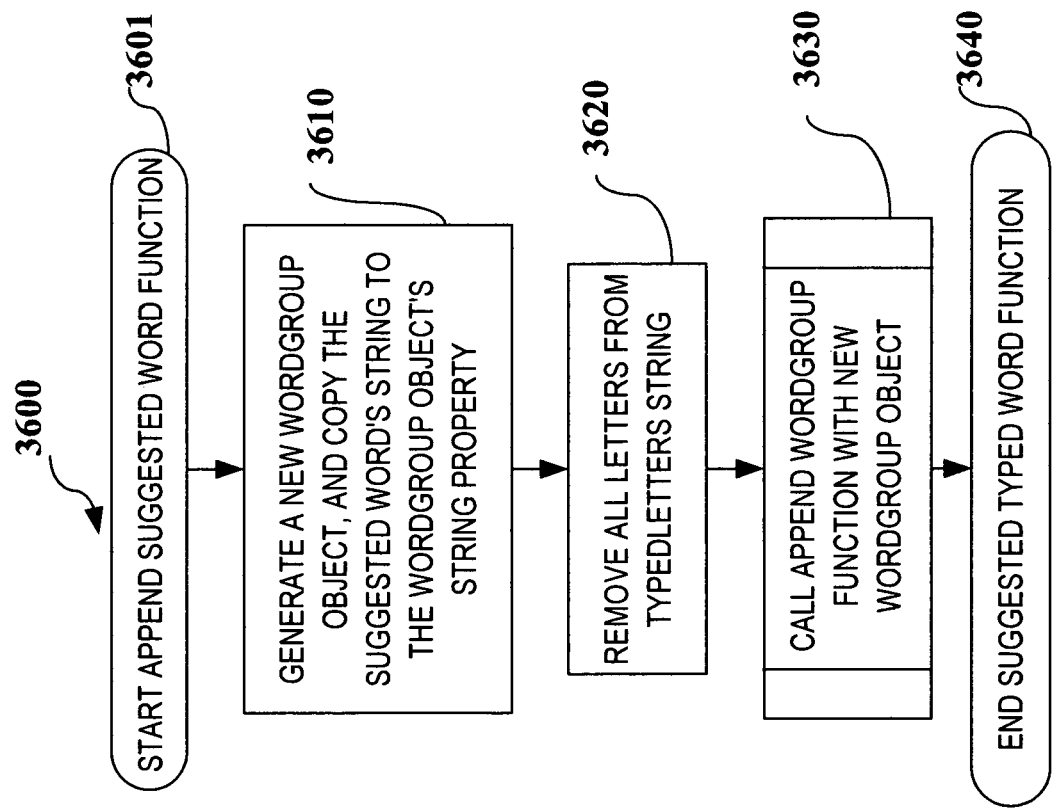

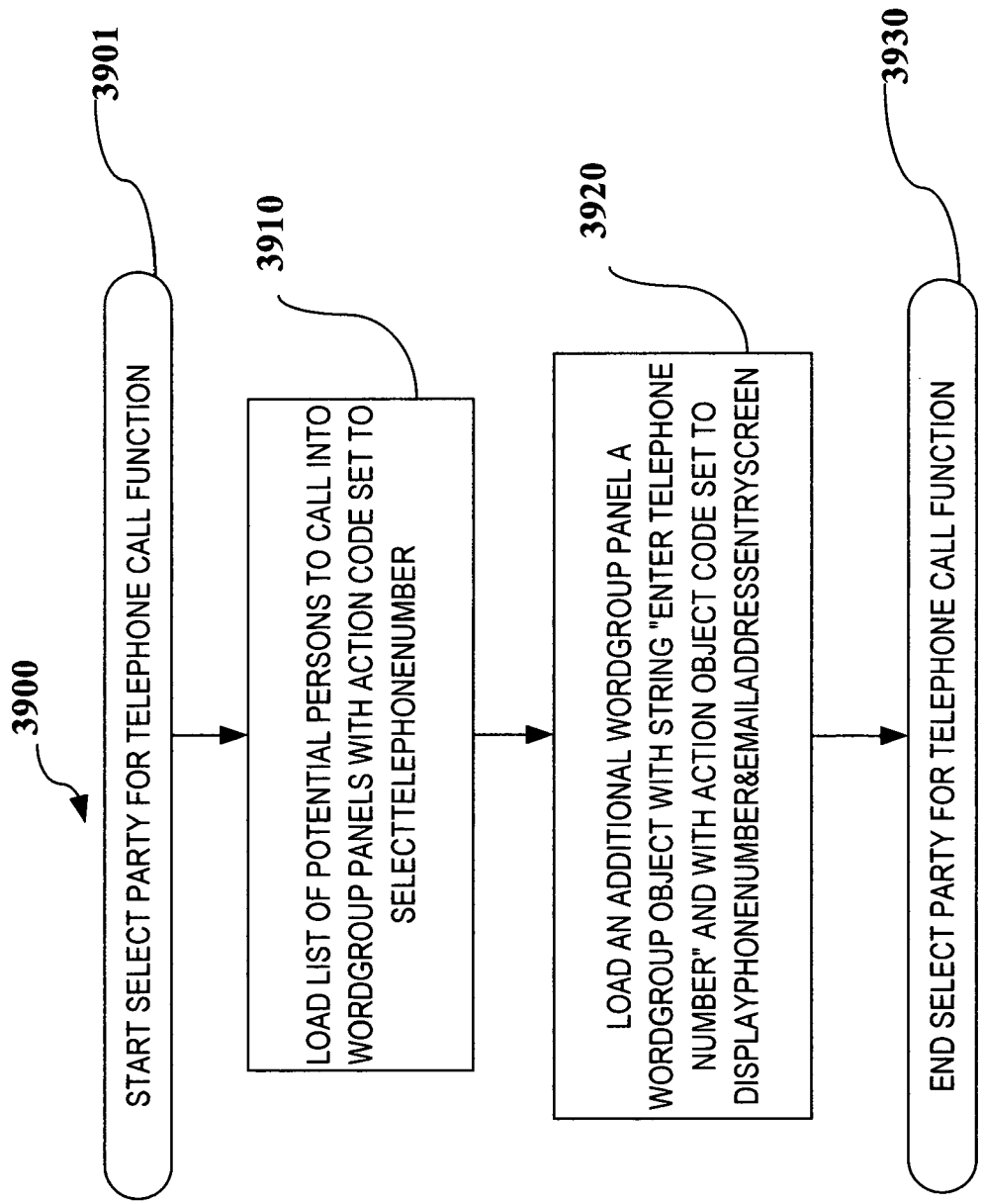

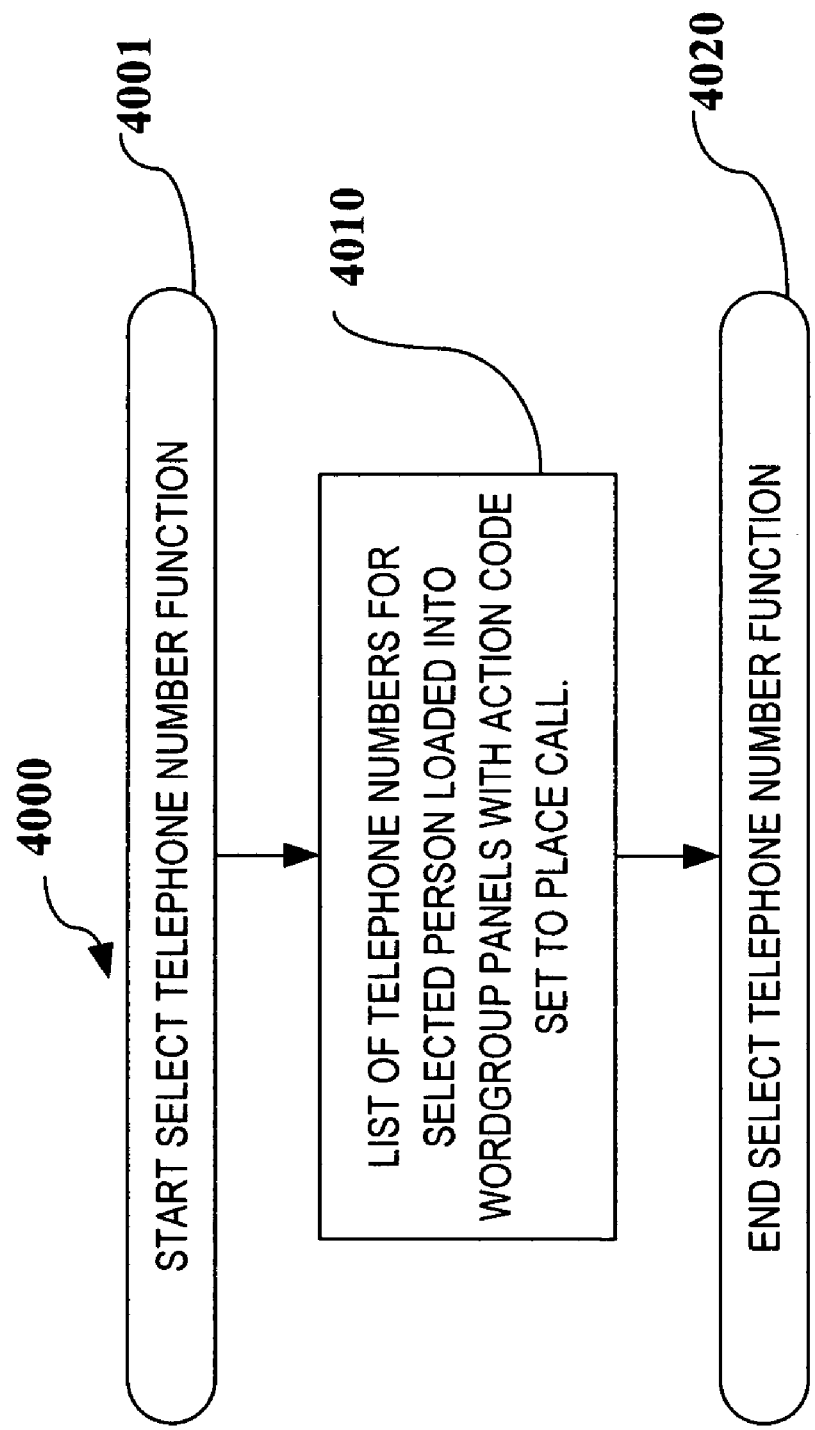

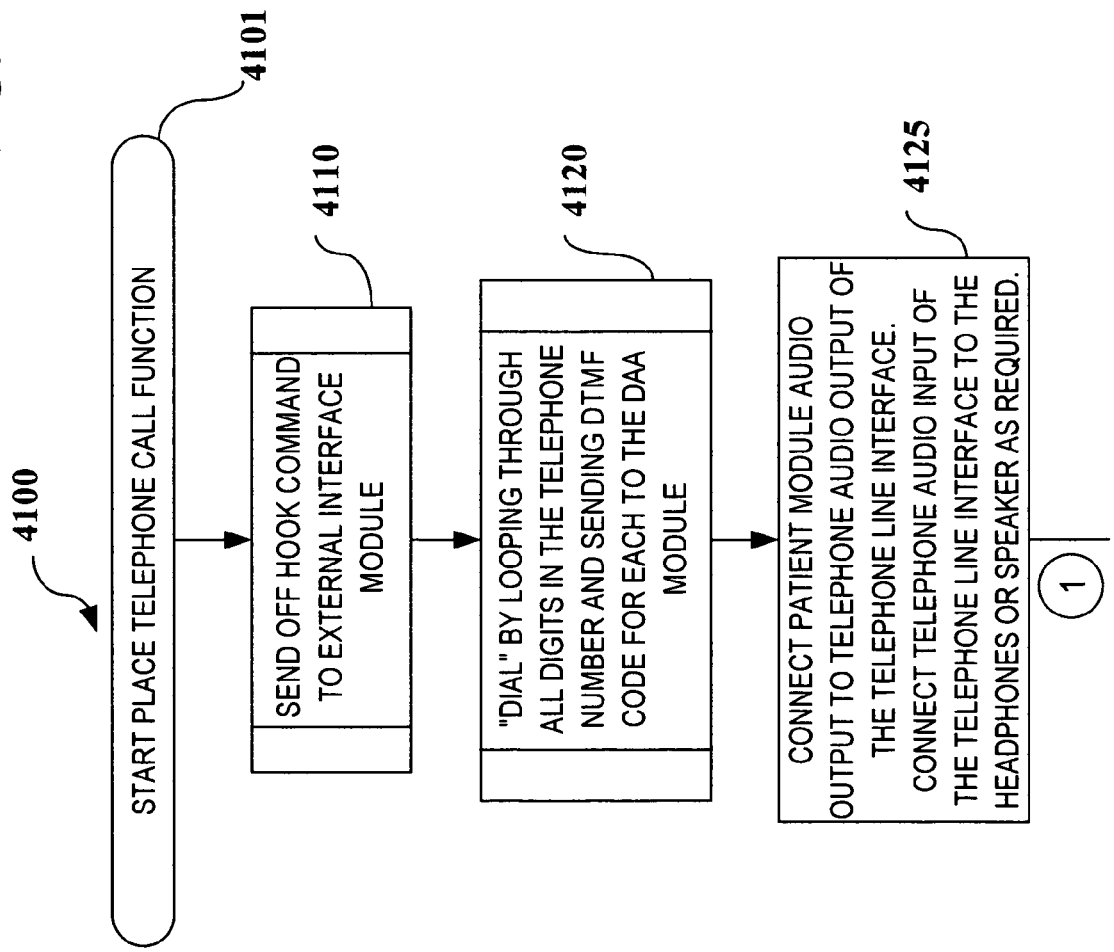

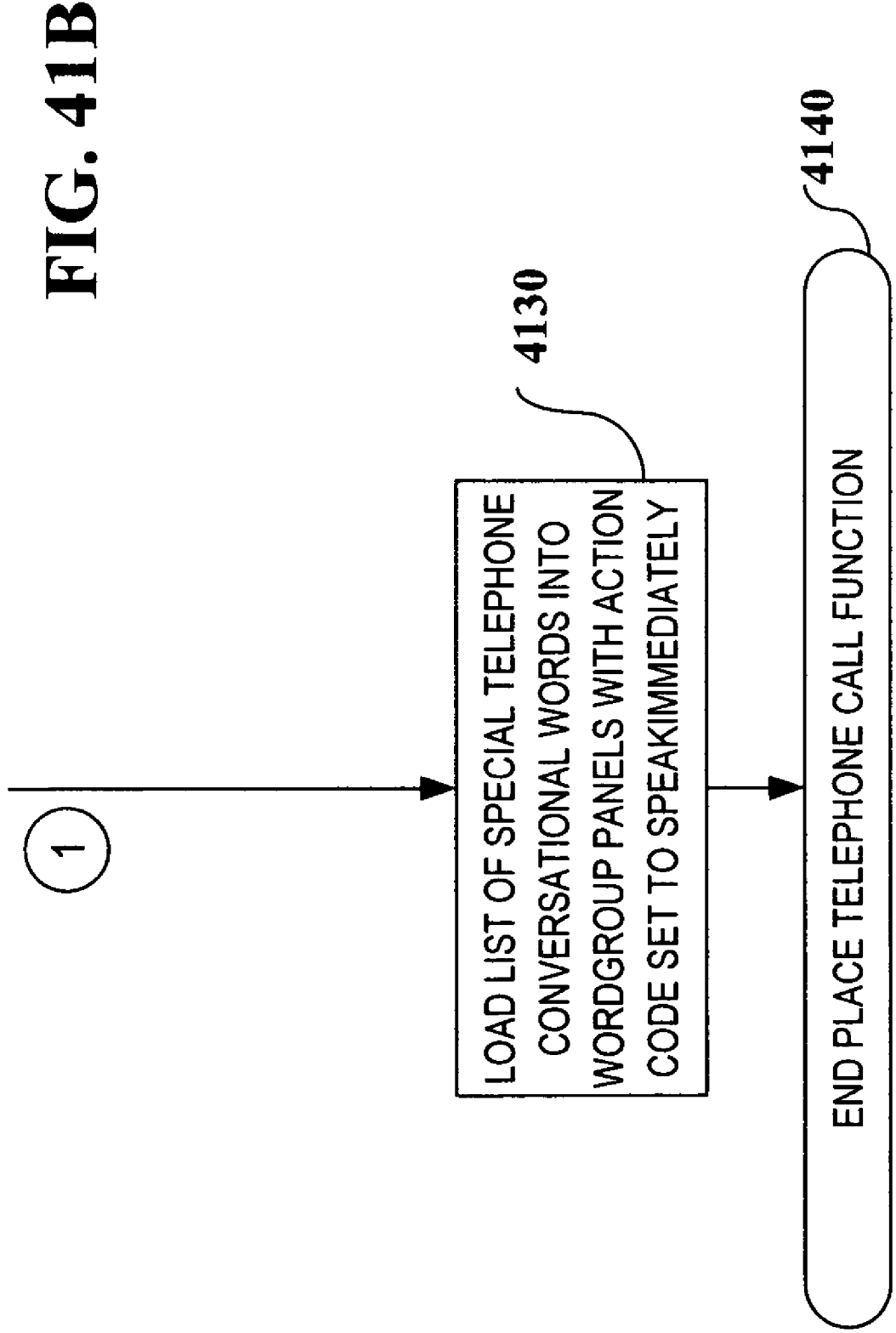

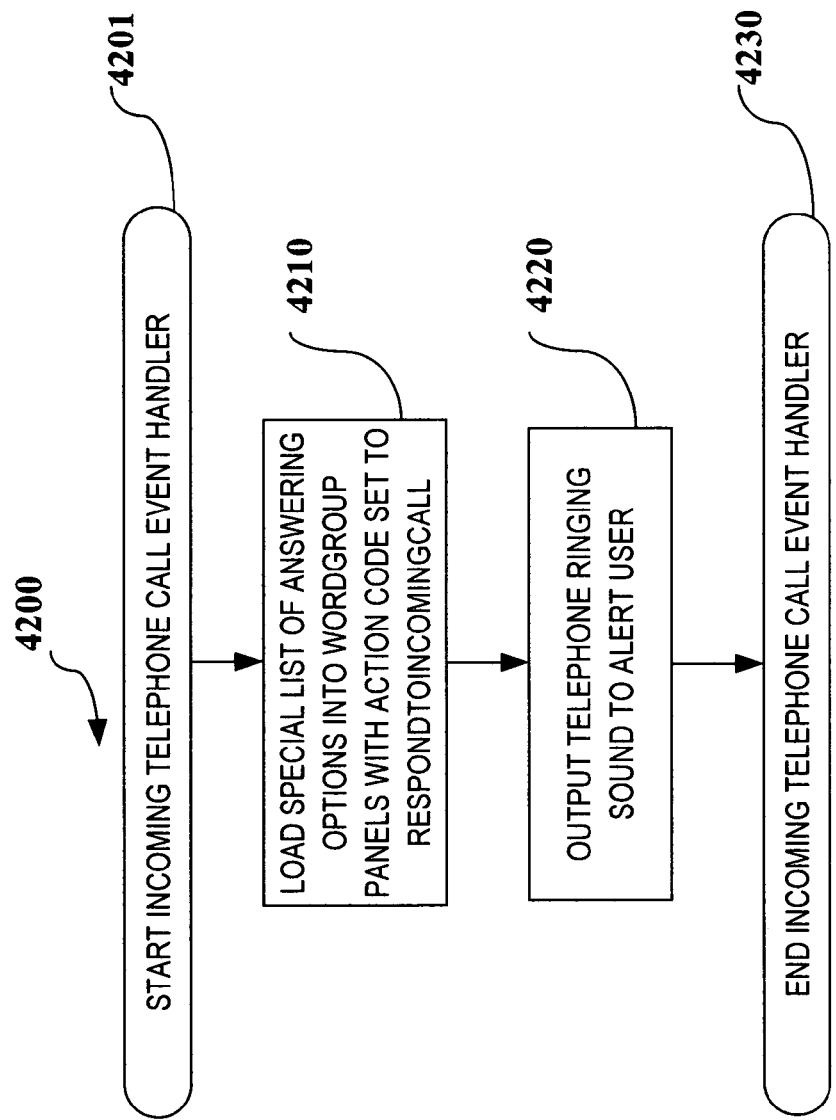

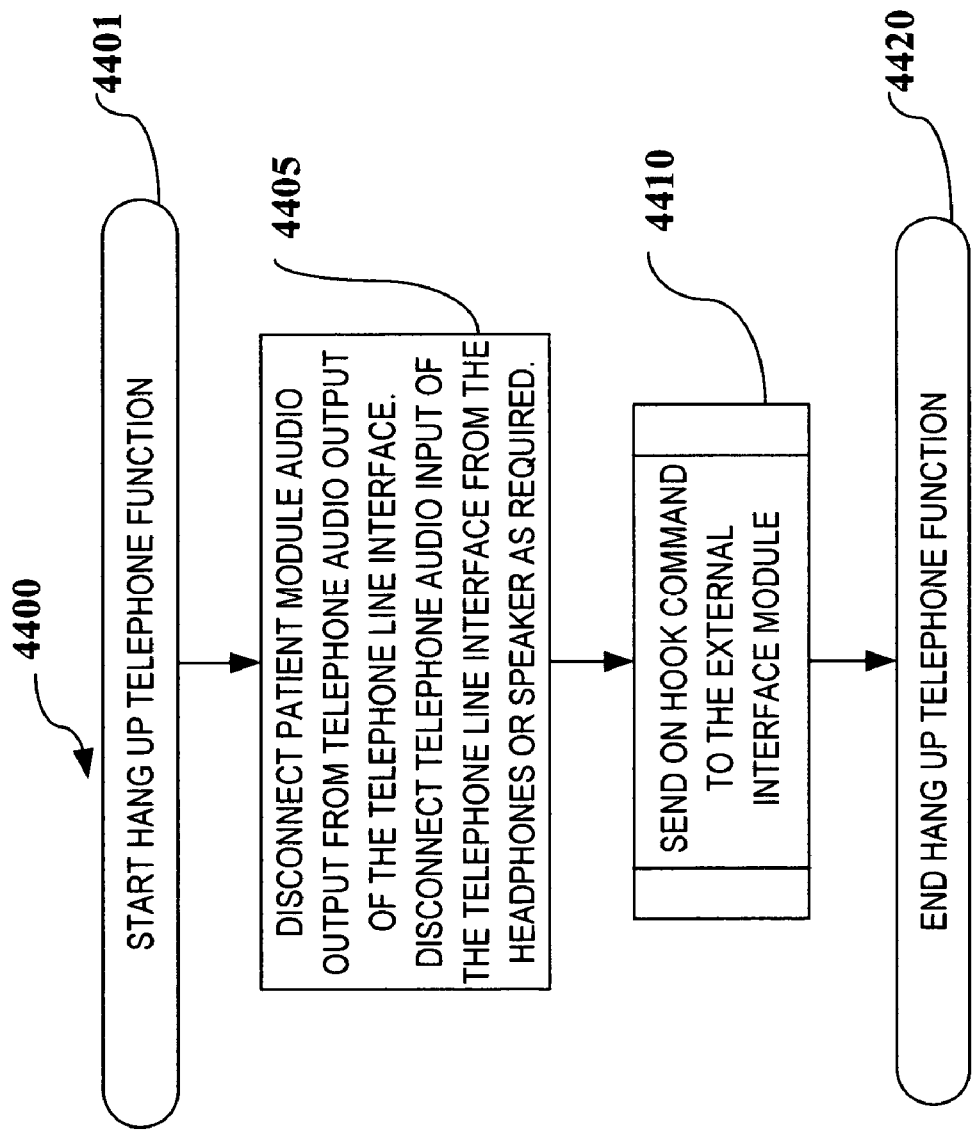

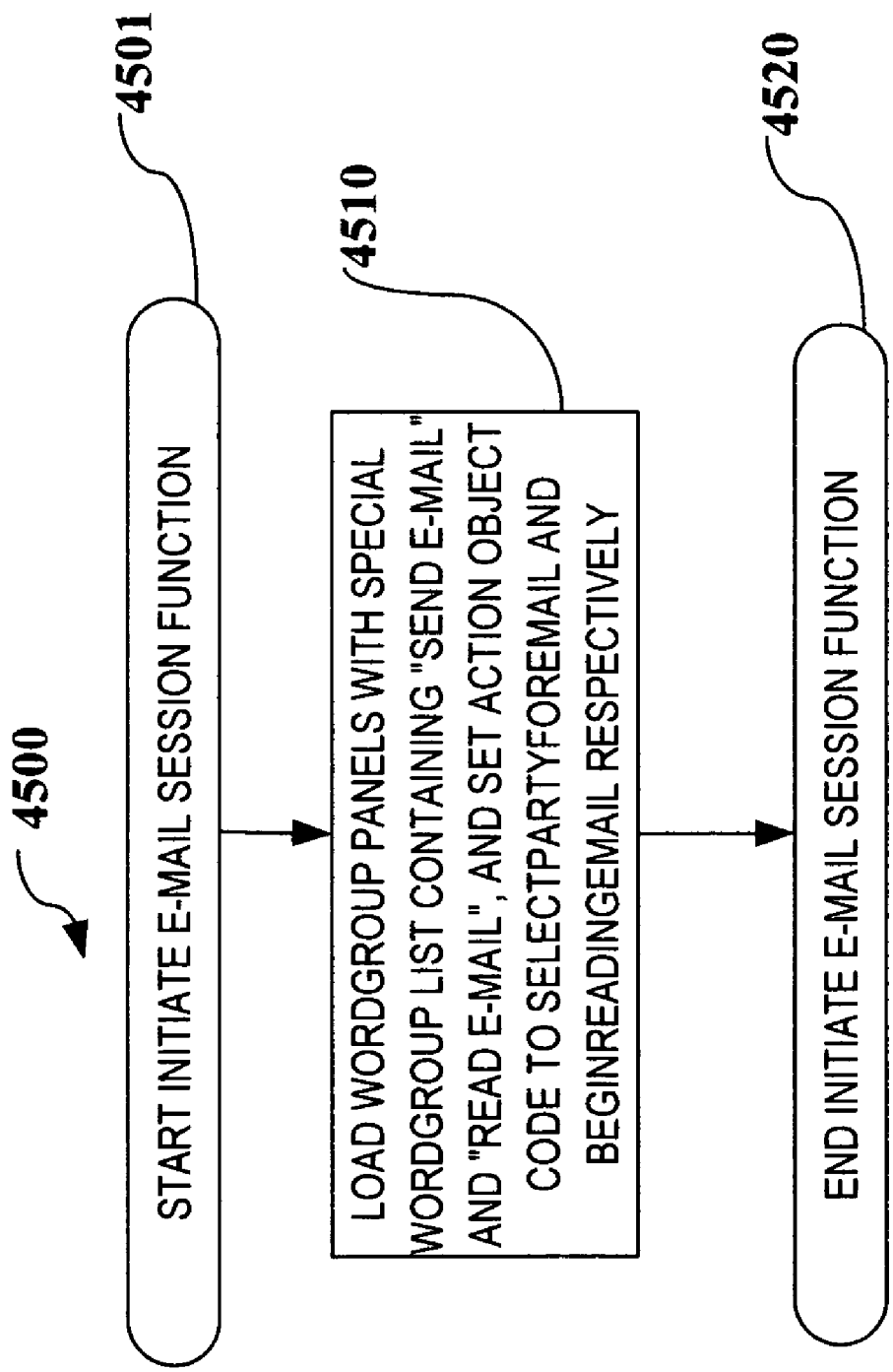

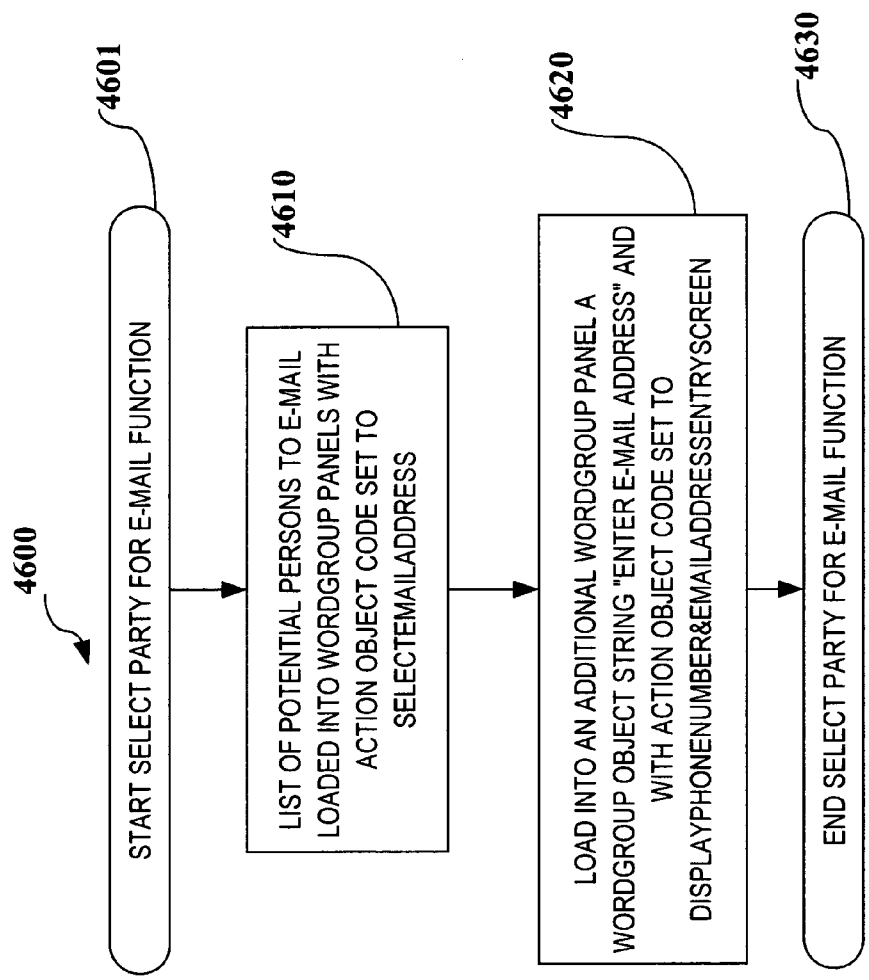

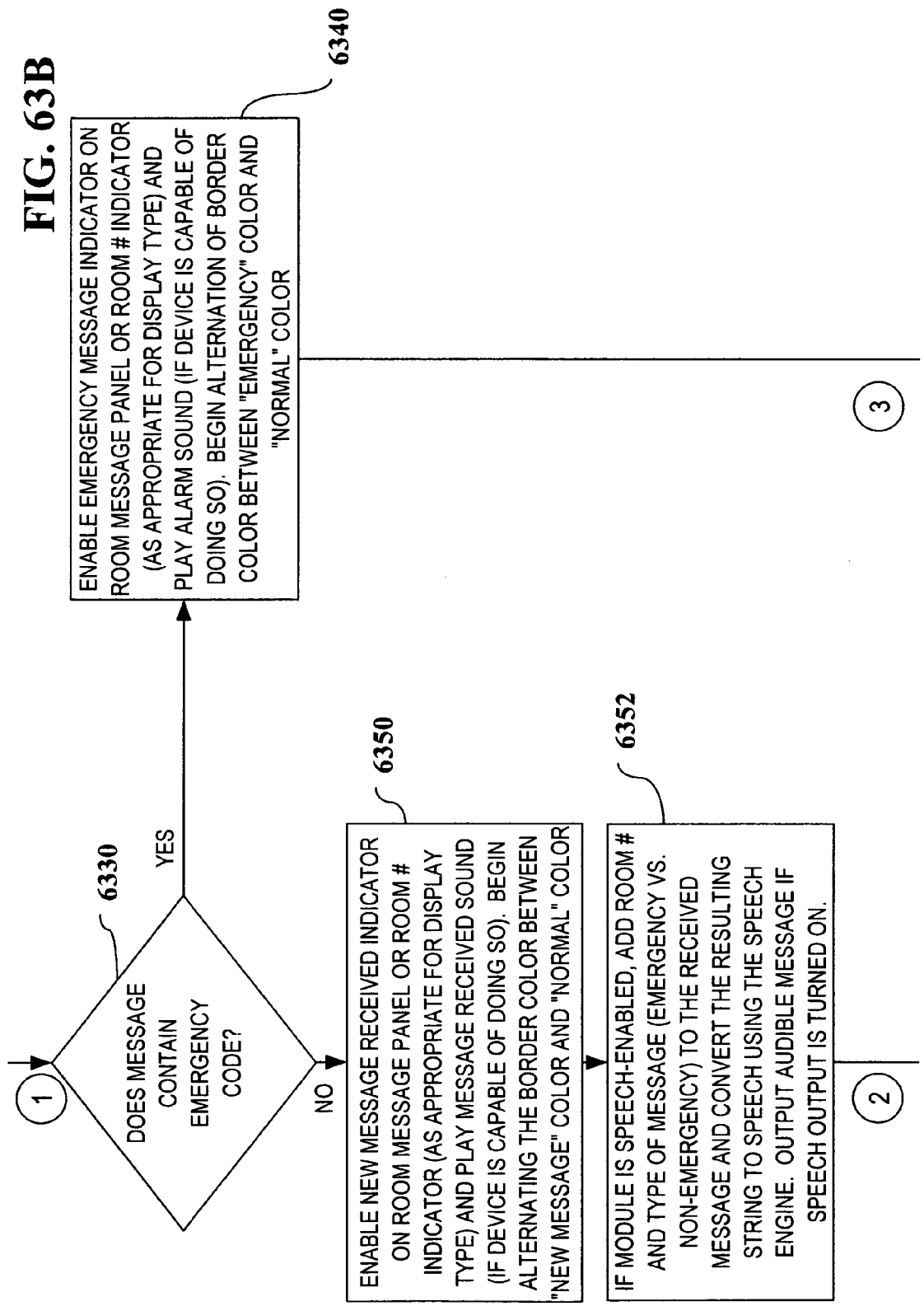

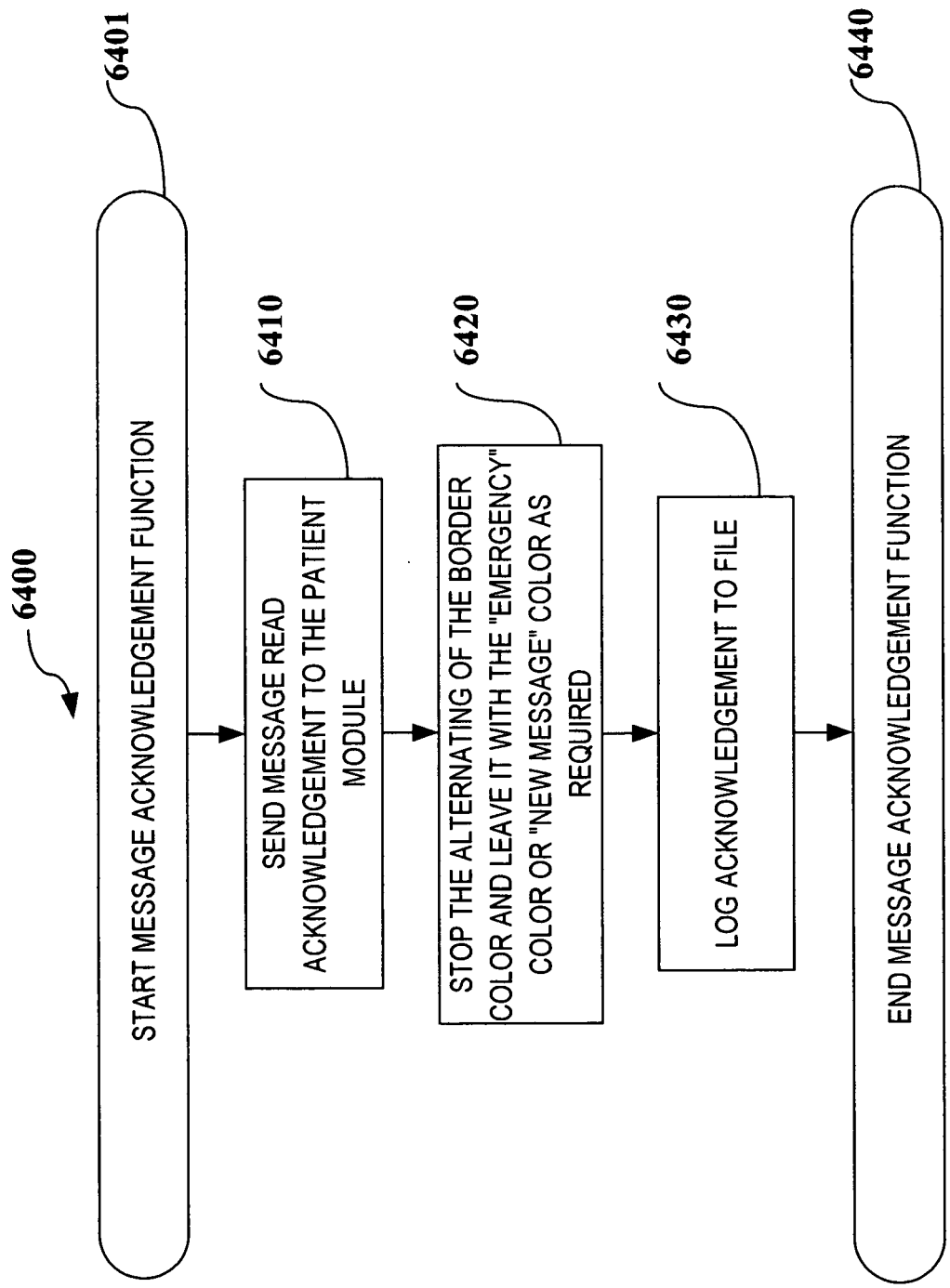

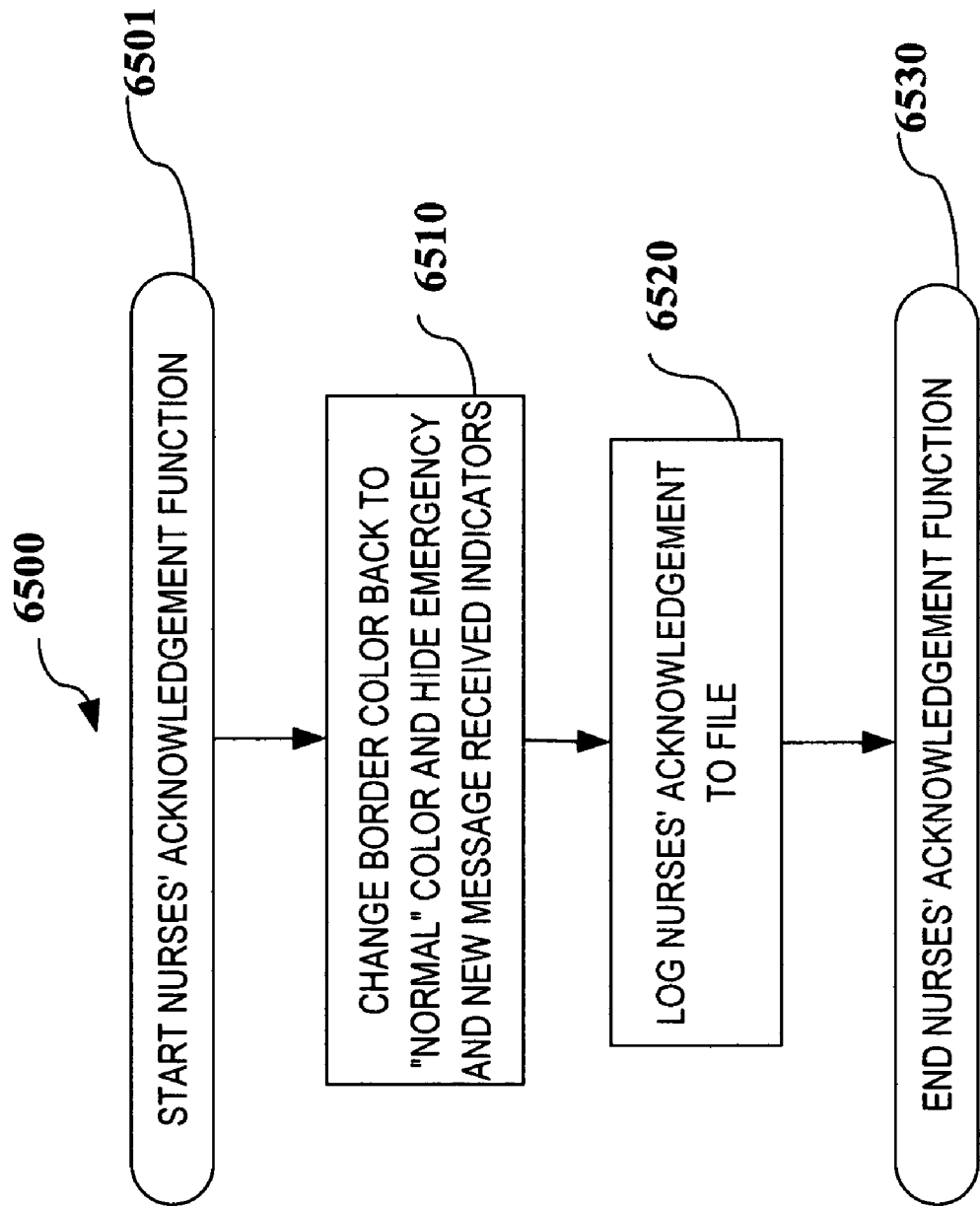

FIG. 72

| HOME | ERASE | HELP |
|------|-------|------|
| SPEAK | MAIN SCREEN | |
| | SPELL | MORE |

I NEED BOY

| BOY | BOYCOTT |
|-----|---------|
| BOYFRIEND | BOYHOOD |
| BOYISH | BOYS |

ASSISTIVE COMMUNICATION DEVICE

CROSS REFERENCE TO RELATED APPLICATION

This claims the benefit of now abandoned, commonly-assigned U.S. Provisional Patent Application No. 60/624,395, filed Nov. 2, 2004, which is hereby incorporated by reference herein in its entirety.

BACKGROUND OF THE INVENTION

This invention relates to assistive communication devices, and particularly to computer-based devices which allow individuals with a temporary or permanent speech impairment to communicate by constructing messages which are output using speech synthesizers, on-screen and remote text display, as well as telephone and e-mail interfaces. More particularly, this invention relates to such devices that can be used by a patient in an acute-care or other healthcare or home setting with little or no instruction from any other person.

Patients in intensive care units in hospitals as well as a significant number of patients in other health-care settings often find themselves temporarily unable to speak and therefore unable to communicate their medical and emotional needs to health care providers or family members. The reasons for the inability to speak are varied, but include stroke, spinal cord injury, head injury, cancer, other degenerative diseases, and intubation associated with mechanical ventilation.

A number of different methods are typically employed to help hospital patients attempt to communicate with medical staff and family members. The most commonly used methods are lip reading, use of alphabet or word boards, handwriting, and gesturing.

General weakness and loss of muscle tone which frequently occur in patients on ventilator support often makes handwriting difficult to interpret. In addition, ventilated patients are frequently restrained (to prevent accidental extubation), further complicating any attempts to communicate via handwriting.

The remainder of the techniques mentioned above (alphabet/word boards, lip reading, and gesturing) are often very tedious, and may require the participation of a trained "communication partner." Even with experience in the use of these alternative communication methods, nurses state that they often leave the room having no idea what the patient was trying to communicate.

Complicating the situation is the fact that ventilated patients not infrequently experience compromised vision, making visually-based methods difficult for these patients. Nursing shortages and demands on nurses' time make it hard for nurses to devote large amounts of time to communication efforts, so that even when these alternative methods are successful, they typically restrict the patient to communicating basic nursing needs rather than more complex concerns, emotions, or feelings.

Another issue related to patient care is the fact that patients who cannot communicate with the nurses' station using the normal method (call button/intercom combination) are at a serious disadvantage in having their medical and emotional needs met. This inability of speech impaired patients to communicate with the nurses' station, also affects the efficiency of the nursing operation, because the nurses' station personnel are unable to assess the reason why the patient pressed the call button, and are therefore hampered in their ability to prioritize their response to the call button event with respect to other patients' needs. Similarly, without knowledge of why the patient pressed the call button, the nurses' station staff are limited in their ability to send an appropriate staff member (e.g., a nurse as opposed to a nurse's aide) to the room, therefore resulting in inefficient use of nursing resources.

The inability of ventilated patients to speak, coupled with the handwriting difficulties mentioned above, results in situations in which proper, complete medical histories are sometimes not obtained from seriously ill patients who enter the hospital suddenly and shortly afterward are put on ventilator support. Because this type of communication difficulty may result in patients not being able to adequately describe previous illnesses, on-going medication needs, and drug allergies, the speech-impaired patient may be at a significantly higher risk for in-hospital complications than his or her speech-capable counterparts.

Patients whose illness or injuries require longer term, in-hospital ventilator support often elicit the help of nursing staff with lip reading expertise to place, or respond to, telephone calls to, or from, family members who are unable to visit the hospital on a regular basis. Nurses who become involved in this "interpretive" role often comment about the tremendous amount of time it takes away from other nursing activities, as well as the fact that they are placed in a very awkward position which prevents the patient from having a confidential conversation without a stranger present.

A variety of assistive communication devices (sometimes referred to as augmentative and alternative communication—i.e., AAC—devices) are available for individuals with long term-medical disabilities (such as amyotrophic lateral sclerosis—i.e., ALS). These systems include touchscreen and switch-activated computers with integrated or add-on speech synthesizer functionality, which may be provided by hardware, software or a combination of both, and which is hereafter referred to as a speech engine. These devices are typically optimized for "face-to-face" verbal communication in a home, school, or work setting but lack key functionality required to fulfill the needs of short-term patients in a hospital or health-care setting. For example, they lack an integrated interface to allow communication to a hospital's nurses' station or to caregivers who are not in the patient's room, and do not address the short-term communication needs of permanently or temporarily visually impaired patients who also are at least temporarily speech-impaired, or the needs of patients who may be temporarily or permanently unable to comprehend written text. In addition, these devices typically require that a professional familiar with the device provide instruction in its use, thus limiting their potential use in a short-term acute-care setting where limited time and resources may exist for such instruction and training, and where a patient may not be in a condition requiring the device for a long enough period of time to justify the instructional effort.

Accordingly, there is a need for an integrated assistive communication system which requires minimal patient training, and which will allow an individual with a temporary speech impairment to easily communicate medical and emotional needs to health-care professionals and family members.

SUMMARY OF THE INVENTION

In accordance with the present invention, there is provided an integrated assistive communication system which requires minimal patient training, and which will allow an individual with a temporary or permanent speech impairment to easily communicate medical and emotional needs to health-care professionals and family members. Such a system preferably has one or more of the following characteristics: (1) it is usable by a broad spectrum of patients, including those with visual impairments; (2) it facilitates the obtaining of the patient's medical history; (3) it enhances "face-to-face" communication between the patient, caregivers, and family members; (4) it facilitates communication between the patient and a nurses' station; and (5) it allows remote communication with family members and health-care providers who may not have the opportunity to be at the patient's location.

To this end, the system of the present invention preferably includes a computer-based Patient Module, which preferably is utilized by the patient to communicate pre-configured messages or user-generated messages. The system also may include one or more of a variety of computer-based or microprocessor-based Nurses' Station or Caregiver Communication Modules which can be used to receive and acknowledge patient messages sent to remote hospital locations or any other remote locations.

The Patient Module, like some existing AAC systems, preferably utilizes a touchscreen display and switch inputs for user interaction, and a speech engine and text display outputs for "face-to-face" communication. However, in addition to the functionality typically present in AAC systems, the system according to the present invention preferably has one or more of the following additional features:

1. A Self-Instruction Mode which, by guiding the user with step-by-step audible instructions, allows a user who had never been instructed in the use of the system, or who has previously been instructed but has lost familiarity with (i.e., has at least partially forgotten how to use) the system, to quickly learn (or re-learn) how to use the system substantially without any assistance, other that of someone who positions the system and its associated switches (if present), and turns the system on. The step-by-step audible instructions of the Self-Instruction Mode may serve a second purpose, allowing fully or partially visually impaired patients, as well as any other patient who is physically or otherwise unable to use the full function of standard computer input devices (such as keyboard and mouse devices) in response to what he or she sees (e.g., is restrained or temporarily partially paralyzed), to substantially fully utilize the system to accomplish the same set of communication tasks as his or her non-impaired counterparts.

2. An integrated telephone interface which preferably allows speech-impaired individuals to place and receive telephone calls and participate in telephone conversations with remote parties equipped only with standard telephones, and which, when coupled with the Self-Instruction Mode, preferably allows speech-impaired users who also are fully or partially visually impaired to do the same.

3. An integrated electronic mail (i.e., e-mail) interface which preferably allows fully or partially visually impaired patients, or any other patient who is physically or otherwise unable to use standard computer input devices (such as keyboard and mouse devices), to generate and receive e-mail messages. In the case of fully or partially visually impaired patients, an incoming e-mail message preferably is read by the system and spoken to the patient via a speech engine, which preferably is built into the system.

4. A Questionnaire Mode which preferably allows patients who are unable to speak or write (including fully or partially visually or physically impaired patients) to execute a standard medical history or other questionnaire.

5. Intelligent, self-optimizing conditional scanning and navigation functionality, which, when combined with the above modes, optimizes the system based on the user mode and current context to minimize the time and effort required by the user to communicate his/her needs.

6. Nurses' Station and Caregiver Communication Module functionality which preferably allows the patient to send emergency and non-emergency messages to a computer-based Nurses' Station Module or to PDA-based, cell phone-based, pager-based, or other microprocessor-based Caregiver Communication Modules, and to receive appropriate acknowledgements when these messages have been received by the devices and when they have been read by the appropriate personnel. If the receiving device (such as a computer, PDA, or cell-phone based system) is capable of audio-output, these remote messages could be output as synthesized speech messages in addition to, or in place of text messages.

The Nurses' Station and Caregiver Communication Modules, in addition to receiving and acknowledging messages sent by one or more Patient Modules, preferably have the ability to display the messages in a format which preferably calls the user's attention to the message and to its urgency level, and, with the exception of pager-based Caregiver Communication Modules, also may contain built-in functionality to facilitate the paging of other staff members as required to address the patient's needs. In addition to the hospital setting, this same functionality could be utilized in any health-care setting, including the home, to allow patients to communicate with caregivers or family members who may be at other locations within the premises or outside the premises. Thus, for example, a bed-ridden, speech-disabled patient, or any other patient who is physically or otherwise unable to use standard computer input devices (such as keyboard and mouse devices), at home could send a message to a family member in the yard, on a shopping trip, or even at work, provided that the receiving device had reception at the receiving location.

It should be pointed out that although the system according to the invention is designed to be easily used with minimal instruction, to facilitate use by patients with short-term needs that might not be consistent with intensive instruction, the system also can be used on a long-term basis. For example, the system includes features that make it useful for visually impaired patients, including those who may have long-term or permanent needs. In the context of the present invention, and in the claims which follow, visual impairment, or being "other than able to see," includes cognitive impairment relative to visual data—i.e., the inability to process visual data, even when the patient can see. For example, a stroke patient who can see may nevertheless be permanently or temporarily unable to process what he or she sees.

Therefore, in accordance with the present invention there is provided an assistive communication device for allowing a speech-impaired user to construct at least one of a statement, a query and a request, and to communicate the at least one of the statement, query and request to another person. The assistive communication device includes an input device that accepts inputs from the user, and a plurality of output devices that communicate with the user and with that other person. The plurality of output devices includes at least a display and a transducer for creating aural output. A processor operates on the inputs and interacts with the user via at least one of the plurality of output devices to construct said at least one of a statement, a query and a request. The processor operates in a first mode when the user is all of (a)

familiar with use of the assistive communication device, (b) able to see, and (c) able to use full function of standard computer input devices, and in at least one other mode different from the first mode when the user is both (a) unfamiliar with use of the assistive communication device, and (b) at least one of (i) visually impaired, and (ii) unable to use full function of standard computer input devices, to allow the user who is both (a) unfamiliar with use of the assistive communication device, and (b) at least one of (i) visually impaired, and (ii) unable to use full function of standard computer input devices, to use the assistive communication device to communicate with that other person.

A caregiver message device for use with the assistive communication device is also provided.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 3 is a representation of a Patient Module screen display in a preferred embodiment of a system according to the present invention after a patient selects the "I need" WordGroup;

FIGS. 11A, 11B, 11C and 11D (hereafter collectively referred to as FIG. 11) are a flowchart representing a preferred embodiment of a DoAction Function in a preferred embodiment of a system according to the present invention;

FIG. 15 is a flowchart representing a preferred embodiment of a Move Highlight Specific Function in a preferred embodiment of a system according to the present invention;

FIG. 17 is a flowchart representing a preferred embodiment of an Erase Function in a preferred embodiment of a system according to the present invention;

FIG. 20 is a flowchart representing a preferred embodiment of a Re-generate Displayed and Spoken Messages Function in a preferred embodiment of a system according to the present invention;

FIGS. 21A, 21B and 21C (hereafter collectively referred to as FIG. 21) are a flowchart representing a preferred embodiment of a Re-generate Displayed Message Function in a preferred embodiment of a system according to the present invention;

FIGS. 22A, 22B, 22C and 22D (hereafter collectively referred to as FIG. 22) are a flowchart representing a preferred embodiment of a Re-generate Spoken Message Function in a preferred embodiment of a system according to the present invention;

FIG. 26 is a flowchart representing a preferred embodiment of a Speak Displayed Message Function in a preferred embodiment of a system according to the present invention;

FIG. 36 is a flowchart representing a preferred embodiment of an Append Suggested Word Function in a preferred embodiment of a system according to the present invention;

FIG. 39 is a flowchart representing a preferred embodiment of a Select Party for Telephone Call Function in a preferred embodiment of a system according to the present invention;

FIG. 40 is a flowchart representing a preferred embodiment of a Select Telephone Number Function in a preferred embodiment of a system according to the present invention;

FIGS. 41A and 41B (hereafter collectively referred to as FIG. 41) are a flowchart representing a preferred embodiment of a Place Telephone Call Function in a preferred embodiment of a system according to the present invention;

FIG. 42 is a flowchart representing a preferred embodiment of an Incoming Telephone Call Event Handler in a preferred embodiment of a system according to the present invention;

FIG. 44 is a flowchart representing a preferred embodiment of a Hang Up Telephone Function in a preferred embodiment of a system according to the present invention;

FIG. 45 is a flowchart representing a preferred embodiment of an Initiate E-mail Session Function in a preferred embodiment of a system according to the present invention;

FIG. 46 is a flowchart representing a preferred embodiment of a Select Party for E-mail Function in a preferred embodiment of a system according to the present invention;

FIGS. 63A, 63B and 63C (hereafter collectively referred to as FIG. 63) are a flowchart representing a preferred embodiment of a Receive Patient Message Event Handler in a preferred embodiment of a system according to the present invention;

FIG. 64 is a flowchart representing a preferred embodiment of a Message Acknowledgement Function in a preferred embodiment of a system according to the present invention;

FIG. 65 is a flowchart representing a preferred embodiment of a Nurse's Acknowledgement Function in a preferred embodiment of a system according to the present invention;

FIG. 72 is a representation of a preferred embodiment of an implementation of a Patient Module Spelling Interface screen in a preferred embodiment of a system according to the present invention after addition of letters "b," "o," and "y" and user selection of the "Suggest" option;

Each of FIGS. 73-78 is a representation of a preferred embodiment of an implementation of a Patient Module Questionnaire Mode Screen in a preferred embodiment of a system according to the present invention;

Each of FIGS. 79-82 is a representation of a preferred embodiment of an implementation of a Patient Module Screen illustrating an aspect of telephone functionality in a preferred embodiment of a system according to the present invention; and Each of FIGS. 83-86 is a representation of a preferred embodiment of an implementation of a Patient Module Screen illustrating an aspect of e-mail functionality in a preferred embodiment of a system according to the present invention.

DETAILED DESCRIPTION OF THE INVENTION

Before describing how the present invention achieves the aforementioned improvements over previously known AAC devices, it is instructive to describe in detail the various hardware and software modules of the system, after which the various combinations of those modules to achieve the results of the invention can more easily be described.

Figure 1:
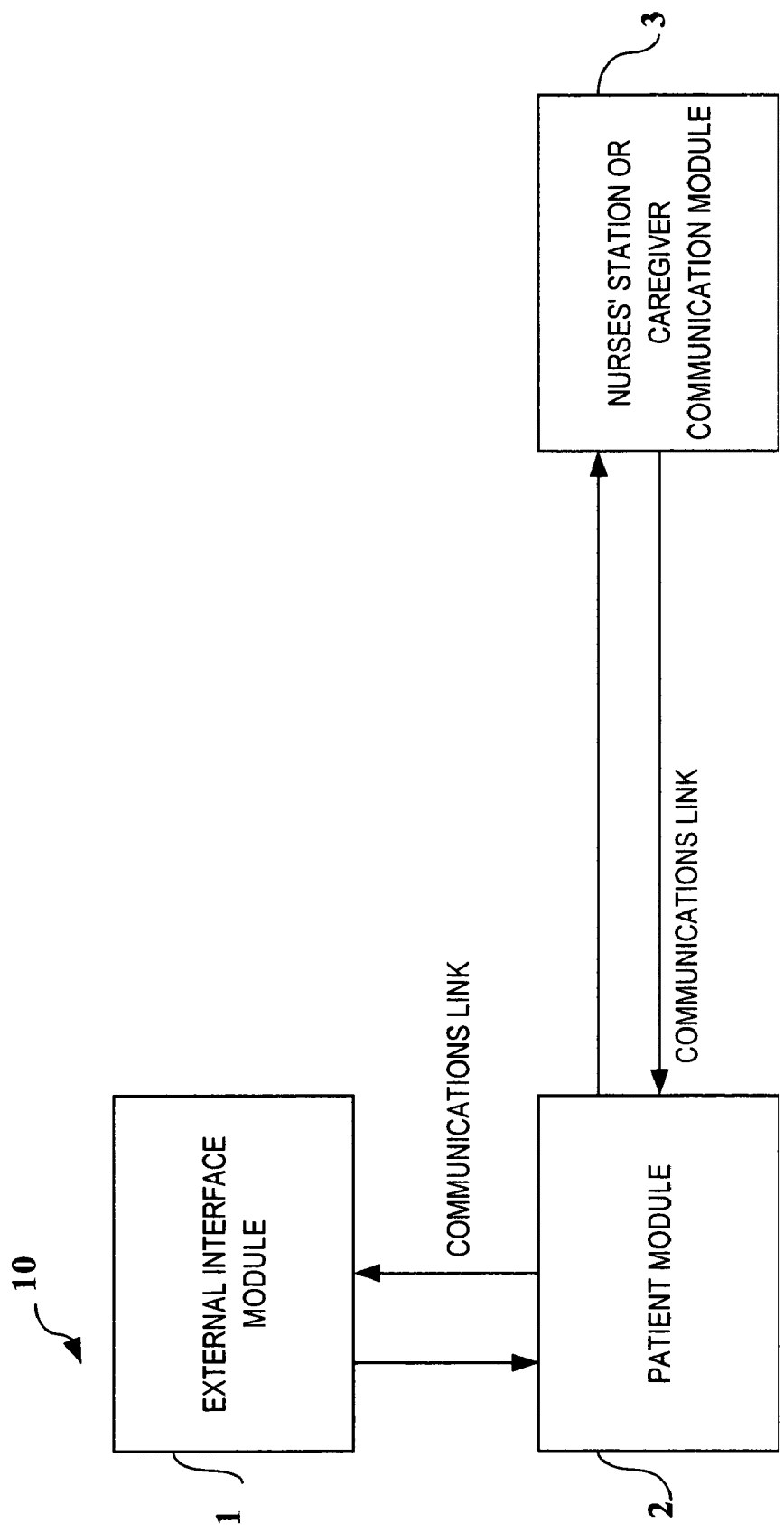
FIG. 1 is a block diagram of a preferred embodiment of a system in accordance with the present invention.
Figure 2:
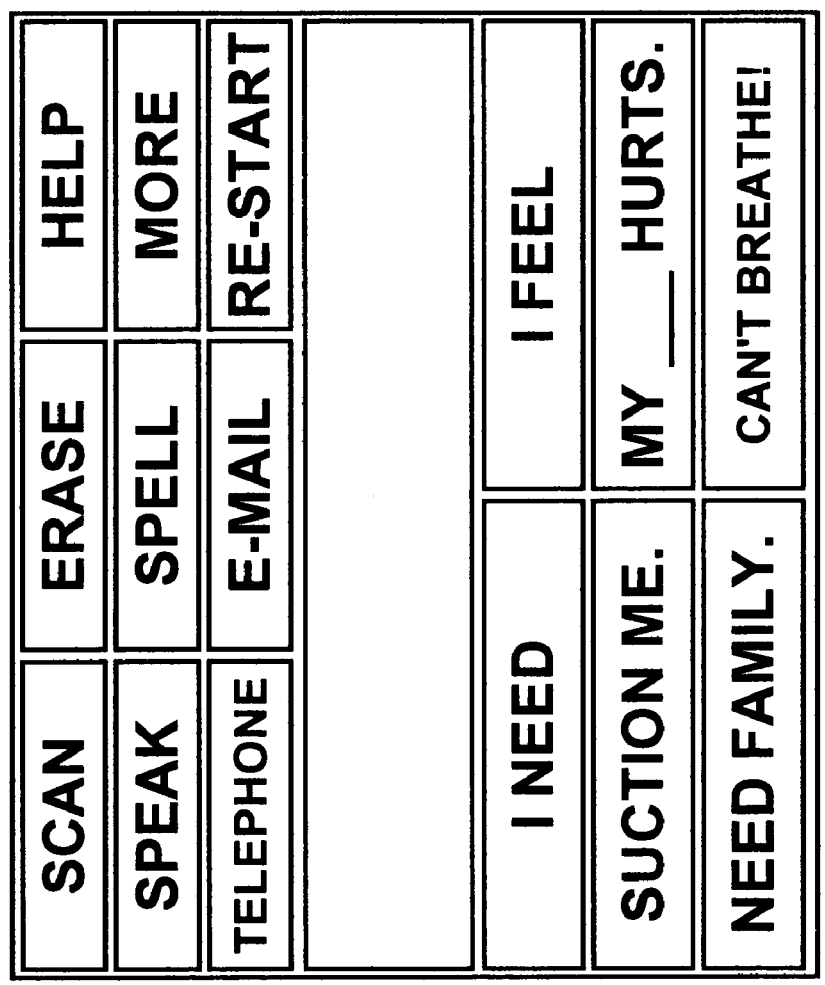
FIG. 2 is a representation of a typical Patient Module screen display in a preferred embodiment of a system according to the present invention prior to any patient activity.
Figure 4:
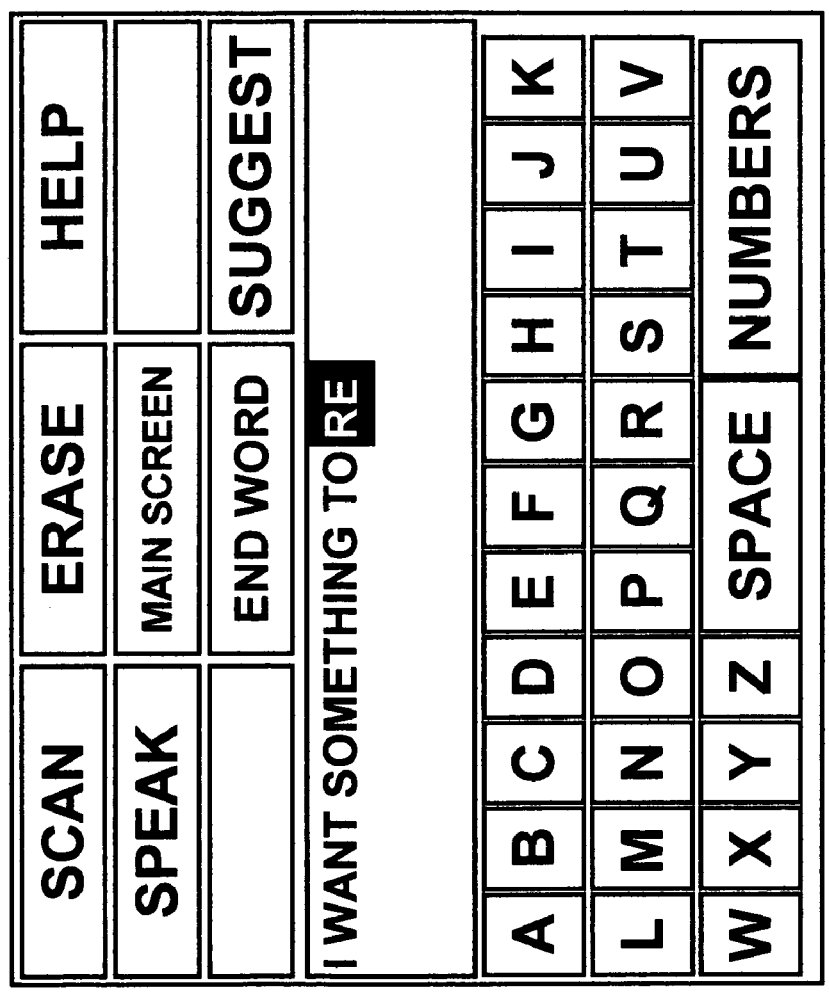
FIG. 4 is a representation of a Patient Module screen display in a preferred embodiment of a system according to the present invention when using the Spell Mode option.
Figure 5:
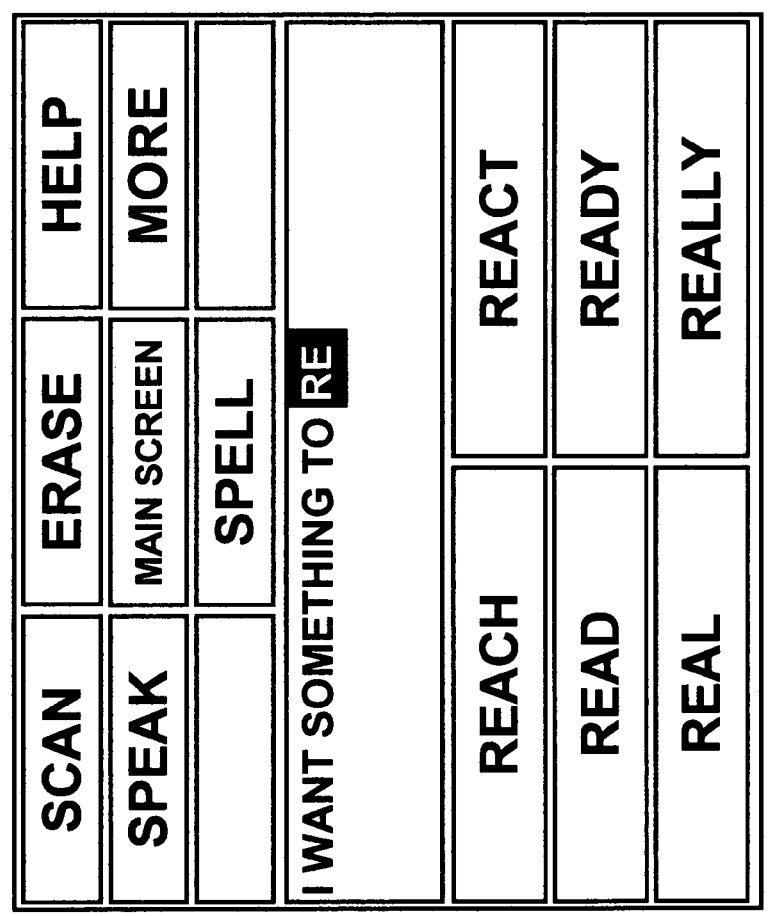
FIG. 5 is a representation of a Patient Module screen display in a preferred embodiment of a system according to the present invention after user selection of the "Suggest" panel.
Figure 6:
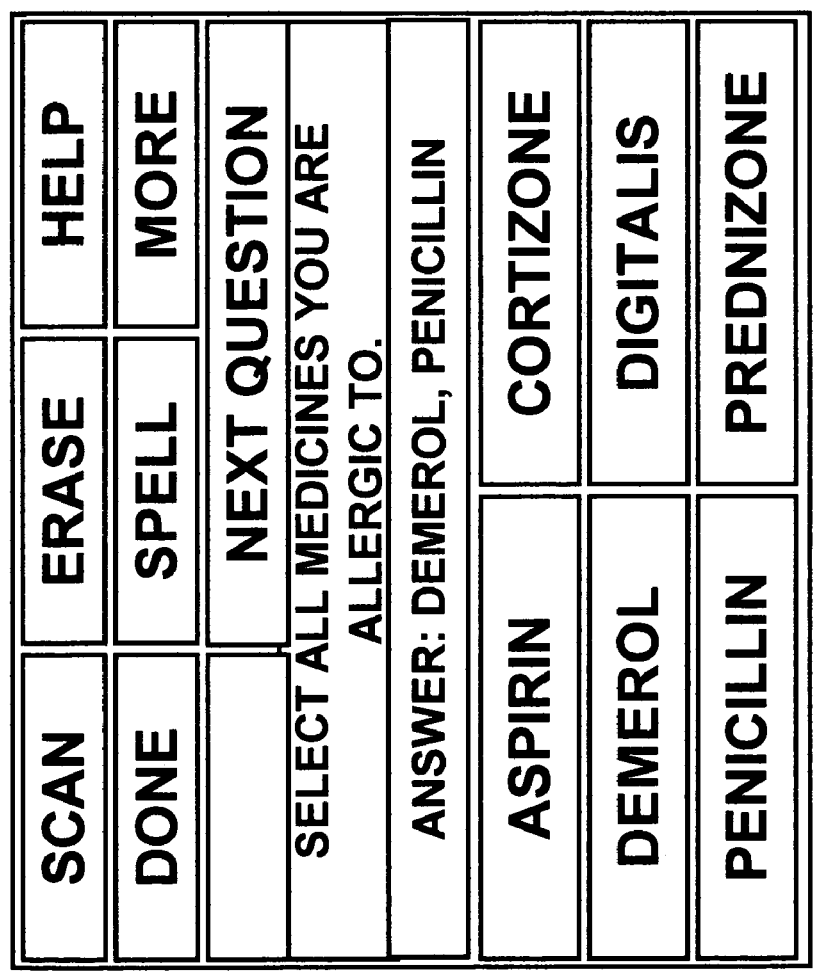
FIG. 6 is a representation of a Patient Module screen in a preferred embodiment of a system according to the present invention when using Questionnaire Mode.

FIG. 1 is a block diagram of major components of a preferred embodiment of a patient and nurses' station/caregiver communication system 10 according to the present invention. The system preferably includes a Patient Module 2, which may be a computer with an integrated touchscreen display or external touchscreen monitor, an External Interface Module 1 which preferably includes electronic circuitry that provides various interfaces to one or more external devices, and a computer-based or microprocessor-based nurses' station or caregiver communication module or message device 3. Each of External Interface Module 1 and nurses' station/caregiver communication module 3 may communicate bidirectionally with Patient Module 2. Patient Module 2 and External Interface Module 1 can be, but need not be, located in the same housing. Each patient utilizing the system in a hospital, health-care or home setting would typically have his or her own dedicated Patient Module 2, whereas a single nurses' station/caregiver communication module 3 typically would communicate with more than one Patient Module 2.

A user preferably interacts with Patient Module 2 either by touching the screen, if he or she is able to do so, or by activating one or more switch-based or switch-emulating sensors connected to External Interface Module 1, or directly to a computer input port of Patient Module 2. External Interface Module 1, in turn, transmits the switch-closure information to Patient Module 2 via an appropriate communications link. Appropriate sensors (not shown) may include a keyboard, mouse, trackball or joystick or any pointing device which emulates the actions of a mouse, trackball or joystick. It should be noted that in the case of user who is able to use standard computer input devices such as a keyboard or pointing device (i.e., mouse, trackball, joystick, etc.), but is unable to use the full function of such devices, some subset of inputs from such devices can be used. For example, a limited number of keys (e.g., the "Enter" key and the space bar) may be used as switch inputs. For more restricted patients, such as patient who has permanently or temporarily lost use of his or her hands or arms, an appropriate sensor might be an eye-blink sensor or pillow switch (not shown).

When the user has generated a message (as described in more detail below) which he or she desires to communicate to someone in his or her local environment, the user can cause Patient Module 2 to generate an electrical signal which, when connected to loudspeakers in External Interface Module 1, preferably results in audible synthetic speech. When the user desires to communicate via a telephone to a remote location, this same electrical signal can be connected to a telephone line interface DAA module within External Interface Module 1, which may be connected directly or wirelessly to a standard hospital or home telephone jack.

When the user desires to send a message to the computer-based nurses' station/caregiver communication module 3, the constructed message preferably is sent to the nurses' station or caregiver module via an appropriate communications link, which may be a wired or wireless network link, or any other suitable computer communications link.

Figure 7:
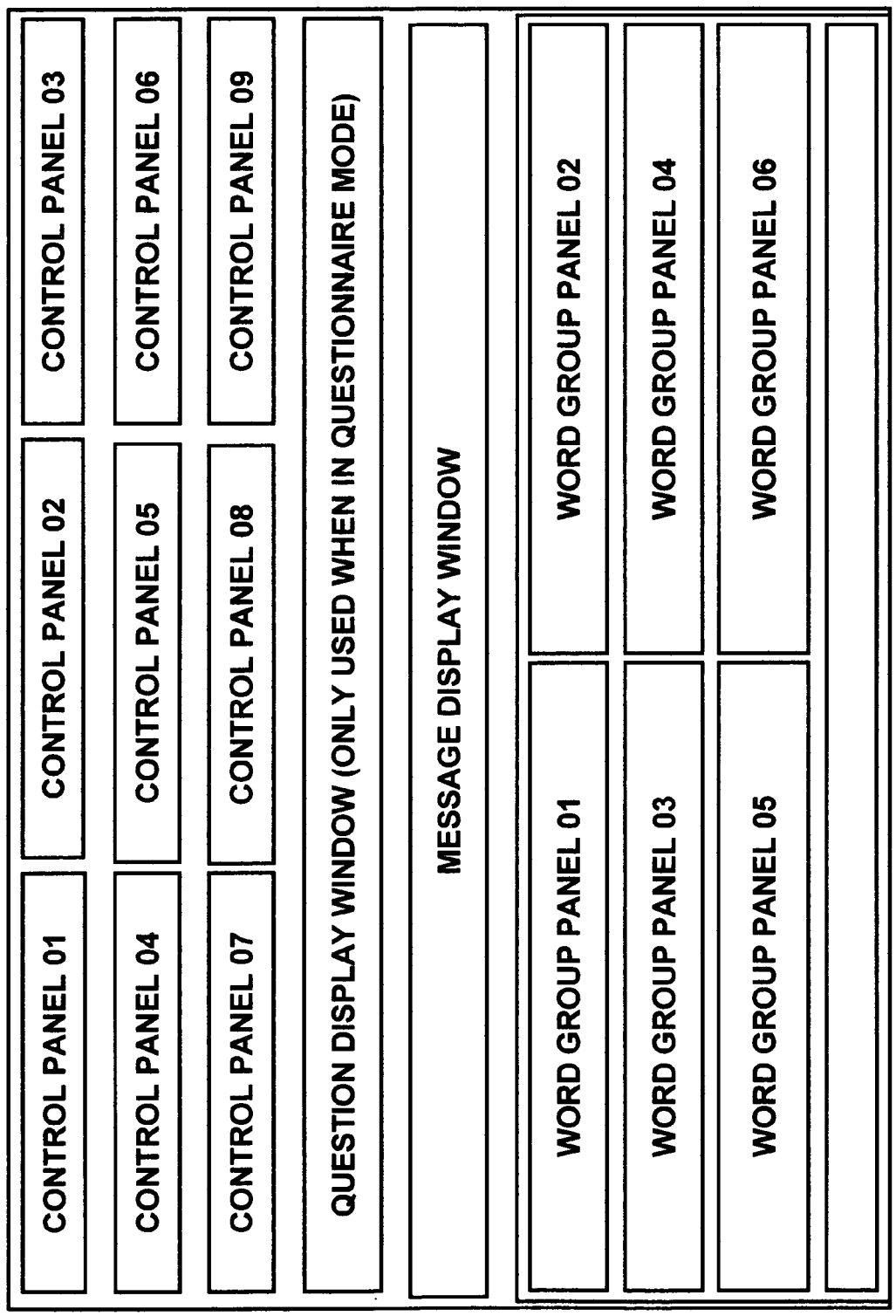
FIG. 7 is a representation of a preferred screen component layout of a Patient Module screen in a preferred embodiment of a system in accordance with the invention.

Each of FIGS. 2-6 shows an example of a display on the screen of a preferred embodiment of Patient Module 2 in accordance with the present invention. Each of the Patient Module screens includes a variety of display areas (hereafter referred to as "panels") and display windows, as illustrated in FIG. 7.

Each panel has associated with it an object in memory (hereafter referred to as an Action Object for the panel). This Action Object preferably is associated with a code identifying the function associated with the display panel, as well as a WordGroup Object which contains a series of character strings (hereafter referred to as strings) used by the Action Object. For example, the text which appears on the panel is one such string, and preferably is included within the WordGroup Object. The terminology used to refer to these display panels is shown in FIG. 7.

The following terms are used herein:

"WordGroup Object" is used to refer to a data structure which preferably is used to store the text strings displayed on WordGroup Panels (such as those in FIG. 2) and other text strings used in association with WordGroup Panels and Command Panels, as well as to store a number of integer and Boolean variables which control how the specific WordGroup Object is to be used or displayed. A configuration utility preferably is provided for use in generating new WordGroup Objects, or to modify existing WordGroup Objects to customize Patient Module 2 to meet the needs of a particular patient.

"WordGroup List" is used to refer to a data structure which stores a list of related WordGroup Objects for use with the WordGroup Panels on the screen. At any given time, the items shown in the WordGroup Panels on the screen (see, e.g., FIGS. 2 and 3) preferably are contained within the same WordGroup List. When a patient selects a WordGroup Panel (for example, by touching it), the WordGroup Object associated with the panel preferably indicates the next WordGroup List, preferably including the next items to be displayed in the WordGroup Panels.

When Patient Module 2 is running, there preferably are three basic modes of user-interaction with the system. These modes are referred to as TouchScreen Mode, Switch Advance Mode, and Scan mode, and are briefly described as follows. In TouchScreen Mode, the user touches an appropriate panel on the Patient Module screen, and the system preferably performs the function associated with the panel. In Switch Advance Mode, user initiated electrical switch closures (detected by digital input/output ports within External Interface Module 1) preferably are used to move a highlight (a special color) from one panel to another, and, when the desired panel is highlighted, a separate switch closure activated by the user preferably causes that panel's function to be performed. In Scan Mode, a timer event preferably causes the highlight to advance to the next panel in sequence, and, when the desired panel is highlighted, a user-actuated switch closure preferably causes that panel's function to be performed. For ease of description, each of these three modes will be described independently. However, more than one of these modes may be enabled simultaneously with little or no modification, as would be apparent to one of ordinary skill in the art.

It should be noted that in addition to using a special color as a "highlight," "highlighting" as described in the previous paragraph also could include a shaded region which surrounds the panel, a colored bar which sits on the top of the panel, a visible "sprite" such as a pointer, a "bouncing ball," or any other visual indicator. In some modes of operation, the "highlight" could even be an aural indicator which announces which panel is "highlighted".

Figure 8A:
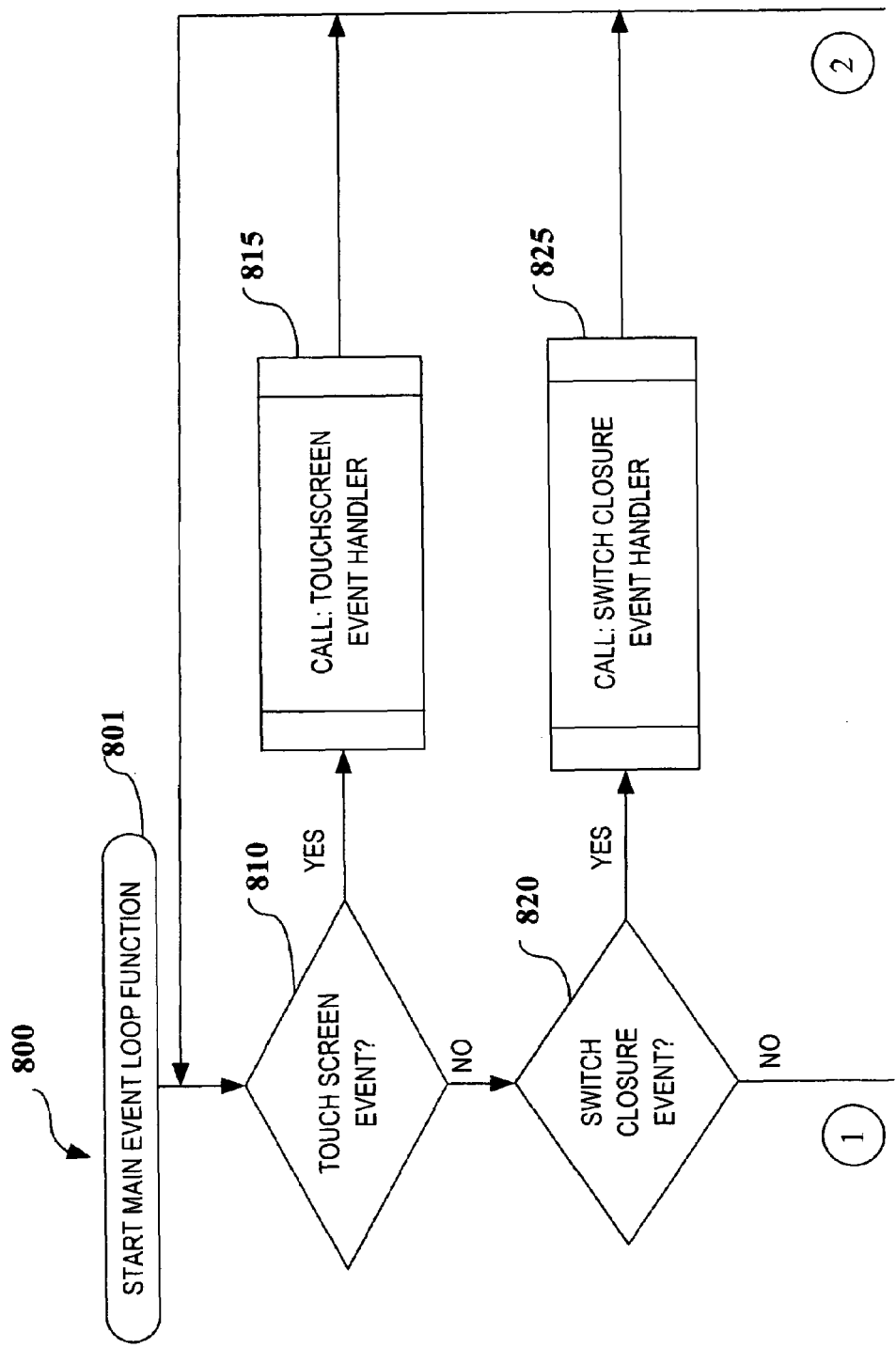
FIGS. 8A, 8B and 8C (hereafter collectively referred to as FIG. 8) are a flowchart representing a preferred embodiment of a Main Event Loop in a preferred embodiment of a system according to the present invention.
Figure 8B:
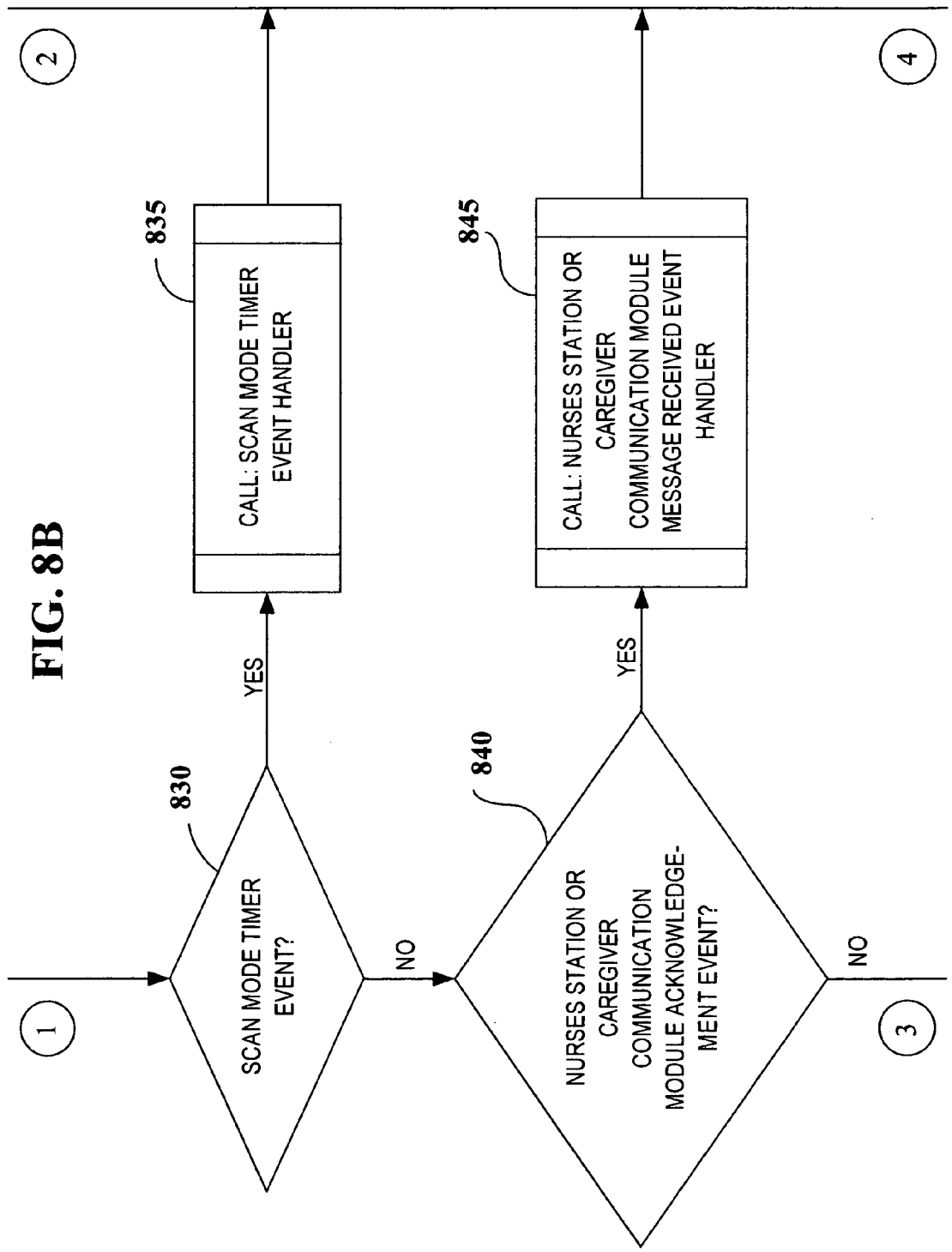
Figure 8C:
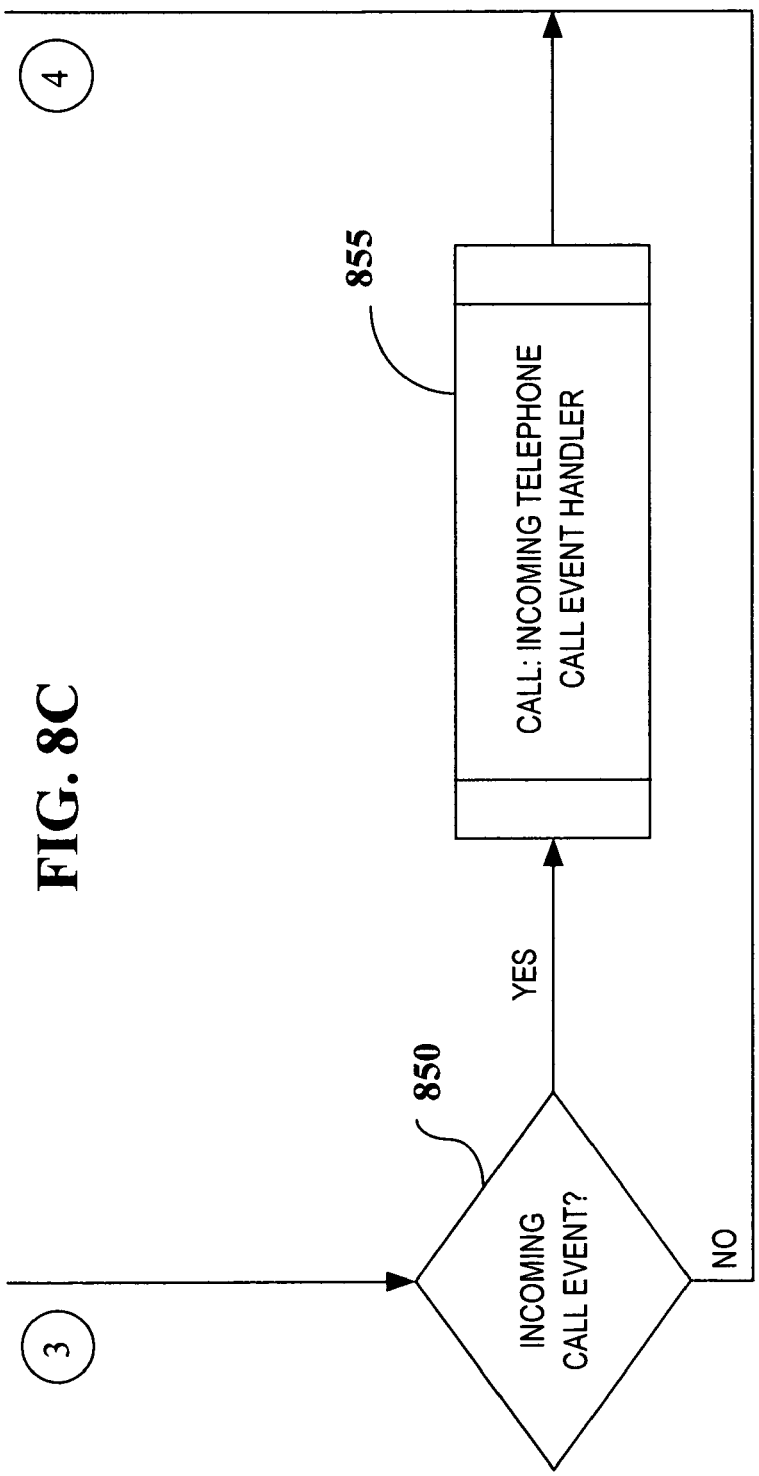

FIG. 8 is a flowchart describing the overall event monitoring loop 800 of the central processor (not shown) of Patient Module 2. Whenever Patient Module 2 is operating, its processor preferably is waiting for a system event including (1) a user-generated event, (2) a "scan timer" event (test 830), or (3) one of a variety of events generated by external devices. The waiting by the system for an event is implemented by the loop of tests 810, 820, 830, 840, 850. The user-generated events preferably include a TouchScreen Event (test 810) and a Switch-Closure Event (test 820). Examples of events generated by external devices are an Incoming Telephone Call Event (test 850) and a Nurses' Station or Caregiver Communication Module Acknowledgement Event (test 840). When any of the system events is detected, the system preferably calls the appropriate event handler routine.

Figure 9A:
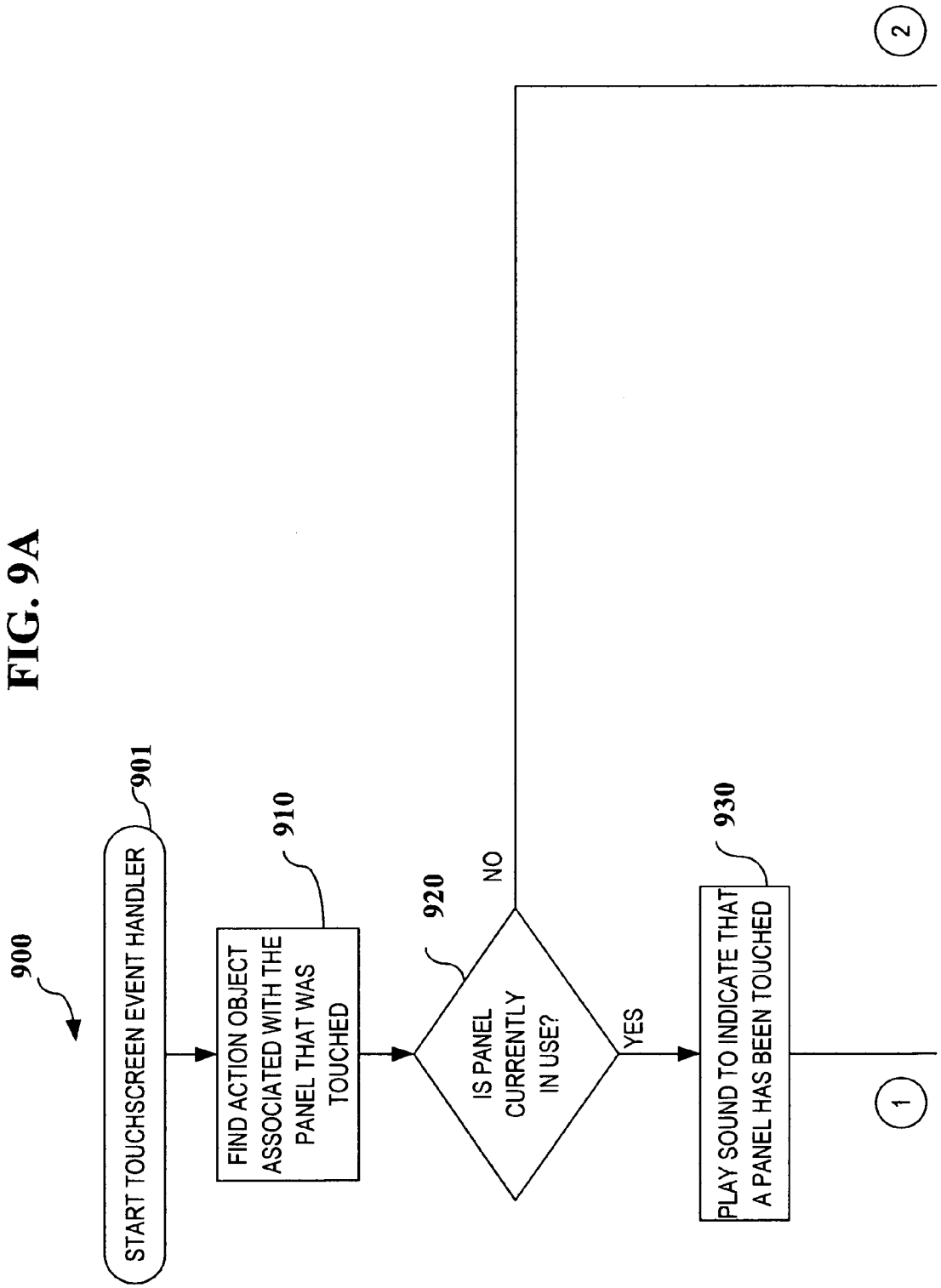
FIGS. 9A and 9B (hereafter collectively referred to as FIG. 9) are a flowchart representing a preferred embodiment of a TouchScreen Event Handler in a system according to the present invention.
Figure 9B:
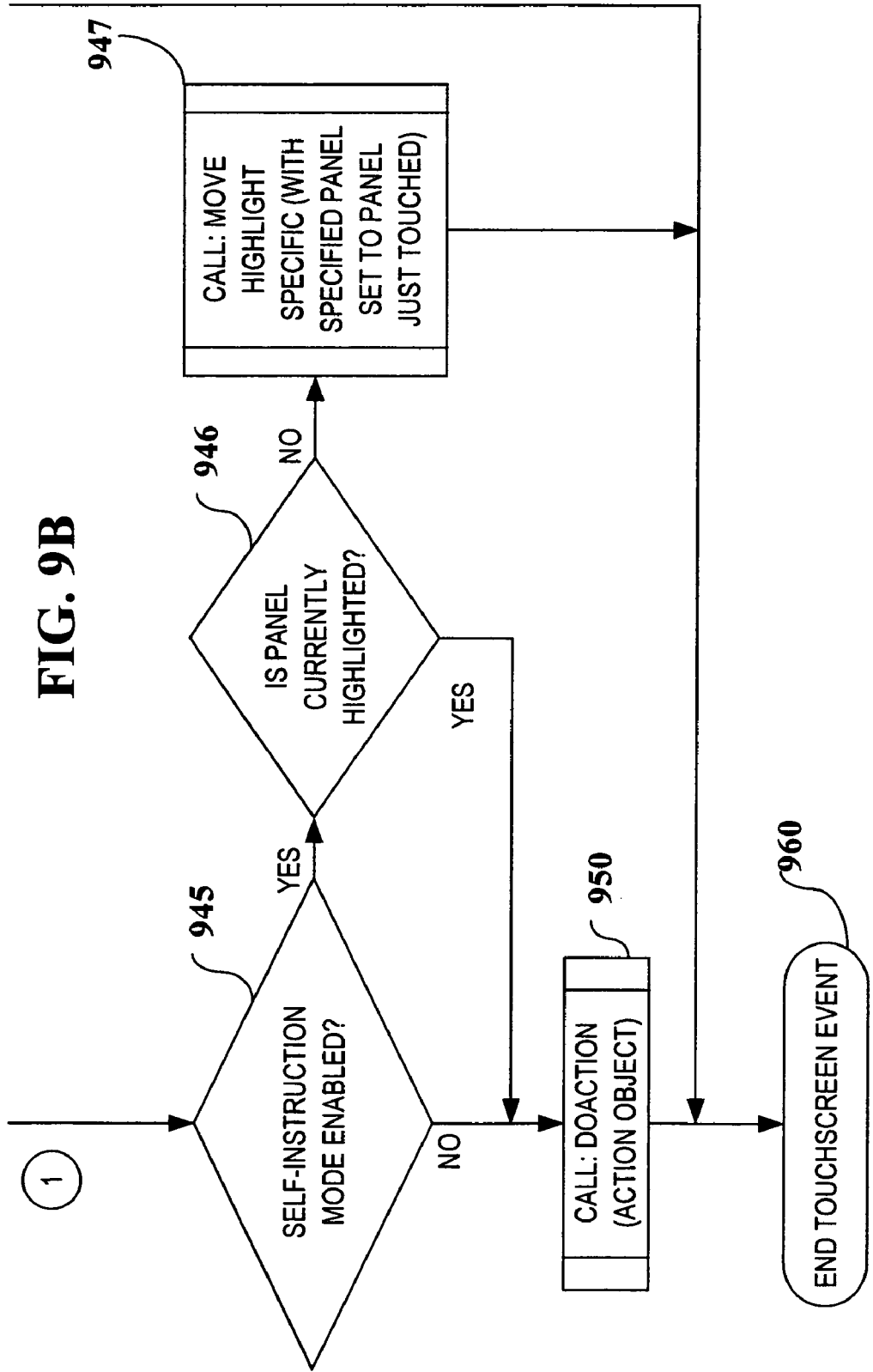

FIG. 9 shows one embodiment of a process 900 for responding to a TouchScreen Event. In step 910, the system identifies the panel which was touched, as well as the Action Object for that panel. In test 920, it is decided whether the panel is in use by seeing whether the caption string for the panel is blank. If the panel is not in use, the remaining steps are skipped and process 900 ends at 960. If the panel is in use, as indicated by Yes, the process proceeds to step 930, where a stored sound is output to indicate that a panel has been touched.

In test 945, it is determined whether or not Self-Instruction Mode is enabled.

If the answer at test 945 is No, test 946 and step 947 are skipped, and in step 950, the DoAction function (see FIG. 11) is called with its argument set to the Action Object associated with the panel that was touched. After the DoAction function performs the functions indicated by the specific Action Object, process 900 ends at 960.

If the answer to test 945 is Yes, test 946 determines if the panel that was touched is highlighted. If the answer to test 946 is No, step 947 calls the Move Highlight Specific function (FIG. 15), with its argument set to the panel which was touched, in order to highlight the panel, and to perform the Instruction function. Step 950 is then skipped at which point process 900 ends at 960.

If the answer to test 946 is Yes (indicating that the Move Highlight function has already been called to highlight this panel and thus, that the instructions for the panel have already been presented to the user), the DoAction function (see FIG. 11) is called with its argument set to the Action Object associated with the panel that was touched, and at the completion of the DoAction function, process 900 ends at 960.

Figure 10A:
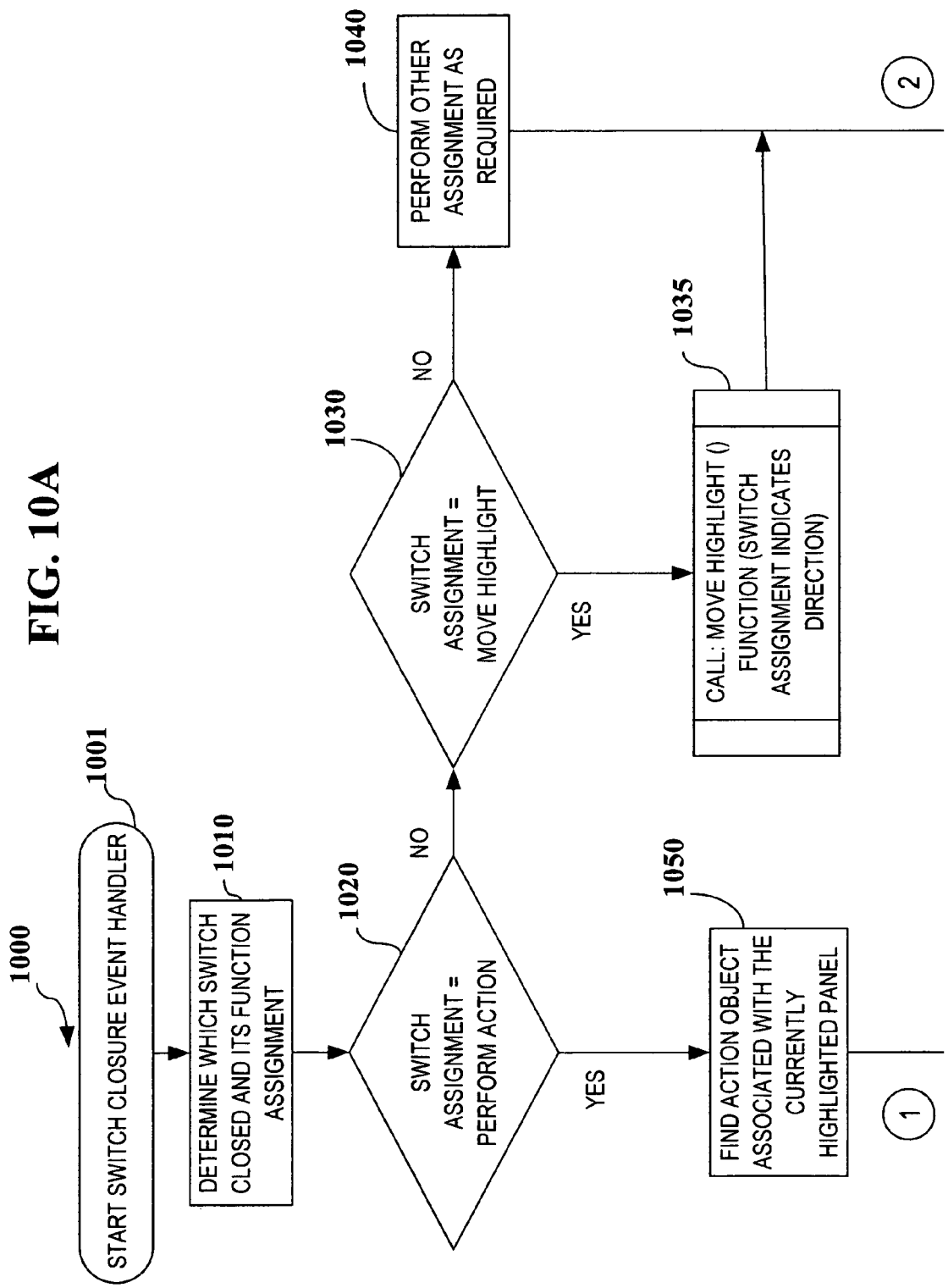
FIGS. 10A and 10B (hereafter collectively referred to as FIG. 10) are a flowchart representing a preferred embodiment of a Switch Closure Event Handler in a preferred embodiment of a system according to the present invention.
Figure 10B:
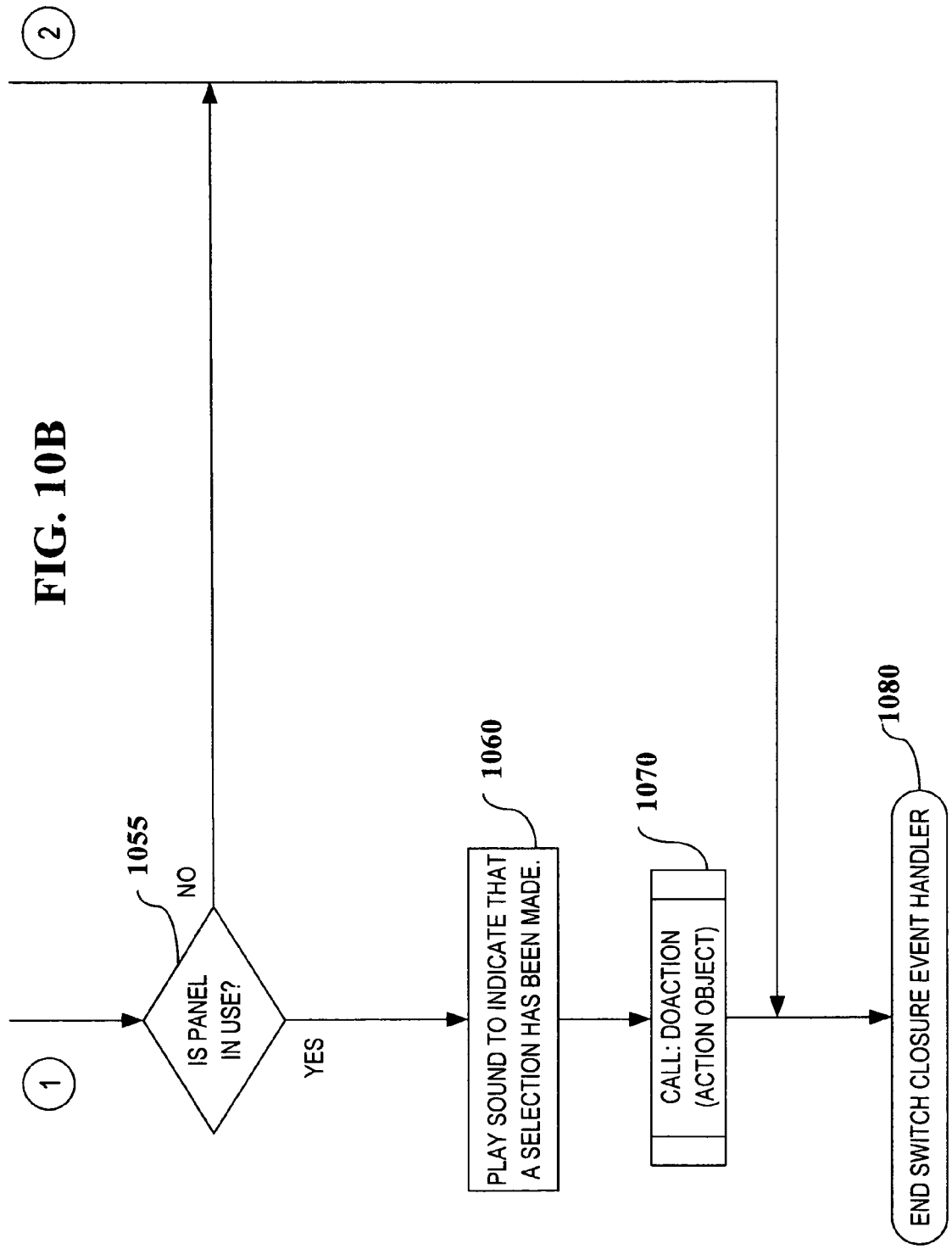

FIG. 10 shows the process 1000 of responding to a Switch Closure Event. In step 1010, the Patient Module identifies which switch was closed by determining which digital input within External Interface Module 1 changed state, and then looks up the current assignment of the switch.

Test 1020 determines if the switch assignment is the Perform Action Assignment. If the answer to test 1020 is Yes, process 1000 proceeds to step 1050 in which the system identifies the panel which was highlighted when the switch closure event occurred, as well as the Action Object for that panel. In test 1055, it is decided whether the panel is in use by determining whether or not the caption string for the panel is blank. If the panel is in use, as indicated by Yes, process 1000 proceeds to step 1060. In step 1060 a stored sound is output to indicate that a panel has been selected. In step 1070, the DoAction function (see FIG. 11) is called with its argument set to the Action Object associated with the panel that was highlighted when the switch closure event occurred. After the DoAction function performs the functions indicated by the specific Action Object, process 1000 ends at 1080.

If the answer to test 1020 is No, test 1030 determines if the switch assignment is one of the four Move Highlight assignments. If the answer to test 1030 is Yes, then step 1035 calls the Move Highlight function (see FIG. 13), passing to it the directional assignment of the switch. After the Move Highlight function completes, process 1000 ends at 1080.

If the answer to test 1030 is No, then the switch assignment is one of the other remaining switch assignments, and the system performs any special operation which may have been assigned to that switch (for example, decreasing or increasing the screen brightness) before exiting process 1000 at 1080. It should be appreciated that one of ordinary skill in the art can easily implement a mouse event handler or keyboard event handler to perform the same general functions as Switch Closure Event Handler 1000.

Figure 11A:
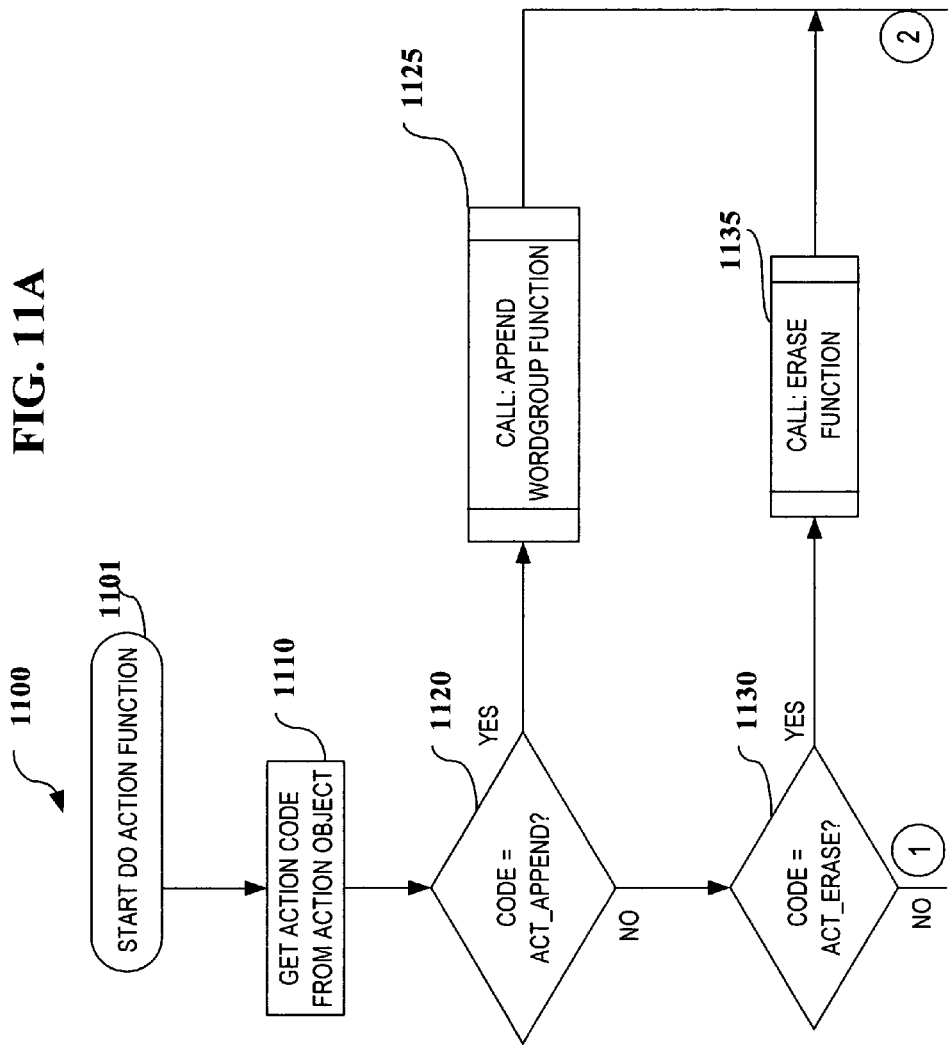
Figure 11B:
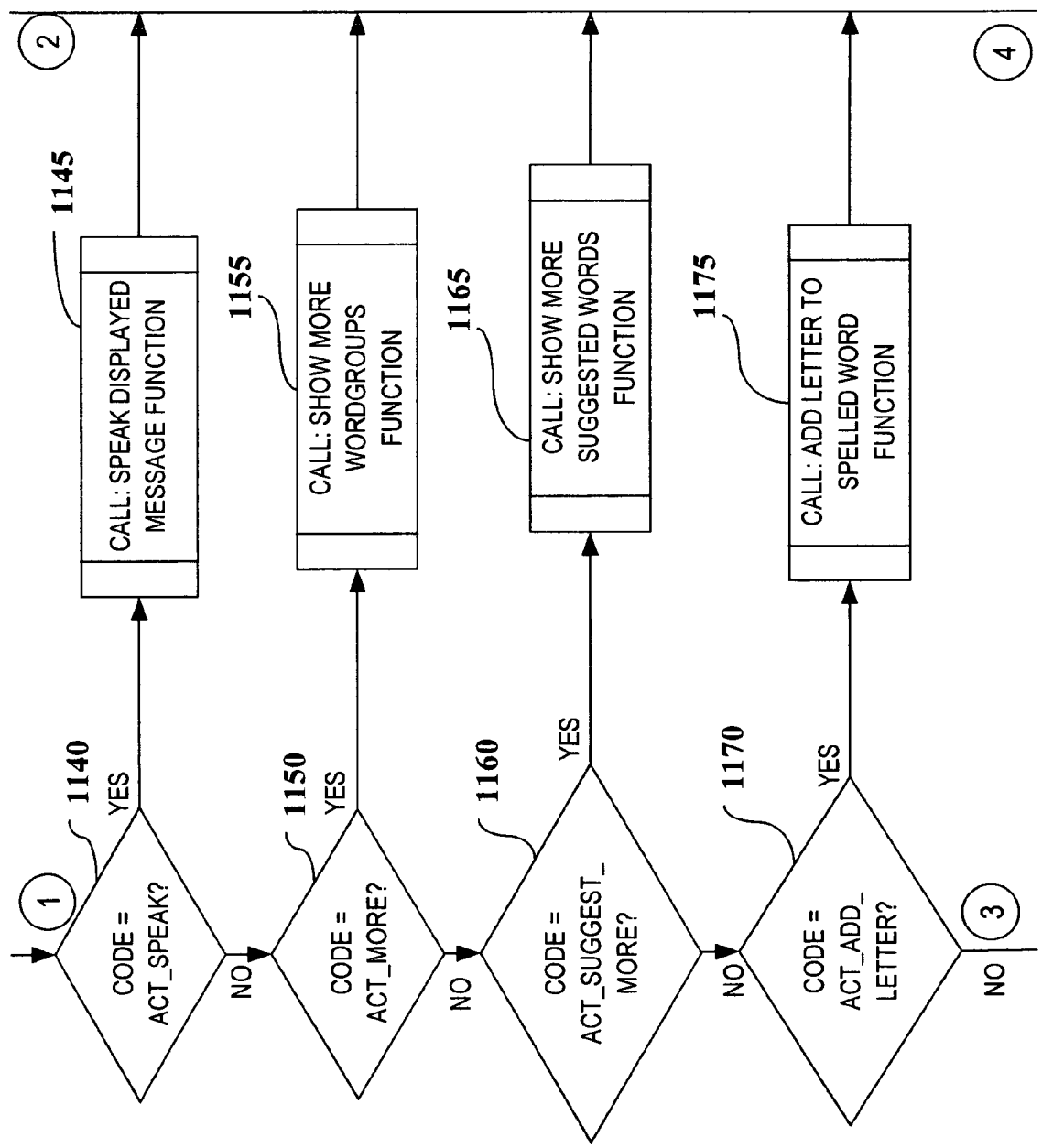
Figure 11C:
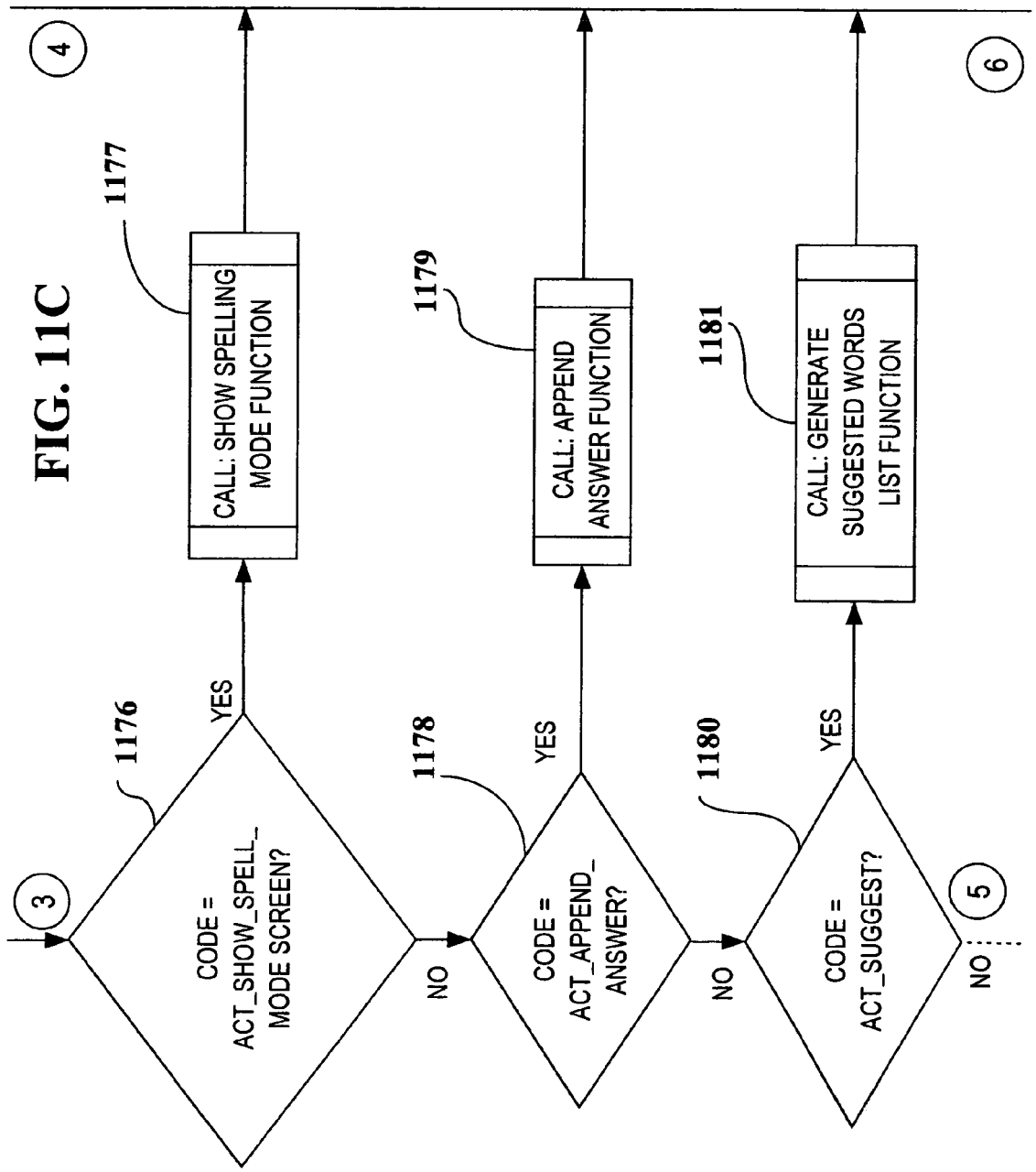

FIG. 11 describes the DoAction function 1100, which is called by user-generated events. Step 1110 extracts the Action Code from the Action Object argument passed to the DoAction function. Based on the Action Code, the system performs the appropriate function, such as (1) appending text strings to the Message Display Window (step 1125), (2) erasing text strings from the Message Display Window (step 1135), (3) speaking text strings in the Message Display Window (step 1145), (4) displaying additional options in the WordGroup Panels (step 1155), (5) displaying more suggested words (step 1165) when the spelling interface is in use, (6) performing various other functions (steps 1170 to 1181) related to the spelling interface screen or the questionnaire mode, or any other function required for system operation (step 1183).

Test 1184 then determines whether the function which was called by the Do Action function changed any of the Control Panels or Word Group Panels currently visible on the screen. If not, the Do Action function is complete, and function 1100 ends at 1199.

The Action Object associated with each panel preferably contains four properties, each of which indicates the index of the next panel to be highlighted when this panel is presently highlighted, and the Move Highlight Directional function (see FIG. 14) is called with its argument set to one of the four possible values (Back, Advance, Up, or Down). If the answer at test 1184 is Yes, then preferably step 1185 computes and stores, for each Control or Word Group Panel on the screen, the four directional properties for the Action Object associated with the panel. Computation of these four directional properties whenever the screen display changes allows the function 1100 to use conditional logic to optimize the panel highlight sequence based on the current screen context, patient- or user-specific settings, and the record of the user's previous actions while using the system. Function 1100 then ends at 1199.

Figure 12:
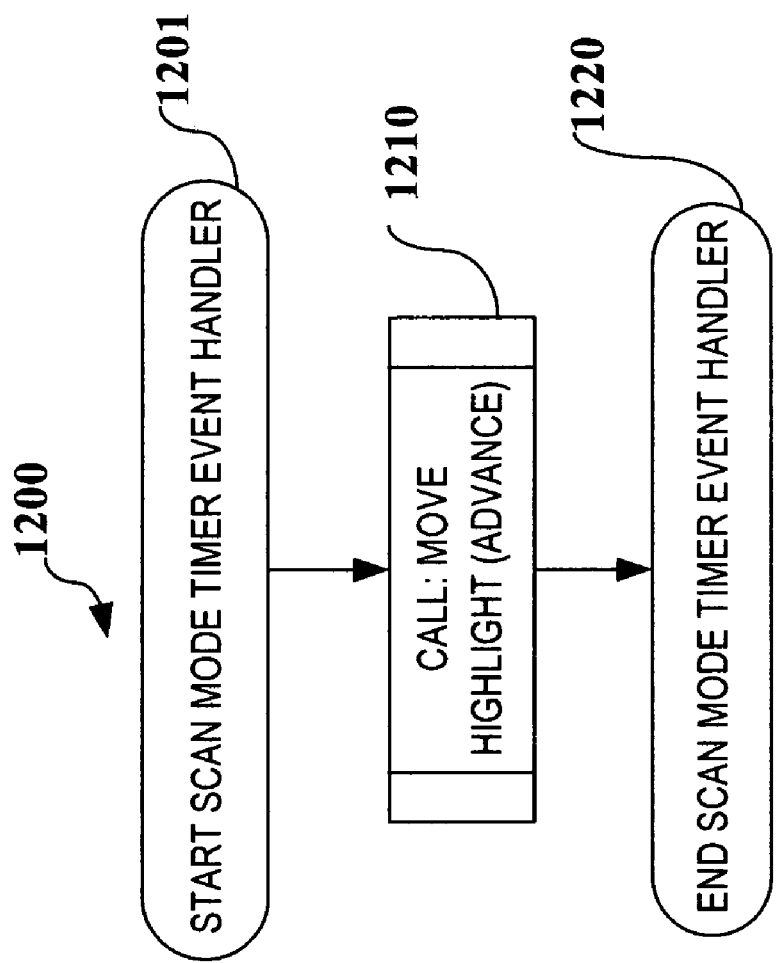
FIG. 12 is a flowchart representing a preferred embodiment of a Scan Mode Timer Event Handler in a preferred embodiment of a system according to the present invention.

FIG. 12 shows process 1200 for responding to a Scan Timer Event. When this event occurs, process 1200 starts at 1201, the Move Highlight function (see FIG. 13) is called at step 1210 with the direction argument set to Advance, and process 1200 ends at 1220.

Figure 13:
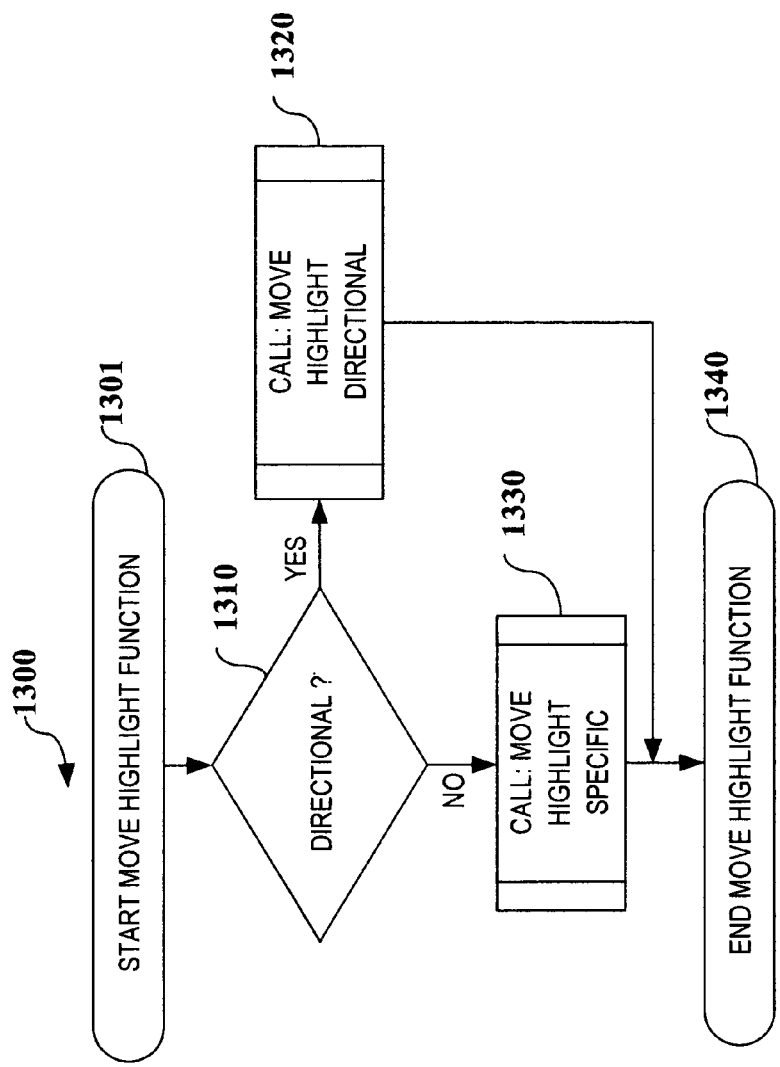
FIG. 13 is a flowchart representing a preferred embodiment of a Move Highlight Function in a preferred embodiment of a system according to the present invention.

FIG. 13 describes the process 1300 for implementing the Move Highlight function. When the Move Highlight function is called, process 1300 starts at 1301 and the system determines (test 1310) whether the argument is a directional argument, or whether it is a request to move the highlight to a specific panel. If the argument is directional, the Move Highlight Directional function (step 1320) is called with the same argument as was passed to the Move Highlight function. If the argument is a specific panel, the Move Highlight Specific function (step 1330) is called with the same argument that was passed to the Move Highlight function. Process 1300 then ends at 1340.

Figure 14A:
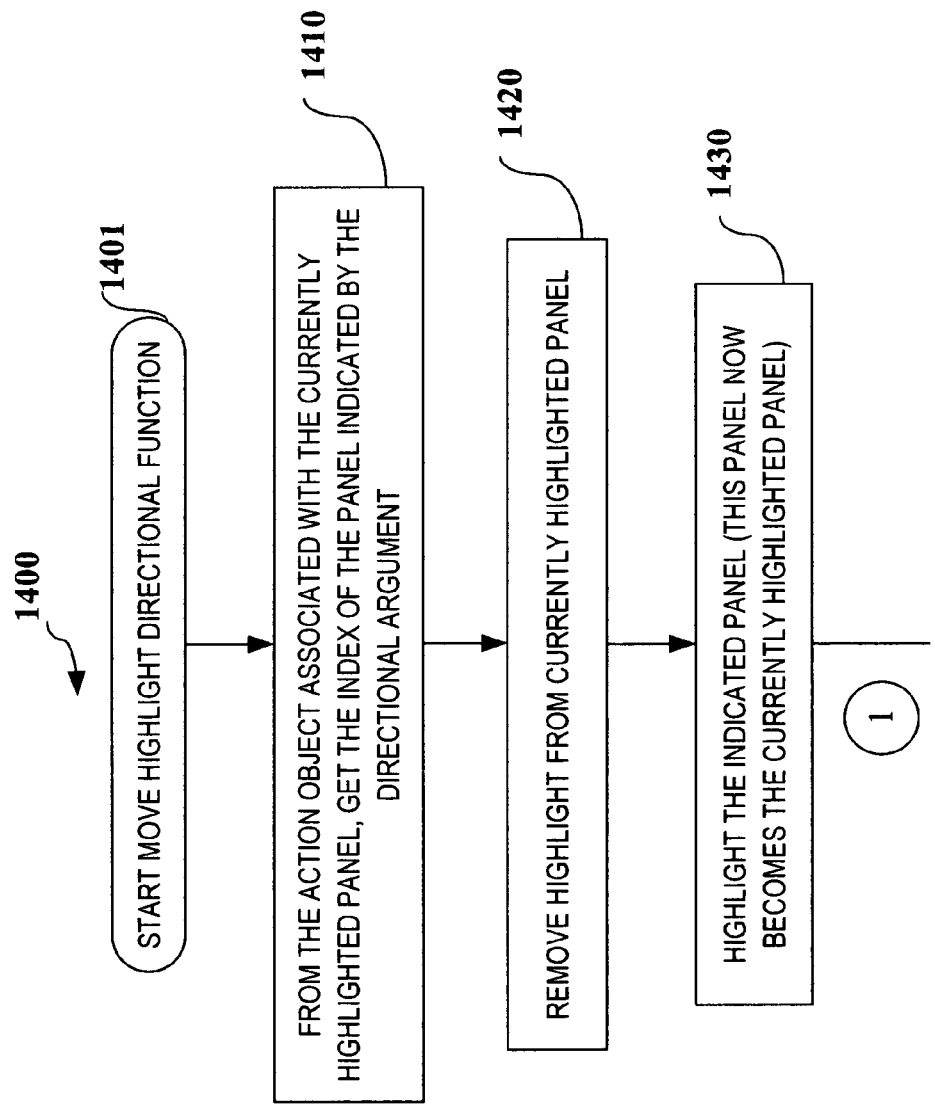
FIGS. 14A and 14B (hereafter collectively referred to as FIG. 14) are a flowchart representing a preferred embodiment of a Move Highlight Directional Function in a preferred embodiment of a system according to the present invention.
Figure 14B:
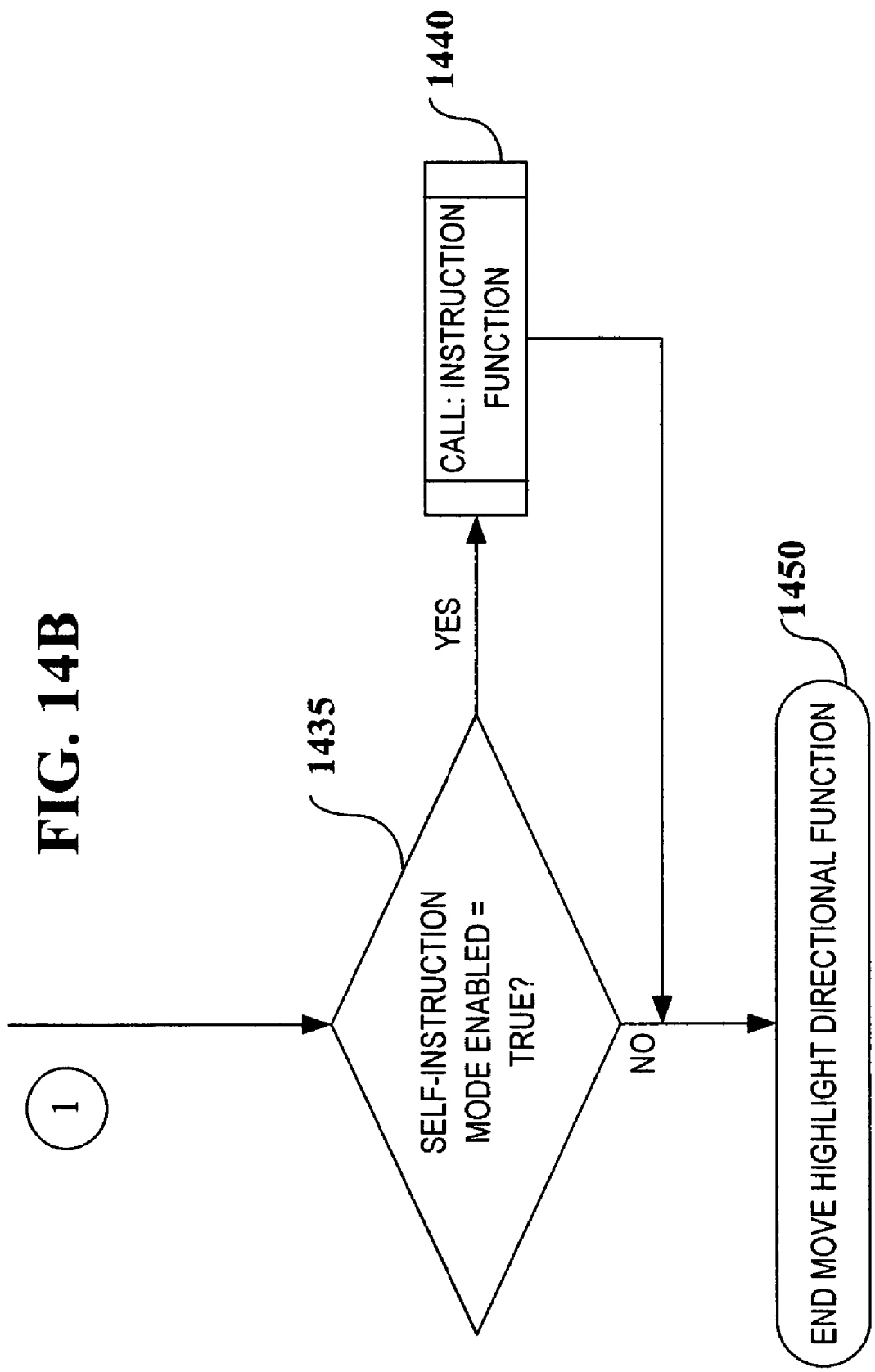

FIG. 14 describes the process 1400, which starts at 1401, for implementing the Move Highlight Directional function. The Action Object associated with each panel contains four properties indicating the index of the next panel to be highlighted when the directional argument passed to Move Highlight Directional is Back, Advance, Up, or Down. In step 1410, the Move Highlight Directional function uses this directional argument to get (from the Action Object of the panel which was highlighted when the Move Highlight function was called) the index of the next panel to be highlighted. It then removes the highlight from the current panel (step 1420), highlights the desired panel (step 1430) and, if Self-Instruction Mode is enabled (test 1435), calls the Instruction function (step 1440) which provides audible instructions for the newly-highlighted panel. Process 1400 ends at 1450.

FIG. 15 describes a preferred embodiment of process 1500, which starts at 1501, for implementing the Move Highlight Specific function. This function simply removes the highlight from the current panel (step 1510), moves the highlight to the specified panel (step 1520) and, if Self-Instruction Mode is enabled (test 1525), calls the Instruction function (step 1530), which provides audible instructions for the newly highlighted panel. Process 1500 ends at 1540.

Figure 16A:
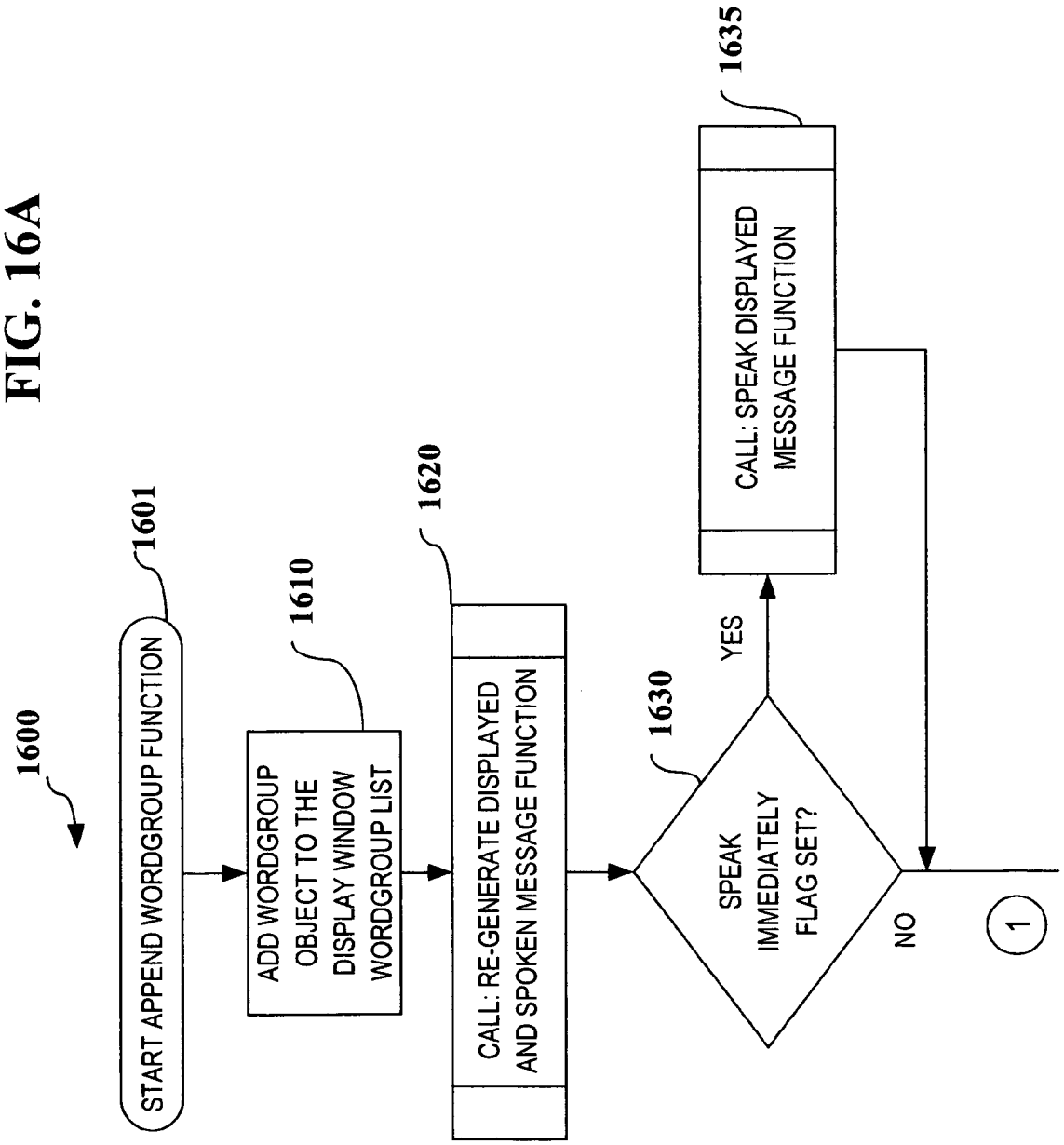
FIGS. 16A, 16B and 16C (hereafter collectively referred to as FIG. 16) are a flowchart representing a preferred embodiment of an Append WordGroup Function in a preferred embodiment of a system according to the present invention.
Figure 16B:
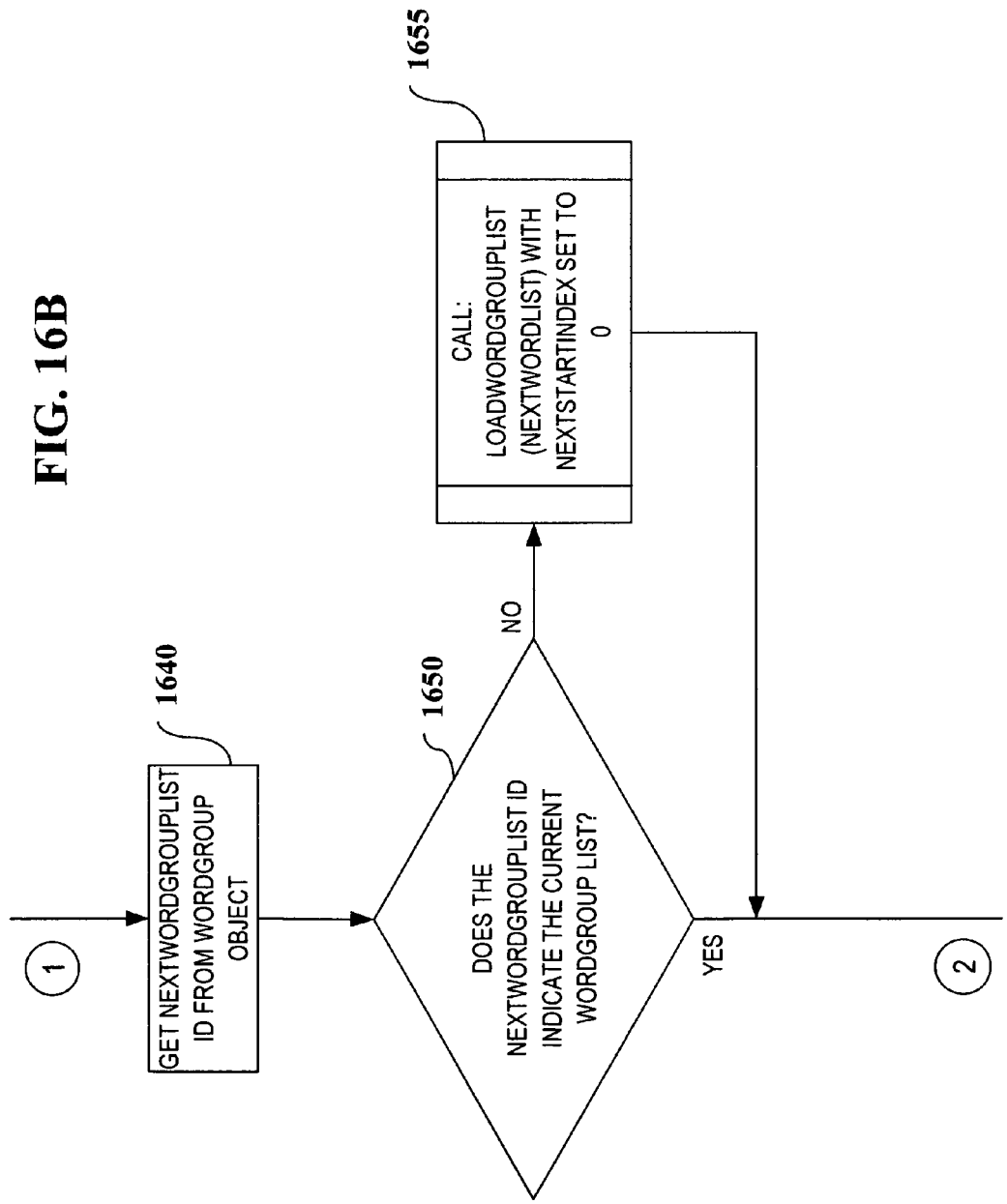
Figure 16C:
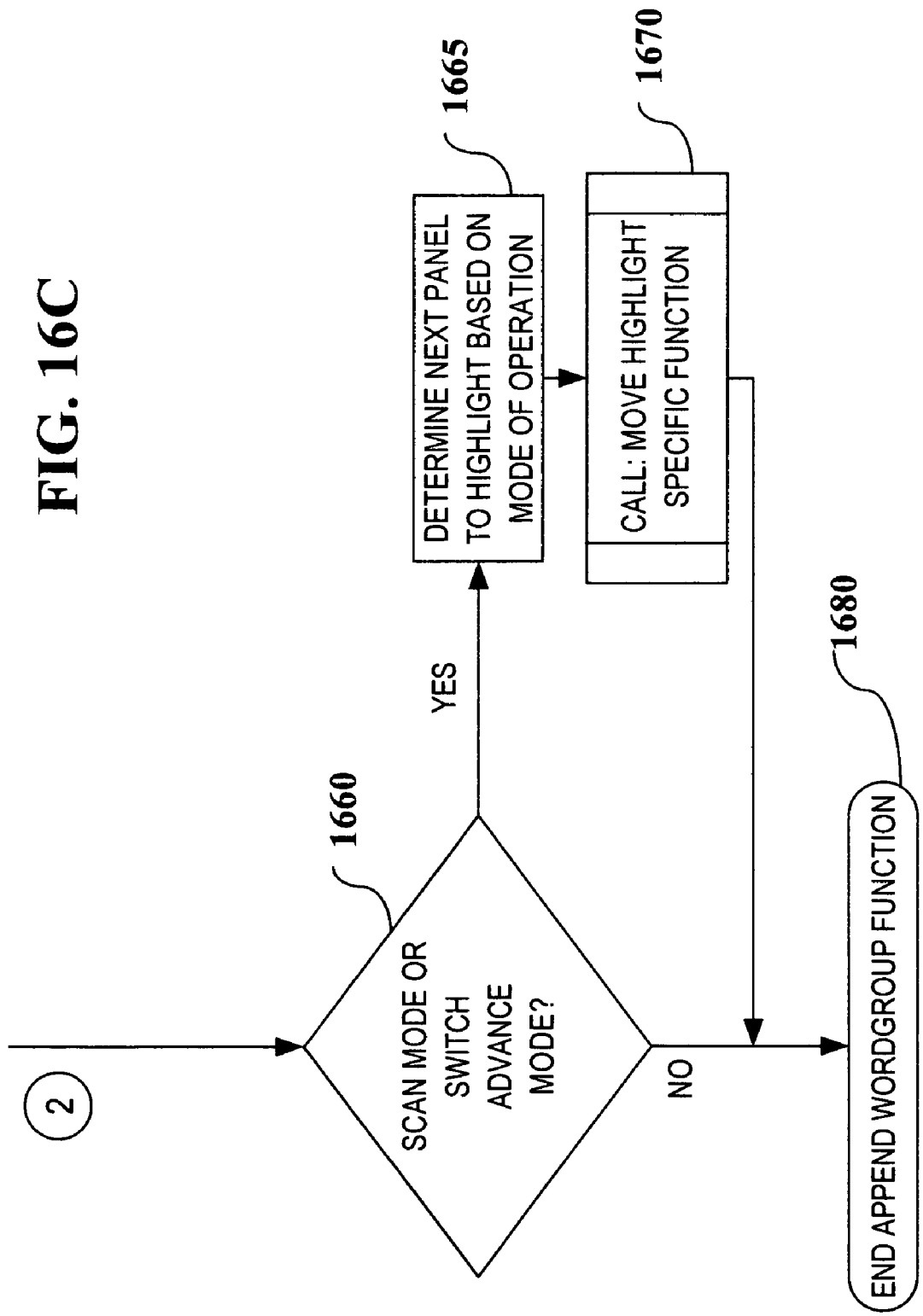

FIG. 16 describes a preferred embodiment of process 1600, which starts at 1601, for implementing the Append WordGroup function, which is called by the DoAction function when the Action Code of the Action Object associated with the panel selected by the user is set to ACT_APPEND. The purpose of this function is to add text strings stored in WordGroup Objects to the currently displayed text strings in the Message Display Window. These WordGroup Objects may be obtained from the Action Object associated with a WordGroup Panel selected by the user in the process of constructing a message, or they may be generated by the spelling interface when the user indicates that he or she has completed spelling a word.

Each subsequent call to the Append WordGroup function adds an additional WordGroup Object to a list of multiple WordGroup Objects. This list of WordGroup Objects is stored in the Message Display Window Object, and is used to generate the displayed text strings in the Message Display Window.

In step 1610, the WordGroup Object generated by the system's spelling interface, or the WordGroup Object of the current Action Object associated with the WordGroup Panel selected by the user, is added to the list of WordGroup Objects of the Message Display Window Object. (The current Action Object is the Action Object associated with the panel which was touched, or was highlighted during a Perform Action Switch-Closure Event.) Step 1620 then calls the Re-generate Displayed and Spoken Messages function which modifies the displayed contents in the Message Display Window based on the WordGroup Object which was appended. For example, if the Message Display Window displayed the string "I want" and the appended WordGroup Object contained the word group "my pain medicine," the Re-generate Displayed and Spoken Messages function might update the Message Display Window to display "I want my pain medicine."

In test 1630, the Speak Immediately property of the current WordGroup Object is checked, and if it is true, the system calls the Speak Displayed Message function, which speaks the currently displayed message.

Each WordGroup Object has a property which indicates the next WordGroup List whose strings are to be displayed in the WordGroup Panels on the screen when that WordGroup Object is appended to the Message Display Window Object. This property is called the NextWordGroupList ID.

Step 1640 gets the NextWordGroupList ID from the last WordGroup Object added to the Message Display Window Object. In test 1650, the system determines if the NextWordGroupList ID identifies the current WordGroup List, and, if not, the LoadWordGroupList function (step 1655) is called to load the new WordGroup List into the WordGroup Panels.

Test 1660 then determines whether the system is operating in Scan Mode or Switch Advance Mode (both of which utilize moving highlights) and, if not, the Append WordGroup function is complete at 1680.

If at test 1660 the system is in Scan Mode or Switch Advance Mode, step 1665 determines what panel to highlight next based on the current mode of operation (Scan Mode vs. Switch Advance Mode), other user-specific configuration settings, the current context, and the record of the user's previous actions while using the system. For example, if the record indicates that the user has very frequently used the Help Panel to call for assistance, or has frequently used the Erase Panel to correct erroneous selections, the next panel to highlight might one chosen for its proximity to the Erase Panel or the Help panel. On the other hand, if the user's previous activity did not indicate the need to facilitate erasure of incorrect entries or calling for help, the next panel to highlight might be chosen based on the current screen context. For example, if the word group just appended to the Message Display Window was intended to complete a sentence (as indicated by a Yes response to test 1650), the next panel to highlight might be the Speak panel. If the word group just appended, on the other hand, is a word group (such as "I need") which results in a No response to test 1650, thereby loading a new WordGroup List, the next panel to highlight might be the panel containing the first word group in the new WordGroup List. In this manner, an appropriate series of conditional statements can optimize the highlight sequence for a particular situation, taking into account the current user settings, the current context, and the record of the user's previous actions while using the system. After determining the next panel to highlight, step 1670 calls the Move Highlight Specific function (FIG. 15), and process 1600 ends at 1680.

FIG. 17 describes a preferred embodiment of process 1700, which starts at 1701, for implementing the Erase function. The purpose of this function is to delete the most recently added text strings from the Message Display Window. In test 1710, it is decided whether there are any individual letters in the Message Display Window which have not yet been converted to a word (see FIGS. 29-36 for discussion of the spelling interface). If there are individual letters (not yet converted to a word) as indicated by a Yes answer to test 1710, the Erase Letter from Spelled Word function (step 1720) is called. If there are no incompletely spelled words, then the Erase Last WordGroup function (step 1730) is called. After either function is called, process 1700 ends at 1740.

Figure 18A:
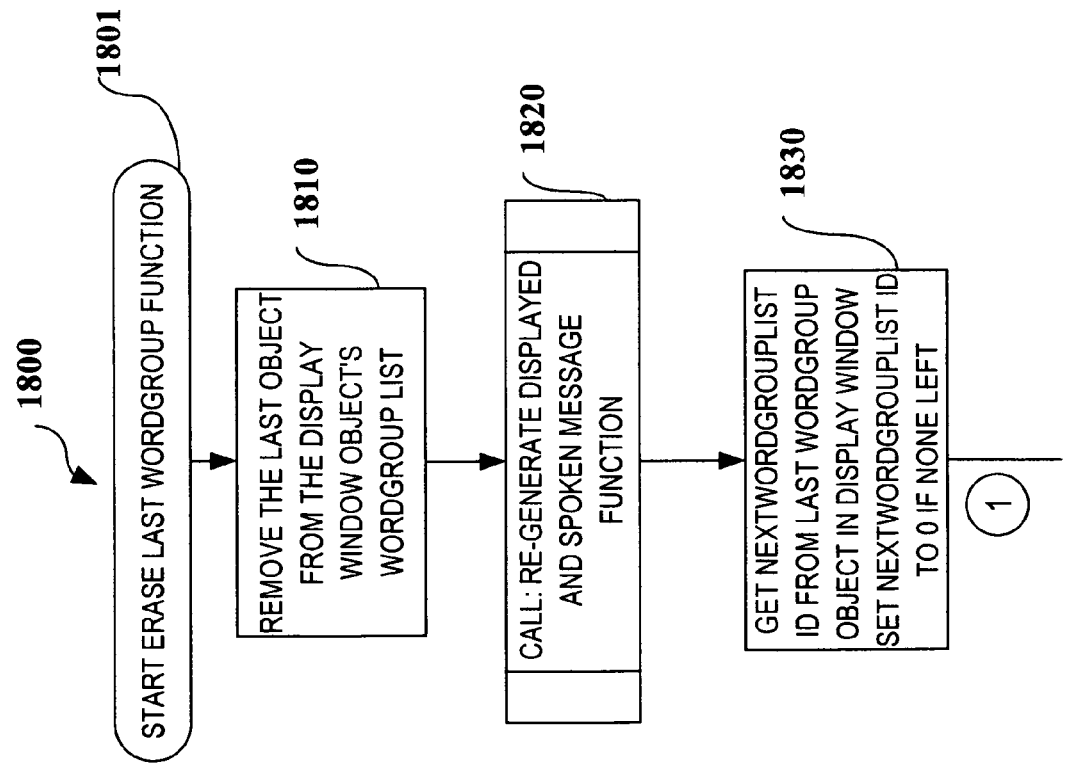
FIGS. 18A and 18B (hereafter collectively referred to as FIG. 18) are a flowchart representing a preferred embodiment of a Erase Last WordGroup Function in a preferred embodiment of a system according to the present invention.
Figure 18B:
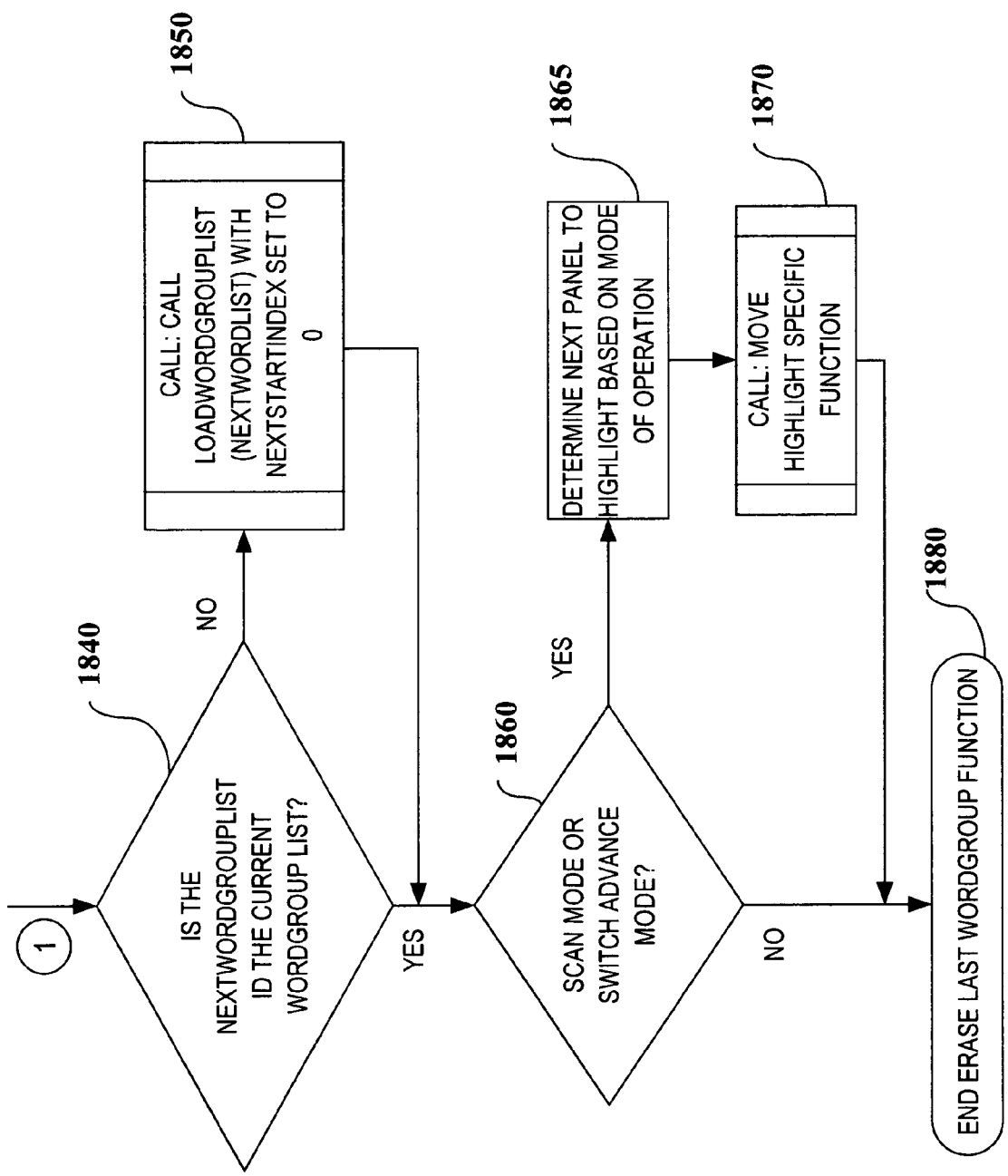

FIG. 18 describes a preferred embodiment of process 1800, which starts at 1801, for implementing the Erase Last WordGroup function. The purpose of this function is to remove the last WordGroup Object which was added to the list of WordGroup Objects associated with the Message Display Window.

In step 1810, the last WordGroup Object added to the list of WordGroup Objects of the Message Display Window Object is deleted from this list. Step 1820 then calls the Re-generate Displayed and Spoken Messages function which restores the displayed contents in the Message Display Window to its status prior to the addition of this last WordGroup Object.

Step 1830 gets the NextWordGroupList ID from the last WordGroup Object in the current Message Display Window list. If there are no WordGroup Objects left in the list, the NextWordGroupList ID is set to zero. In test 1840, the system determines if the NextWordGroupList ID identifies the current WordGroup List, and, if not, the LoadWordGroupList function (step 1850) is called to load the new WordGroup List into the WordGroup Panels.

Either way, test 1860 determines whether the system is operating in Scan Mode or Switch Advance Mode (both of which utilize moving highlights) and, if not, the Append WordGroup function is complete at 1880.

If the system is in Scan Mode or Switch Advance Mode, step 1865 determines what panel to highlight next based on, preferably, user-specific settings, the current mode of operation, the current context and the record of the user's previous actions. After determining the next panel to highlight, step 1870 calls the Move Highlight Specific function, and process 1800 ends at 1880.

Figure 19:
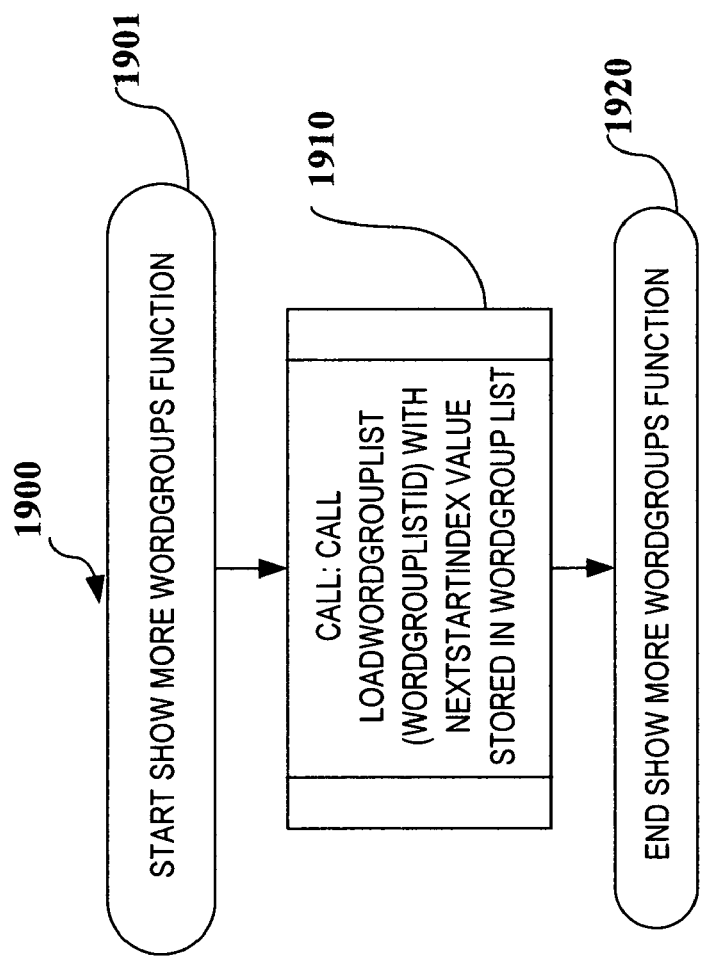
FIG. 19 is a flowchart representing a preferred embodiment of a Show More WordGroups Function in a preferred embodiment of a system according to the present invention.

FIG. 19 describes a preferred embodiment of process 1900, which starts at 1901, for implementing the Show More WordGroups function. The purpose of this function is to replace the WordGroups currently shown on the screen with the next set of WordGroups from within the current WordGroup List. (This allows WordGroup Lists to have more WordGroups than the number of WordGroups which can simultaneously be displayed on the screen). When this function is called, the NextStartIndex variable associated with the WordGroup List currently displayed on the screen is determined, and the LoadWordGroupList function (step 1910) is called with the same WordGroup List ID and the new starting index set to NextStartIndex. Process 1900 then ends at 1920.

FIG. 20 describes a preferred embodiment of process 2000, which starts at 2001, for implementing the Re-Generate Displayed and Spoken Messages function. Step 2010 calls the Re-Generate Displayed Message function, and step 2020 then calls the Re-Generate Spoken Message function. Process 2000 then ends at 2030.

Figure 21A:
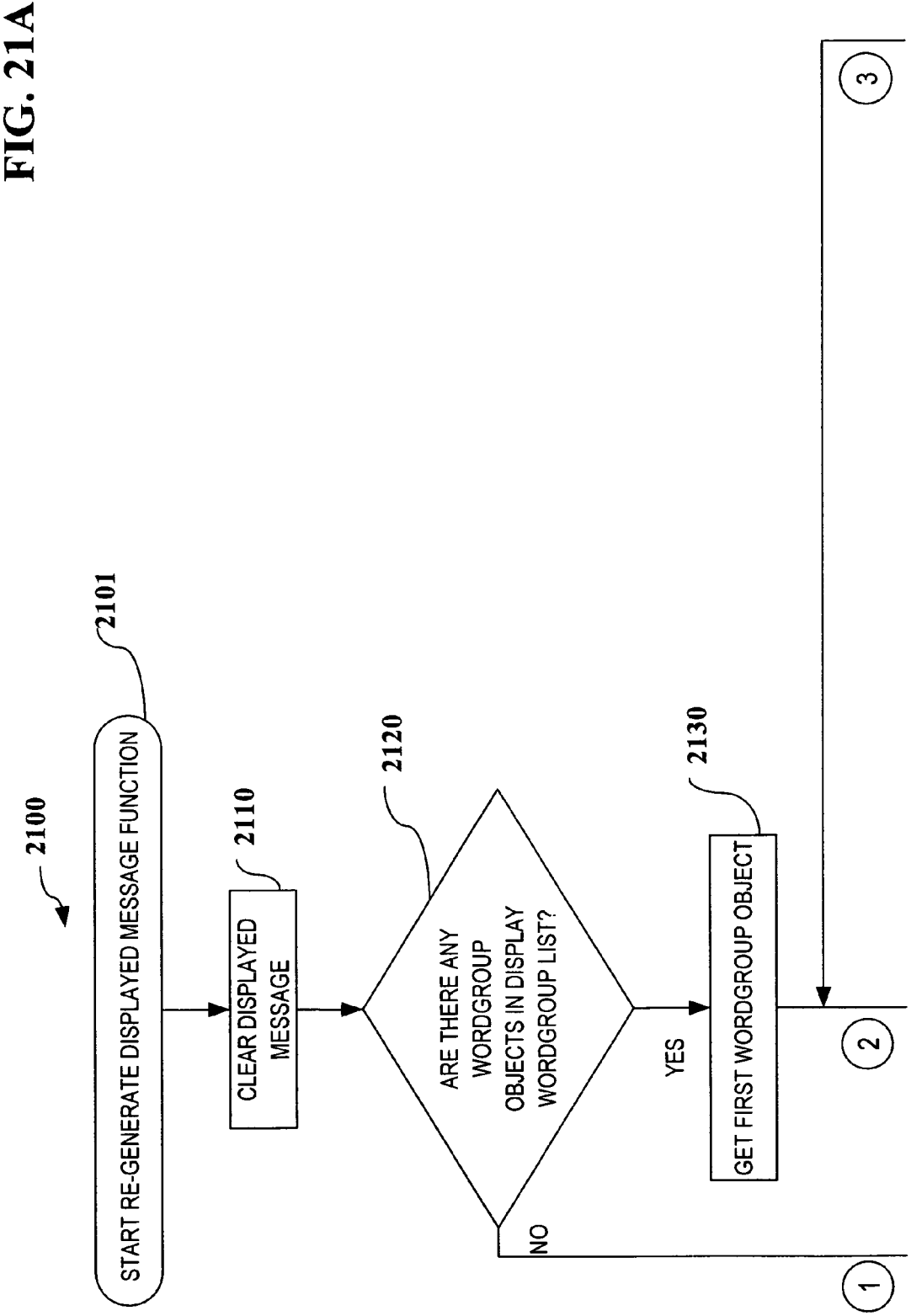
Figure 21B:
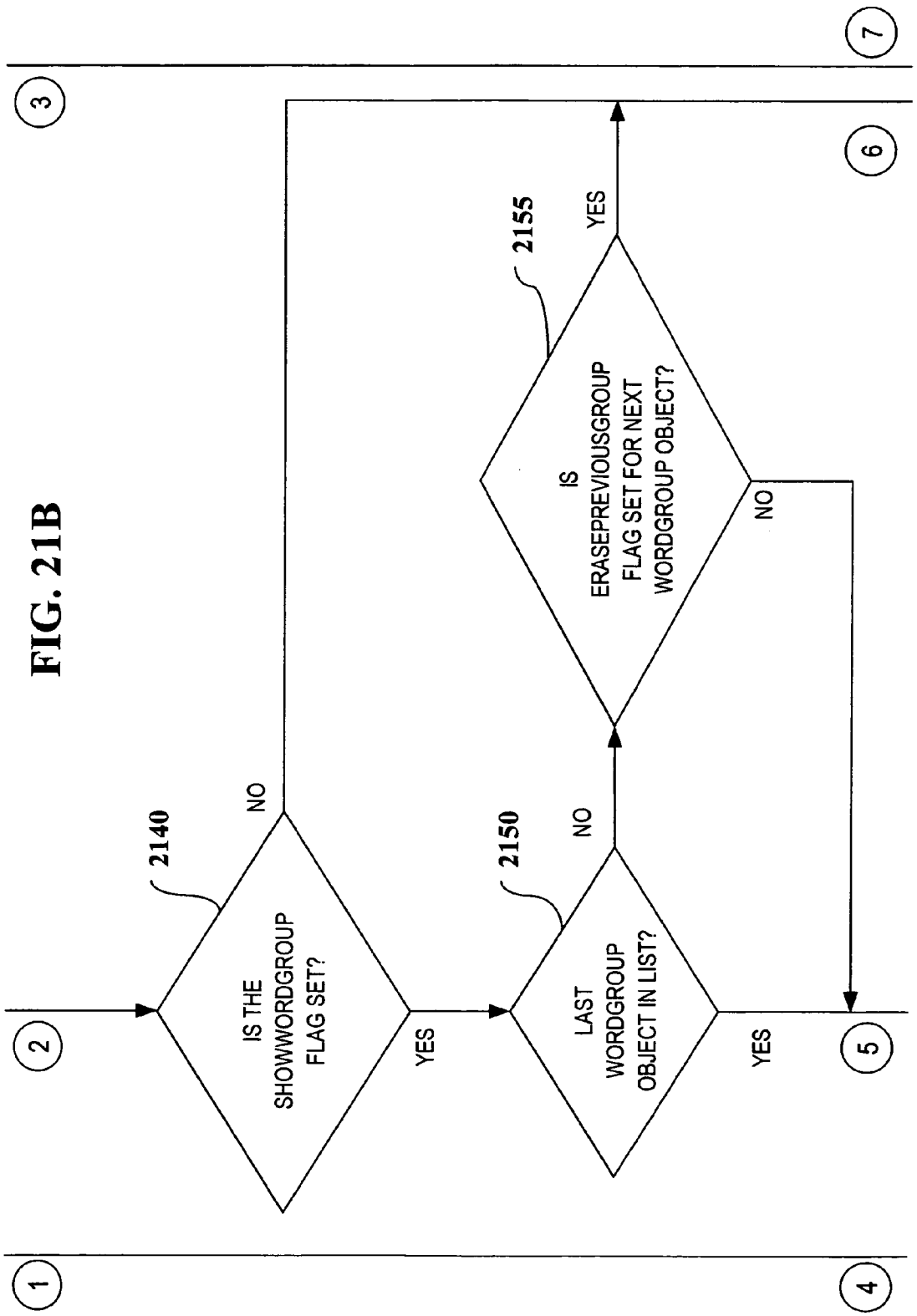

FIG. 21 describes a preferred embodiment of process 2100, which starts at 2101, for implementing the Re-Generate Displayed Message function. Step 2110 clears the Displayed Message String variable (which stores the message currently displayed in the Message Display Window).

In test 2120 it is decided whether there are any WordGroup Objects in the Message Display Window WordGroup List, and if the answer is No, the remaining steps of the function are skipped, and process 2100 ends at 2190. If the answer is Yes, step 2130 gets the first WordGroup Object in the list, and makes it the current WordGroup Object. Test 2140 determines whether the current WordGroup Object is intended to be displayed in the Message Display Window by determining whether the ShowWordGroup Flag is true. The ShowWordGroup Flag, while not essential for system operation, preferably is a property of each WordGroup Object which provides the person setting up the system with the flexibility to specify that the message in the Message Display Window should or should not change when the panel associated with the WordGroup Object is selected. For example, setting the ShowWordGroup Flag to false for a WordGroup Panel labeled "medicines" allows the system to respond to a user selection of that panel by loading a list containing types of medicines into the WordGroup Panels without changing any message currently in the Message Display Window.

If the answer to test 2140 is No, steps 2150 through 2170 are skipped. If the ShowWordGroup Flag is true, and the current WordGroup Object is not the last WordGroup Object in the list (test 2150), test 2155 determines whether the next WordGroup Object in the list requires "erasure" of the previous WordGroup from the Message Display Window. If the answer is Yes, steps 2160 through 2170 are skipped.

If the answer to test 2155 is No, then test 2160 determines whether an Alternate Display String is present in the WordGroup Object. If it is present, then Step 2165 adds the Alternate Display String to the Displayed Message string. If an Alternate Display String is not present, then Step 2170 adds the Default Display String of the current WordGroup Object to the Displayed Message string.

The Default Display String is the string which is used to visually label the WordGroup Panel. An Alternate Display String may be a different string, which is related in some way to the Default Display String, but might, for example, be too long to be displayed on the WordGroup Panel. By utilizing an Alternate Display String where necessary, the system has the capability to add a longer or more appropriately worded string to the Message Display Window in order to improve the clarity of the resulting message. Thus, for example, the Default Display String associated with a panel might be: "My _____ hurts.", but the Alternate Display String might be: "The following part of my body hurts:". Similarly, the Default Display String for a panel might be "bathroom" but the Alternate Display String could be "to go to the bathroom."

Test 2180 determines whether the current WordGroup Object is the last WordGroup Object in the Message Display Window's list of WordGroup Objects. If the answer is Yes, the Re-Generate Displayed Message function is complete at 2190. If the answer is No, then step 2185 gets the next WordGroup Object, and the procedure returns to test 2140.

Figure 22B:
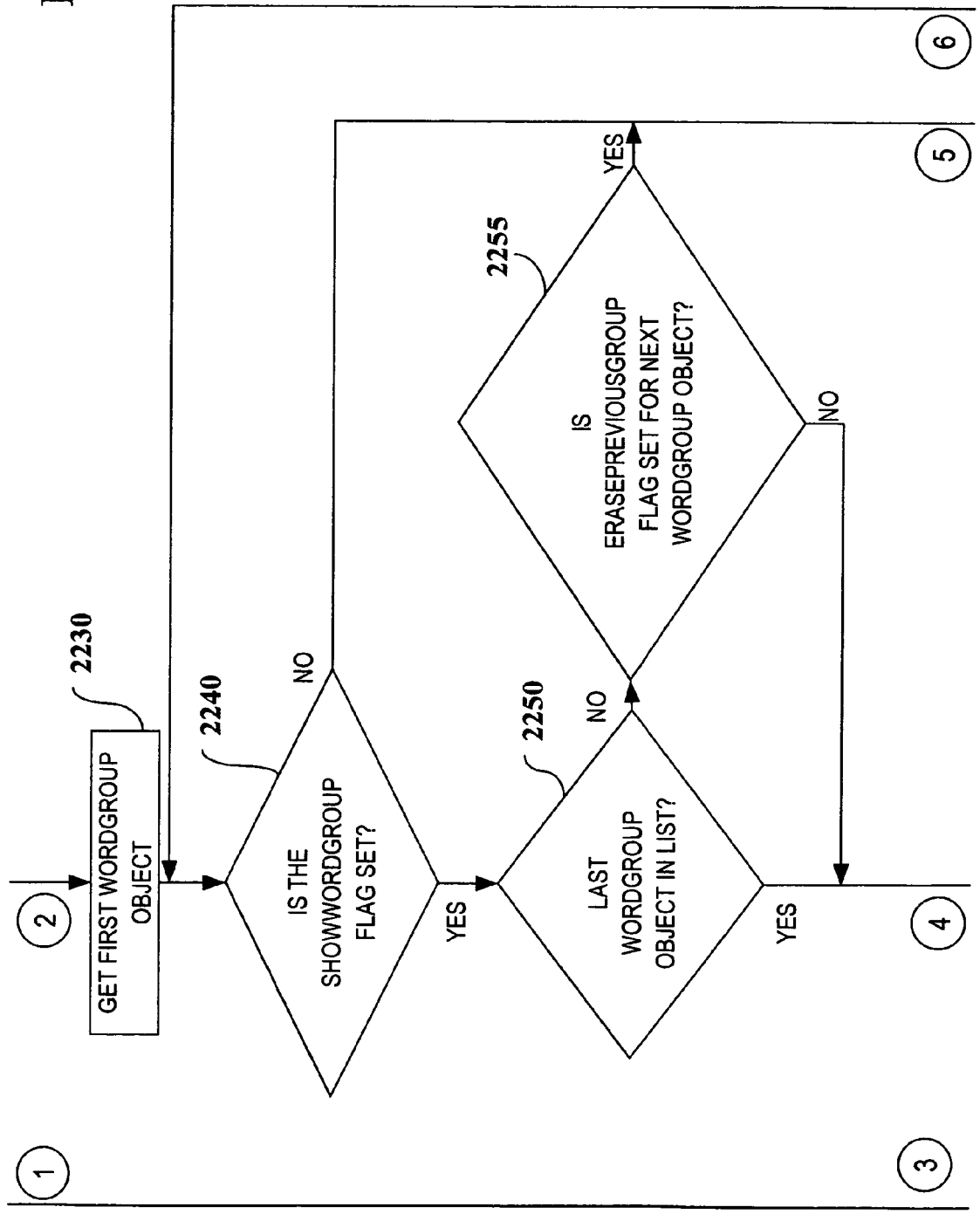
Figure 22C:
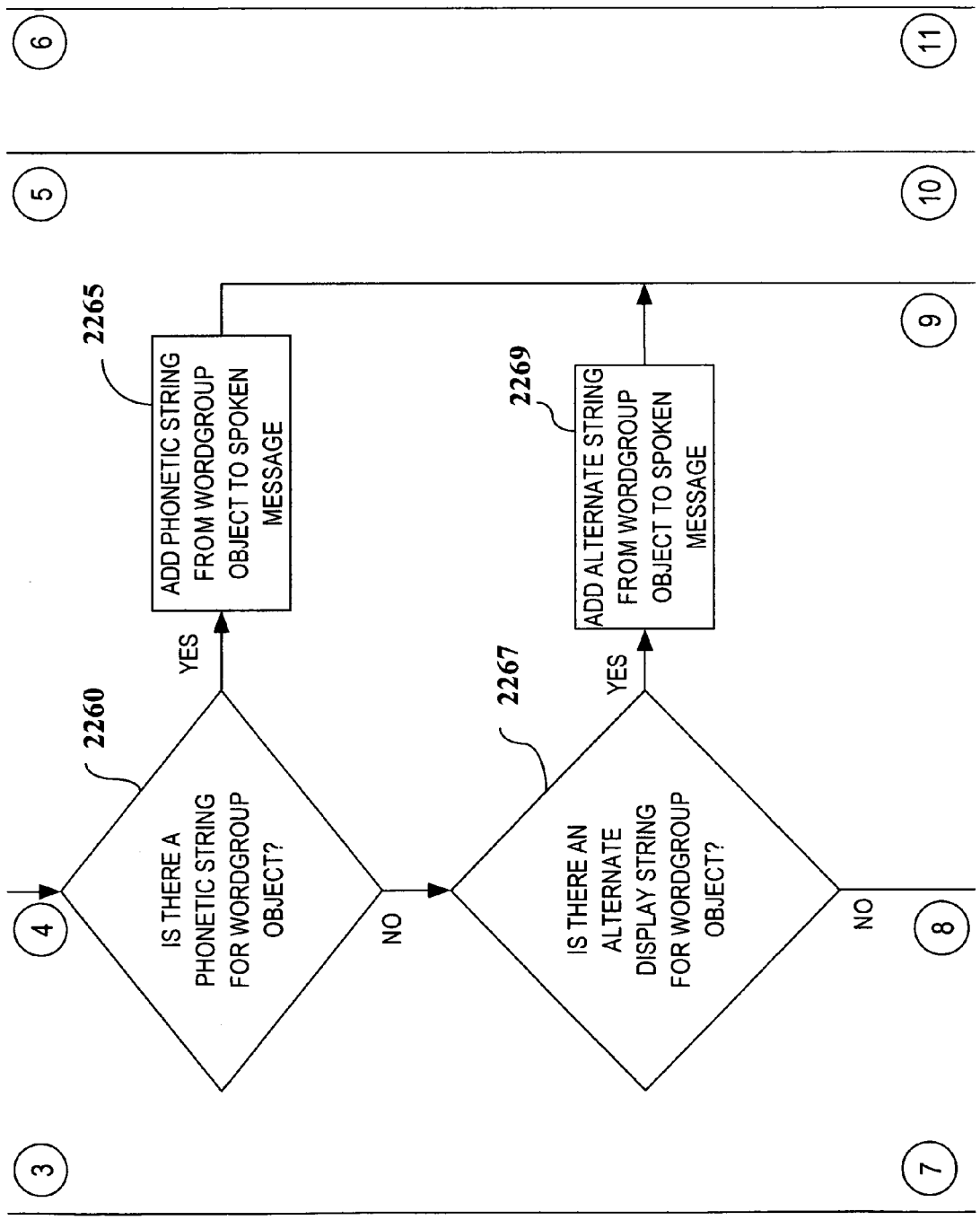
Figure 22D:
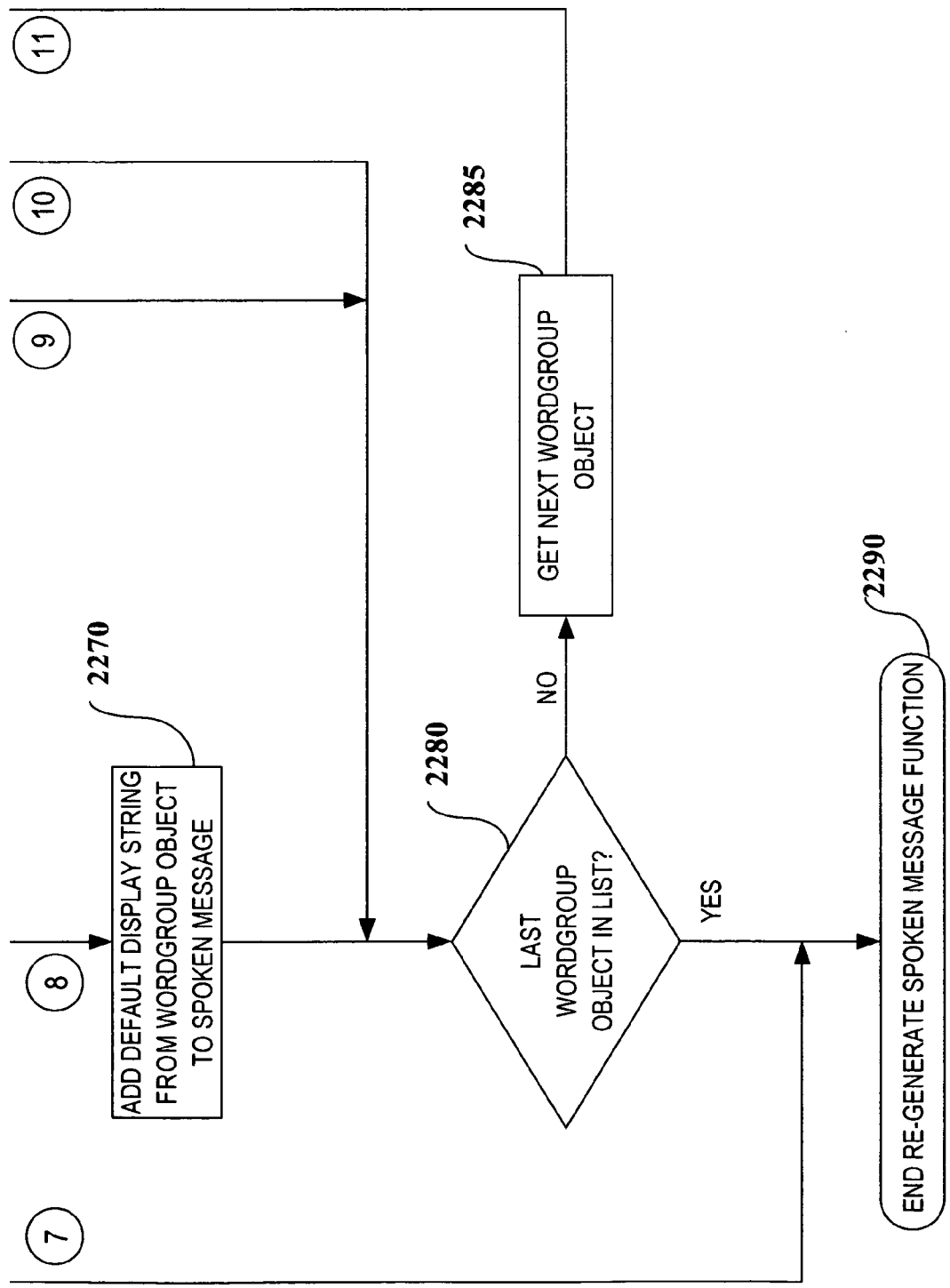

FIG. 22 describes a preferred embodiment of process 2200, which starts at 2201, for implementing the Re-Generate Spoken Message function. Step 2210 clears the Spoken Message String variable (which stores the spoken message currently associated with the Message Display Window Object).

In test 2220 it is decided whether there are any WordGroup Objects in the Message Display Window WordGroup List, and if the answer is No, the remaining steps of the function are skipped and process 2200 ends at 2290. If the answer is Yes, step 2230 gets the first WordGroup Object in the list, and makes it the current WordGroup Object. Test 2240 determines whether the current WordGroup Object is intended to be added to the Spoken Message String for the Message Display Window, by determining whether the Show WordGroup Object variable is true. If it is not true, steps 2250 through 2270 are skipped and process 2200 proceeds to test 2280.

If the Show WordGroup variable is true, and the current WordGroup Object is not the last WordGroup Object in the list, test 2255 determines whether the next WordGroup Object in the list requires "erasure" of the previous WordGroup from the Message Display Window. If the answer is Yes, steps 2260 through 2270 are skipped and process 2200 proceeds to test 2280. If the answer is No, then test 2260 determines whether a Phonetic String, which is simply an alternate spelling for a word whose normal spelling is not properly pronounced by the currently used speech engine, is present in the current WordGroup Object. If it is present, then step 2265 adds the Phonetic String to the Spoken Message String. If a Phonetic String is not present, then test 2267 determines whether an Alternate Display String is present in the WordGroup Object. If it is present, then Step 2269 adds the Alternate Display String to the Spoken Message String. If an Alternate Display String is not present, then Step 2270 adds the Default Display String of the current WordGroup Object to the Spoken Message String.

Test 2280 determines whether the current WordGroup Object is the last WordGroup Object in the Message Display Window's list of WordGroup Objects. If the answer is Yes, the Re-Generate Spoken Message function is complete and process 2200 ends at 2290. If the answer is No, then step 2285 gets the next WordGroup Object, and the process 2200 returns to test 2240.

Figure 23A:
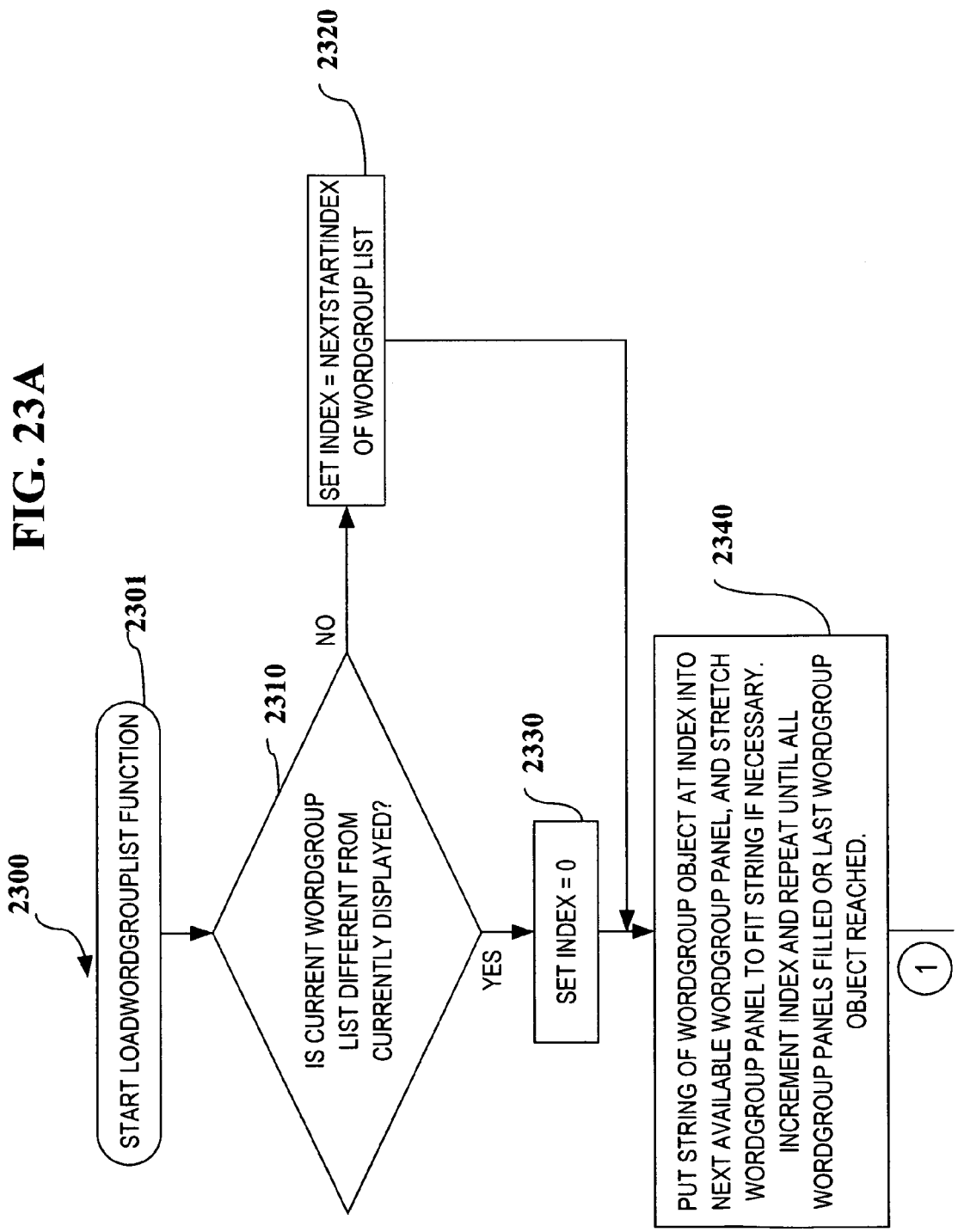
FIGS. 23A and 23B (hereafter collectively referred to as FIG. 23) are a flowchart representing a preferred embodiment of a LoadWordGroupList Function in a preferred embodiment of a system according to the present invention.
Figure 23B:
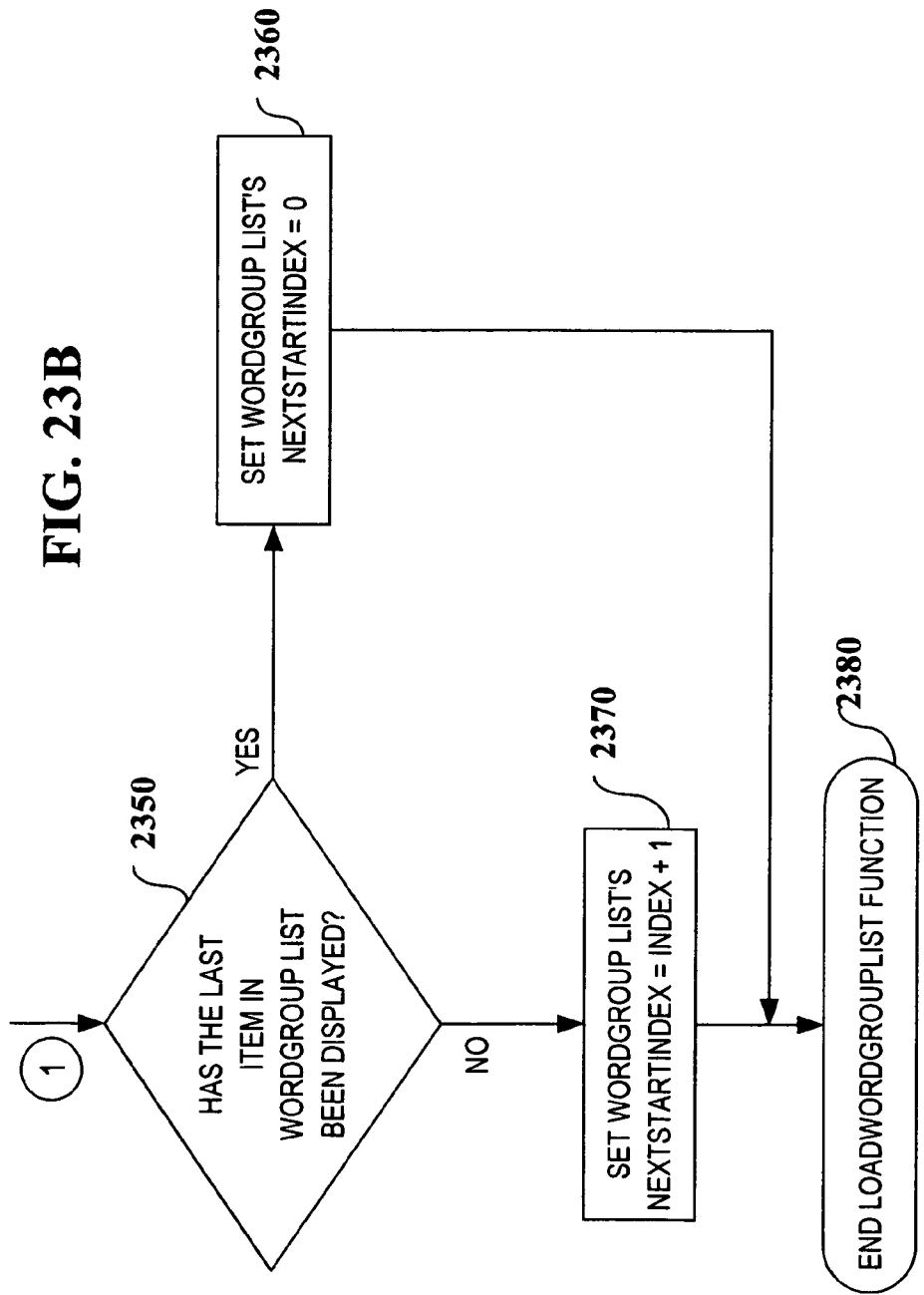

FIG. 23 describes a preferred embodiment of process 2300, which starts at 2301, for implementing the LoadWordGroupList function. In test 2310 it is decided whether the WordGroup list requested to be loaded is different than the currently displayed WordGroup list. If the answer is Yes, step 2330 sets the index counter to zero, so that the first WordGroup object in the WordGroup list is the first to be displayed. If the answer is No, step 2320 sets the index counter to the NextStartIndex property of the WordGroup list, so that the next undisplayed WordGroup Object in the WordGroup list is the next to be displayed.

Next, step 2340 represents a loop in which the String property of successive WordGroup objects are loaded into available WordGroup Panel objects, stretching the WordGroup Panel objects as necessary to accommodate the length of the String.

In test 2350 it is decided whether the last WordGroup object displayed is the last WordGroup object in the WordGroup list. If the answer is Yes, Step 2360 sets the NextStartIndex property of the WordGroup list to zero, so that the next call to the LoadWordGroupList function will start at the beginning of the WordGroup List, and process 2300 ends at 2380. If the answer is No, step 2370 sets the NextStartIndex property of the WordGroup list to the index counter+1, so that the next call to the LoadWordGroupList function will start at the first undisplayed WordGroup object, and process 2300 ends at 2380.

Figure 24A:
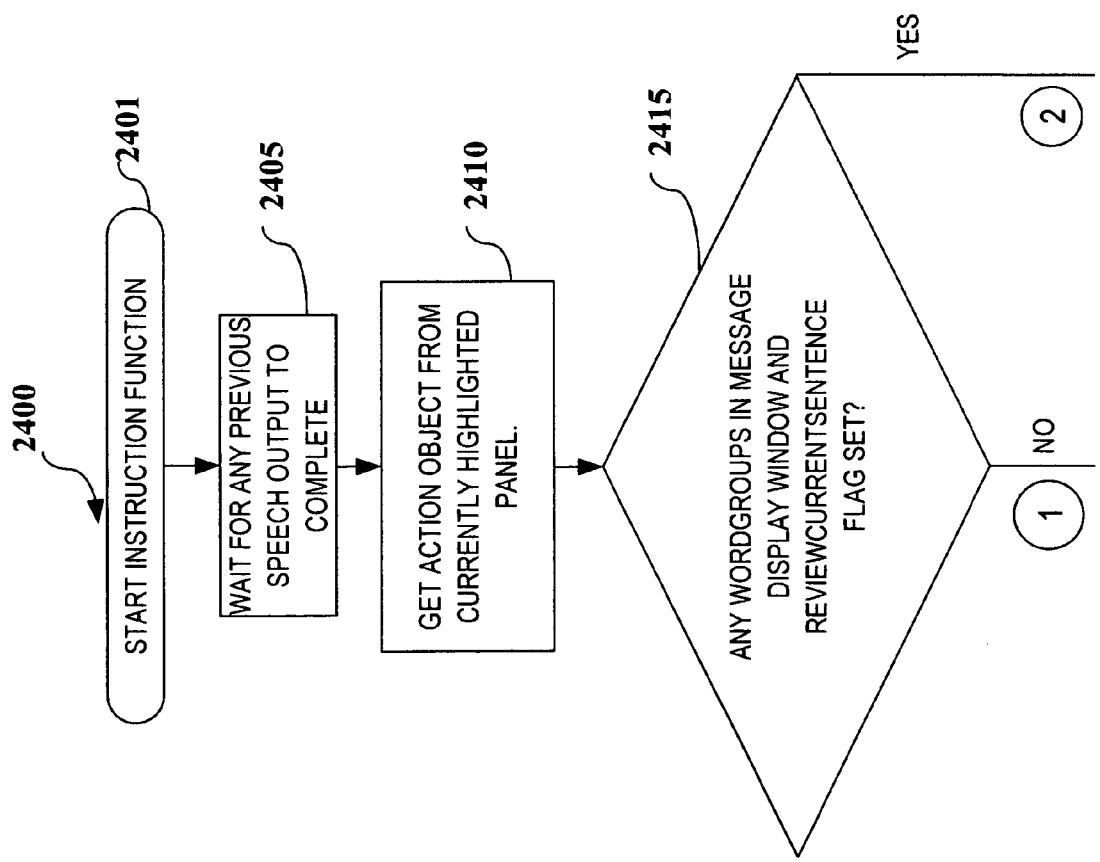
FIGS. 24A, 24B and 24C (hereafter collectively referred to as FIG. 24) are a flowchart representing a preferred embodiment of an Instruction Function in a preferred embodiment of a system according to the present invention.
Figure 24B:
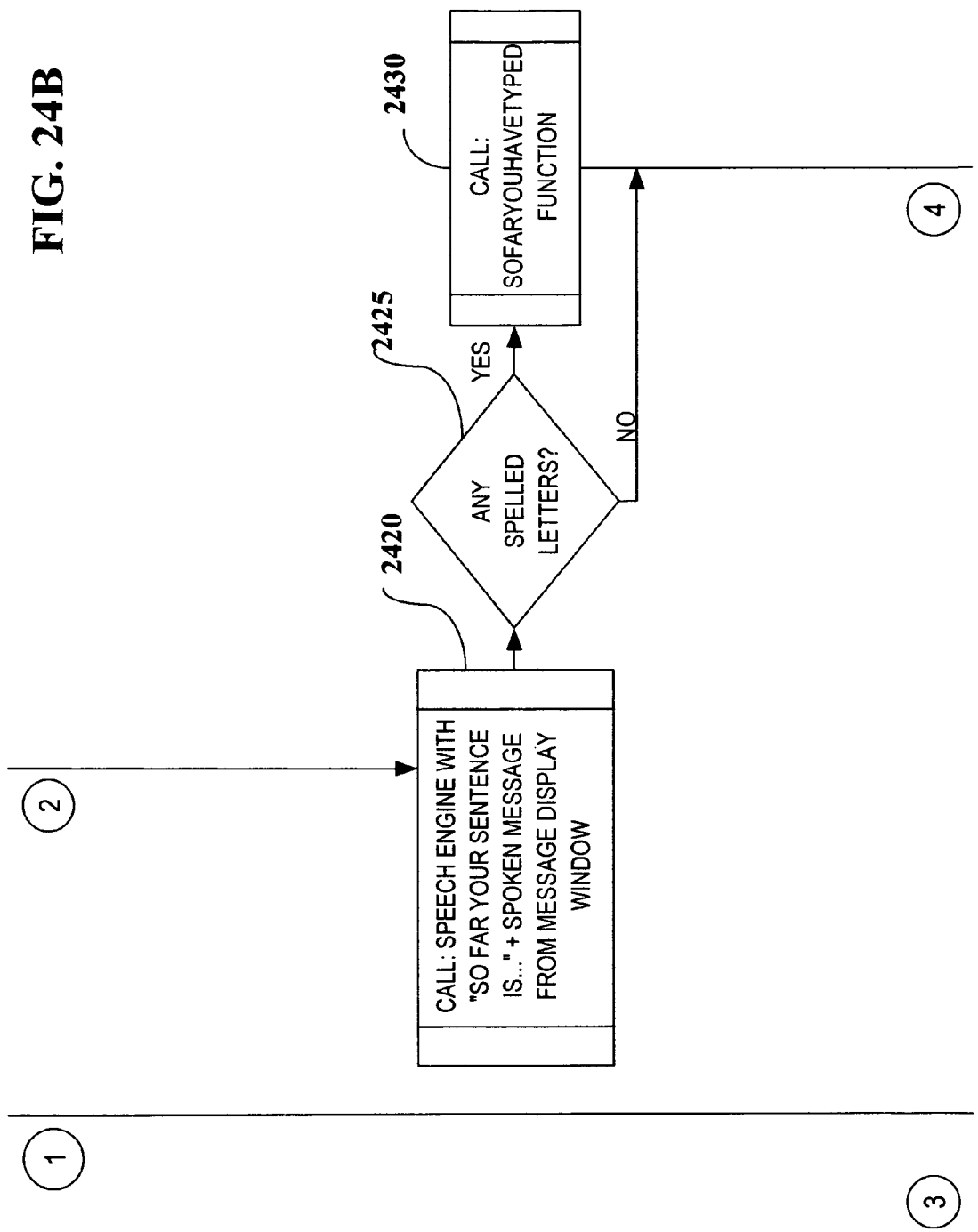
Figure 24C:
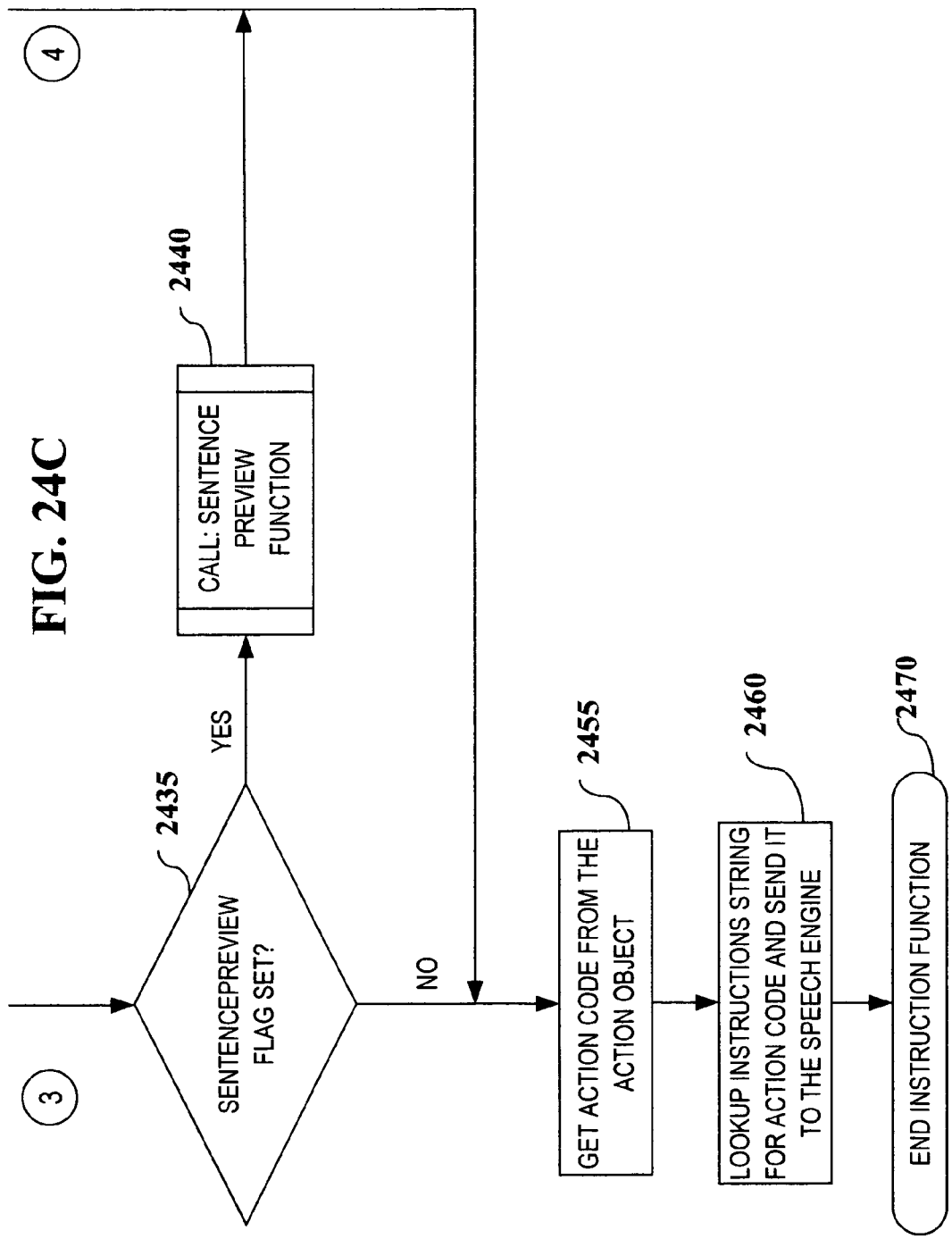

FIG. 24 describes a preferred embodiment of process 2400, which starts at 2401, for implementing the Instruction function. Step 2405 waits for the completion of any speech output which was in progress when the Instruction function was called. Step 2410 gets the Action Object associated with the currently highlighted panel, the WordGroup Object associated with that Action Object, and the ReviewCurrentSentence Flag which is a property of the Action Object.

Figure 28:
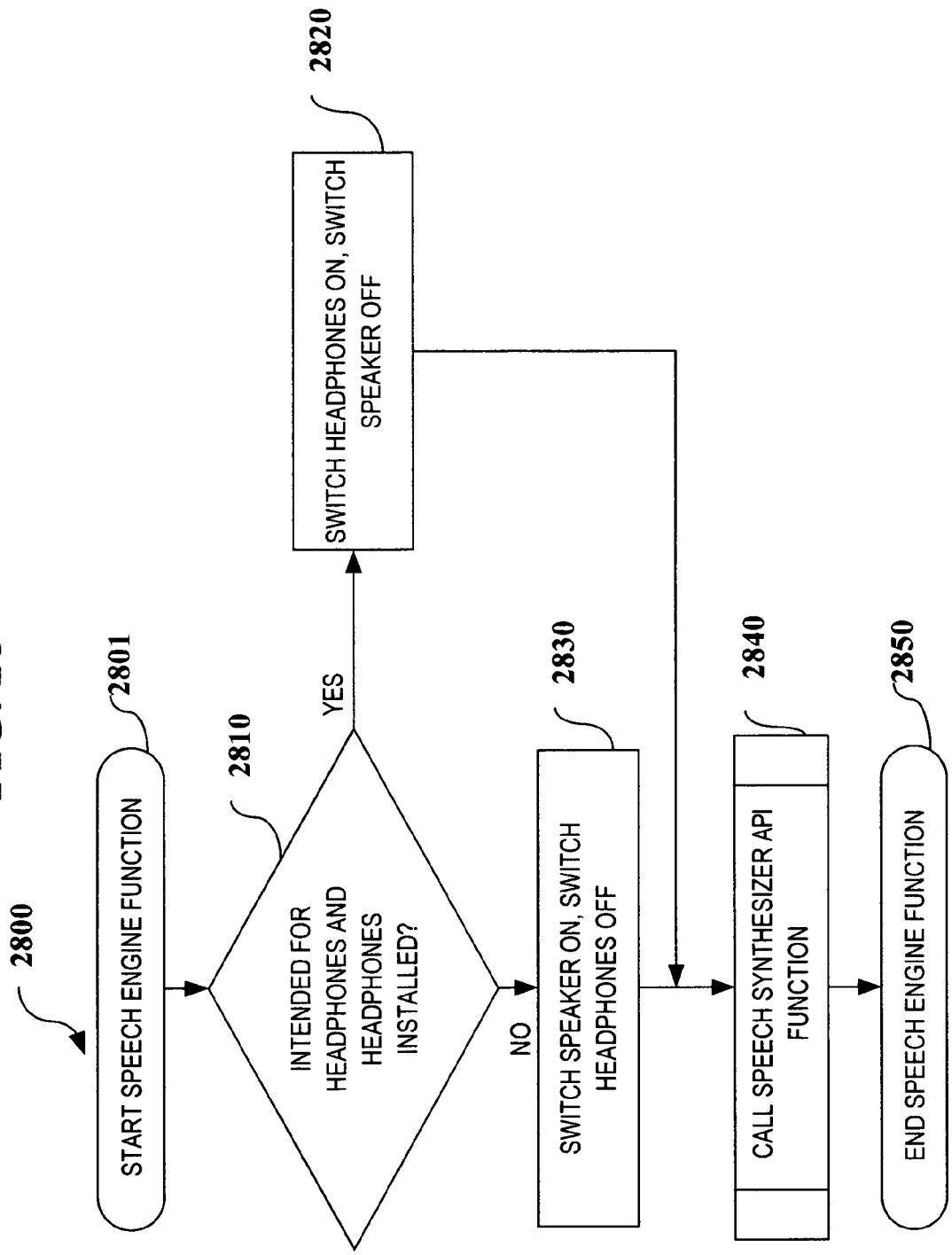
FIG. 28 is a flowchart representing a preferred embodiment of a Speech Engine Function in a preferred embodiment of a system according to the present invention.

In test 2415 it is decided if the Message Display Window contains text and whether the ReviewCurrentSentence Flag is set. If the answer to both are Yes, Step 2420 pre-appends the string "So far your message is" to the Spoken Message String for the Message Display Window and sends the resulting string to Speech Engine function 2800 (FIG. 28). Test 2425 then determines if the user is in the process of constructing a (presently incomplete) word by adding individual letters to the Message Display Window. If the answer is Yes, Step 2430 calls the SoFarYouHaveTyped function, which outputs a string to Speech Engine function 2800 so that the speech engine can tell the user what letters have been added to the yet-to-be completed word.

If the answer to test 2415 is No, step 2435 decides whether the SentencePreview Flag for the Action Object is set. If the answer is Yes, Step 2440 calls the SentencePreview function, which outputs a string to the speech engine which tells the user what the sentence in the Message Display Window would become if the user were to select the currently highlighted panel.

If the answer to test 2435 is No, step 2455 gets the Action Code from the Action Object. Step 2460 then looks up the instruction string associated with the Action Code, and sends the instruction string to the speech engine. For example, if the Action Code is ACT_SEND_NURSE_MSG, the instruction might be "If you click now, your message will be sent to the Nurses' Station." Alternatively, the instruction could be an imperative form, such as: "Click now to send your message to the Nurses' Station." Process 2400 ends at 2470.

Figure 25A:
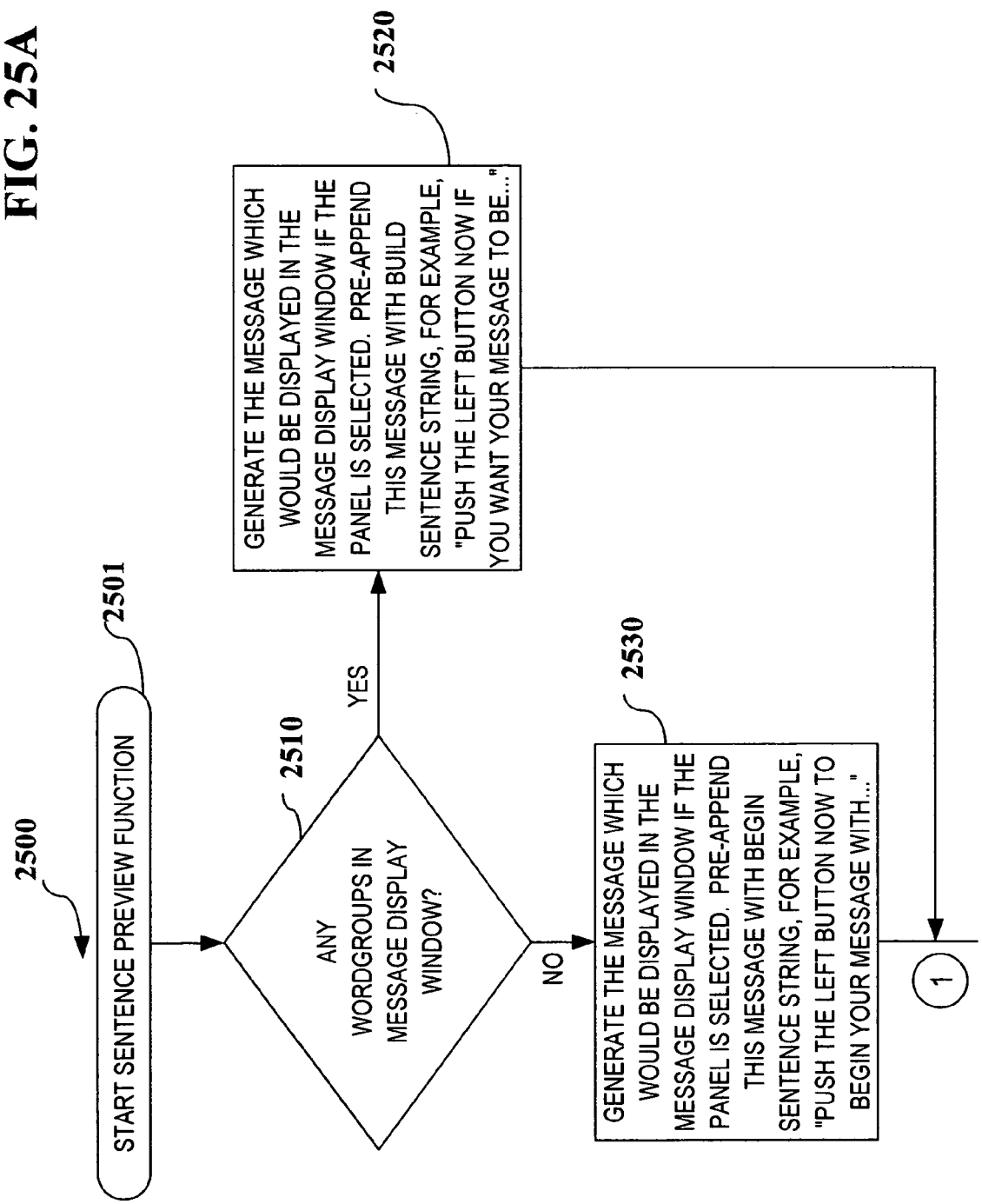
FIGS. 25A and 25B (hereafter collectively referred to as FIG. 25) are a flowchart representing a preferred embodiment of a Sentence Preview Function in a preferred embodiment of a system according to the present invention.
Figure 25B:
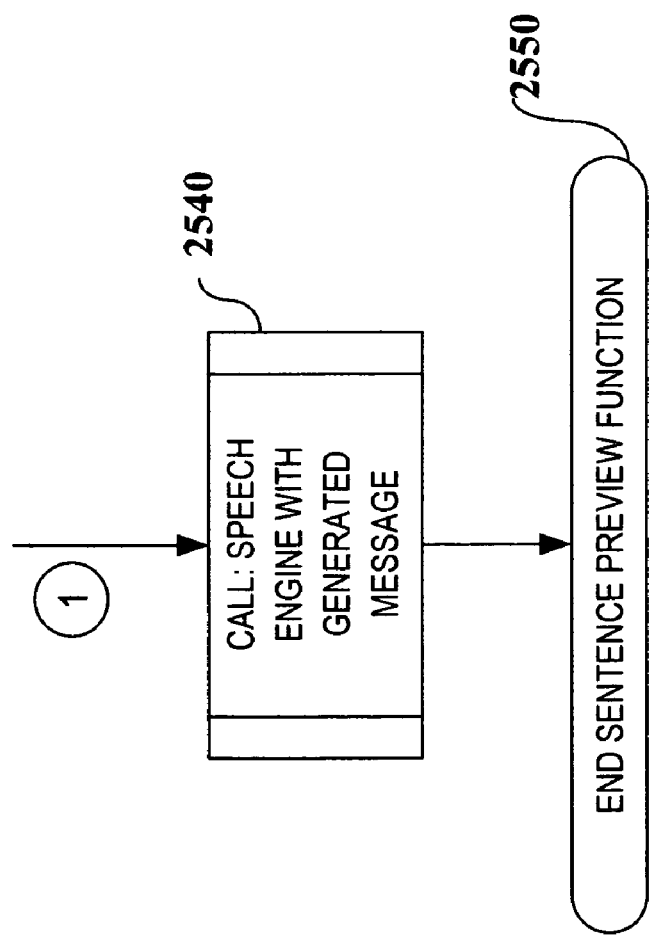

FIG. 25 describes a preferred embodiment of process 2500, which starts at 2501, for implementing the Sentence Preview function. In test 2510 it is determined whether there are any WordGroups in the Message Display Window. If the answer is No, step 2530 generates the new message which would appear in the Message Display Window if the highlighted WordGroup Panel is selected, and pre-appends this message with the Begin Sentence String, which, for example, might be: "Push the left button now to begin your message with . . . "

If the answer to step 2510 is Yes, step 2520 generates the revised message which would appear in the Message Display Window if the highlighted WordGroup Panel is selected, and pre-appends this message with the Build Sentence String, which, for example, might be: "Push the left button now if you want your message to be . . . "

Next, step 2540 sends the resulting string generated by step 2520 or step 2530 to the Speech Engine function (FIG. 28), and process 2500 ends at 2550.

FIG. 26 describes a preferred embodiment of process 2600, which starts at 2601, for implementing the Speak Displayed Message function. Step 2610 gets the Spoken Message String from the Message Display Window Object. Step 2620 sends the Spoken Message String to the speech engine. Step 2630 determines what panel to highlight next based on, preferably, user-specific settings, the current mode of operation, the current context and the record of the user's previous actions, and then calls the Move Highlight Specific function. Process 2600 ends at 2640.

Figure 27:
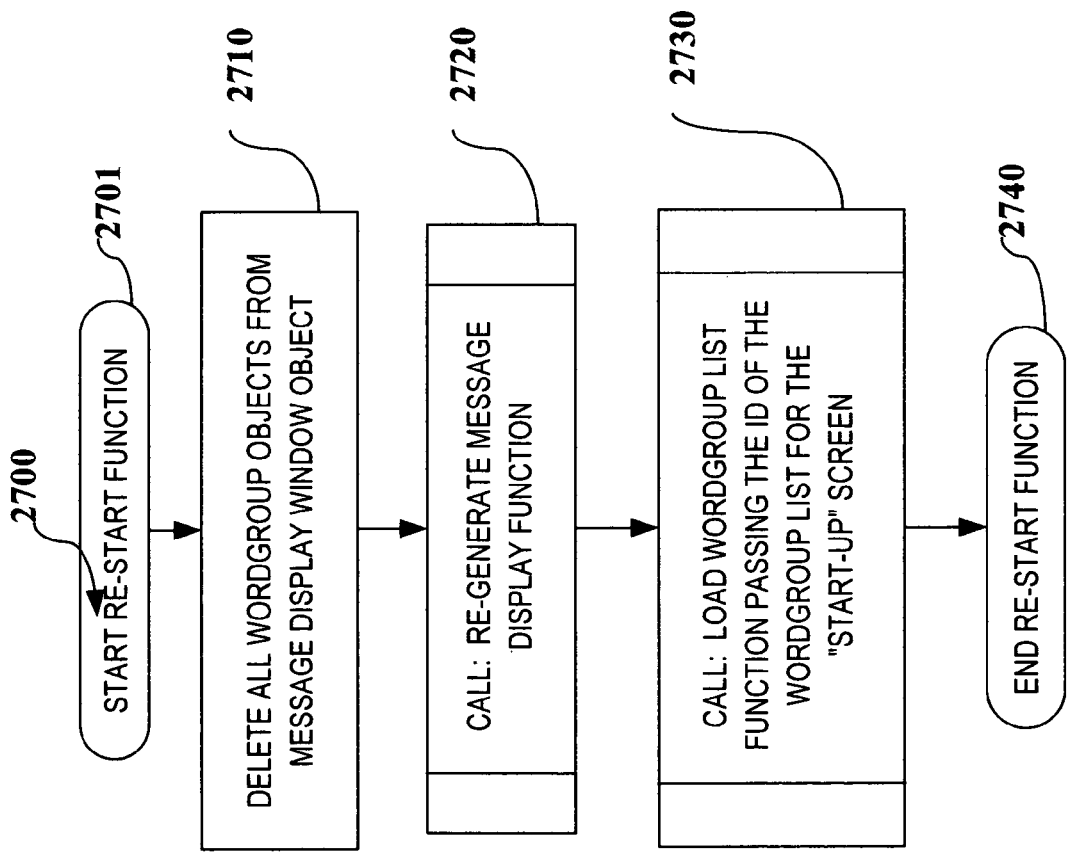
FIG. 27 is a flowchart representing a preferred embodiment of a Re-Start Function in a preferred embodiment of a system according to the present invention.

FIG. 27 describes a preferred embodiment of process 2700, which starts at 2701, for implementing the Re-Start function. Step 2710 deletes all the WordGroup Objects from the Message Display Window's WordGroup List. Step 2720 calls the Re-generate Displayed and Spoken Messages function. Step 2730 calls the LoadWordGroupList function, passing to it the WordGroup List designated for the system's "start-up screen." Process 2700 ends at 2740.

FIG. 28 describes a preferred embodiment of process 2800, which starts at 2801, for implementing the Speech Engine function. Test 2810 determines whether the text output is intended for the headphones and whether the headphones are installed. If the answer to test 2810 is Yes, step 2820 sends a command to the External Interface Module which switches the headphones on and the speaker off. If the answer to test 2810 is No, step 2830 switches the speaker on and the headphones off. Step 2840 passes the text string originally passed to the Speech Engine function to the speech synthesizer API function. Process 2800 ends at 2850.

Figure 29:
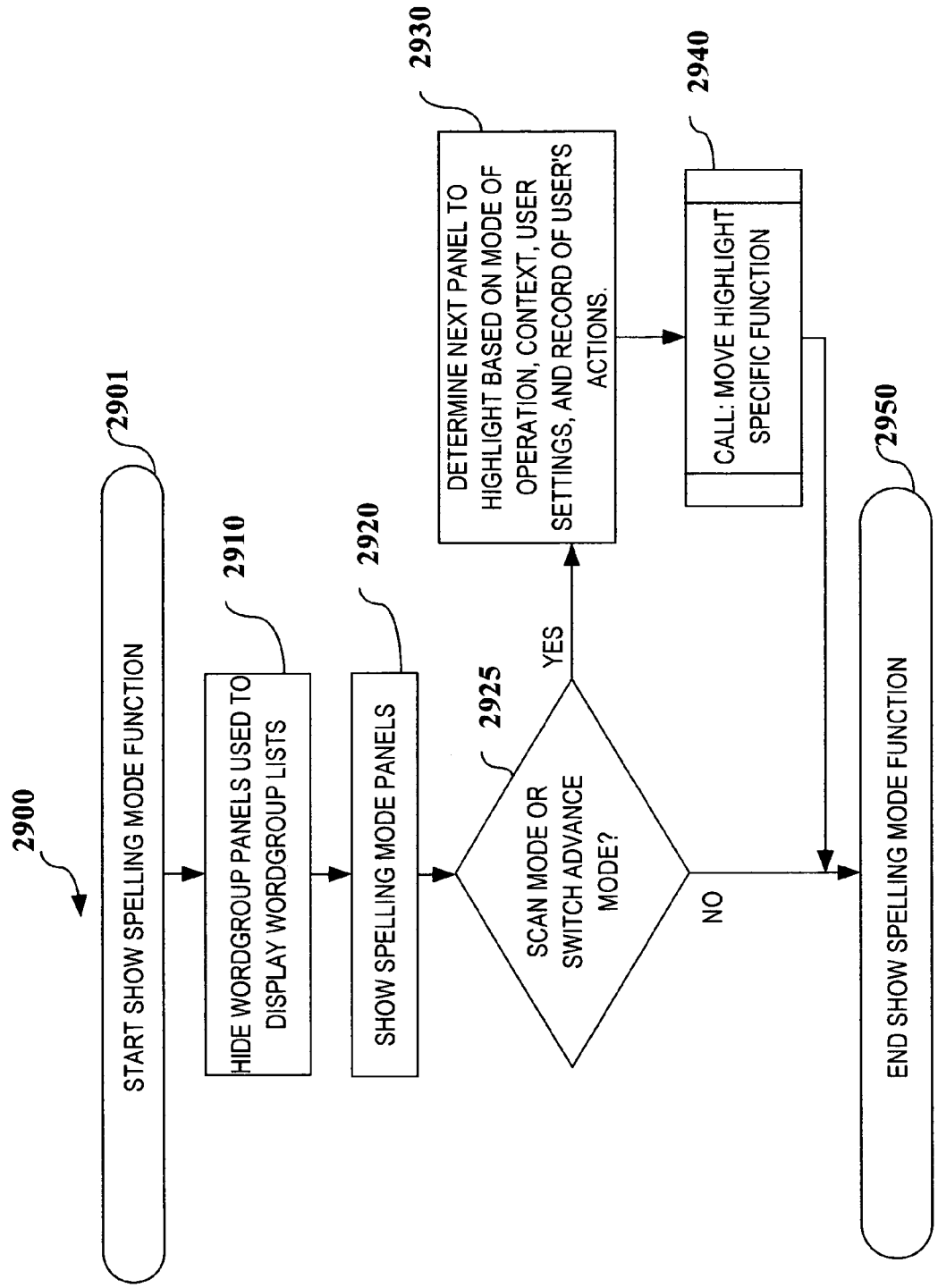
FIG. 29 is a flowchart representing a preferred embodiment of a Show Spelling Mode Function in a preferred embodiment of a system according to the present invention.

FIG. 29 describes a preferred embodiment of process 2900, which starts at 2901, for implementing the Show Spelling Mode function. Step 2910 hides the WordGroup Panels used to display WordGroup Lists. Step 2920 displays a special set of panels used to display individual characters and special commands used in spelling mode (see FIG. 4). If the system is in Scan Mode or Switch Advance Mode (test 2925), step 2930 determines what panel to highlight next based on, preferably, user-specific settings, the current mode of operation, the current context and the record of the user's previous actions. After determining the next panel to highlight, step 2940 calls the Move Highlight Specific function. Process 2900 ends at 2950.

Figure 30:
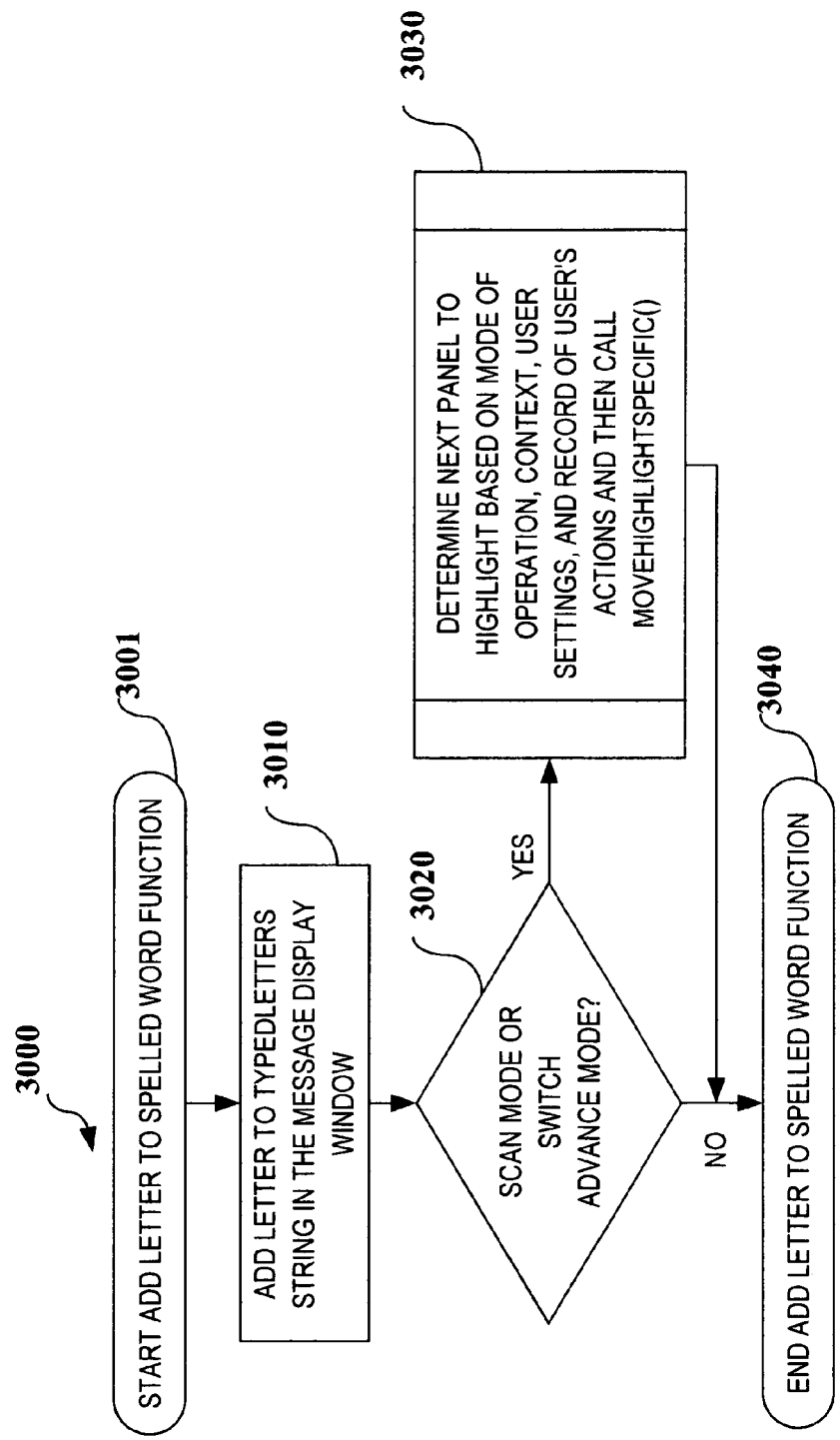
FIG. 30 is a flowchart representing a preferred embodiment of an Add Letter to Spelled Word Function in a preferred embodiment of a system according to the present invention.

FIG. 30 describes a preferred embodiment of process 3000, which starts at 3001, for implementing the Add Letter to Spelled Word function. Step 3010 adds the selected letter to the TypedLetters String in the Message Display Window. If the system is in Scan Mode or Switch Advance Mode (test 3020), step 3030 determines what panel to highlight next based on, preferably, user-specific settings, the current mode of operation and the current context. For example, in normal operation, the next panel to highlight would be the panel whose Action Object contained an Action Code linked to the Generate Suggested Words function, shown in FIG. 33. After determining the next panel to highlight, step 3030 calls the Move Highlight Specific function. Process 3000 ends at 3040.

Figure 31:
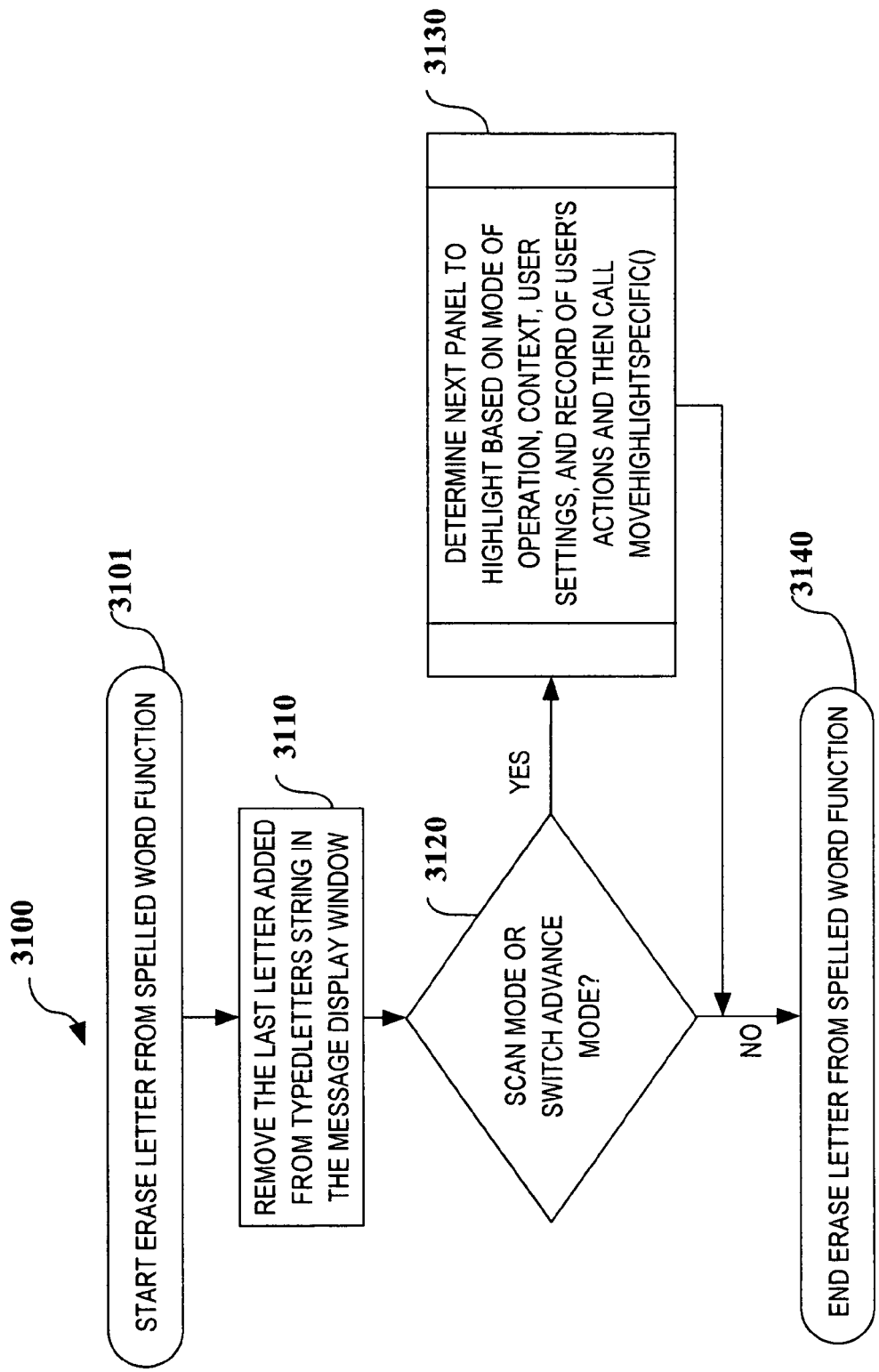
FIG. 31 is a flowchart representing a preferred embodiment of a Erase Letter from Spelled Word Function in a preferred embodiment of a system according to the present invention.

FIG. 31 describes a preferred embodiment of process 3100, which starts at 3101, for implementing the Erase Letter from Spelled Word function. Step 3110 deletes the last letter from the TypedLetters String in the Message Display Window. If the system is in Scan Mode or Switch Advance Mode, test 3120 determines what panel to highlight next based on, preferably, user-specific settings, the current mode of operation and the current context. After determining the next panel to highlight; step 3130 calls the Move Highlight Specific function. Process 3100 ends at 3140.

Figure 32:
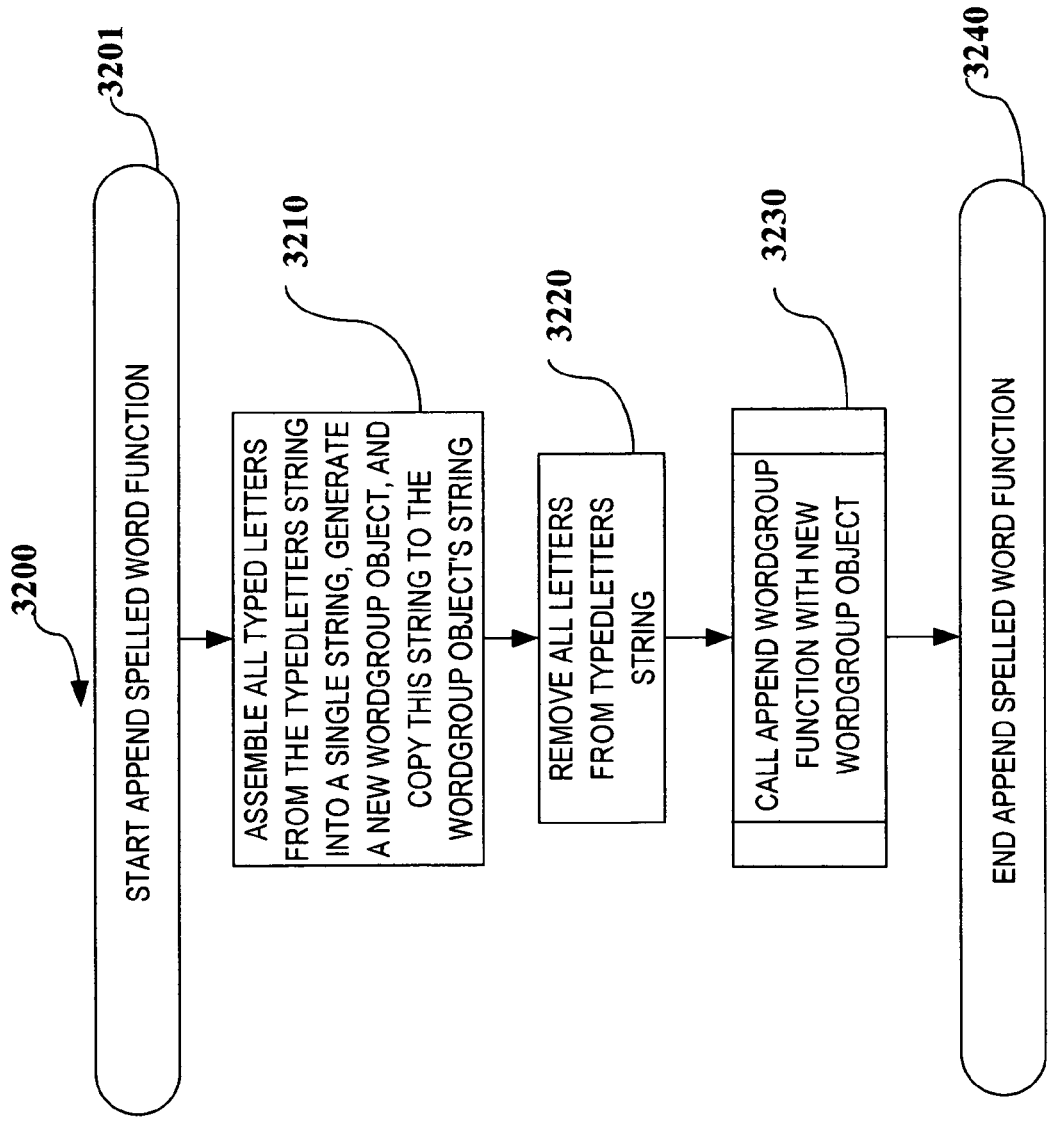
FIG. 32 is a flowchart representing a preferred embodiment of an Append Spelled Word Function in a preferred embodiment of a system according to the present invention.

FIG. 32 describes a preferred embodiment of process 3200, which starts at 3201, for implementing the Append Spelled Word function. When the user selects a panel labeled "End Word" or a "space" character to indicate that the spelled word in process is complete, step 3210 generates a new WordGroup Object and copies the TypedLetters String into the WordGroup Object's string property. Step 3220 removes all letters from the TypedLetters String. Step 3230 calls the Append WordGroup function with the new WordGroup Object as an argument.

Figure 33:
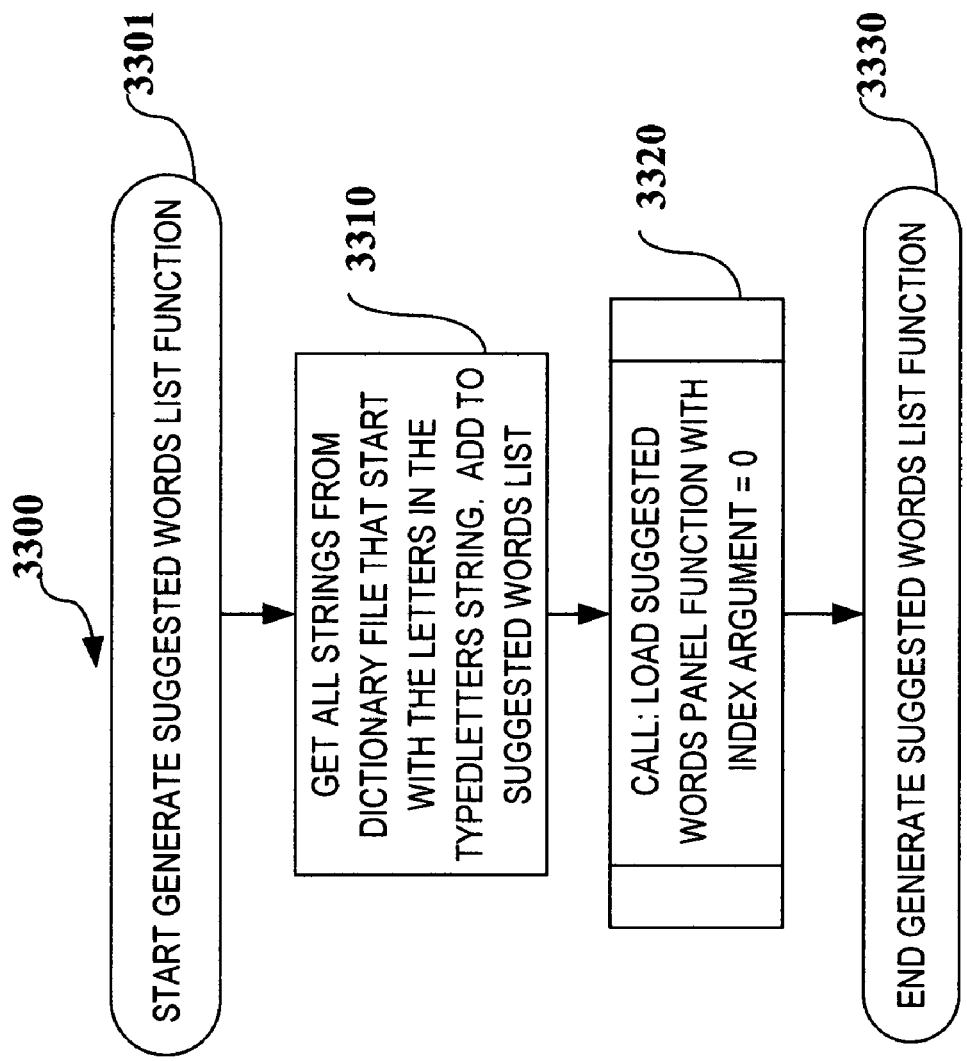
FIG. 33 is a flowchart representing a preferred embodiment of a Generate Suggested Words List Function in a preferred embodiment of a system according to the present invention.

FIG. 33 describes a preferred embodiment of process 3300 which starts at 3301, for implementing the Generate Suggested Words function. Step 3310 opens a dictionary file and copies all the words which begin with the TypedLetters String into the Suggested Words List. Step 3320 calls the Load Suggested Words Panel function with the index argument set to zero. Process 3300 ends at 3330.

Figure 34:
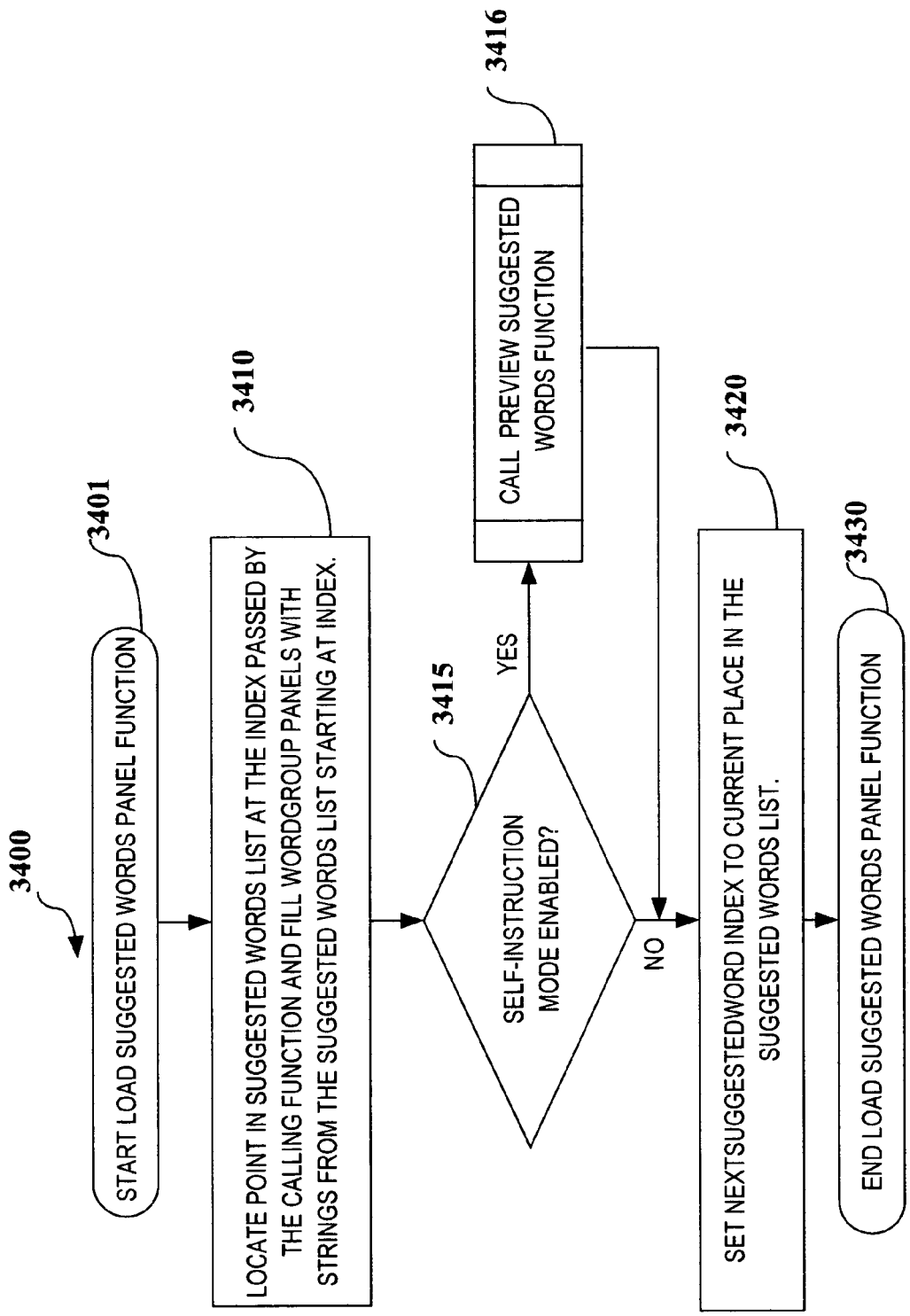
FIG. 34 is a flowchart representing a preferred embodiment of a Load Suggested Words Panel Function in a preferred embodiment of a system according to the present invention.

FIG. 34 describes a preferred embodiment of process 3400, which starts at 3401, for implementing the Load Suggested Words Panel function. Step 3410 fills the WordGroup panels with the strings from the Suggested Words List, starting at the index within the Suggested Words List passed to it by the calling function. Test 3415 determines whether Self-Instruction Mode is enabled. If the answer is Yes, step 3416 calls the Preview Suggested Words function, which might speak the list of suggested words on the screen (to assist visually impaired users or other users who have difficulty reading or comprehending written text). Step 3420 sets the NextSuggestedWordIndex to one index beyond the index of the last word loaded into the WordGroup panels. Process 3400 ends at 3430.

Figure 35:
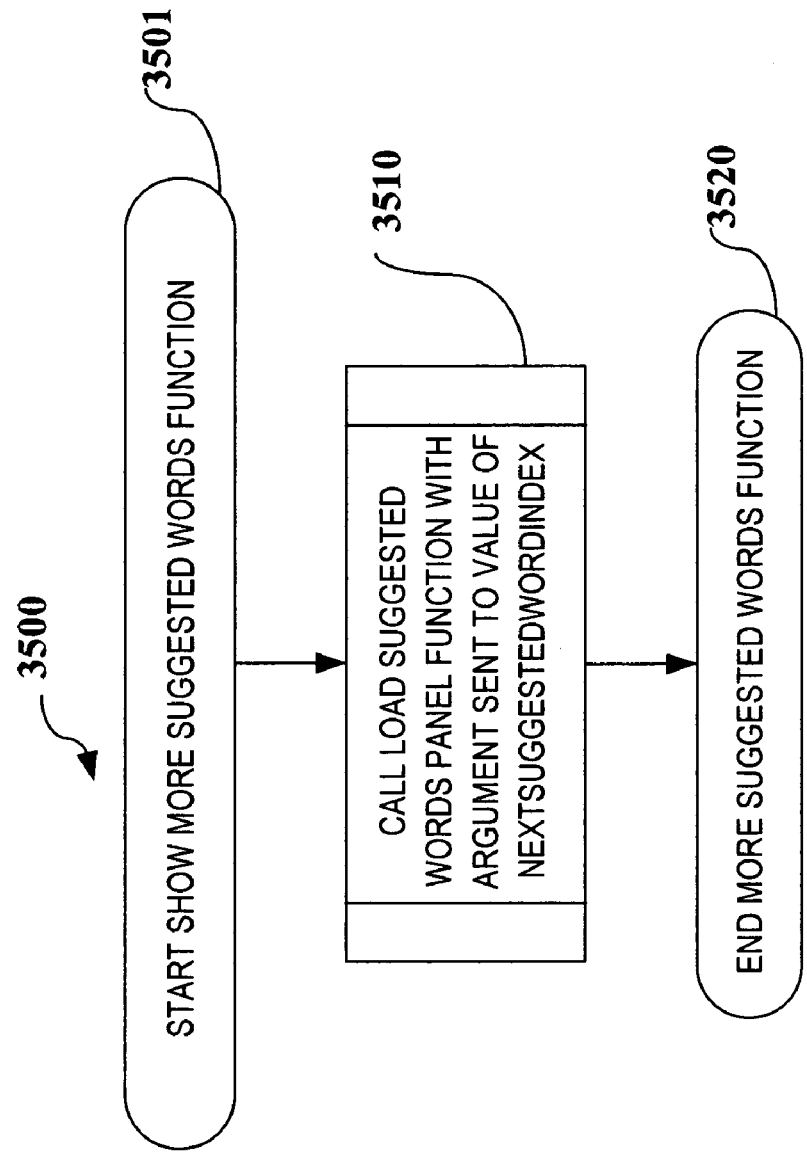
FIG. 35 is a flowchart representing a preferred embodiment of a Show More Suggested Words Function in a preferred embodiment of a system according to the present invention.

FIG. 35 describes a preferred embodiment of process 3500 which starts at 3501, for implementing the Show More Suggested Words function. Step 3510 calls the Load Suggested Words Panel function with the argument set to the NextSuggestedWordIndex. Process 3500 ends at 3520.

FIG. 36 describes a preferred embodiment of process 3600, which starts at 3601, for implementing the Append Suggested Word function, which is called when a user-generated event selects a WordGroup Panel containing a suggested word. Step 3610 generates a new WordGroup Object and copies the suggested word string associated with the selected WordGroup Panel into the new WordGroup Object's string property. Step 3620 removes all letters from the TypedLetters String. Step 3630 calls the Append WordGroup function with the new WordGroup Object as an argument. Process 3600 ends at 3640.

Figure 37A:
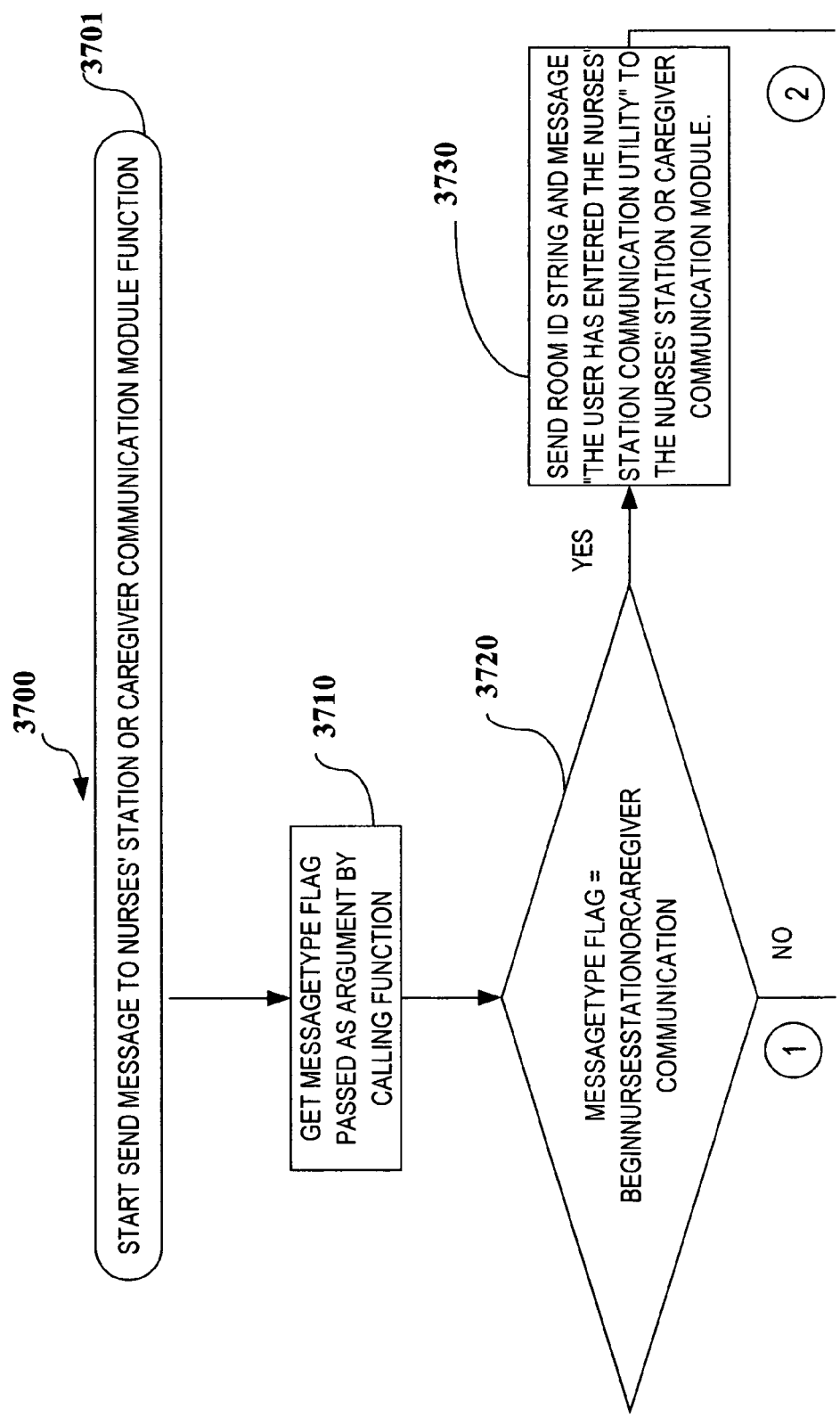
FIGS. 37A, 37B and 37C (hereafter collectively referred to as FIG. 37) are a flowchart representing a preferred embodiment of a Send Message to Nurses' Station or Caregiver Communication Module Function in a preferred embodiment of a system according to the present invention.
Figure 37B:
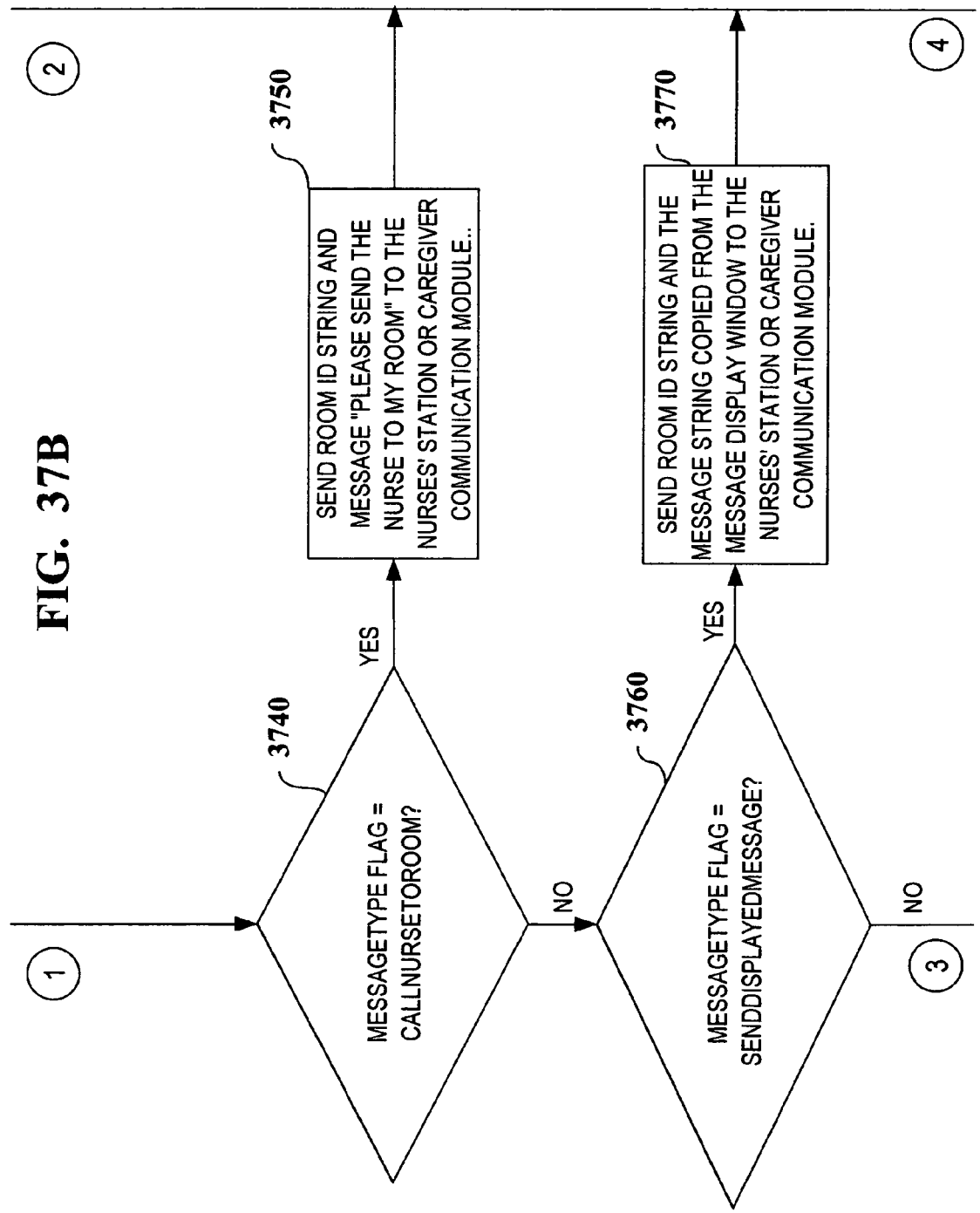
Figure 37C:
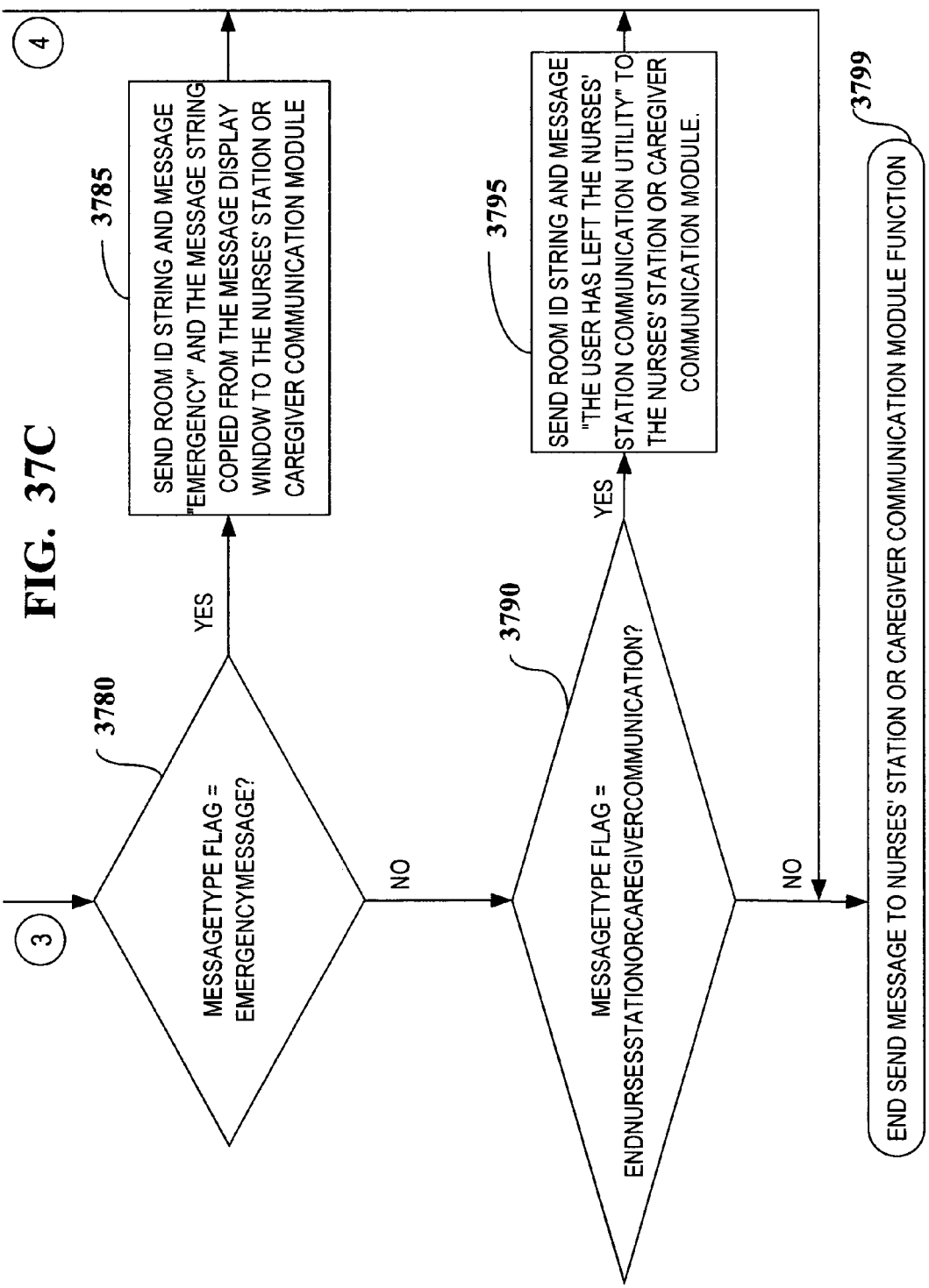

FIG. 37 describes a preferred embodiment of process 3700, which starts at 3701, for implementing the Send Message to Nurses' Station or Caregiver Communication Module function. Step 3710 gets the MessageType Flag which was passed as an argument by the calling function. Test 3720 determines if the flag is equal to the BeginNursesStationOrCaregiverCommunication Flag. If the answer to test 3720 is Yes, step 3730 sends the Room ID string, and an appropriate message (for example, "The user has entered the nurses' station communication module") to the Nurses' Station or Caregiver Communication Module via an appropriate communications link, which could be (but is not restricted to) a wireless computer link, a wireless pager radio link, cell phone text messaging link, or any other appropriate link.

If the answer to test 3720 is No, test 3740 determines if the MessageType Flag is equal to the CallNurseToRoom Flag. If the answer to test 3740 is Yes, step 3750 sends the Room ID string, and an appropriate message (for example, "Please send the nurse to my room") to the Nurses' Station or Caregiver Communication Module via an appropriate communications link.

If the answer to test 3740 is No, test 3760 determines if the MessageType Flag is equal to the SendDisplayedMessage Flag. If the answer to test 3760 is Yes, step 3770 sends the Room ID string and the Displayed Message String from the Message Display Window to the Nurses' Station or Caregiver Communication Module via an appropriate communications link.

Test 3780 determines if the EmergencyMessage Flag is set. If the answer to test 3780 is Yes, step 3785 appends the Displayed Message String to the string "Emergency:" and sends the resulting string, together with the Room ID string, to the Nurses' Station or Caregiver Communication Module via an appropriate communications link.

Test 3790 determines if the flag is equal to the EndNursesStationOrCaregiverCommunication Flag. If the answer to test 3790 is Yes, step 3795 sends the Room ID string, and an appropriate message (for example, "The user has exited the nurses' station communication module") to the Nurses' Station or Caregiver Communication Module via an appropriate communications link. Process 3700 ends at 3799.

Figure 38:
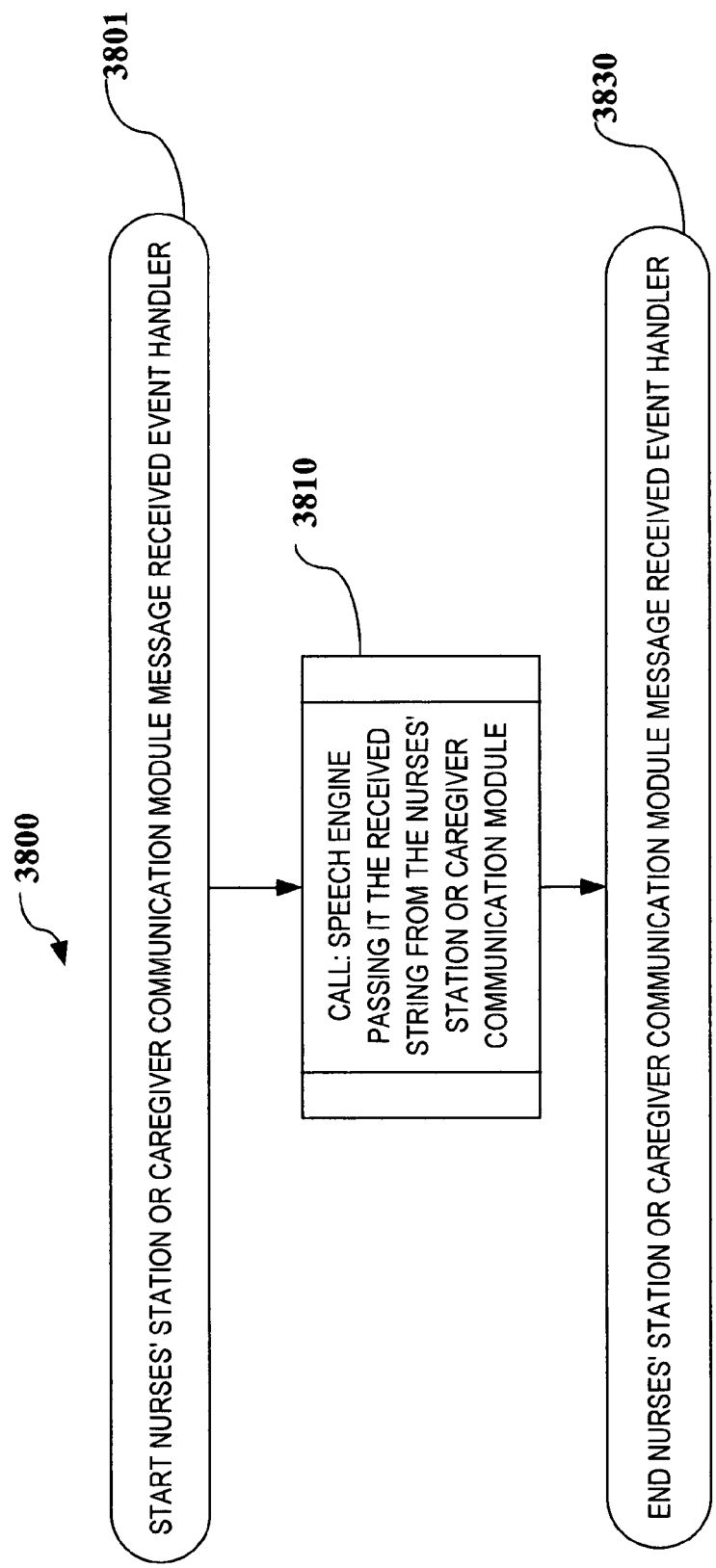
FIG. 38 is a flowchart representing a preferred embodiment of a Nurses' Station or Caregiver Communication Module Message Receipt Event Handler in a preferred embodiment of a system according to the present invention.

FIG. 38 describes a preferred embodiment of process 3800, which starts at 3801, for implementing the Nurses' Station or Caregiver Communication Module Message Receipt Event Handler. Event handler 3800 is called on receipt, via an appropriate communications link, of a communication string from the Nurses' Station or Caregiver Communication Module. Step 3810 sends the received communication string, which was constructed by the Nurses' Station Module or Caregiver Communication Module (e.g., "Your message: 'Please send the nurse to my room,' has been received at the nurses' station."), to the speech engine. Process 3800 ends at 3830.

FIG. 39 describes a preferred embodiment of process 3900, which starts at 3901, for implementing the Select Party for Telephone Call function. Step 3910 loads the List of Potential Persons to Call into WordGroup Panels, with the Action Code for the Action Object associated with each panel set to SelectTelephoneNumber. Step 3920 loads a label similar to "EnterTelephone#" into an additional WordGroup Panel, with the Action Code for the Action Object associated with this panel set to DisplayPhoneNumberAndE-mailAddressEntryScreen (a modified version of the spelling mode screen, which operates identically with the exception that there is a dedicated display window for the constructed telephone number or e-mail address). Process 3900 ends at 3930.

FIG. 40 describes a preferred embodiment of process 4000, which starts at 4001, for implementing the Select Telephone-Number function. Step 4010 loads the List of Telephone Numbers for the selected person into the WordGroup Panels, with the Action Code for the Action Object associated with each panel set to PlaceCall. Process 4000 ends at 4020.

FIG. 41 describes a preferred embodiment of process 4100, which starts at 4101, for implementing the Place Telephone Call function. Step 4110 sends a command to the External Interface Module instructing its telephone interface to go "off-hook." Step 4120 represents a loop in which the DTMF code for each digit of the telephone number is sent to the telephone interface DAA module, in order to "dial" the requested phone number. Step 4125 sends an appropriate command to the External Interface Module instructing it to connect the Patient Module Audio Signal Output to the Telephone Audio Out line of the DAA telephone interface module, and to connect the Telephone Audio In line of the DAA module to the headphone jack or speaker, as required. Step 4130 loads a list of Special Conversational Telephone words into the WordGroup Panels, with the Action Code for the Action Object associated with each panel set to Speak Immediately, so that whenever any of these panels are selected, its associated string is immediately sent to the speech engine, rather than being appended to the Message Display Window. Process 4100 ends at 4140.

FIG. 42 describes a preferred embodiment of process 4200, which starts at 4201, for implementing the Incoming Telephone Call Event Handler. Step 4210 loads the List of Answering Options into the WordGroup Panels with the Action Code for the Action Object associated with each panel set to RespondToIncomingCall. The list of Answering Options may, e.g., include "Answer" and "Ignore." Step 4220 outputs a telephone ringing sound to alert the user to the incoming call. Process 4200 ends at 4230.

Figure 43A:
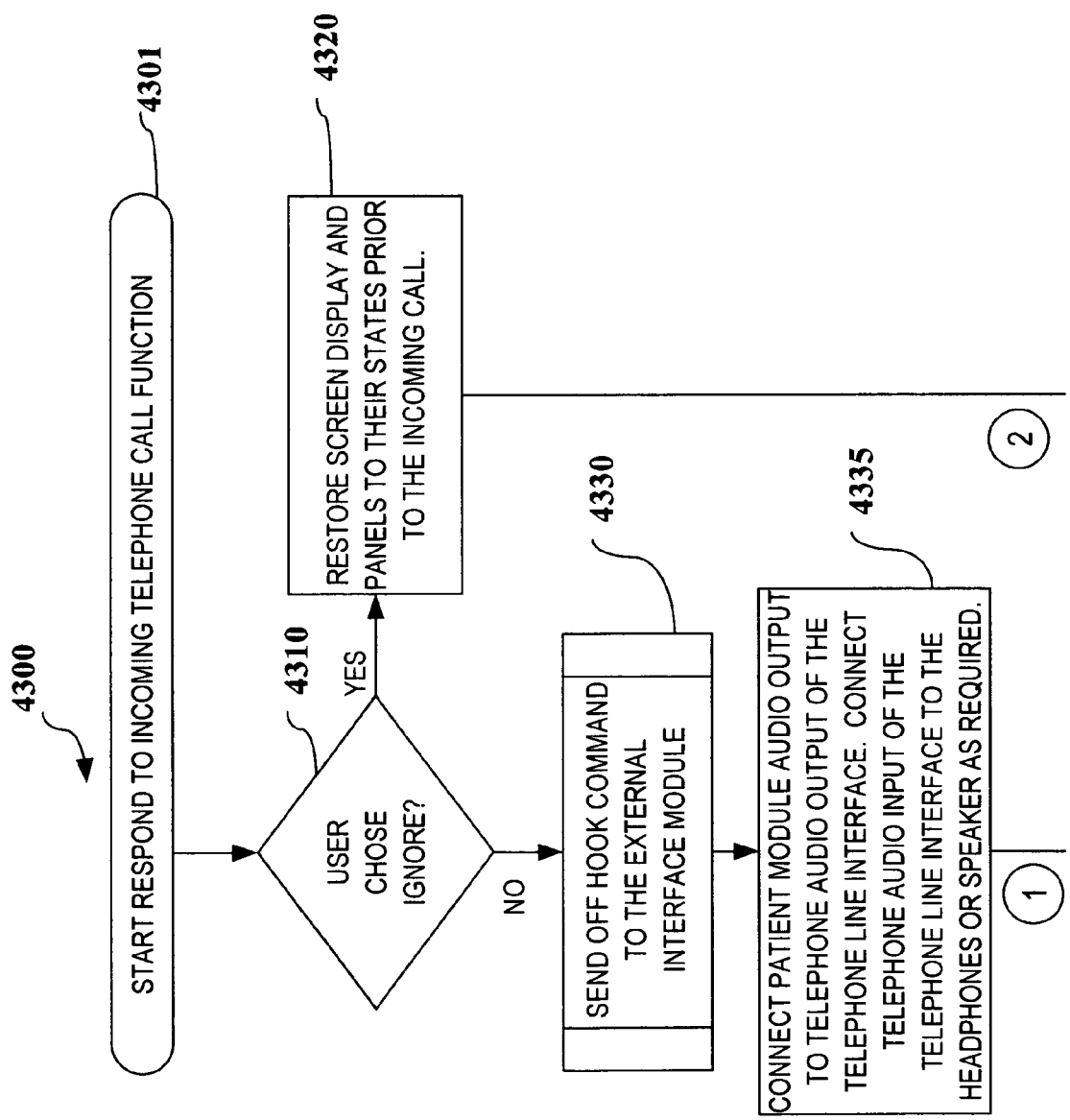
FIGS. 43A and 43B (hereafter collectively referred to as FIG. 43) are a flowchart representing a preferred embodiment of a Respond to Incoming Telephone Call Function in a preferred embodiment of a system according to the present invention.
Figure 43B:
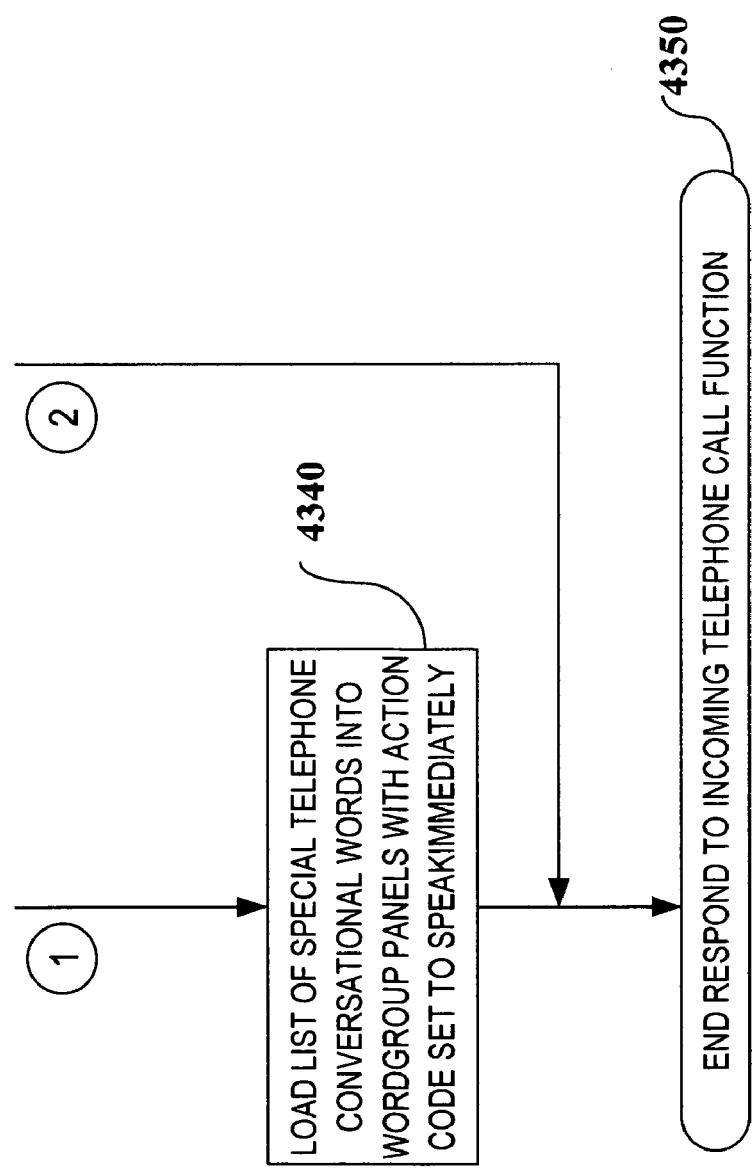

FIG. 43 describes a preferred embodiment of process 4300, which starts at 4301, for implementing the Respond to Incoming Telephone Call function. Test 4310 determines whether the user has selected "Ignore". If the answer to test 4310 is Yes, step 4320 restores the screen display and associated panels to their states prior to the incoming telephone call.

If the answer to test 4310 is No, step 4330 sends a command to the External Interface Module instructing its telephone interface to go "off-hook." Step 4335 sends an appropriate command to the External Interface Module instructing it to connect the Patient Module Audio Signal Output to the Telephone Audio Out line of the DAA telephone interface module, and to connect the Telephone Audio In line of the DAA module to the headphone jack or speaker, as required. Step 4340 loads the List of Special Conversational Telephone words into the WordGroup Panels, with the Action Code for the Action Object associated with each panel set to SpeakImmediately. Process 4300 ends at 4350.

FIG. 44 describes a preferred embodiment of process 4400, which starts at 4401, for implementing the Hang Up Telephone function. Step 4405 sends an appropriate command to the External Interface Module instructing it to disconnect the Patient Module Audio Signal Output from the Telephone Audio Out line of the DAA telephone interface module, and to disconnect the Telephone Audio In line of the DAA module from the headphone jack or speaker, as required. Step 4410 sends a command to the External Interface Module instructing its telephone interface to go "on-hook." Process 4400 ends at 4420.

FIG. 45 describes a preferred embodiment of process 4500, which starts at 4501, for implementing the Initiate E-mail Session function. The provision of e-mail functionality requires that the Patient Module is connected via some wired or wireless interface to the Internet. Step 4510 loads WordGroup Panels with the labels "Send E-mail" and "Read E-mail", with the Action Code for the Action Object associated with "Send-Email" panel set to SelectPartyforE-mail, and the Action Code for the Action Object associated with "Read E-mail" panel set to BeginReadingE-mail. Process 4500 ends at 4520.

FIG. 46 describes a preferred embodiment of process 4600, which starts at 4601, for implementing the Select Party for E-mail function. Step 4610 loads the List of Potential Persons to E-mail into the WordGroup Panels, with the Action Code for the Action Object associated with each such panel set to SelectE-mailAddress. Step 4620 loads a label similar to "Enter E-mail Address" into an additional WordGroup Panel, with the Action Code for the Action Object associated with this panel set to DisplayPhoneNumberAndE-mailAddressEntryScreen. As described above, the Phone Number And E-mail Address Entry Screen is a screen which allows manual entry of telephone numbers or e-mail addresses. At the completion of manual e-mail address entry, an appropriate Control Panel on that screen is preferably enabled, which, when selected, calls the Execute E-mail Output function. Process 4600 ends at 4630.

Figure 47:
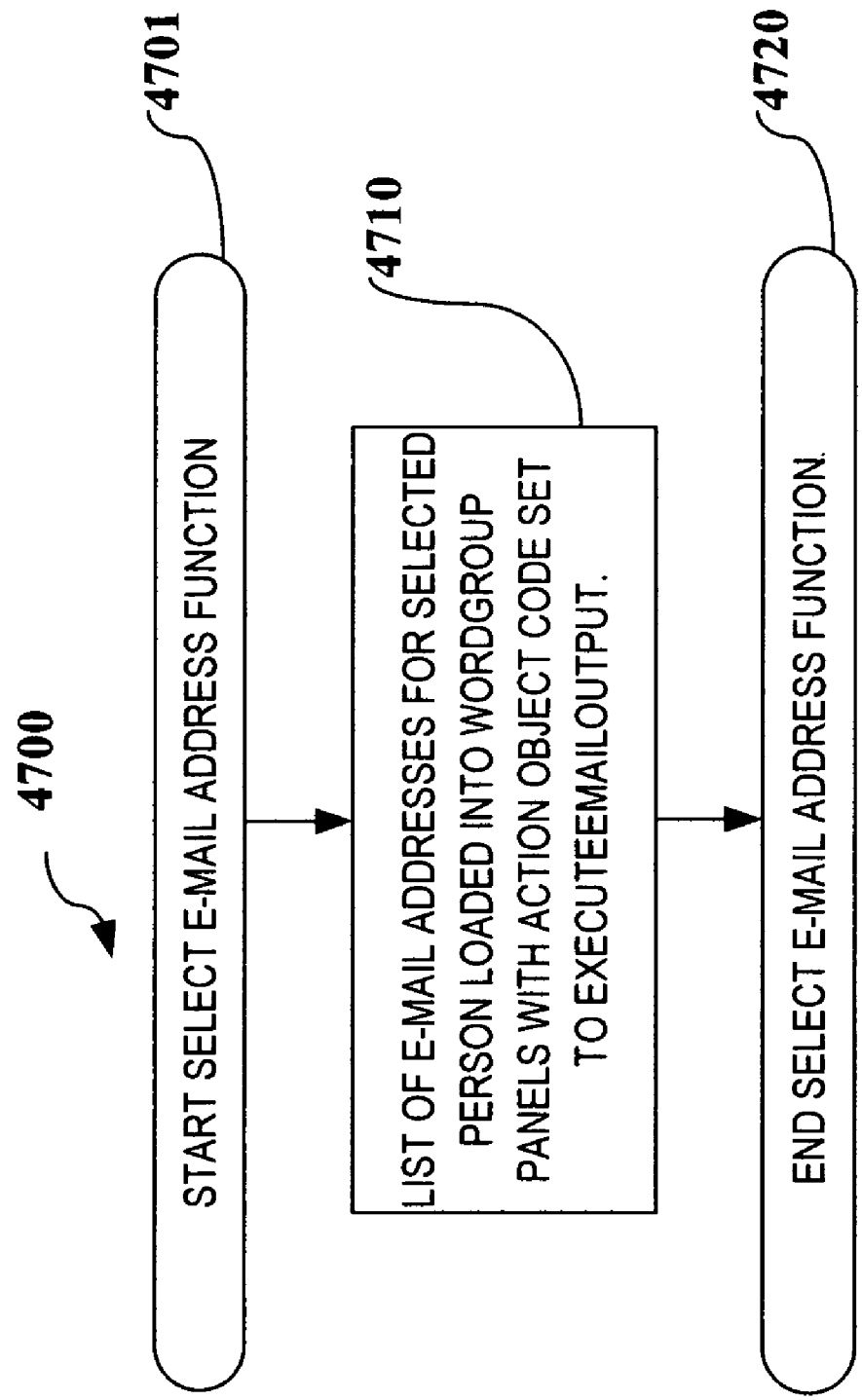
FIG. 47 is a flowchart representing a preferred embodiment of a Select E-mail Address Function in a preferred embodiment of a system according to the present invention.

FIG. 47 describes a preferred embodiment of process 4700, which starts at 4701, for implementing the Select E-mail Address function. Step 4710 loads the List of e-mail addresses for the selected person into the WordGroup Panels, with the Action Code for the Action Object associated with each panel set to ExecuteE-mailOutput. Process 4700 ends at 4720.

Figure 48A:
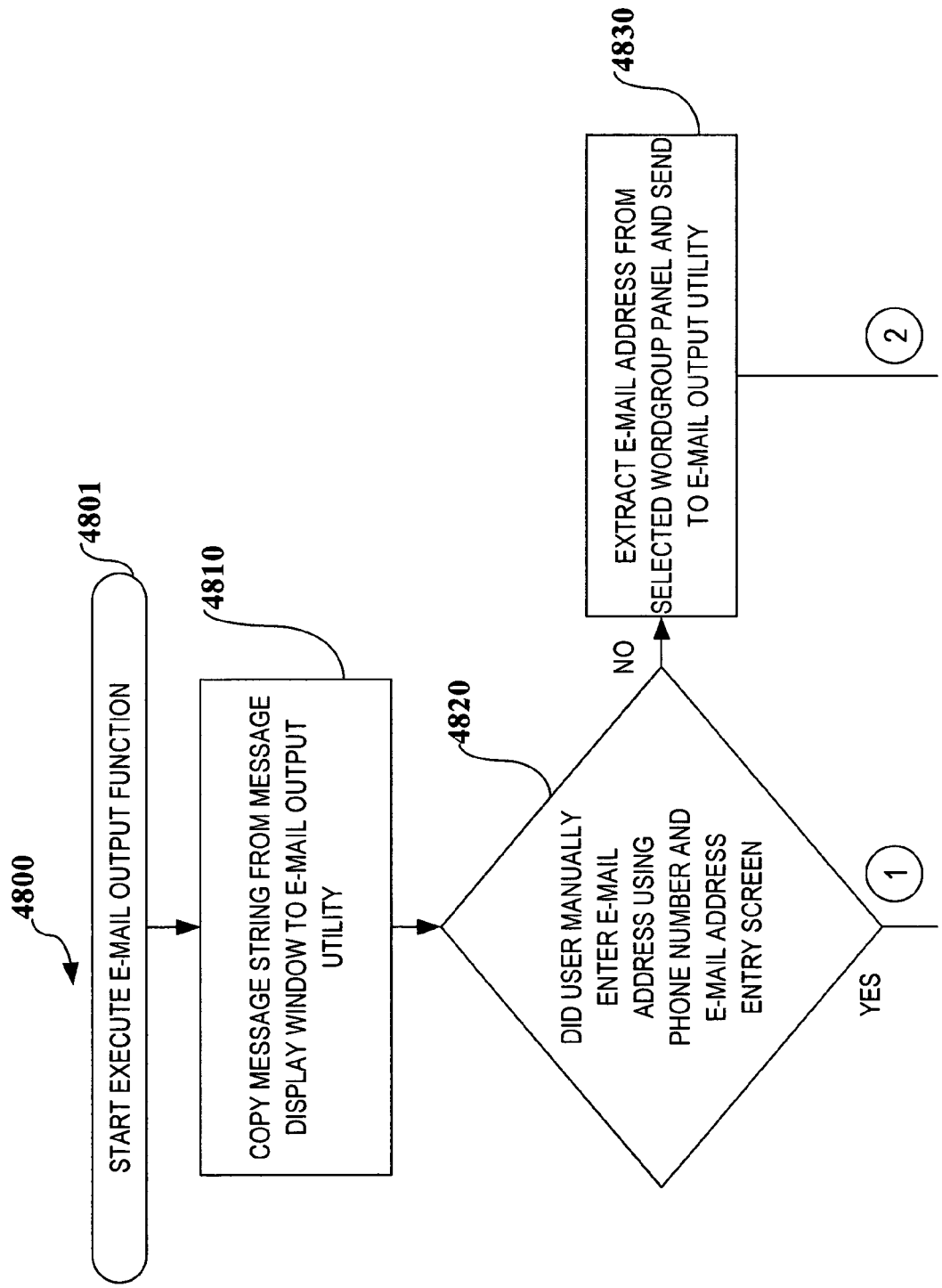
FIGS. 48A and 48B (hereafter collectively referred to as FIG. 48) are a flowchart representing a preferred embodiment of a Execute E-mail Output Function in a preferred embodiment of a system according to the present invention.
Figure 48B:
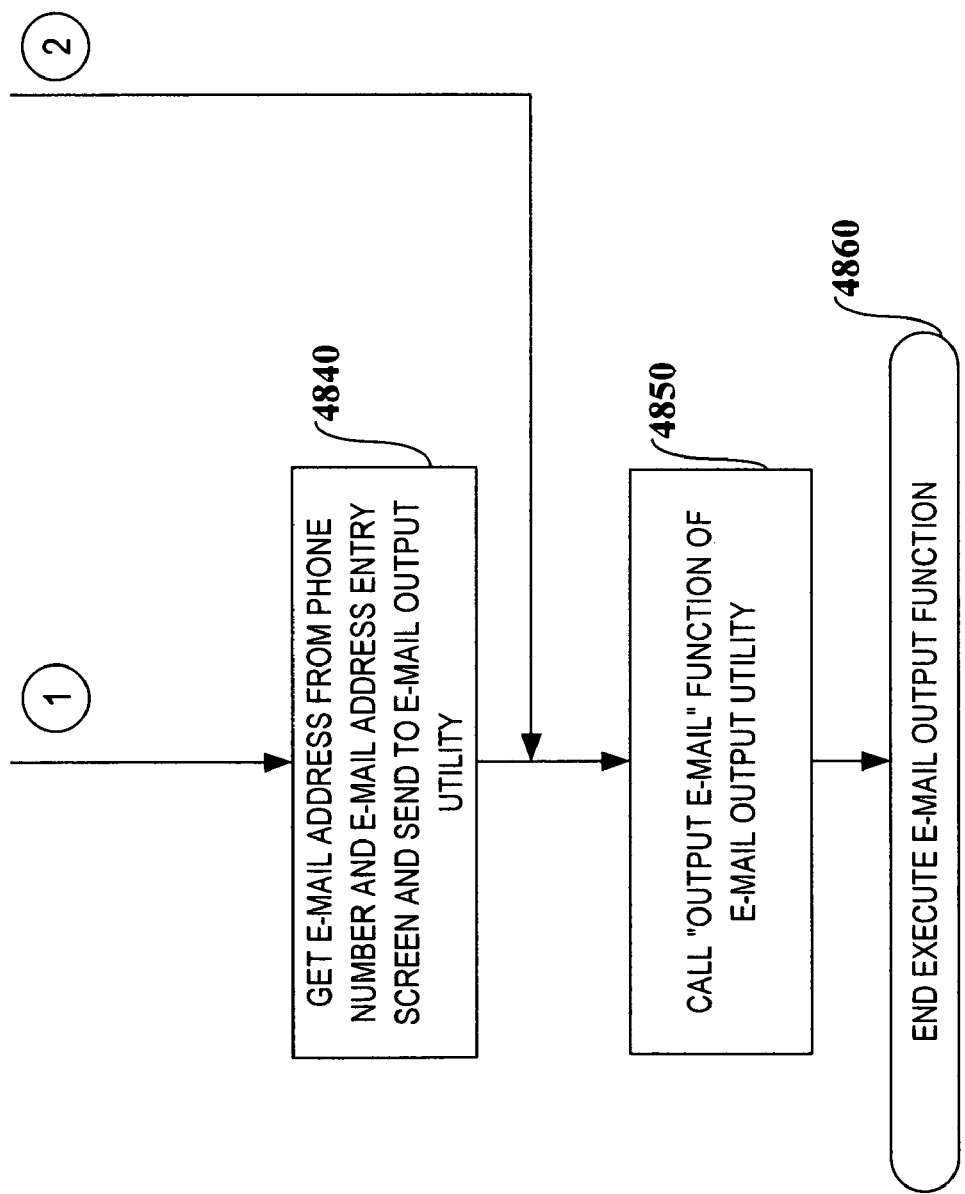

FIG. 48 describes a preferred embodiment of process 4800, which starts at 4801, for implementing the Execute E-mail Output function. Step 4810 copies the Message String from the Message Display Window into the message string property of a commercial e-mail output utility. Test 4820 determines whether the e-mail address was manually entered using the Phone Number and E-mail Address Entry Screen. If the answer to test 4820 is No, step 4830 extracts the e-mail mail address associated with the WordGroup Panel selected by the user, and places this address into the address variable for the commercial e-mail output utility.

If the answer to test 4820 is Yes, step 4840 gets the e-mail address manually input by the user using the Phone Number and E-mail Address Entry Screen, and places this address into the address variable for the commercial e-mail output utility.

Step 4850 calls an appropriate "output e-mail" function of the commercial e-mail output utility. Process 4800 ends at 4860.

Figure 49:
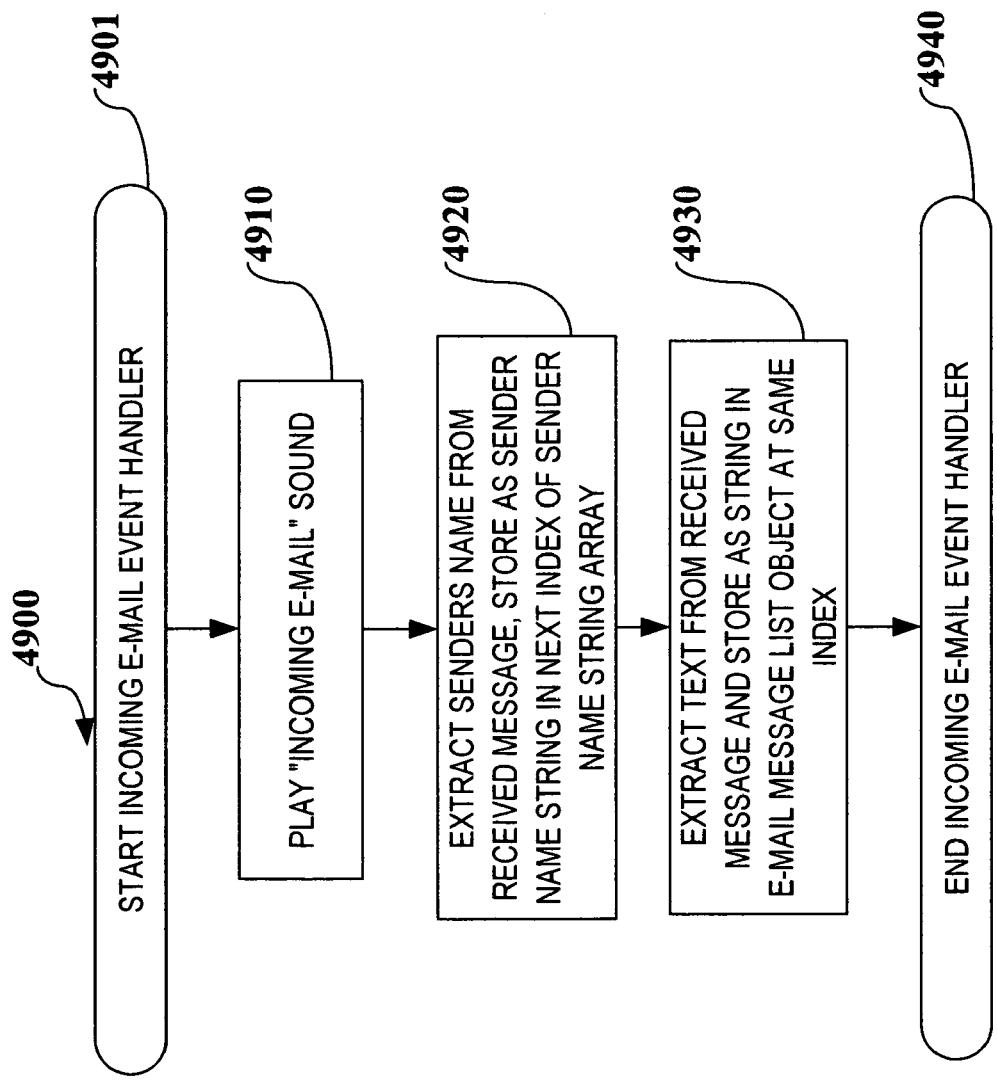
FIG. 49 is a flowchart representing a preferred embodiment of a Incoming E-mail Event Handler in a preferred embodiment of a system according to the present invention.

FIG. 49 describes a preferred embodiment of process 4900, which starts at 4901, for implementing the Incoming E-mail Event Handler. Step 4910 outputs an appropriate sound to indicate the receipt of a new e-mail message. Step 4920 extracts the sender's name from the received message, and stores the name in a sender name string array at the next available index. Step 4930 extracts the text from the body of the e-mail message and stores this text in an e-mail message list object, at the same index used to store the sender name string. Process 4900 ends at 4940.

Figure 50:
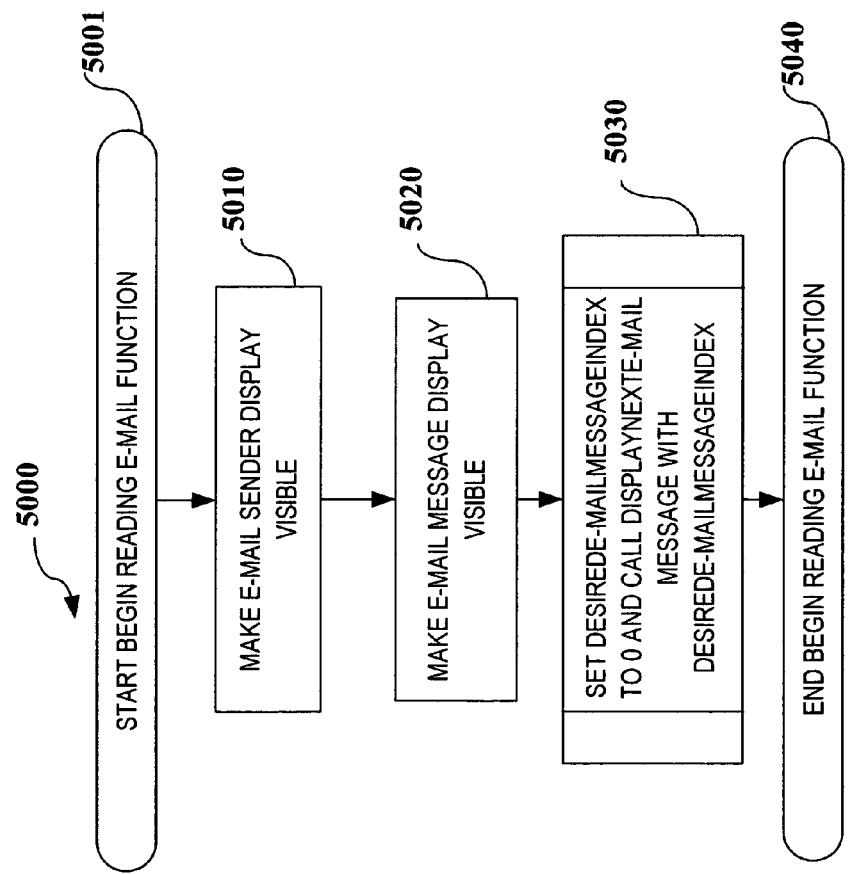
FIG. 50 is a flowchart representing a preferred embodiment of a Begin Reading E-mail Function in a preferred embodiment of a system according to the present invention.

FIG. 50 describes a preferred embodiment of process 5000, which starts at 5001, for implementing the Begin Reading E-mail function. Step 5010 makes visible a special window for displaying the name of the e-mail sender. Step 5020 makes visible a special window for displaying the body of the e-mail message. Step 5030 sets the DesiredE-mailMessageIndex to 0, and calls the DisplayNextE-mailMessage with the DesiredE-mailMessageIndex passed as the parameter. Process 5000 ends at 5040.

Figure 51A:
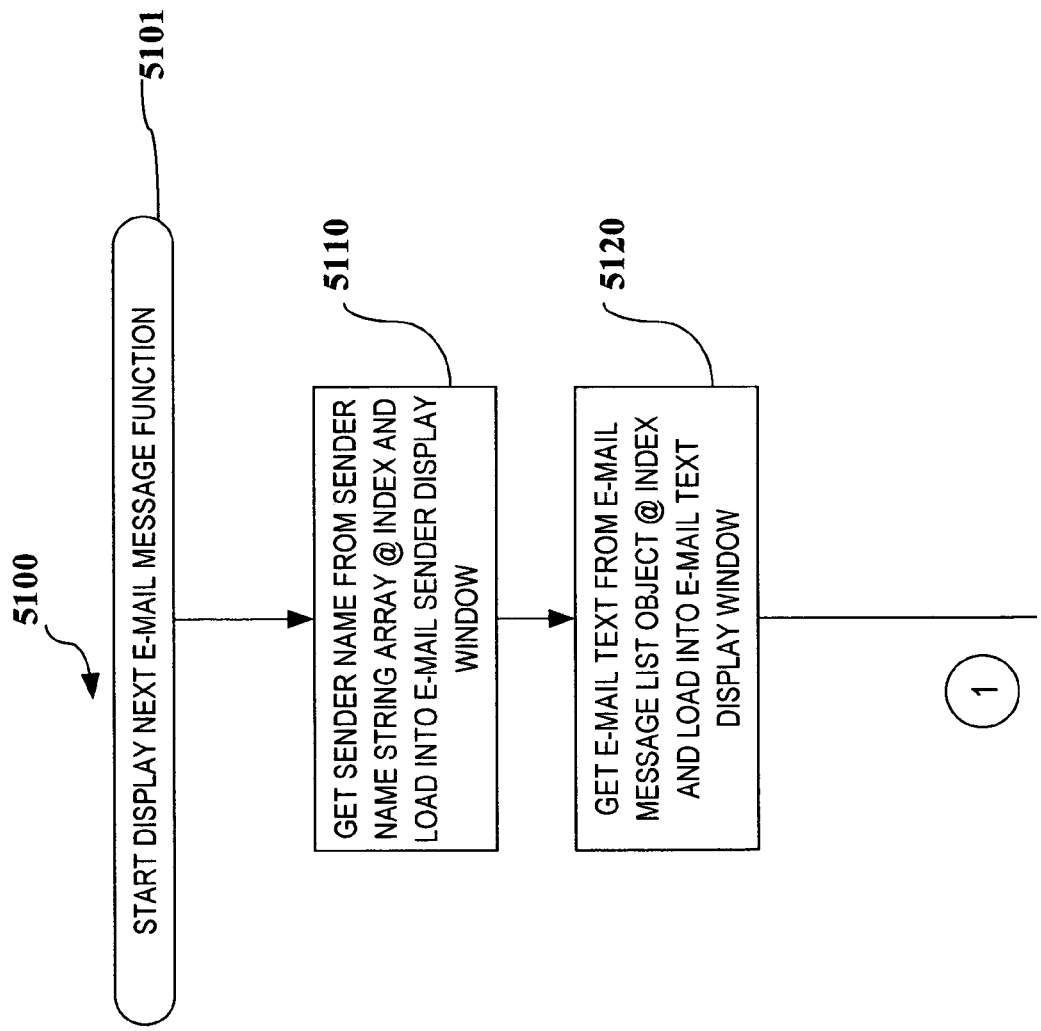
FIGS. 51A and 51B (hereafter collectively referred to as FIG. 51) are a flowchart representing a preferred embodiment of a Display Next E-mail Message Function in a preferred embodiment of a system according to the present invention.
Figure 51B:
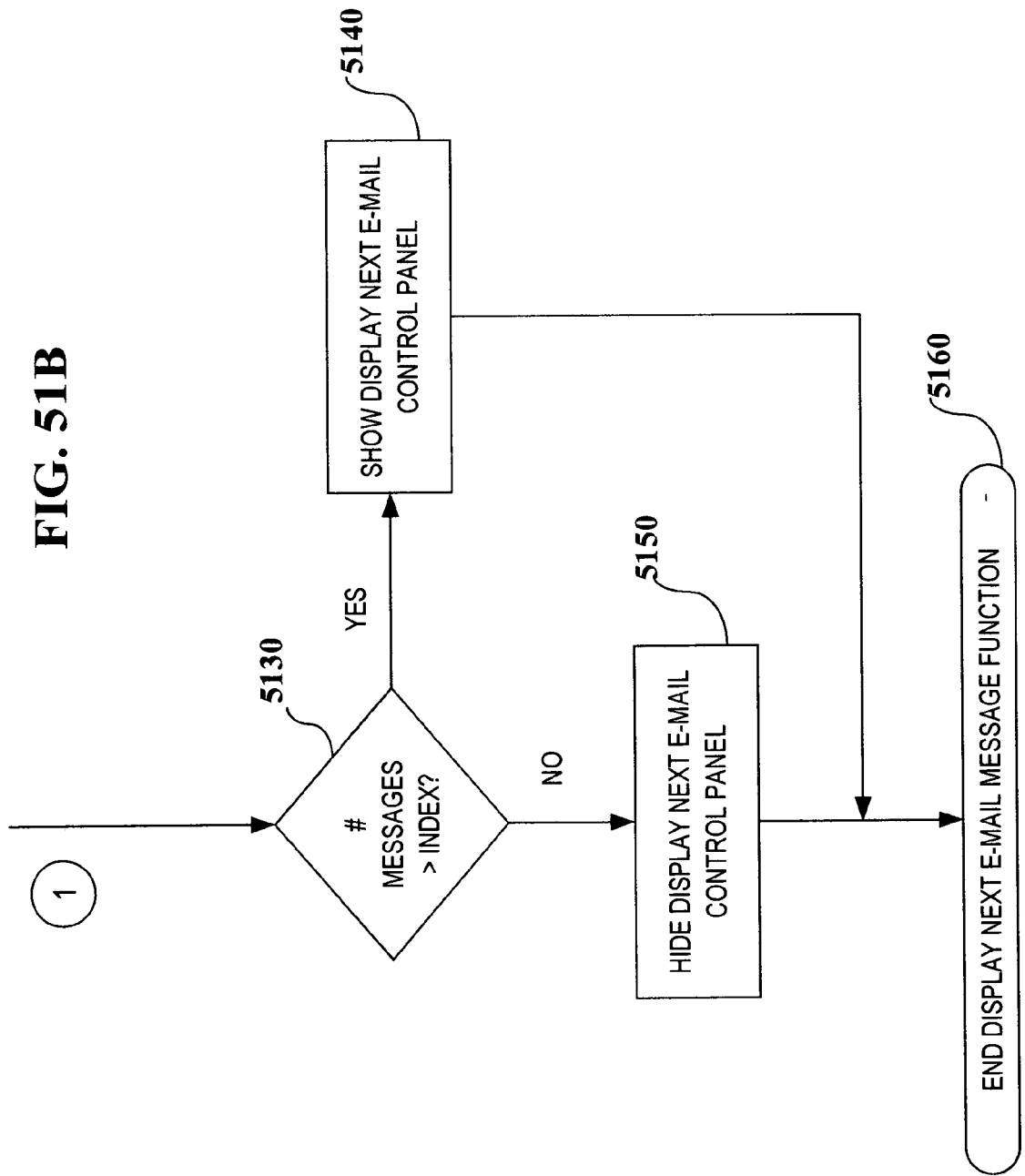

FIG. 51 describes a preferred embodiment of process 5100, which starts at 5101, for implementing the Display Next E-mail Message function. Step 5110 copies the sender name from the desired index within the sender name string array into the display window for the e-mail sender name. Step 5120 copies the body of the e-mail message stored at the corresponding index within the e-mail message list object into the display window for the body of the text. Test 5130 checks to see if the number of messages in the e-mail message list object is greater than the current index. If the answer to test 5130 is Yes, step 5140 makes visible an appropriate Control Panel labeled "Display Next E-mail". If the answer to test 5130 is No, step 5150 hides the Control Panel labeled "Display Next E-mail". Process 5100 ends at 5160.

Figure 52:
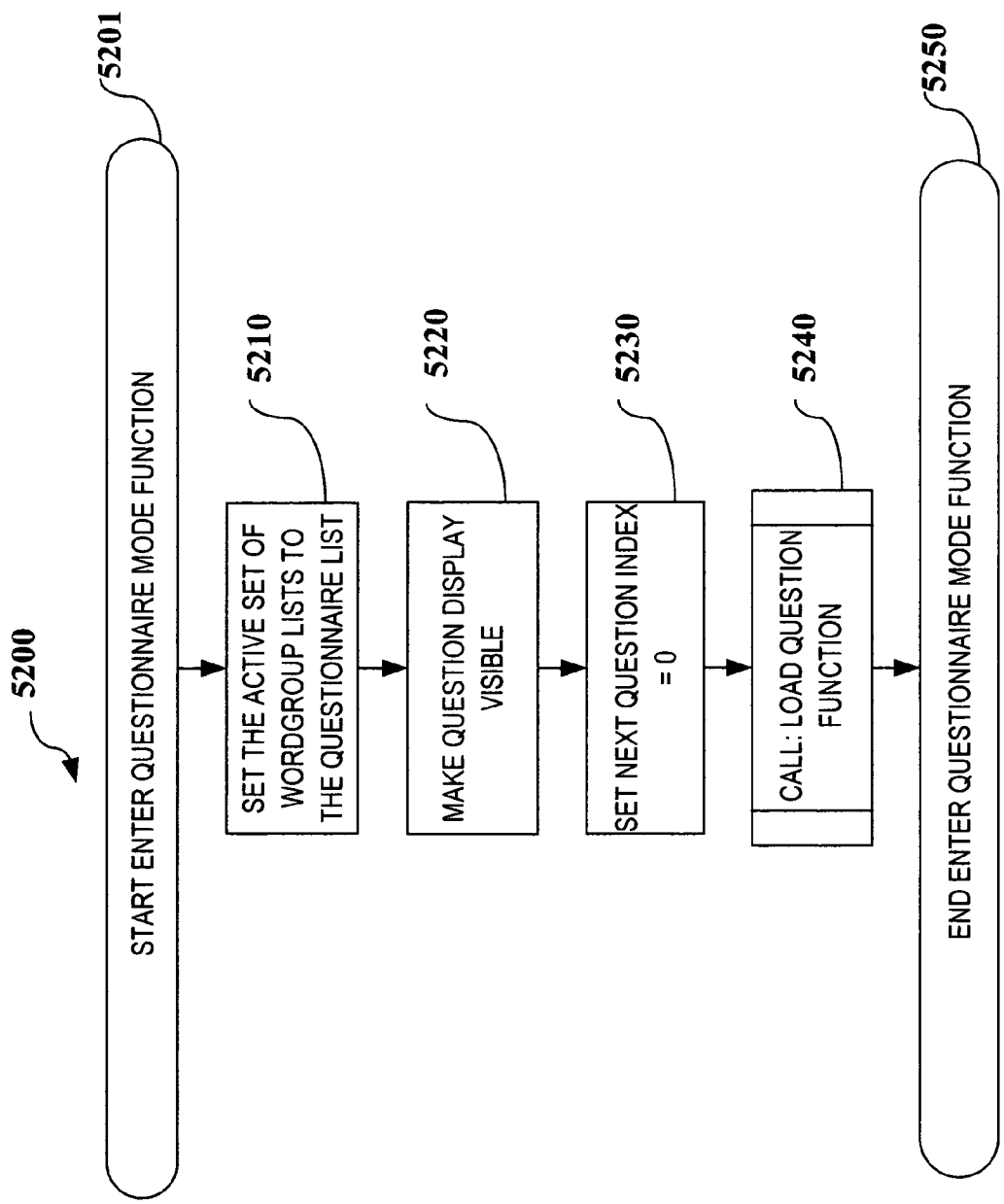
FIG. 52 is a flowchart representing a preferred embodiment of an Enter Questionnaire Mode Function in a preferred embodiment of a system according to the present invention.

FIG. 52 describes a preferred embodiment of process 5200, which starts at 5201, for implementing the Enter Questionnaire Mode function. This function changes the Active Set of WordGroup lists used by the Patient Module from a standard set designed to allow the patient to communicate with caregivers or family members to a special set of WordGroup lists designed to allow a non-speaking patient to answer a questionnaire (such as, a standard medical intake questionnaire). Each of the WordGroup lists used in the Questionnaire Mode has an associated Question String, and each WordGroup object in the WordGroup list is a potential answer to the question posed by the Question String. Each such WordGroup object may have a link to another WordGroup list which represents a follow-up question for that specific answer.

In step 5210, the Active Set of WordGroup Lists is changed to the set of WordGroup lists for the particular questionnaire. In step 5220, a special Question Display Window is made visible on the screen. Step 5230 sets the Next Question Index to 0 (i.e. pointing to the first WordGroup List, which contains the first question in the questionnaire). Step 5240 then loads this first WordGroup List by calling the Load Question function. Process 5200 ends at 5250.

Figure 53A:
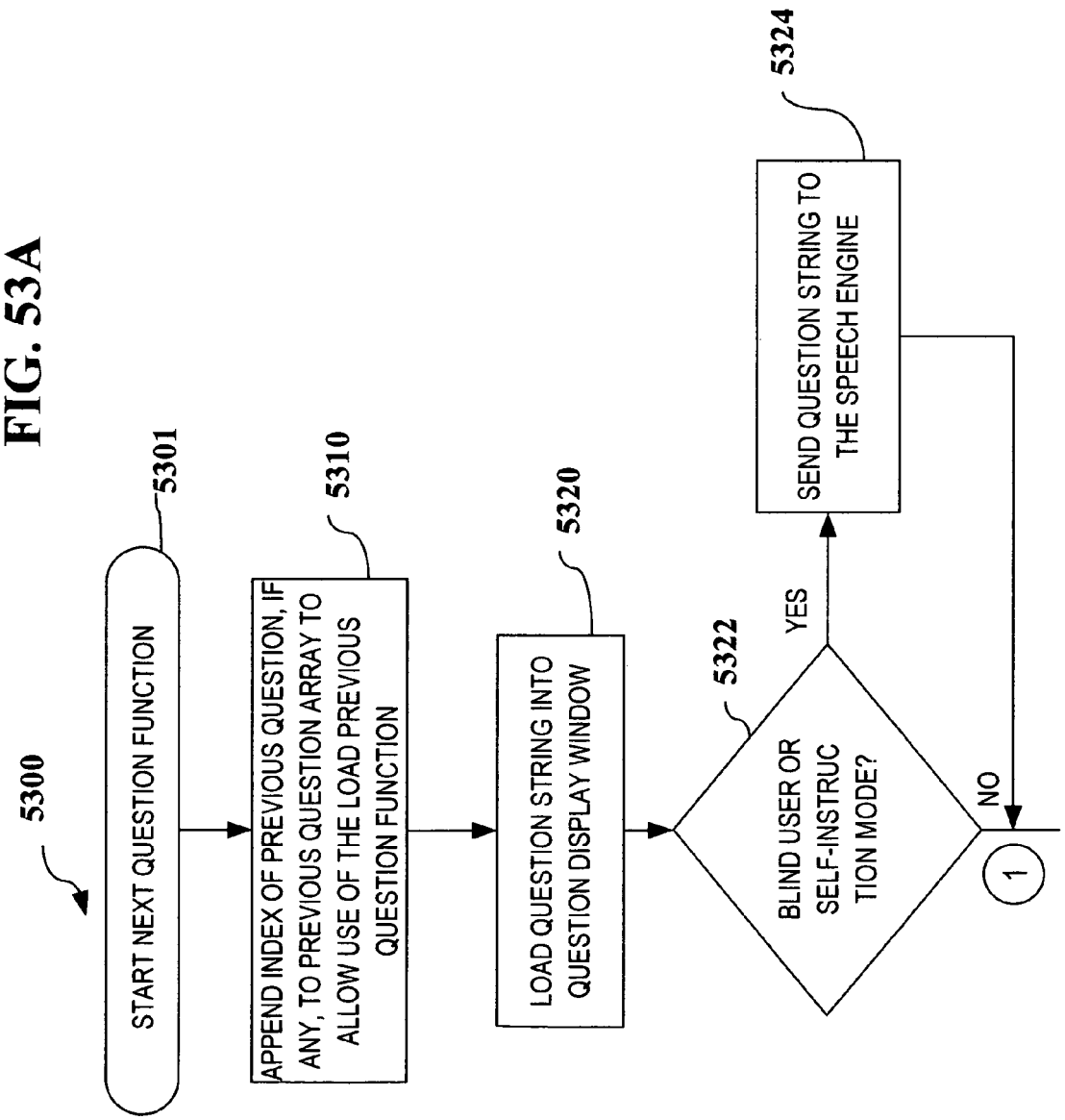
FIGS. 53A, 53B and 53C (hereafter collectively referred to as FIG. 53) are a flowchart representing a preferred embodiment of a Load Question Function in a preferred embodiment of a system according to the present invention.
Figure 53B:
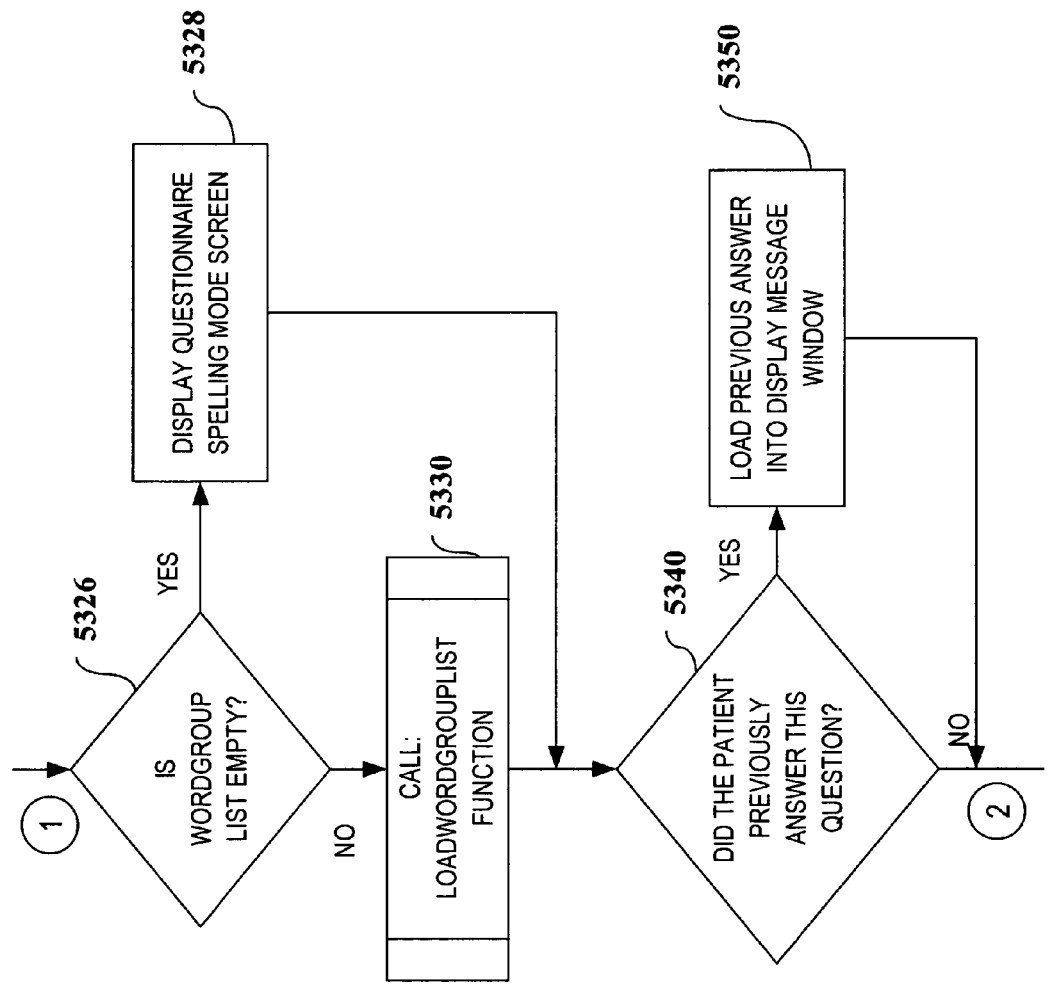
Figure 53C:
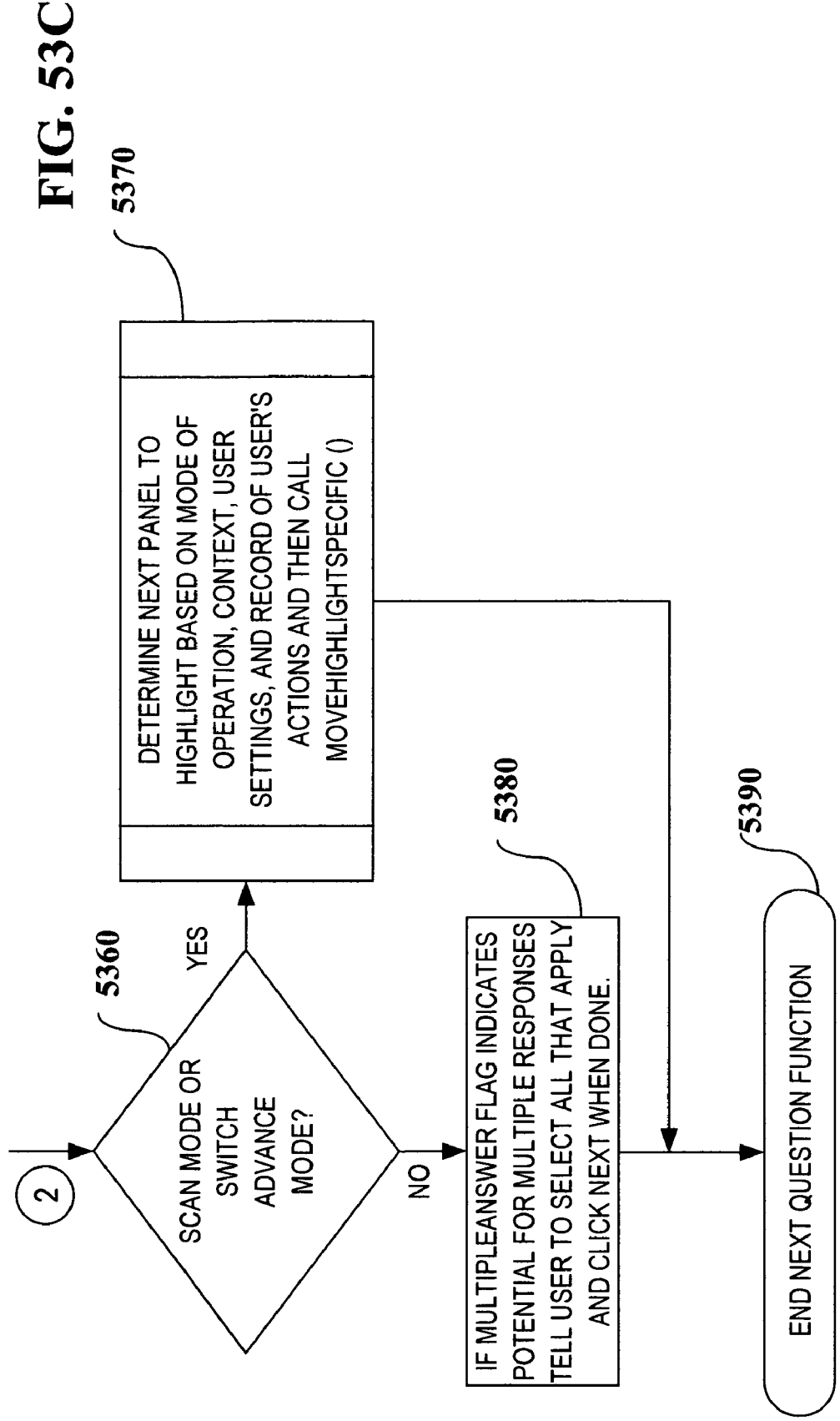

FIG. 53 describes a preferred embodiment of process 5300, which starts at 5301, for implementing the Load Question function. This function puts the Question String from the WordGroup List in the Question Display Window, loads WordGroup objects into the WordGroup Panels as potential answers to the above question, and, if the user has previously answered this question, displays the previous answer in the Message Display Window. In the case where the WordGroup object list is empty (indicating that there are no predictable answers to the question), the system automatically displays a special Questionnaire Mode spelling screen (similar to FIG. 4), in order to allow the patient to spell out a response to the question. In addition, since certain questions may have a small number of highly likely responses (which can be presented in WordGroup Panels, as well as a large number of less likely, but potentially important responses, a property of the WordGroup List can be used to store the name of a "dictionary" of potential responses, which can be pre-appended to the normal dictionary when the user chooses to go to the spelling mode in the process of answering a question. Thus, for example, a question regarding "What medications are you allergic to?" could have a small number of potential answers which list common medications which significant numbers of patients are allergic to, but if the user is allergic to a more obscure medication, he or she could go to the spelling mode and begin to spell it out, with the result that the suggested word list would begin with medications.

In step 5310, the index of the previous question (if any) is stored in the Previous Question Array to be used by the Load Previous Question function which may be called at some time in the future. Step 5320 puts the Question String from the WordGroup List into the Question Display Window. Test 5322 determines whether the system is operating in either of Blind User Mode and Self-Instruction Mode. If the answer to test 5322 is Yes, step 5324 sends the Question String to the Speech Engine to read the question to the user.

Test 5326 determines whether the WordGroup List is empty. If the answer to test 5326 is Yes, step 5328 displays the Questionnaire Mode spelling screen. If the answer to test 5326 is No, step 5330 calls the LoadWordGroupList function, which loads the WordGroup List's WordGroup objects into the WordGroup Panels. (These WordGroup objects contain potential answers to the posed question.)

Test 5340 determines if the user has previously answered this question (e.g., by seeing whether there is an answer to the question in a patient answer file). If the answer to step 5340 is Yes, step 5350 puts the string from the previous answer in the Display Message Window.

Test 5360 determines whether the system is operating in Scan Mode or Switch Advance Mode (both of which utilize moving highlights). If the answer to test 5360 is Yes, step 5370 determines what panel to highlight next based on, preferably, user-specific settings, the current mode of operation, the current context and the record of the user's previous actions, and then calls the Move Highlight Specific function.

Test 5380 determines if the MultipleAnswer flag associated with the current WordGroup List is set. If it is, a string is sent to the Speech Engine telling the user to "Select all answers which apply, then click 'Next' when done." Process 5300 ends at 5390.

Figure 54A:
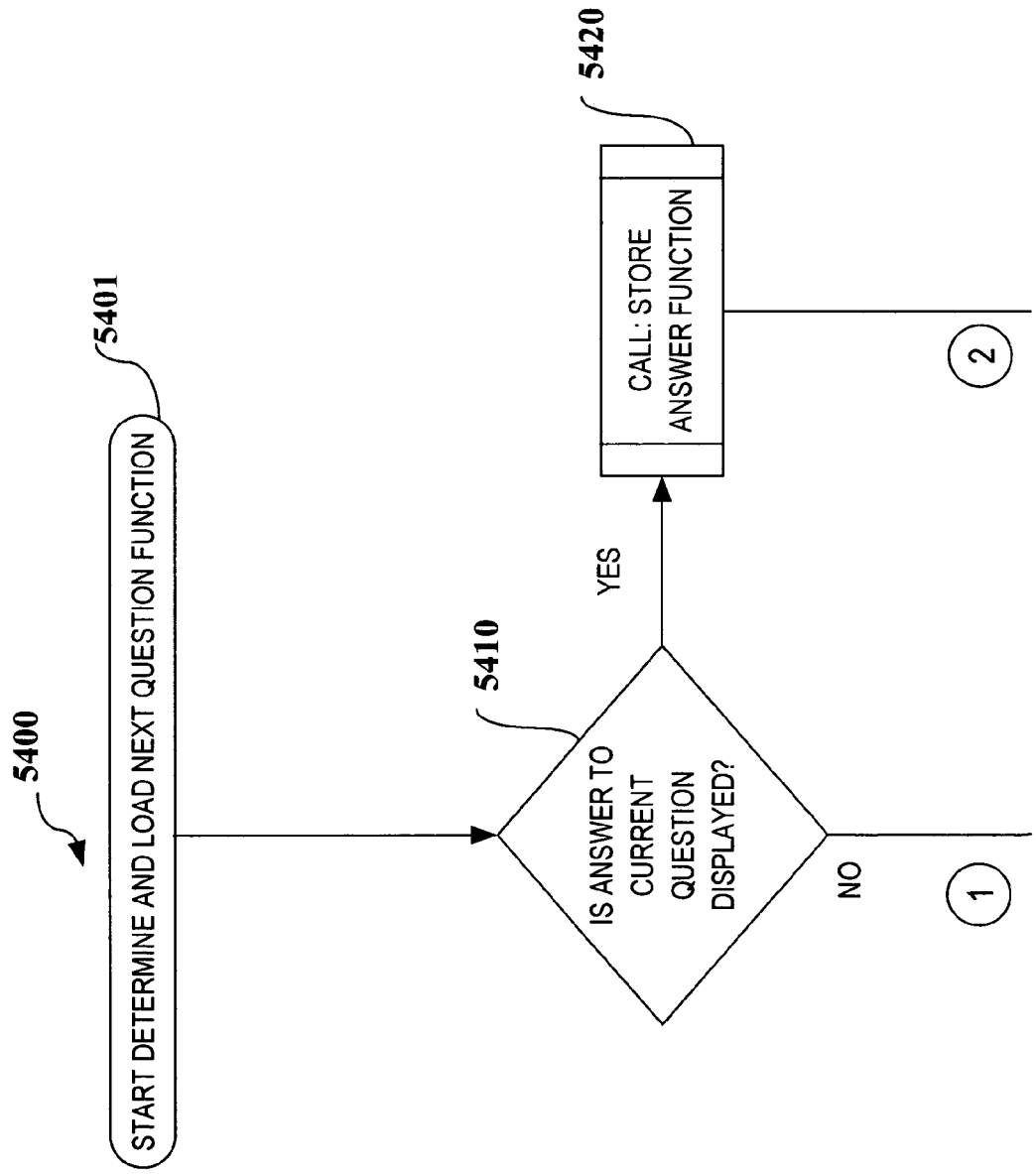
FIGS. 54A and 54B (hereafter collectively referred to as FIG. 54) are a flowchart representing a preferred embodiment of a Determine and Load Next Question Function in a preferred embodiment of a system according to the present invention.
Figure 54B:
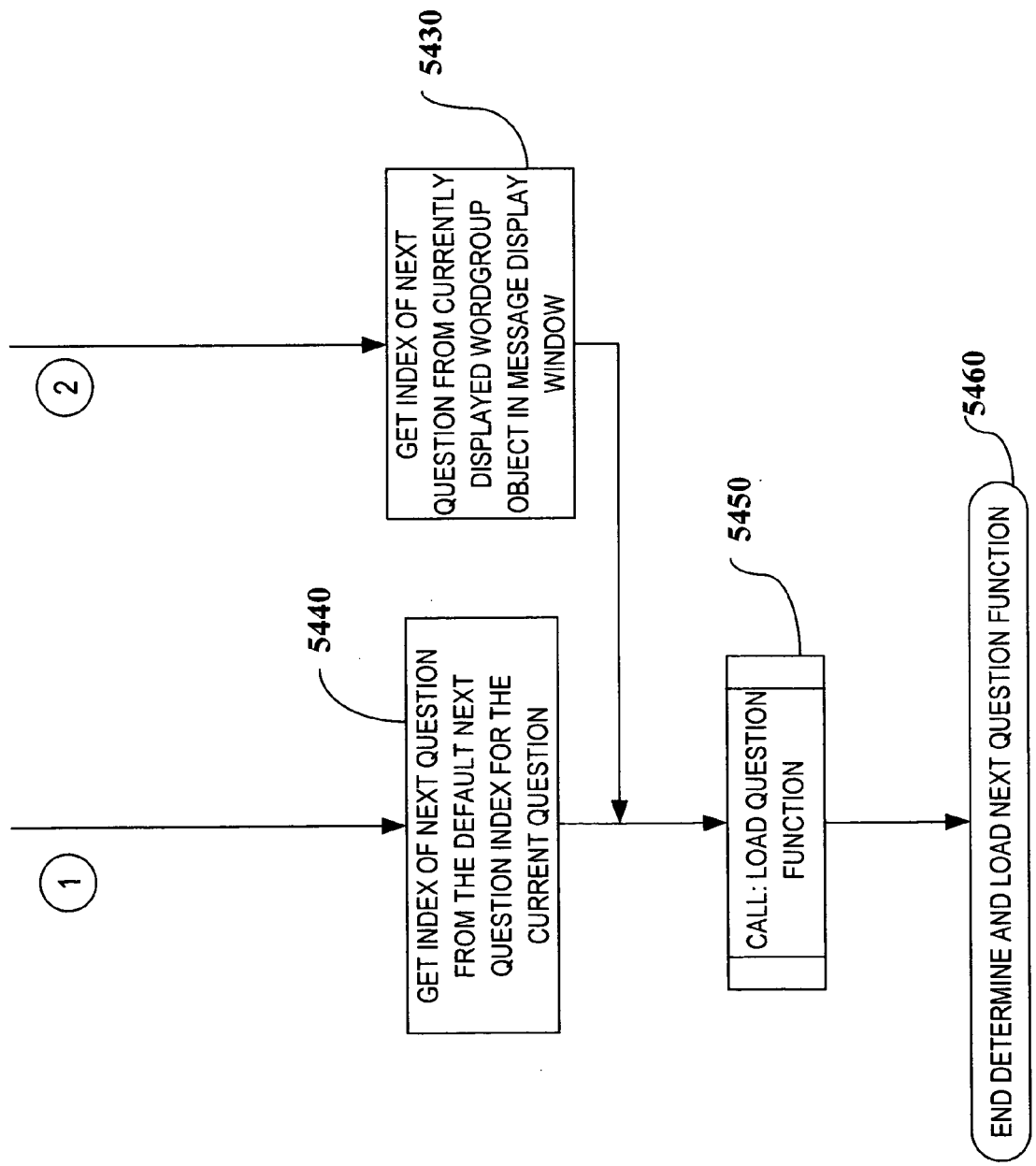

FIG. 54 describes a preferred embodiment of process 5400, which starts at 5401, for implementing the Determine and Load Next Question function. Test 5410 determines if an answer to the current question is presently displayed in the Message Display Window.

If the answer to test 5410 is Yes, step 5420 calls the Store Answer function so that the answer to the current question is stored prior to displaying the next question. Step 5430 gets the NextQuestionIndex from the currently displayed WordGroup Object in the Message Display Window. This NextQuestionIndex could represent the index of an appropriate follow-up question based on the answer displayed in the Message Display Window.

If the answer to test 5410 is No, step 5440 gets the NextQuestionIndex from the DefaultNextQuestionIndex for the currently displayed question. Step 5450 then calls the Load Question function with the NextQuestionIndex as the argument. Process 5400 ends at 5460.

Figure 55:
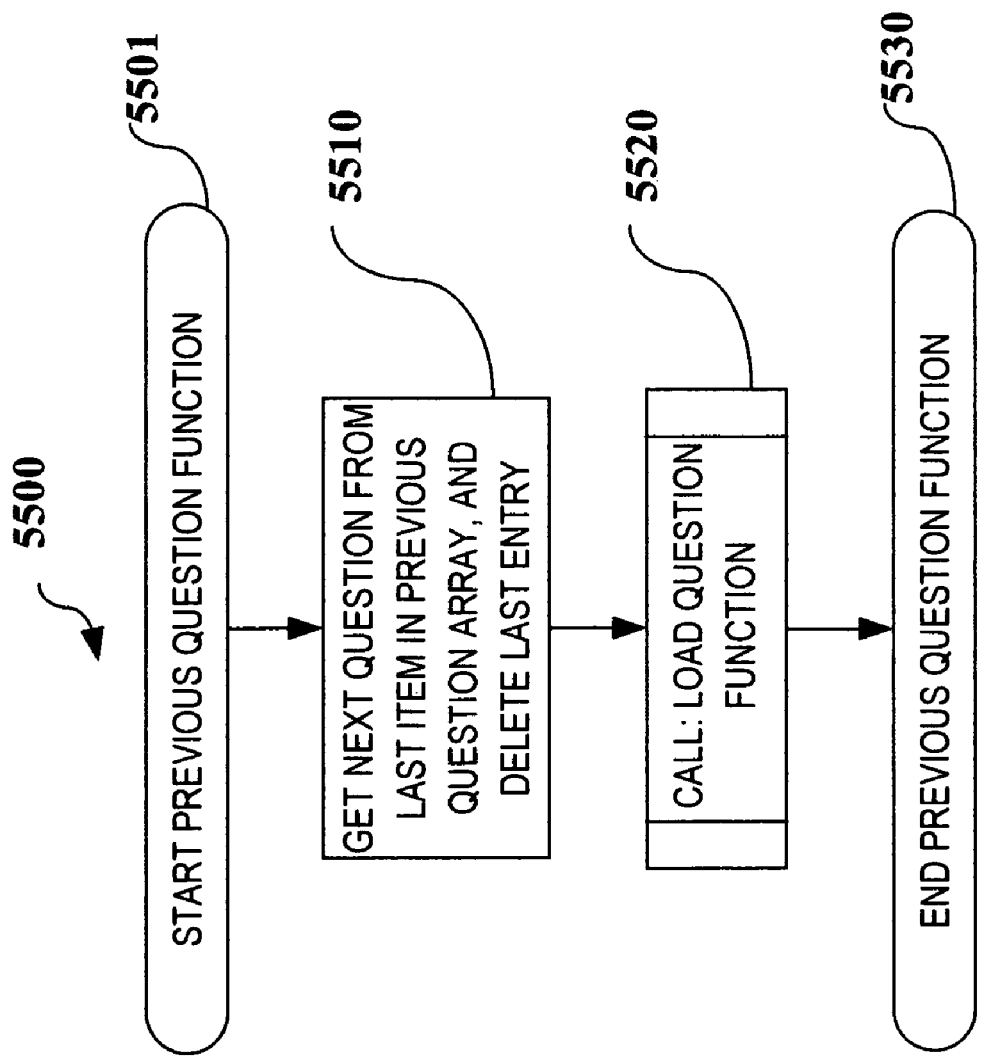
FIG. 55 is a flowchart representing a preferred embodiment of a Load Previous Question Function in a preferred embodiment of a system according to the present invention.

FIG. 55 describes a preferred embodiment of process 5500, which starts at 5501, for implementing the Load Previous Question function, which allows the user to return to the preceding question. Step 5510 gets the NextQuestionIndex from the last entry in the Previous Question Array, and then deletes this last entry from the Previous Question Array. Step 5520 then calls the Load Question function with the NextQuestion Index as the argument. Process 5500 ends at 5530.

Figure 56:
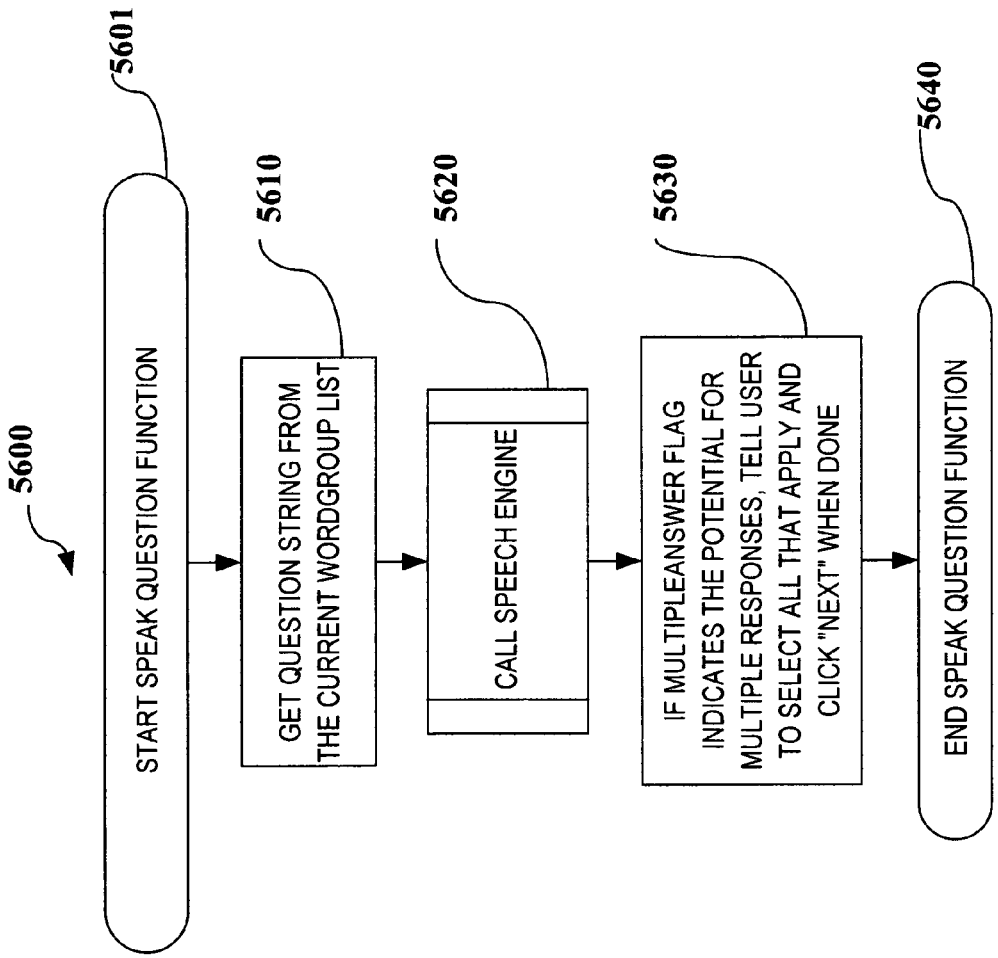
FIG. 56 is a flowchart representing a preferred embodiment of a Speak Question Function in a preferred embodiment of a system according to the present invention.

FIG. 56 describes a preferred embodiment of process 5600, which starts at 5601, for implementing the Speak Question function. Step 5610 gets the Question String from the current WordGroup List, and step 5620 sends that string to the Speech Engine. Step 5630 determines if the MultipleAnswer flag associated with the current WordGroup List is set. If it is, a string to the Speech Engine telling the user to "Select all answers which apply then click "Next" when done." Process 5600 ends at 5640.

Figure 57A:
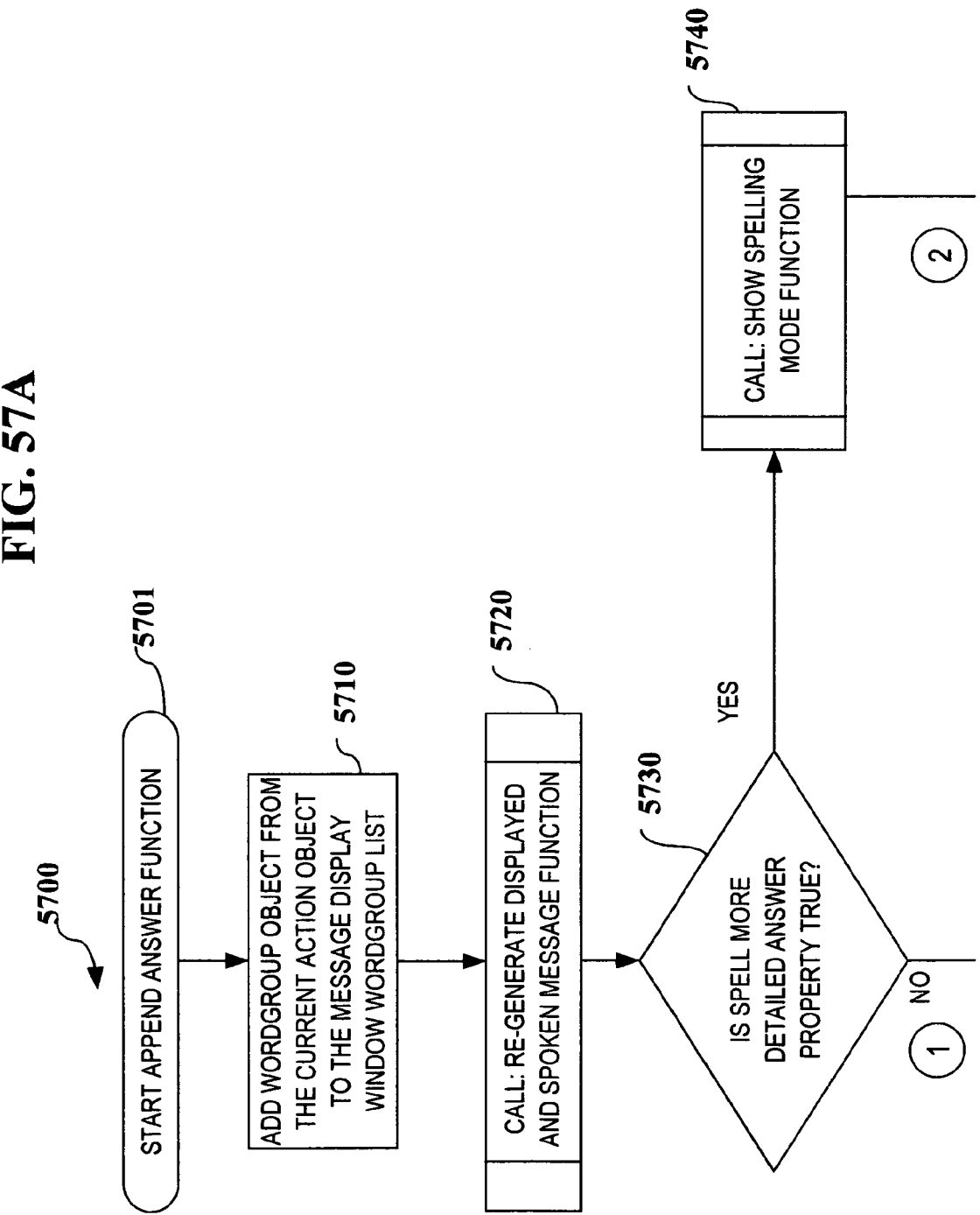
FIGS. 57A and 57B (hereafter collectively referred to as FIG. 57) are a flowchart representing a preferred embodiment of an Append Answer Function in a preferred embodiment of a system according to the present invention.
Figure 57B:
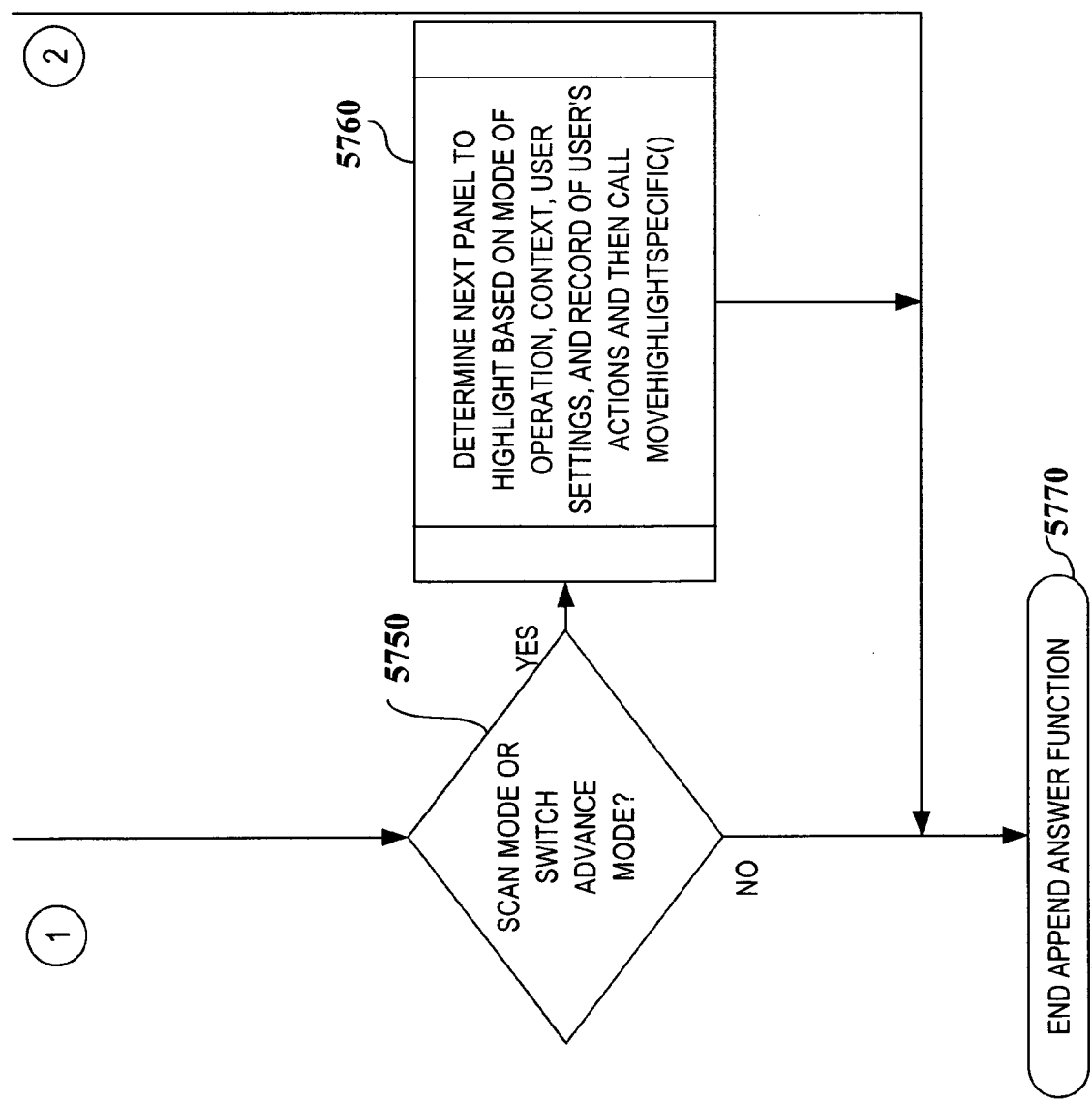

FIG. 57 describes a preferred embodiment of process 5700, which starts at 5701, for implementing the Append Answer function, which is called by the DoAction function, when the user selects one of the WordGroup Panels which contains a potential answer to the displayed question. The purpose of this function is to add answer strings stored in the WordGroup Object variable of an Action Object (associated with a WordGroup Panel) to the currently displayed answer strings in the Message Display Window. The Message Display Window Object has a list of multiple WordGroup Objects which are added to the Message Display Window list in the order in which the Append Answer function adds them.

In step 5710, the WordGroup Object of the current Action Object is added to the list of WordGroup Objects of the Message Display Window. (The current Action Object is the Action Object associated with the panel which was touched, or was highlighted during a Perform Action Switch-Closure Event.) Step 5720 then calls the Re-generate Displayed and Spoken Messages function which modifies the contents of the Message Display Window Object based on the WordGroup Object which was appended.

In test 5730, it is determined if the Spell More Detailed Answer property of the current Action Object is true, indicating that the answer selected by the user is one which requires the user to spell out additional information in order to complete the answer. If the answer to test 5730 is Yes, step 5740 calls the Show Spelling Mode function (which allows the user to construct an answer to the current question on a letter by letter basis).

Test 5750 determines whether the system is operating in Scan Mode or Switch Advance Mode (both of which utilize moving highlights) and, if not, the Append Answer function is complete.

If the system is in Scan Mode or Switch Advance Mode, step 5760 determines what panel to highlight next based on, preferably, user-specific settings, the current mode of operation, the current context and the record of the user's previous actions, and then calls the Move Highlight Specific function. Process 5700 ends at 5770.

Figure 58:
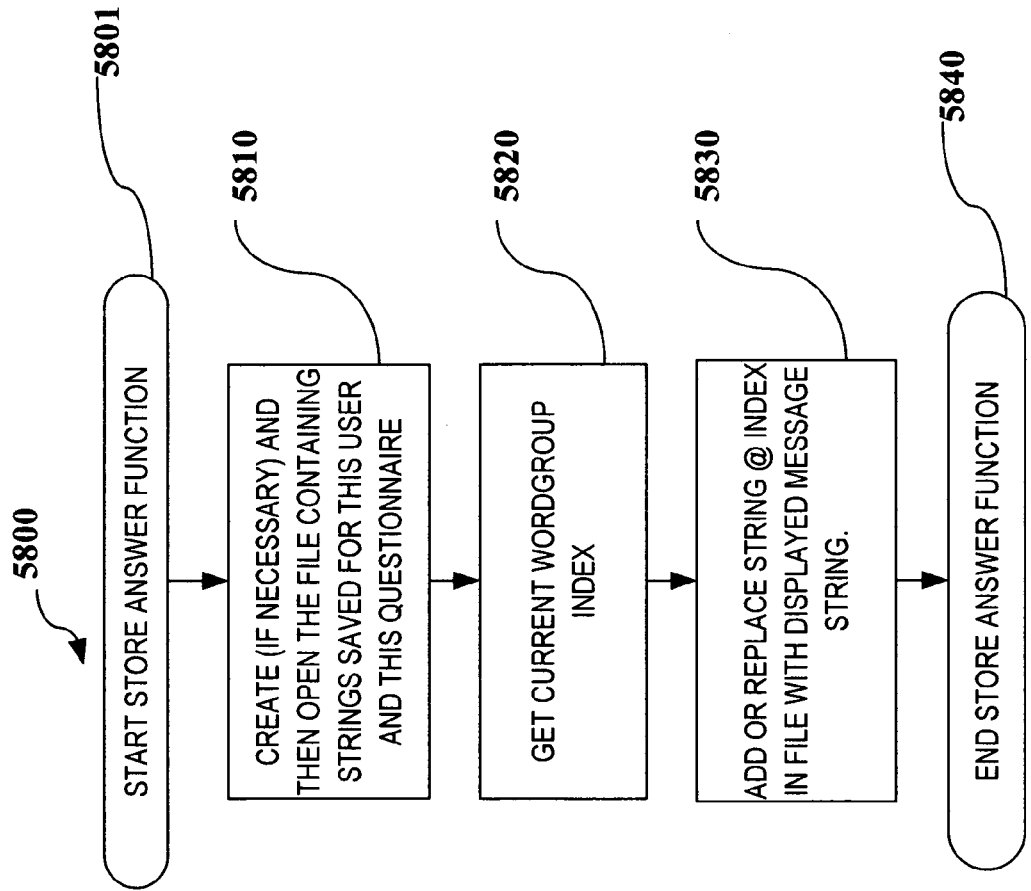
FIG. 58 is a flowchart representing a preferred embodiment of a Store Answer Function in a preferred embodiment of a system according to the present invention.

FIG. 58 describes a preferred embodiment of process 5800, which starts at 5801, for implementing the Store Answer function. Step 5810 determines if there is already an Answers File associated with the current user and the current Questionnaire. If the file already exists, it is opened and if not, it is created and then opened.

Step 5820 gets the index of the current WordGroup List. Step 5830 searches the Answers File for an Answer String associated with the index of the current WordGroup List. If one is found, it is deleted, so that any previous answer to the same question can be replaced by the current answer. Then, the string contents of the Display Message Window (i.e. the answer) is stored along with the index of the current WordGroup List. Process 5800 ends at 5840.

Figure 59:
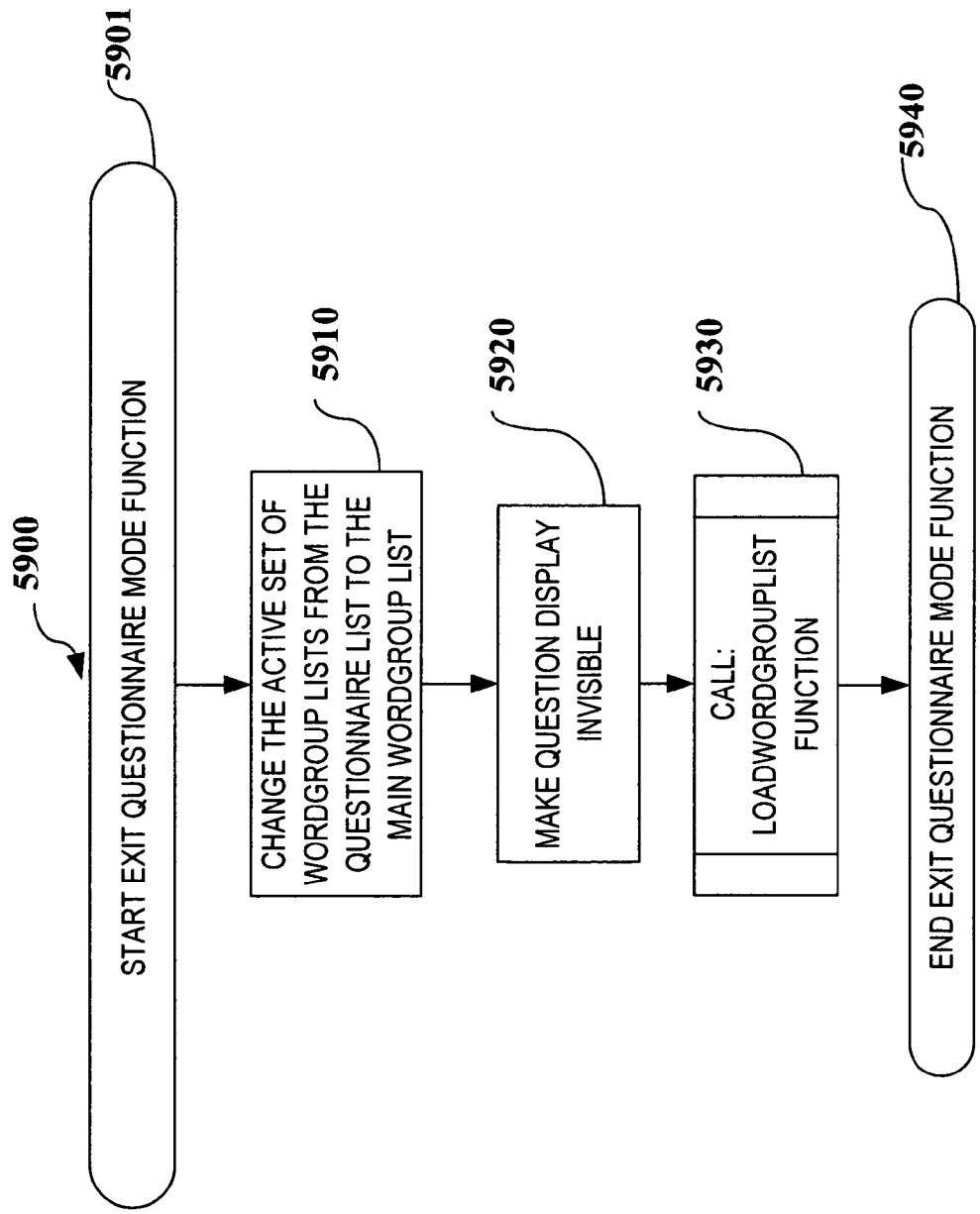
FIG. 59 is a flowchart representing a preferred embodiment of an Exit Questionnaire Mode Function in a preferred embodiment of a system according to the present invention.

FIG. 59 describes a preferred embodiment of process 5900, which starts at 5901, for implementing the Exit Questionnaire Mode function. This function changes the Active Set of WordGroup lists used by the Patient Module from the special set of WordGroup lists, designed to allow a non-speaking patient to answer a questionnaire, back to a standard set designed to allow the patient to communicate with caregivers or family members.

In step 5910, the Active Set of WordGroup Lists is changed back to the standard set of WordGroup lists for the particular patient.

Preferably, a set of WordGroup Lists contains all of the WordGroup Lists (and WordGroup Objects) for a given patient, or type of patient, or situation. These WordGroup Lists can be modified, as required, to customize the system for the specific needs of a particular patient, the needs of a particular type of patients, or for the needs of the particular health-care facility. For example, medical personnel may create new WordGroup Lists or modify a subset of WordGroup Lists to optimize the system for the needs of stroke patients; a patient's family may create or modify other WordGroup Lists containing personal information and WordGroups specific to that patient; or a hospital may create a special set of WordGroup Lists for Questionnaire Mode, containing the specific medical intake questions required for that hospital.

In step 5920, the special Question Display Window is made invisible. In step 5930 the LoadWordGroupList function is called to load the first WordGroup List from the standard set used for normal patient to caregiver communication. Process 5900 at 5940.

Figure 60:
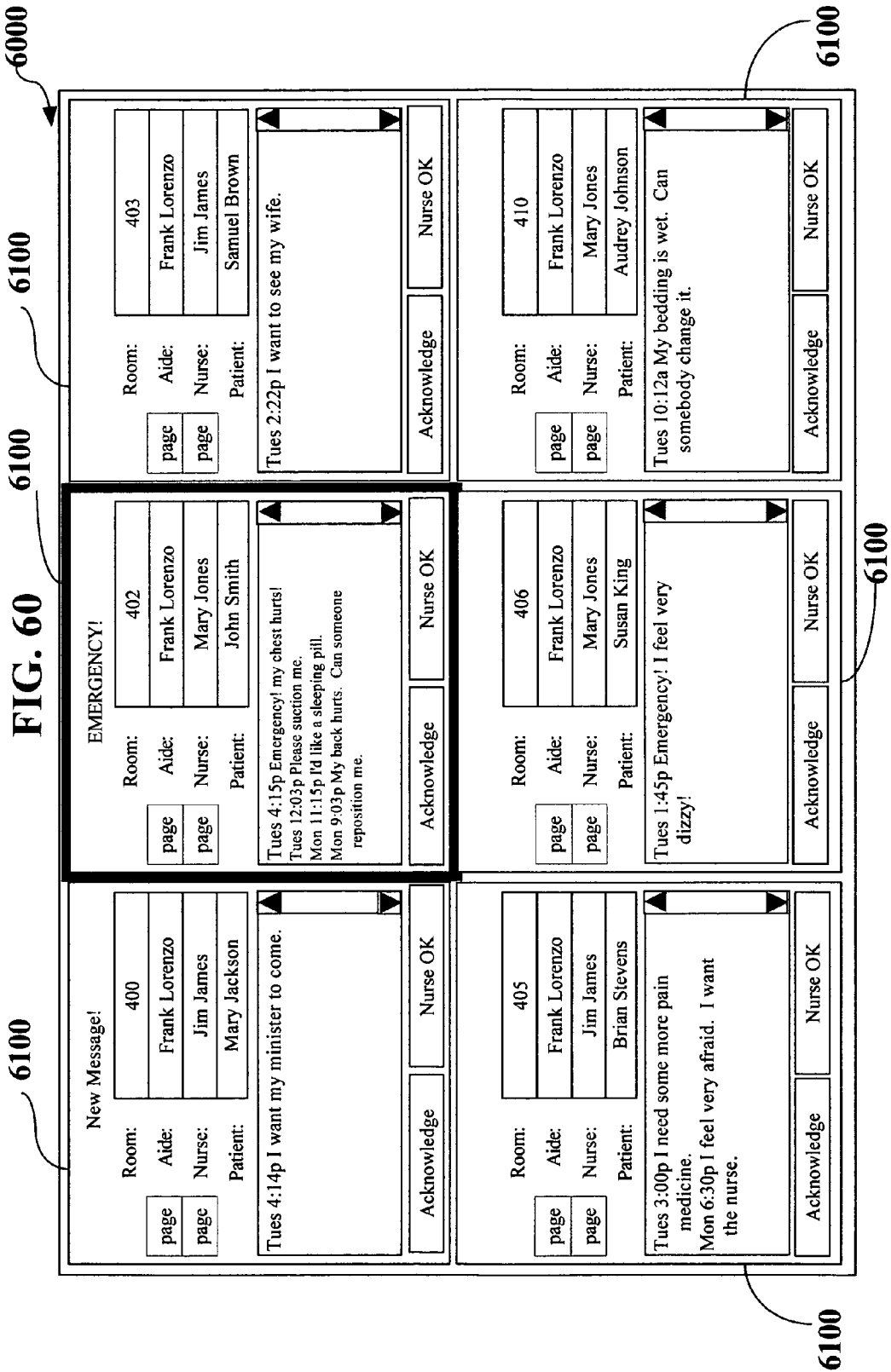
FIG. 60 is a representation of a preferred embodiment of a Nurses' Station Module Screen in a preferred embodiment of a system according to the present invention.
Figure 61:
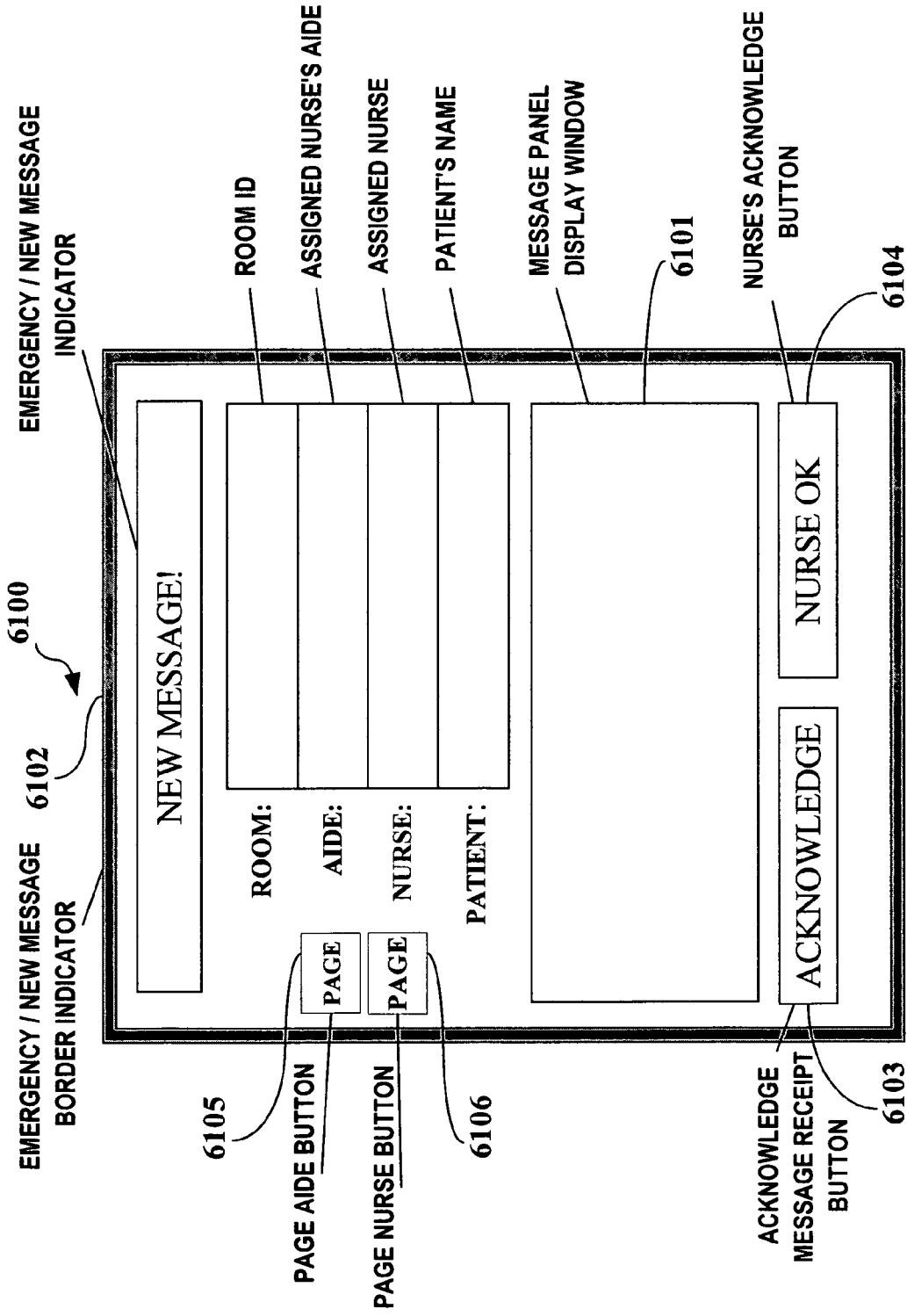
FIG. 61 is a representation of a Room Message Panel in a preferred embodiment of a system according to the present invention.

The following section describes the operation of a preferred embodiment of a Nurses' Station or a Caregiver Communication Module:

The screen 6000 shown in FIG. 60 is an example of one embodiment of the screen in the Nurses' Station or Caregiver Communication Module of the present invention. The screen preferably includes one or more Room Message Panels 6100, which themselves include a variety of panels and display windows, as defined above and as shown in FIG. 61.

Figure 62:
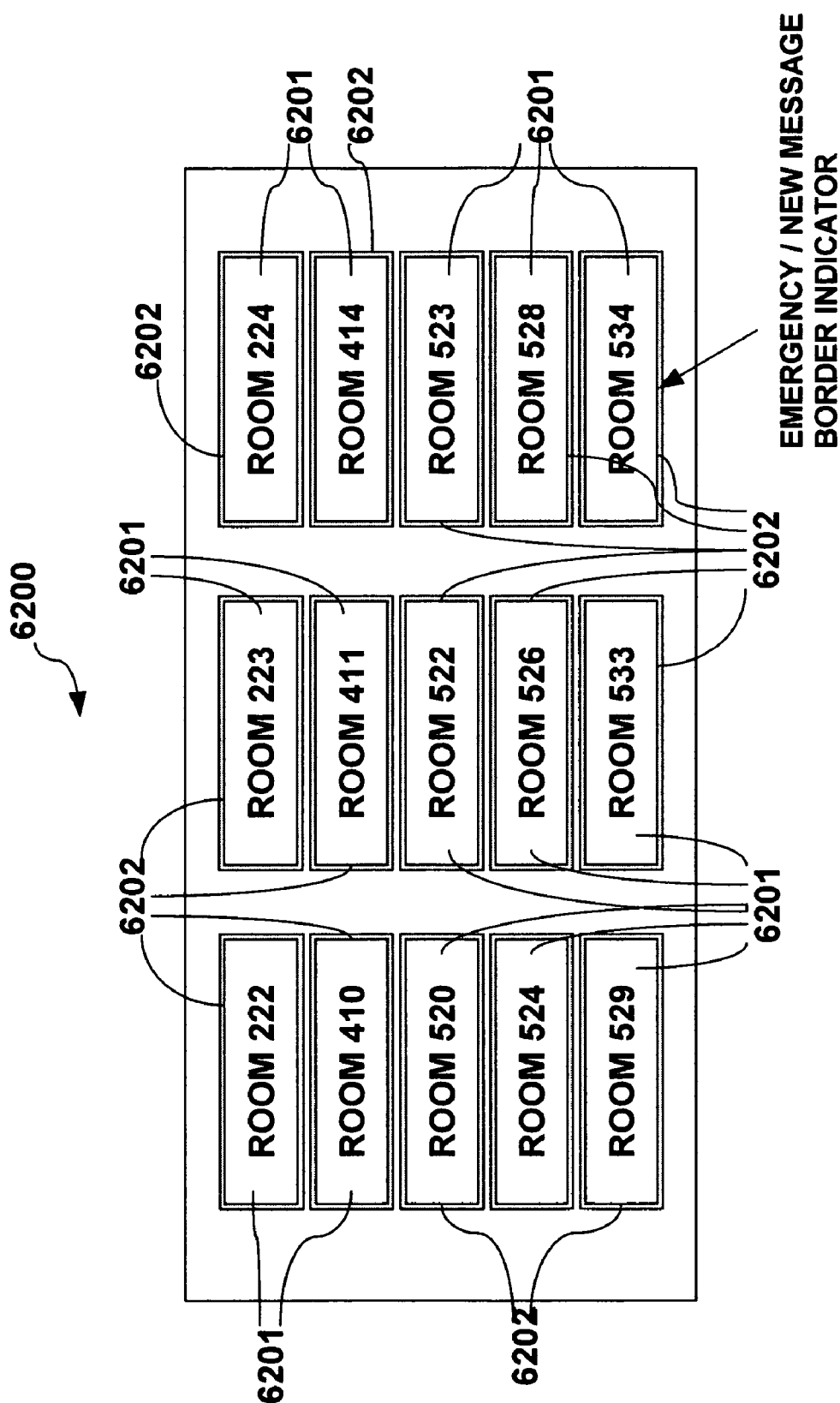
FIG. 62 is a representation of an alternate layout of a Nurses' Station or Caregiver Communication Screen in a preferred embodiment of a system according to the present invention.

FIG. 62 shows another embodiment of a Nurses' Station or Caregiver Communication Module screen 6200 which might be more appropriate for use in cases in which the total number of rooms is large with respect to the size of the screen display. This might be the case either for a health-care facility in which a single Nurses' Station Module was responsible for monitoring a large number of rooms, or in cases in which the Caregiver Communication Module was a PDA, cell phone, pager, or similar device with a relatively small display. In cases in which a screen similar to that of FIG. 62 represented the primary system display, a flashing border 6202 surrounding one or more of the room number displays 6201 or some other alerting mechanism (such as synthesized speech output or change of background color, etc.) preferably would indicate that a new message had been received from that room. An appropriate action by the caregiver could then bring up the detailed information for that room, perhaps on a display similar to that shown in FIG. 61.

It should be clear that, depending on the amount of screen space available and the required number of room displays, all gradations between the screen shown in FIG. 60 and the screen shown in FIG. 62 are possible. Thus another potential embodiment of a Nurses' Station or Caregiver Communication Module screen might be a screen similar in some aspects to FIG. 62, but possessing one or more of the other features shown in FIG. 61 in addition to the room number indicator. Thus, for example, one might have a screen which, in addition to the room number showed the patient's name, or perhaps the last message received from the patient.

Figure 63A:
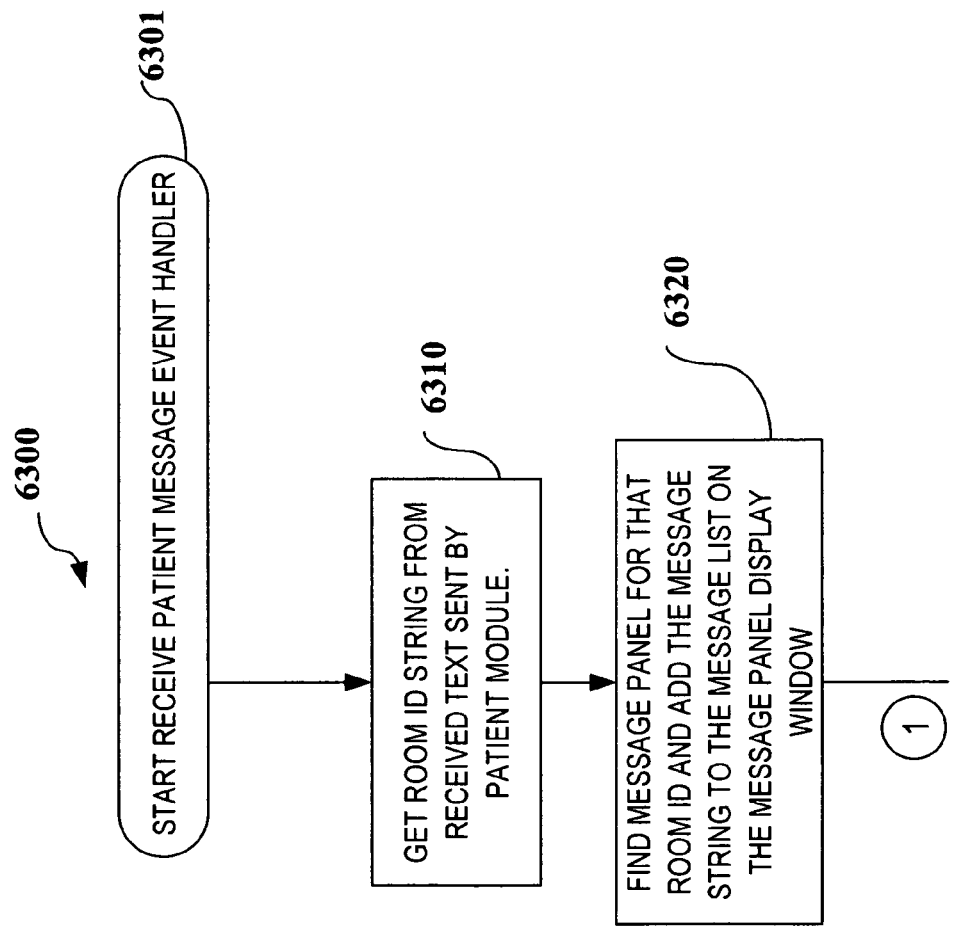
Figure 63C:
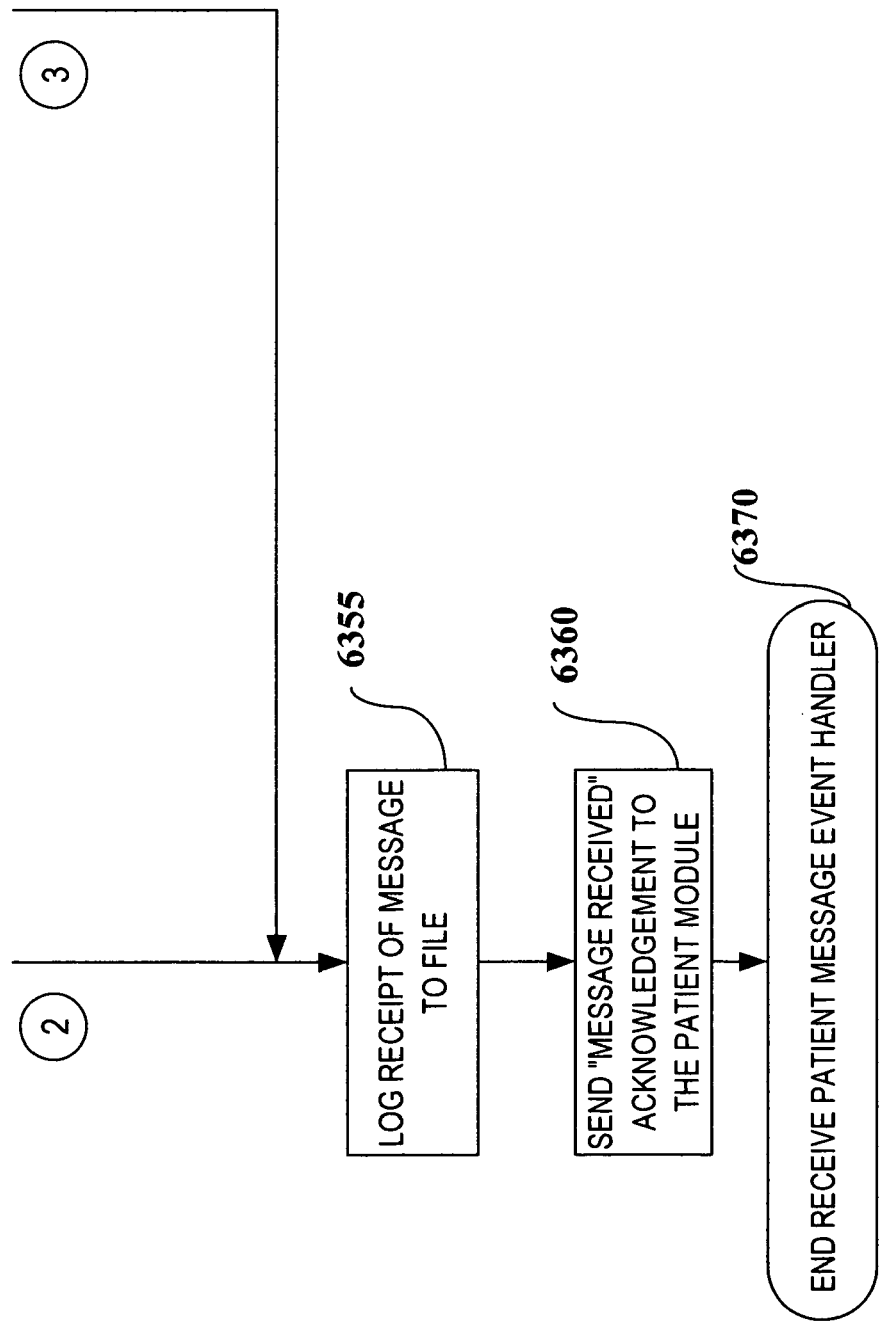

FIG. 63 describes a preferred embodiment of process 6300, which starts at 6301, for implementing the Receive Patient Message Event Handler at a Nurse's Station or Caregiver Communication Module 3. Step 6310 gets the Room ID String from the text (sent by Patient Module 2) received by the Nurses' Station or Caregiver Communication Module 3. Step 6320 performs a lookup to identify the Room Message Panel 6100 assigned to that room, and adds the message string to the list of messages displayed in the Message Panel Display Window 6101. In the case of a system with a primary display similar to that shown in FIG. 62, the appropriate Room Message Panel displays are updated, regardless of whether or not that particular Room Message Panel is currently visible.

Test 6330 determines whether an Emergency code exists within the received message. If the answer to test 6330 is Yes, step 6340 displays an Emergency Message Indicator on the Room Message Panel 6100 or Room Number Indicator 6201 (as appropriate), sounds an appropriate audible Emergency Alarm (if the device is capable of doing so), changes the background color of the Room Message Panel border 6102 or Room Number Indicator border 6202 to a predefined "Emergency color", and starts a timer (if available) which periodically alternates the border color between the "normal color" and the "emergency color" in order to draw attention to the existence of an un-acknowledged emergency message. Other usual alerts might be used instead of changing the border color. For example, in a monochrome caregiver display, the shading of the border 6102 or 6202 might change. Alternatively, regardless of the caregiver display type, instead of affecting the border 6102 or 6202, a reverse video effect could be applied to the entire Room Message Panel 6100 or Room Number Indicator 6201 affected.

If the answer to test 6330 is No, step 6350 displays a New Message Received Indicator on the Room Message Panel 6100 or Room Number Indicator 6201 (as appropriate), sounds an appropriate audible New Message Received Tone (if the device is capable of doing so). Preferably, step 6350 also changes the background color of the Room Message Panel border 6102 or Room Number Indicator border 6202 to pre-defined "new-message color," and starts a timer (if available) which periodically alternates the border color between the "normal color" and the "new-message color" in order to draw attention to the existence of an un-acknowledged new message. The new message effect (color, shading, etc.) would preferably differ from the Emergency effect (color, shading, etc.).

Step 6352 adds the room number and type of message (Emergency vs. non-Emergency) to the received message string, converts the resulting combined text to speech, and speaks the resulting message on the Nurses' Station or Caregiver Communication Module, if it is speech-enabled and the speech-output option is turned on.

Step 6355 adds the type of message (Emergency vs. non-Emergency) and the date and time of message receipt to the received message, and writes the resulting time-stamped message to a user-specific message log file, if available.

Step 6360 sends an appropriate Message Received Acknowledgement (for example: "Your message: 'I have a lot of pain,' has been received at the nurses' station") to Patient Module 2, if the device provides for bidirectional communication with the Patient Module 2. Process 6300 ends at 6370.

FIG. 64 describes a preferred embodiment of process 6400, which starts at 6401, for implementing the Message Acknowledgement function. When personnel at the Nurses' Station or the person with a bidirectional Caregiver Communication Module performs some action (for example, pushing an "Acknowledge" button 6103, pressing a preselected key, or issuing a voice command to be processed by speech recognition software) to indicate that a newly-received patient message has been read, step 6410 sends a Message Read Acknowledgement (for example: "Your message: I have a lot of pain, has been read at the nurses' station") to Patient Module 2. Step 6420 disables the flashing of the Room Message Panel border 6102 or Room Number Indicator border 6202, leaving the border in the "emergency color" or the "new-message color" (as appropriate) to indicate that the message has not yet been read or acted upon by the assigned nurse. Step 6430 logs the time of the message acknowledgement to the user-specific message log file, if available. Process 6400 ends at 6440.

FIG. 65 describes a preferred embodiment of process 6500, which starts at 6501, for implementing the Nurse's Acknowledgement function. When the assigned nurse performs some action (for example, pushing a "Nurse OK" button 6104, pressing a preselected key, or issuing a voice command) to indicate that he or she has read or acted upon (depending on the health care facility's policies) the newly-received patient message, step 6510 returns the Room Message Panel border 6102 or Room Number Indicator border 6202 to the "normal" background color, and hides the Emergency Message Indicator or New Message Indicator (as appropriate). Step 6520 logs the time of the nurse's acknowledgement to the user-specific message log file, if available. Process 6500 ends at 6530.

Figure 66:
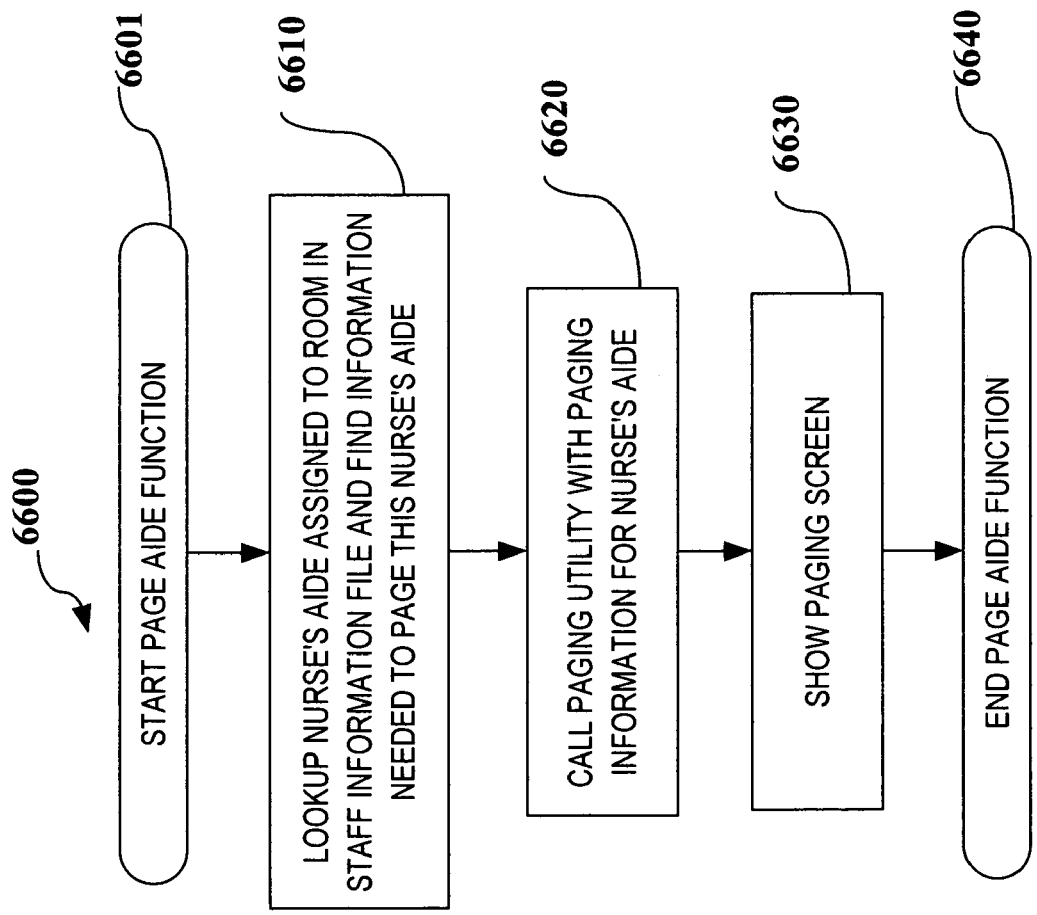
FIG. 66 is a flowchart representing a preferred embodiment of a Page Aide Function in a preferred embodiment of a system according to the present invention.

FIG. 66 describes a preferred embodiment of process 6600, which starts at 6601, for implementing the Page Aide function. When the Nurses' Station personnel or the person with a bidirectional Caregiver Communication Module performs some action (for example, pushing a "Page Aide" button 6105, pressing a preselected key, or issuing a voice command) to initiate a page of an aide, step 6610 performs a lookup (of previously entered staff information) to identify the aide assigned to the room as well as any required telephone numbers or other information required to page the individual. Step 6620 extracts the telephone number or other paging codes required to send a paging request, and passes that information to an appropriate paging software interface. This software could have the ability to send text messages to standard alphanumeric pagers, or text or voice messages to cellular telephones, PDAs, wireless computers, or other electronic communication devices. Step 6630 displays a special paging screen, which allows the user to either relay the text message sent by Patient Module 2, or alternatively to send previously stored or custom generated messages to the aide's communication device. Process 6600 ends at 6640.

Figure 67:
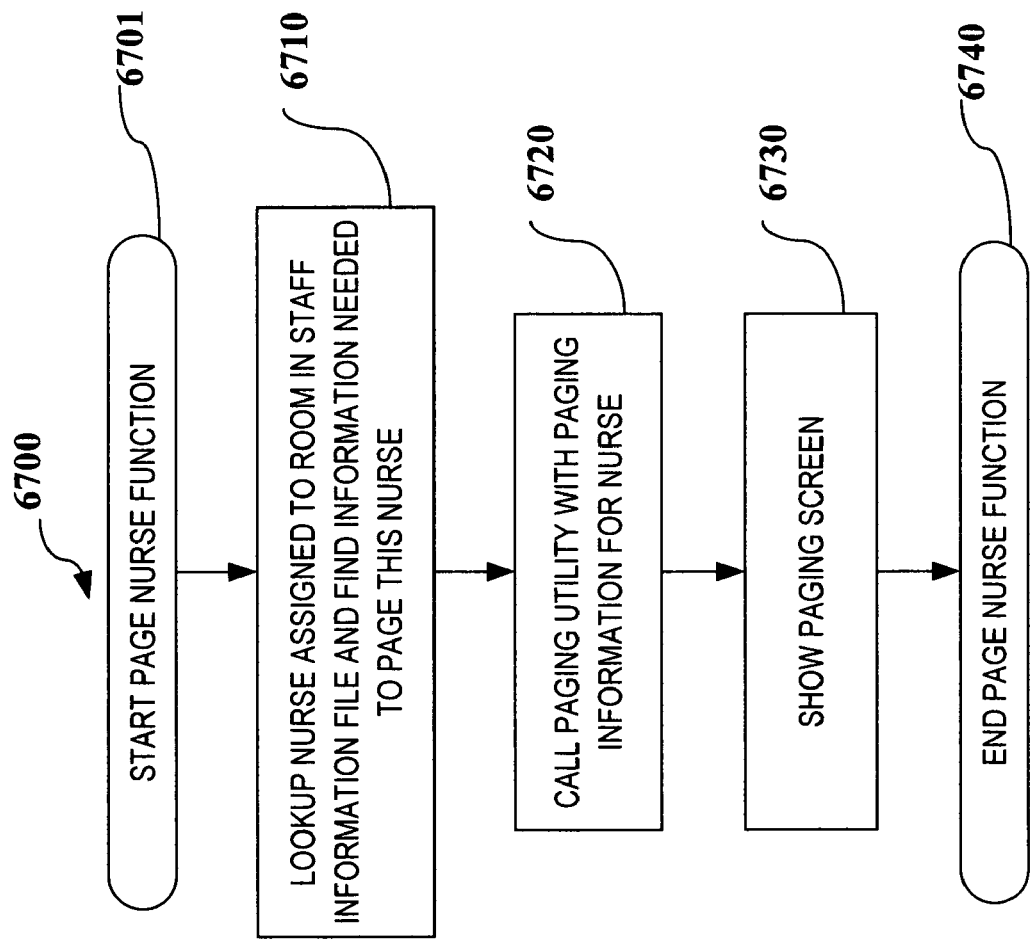
FIG. 67 is a flowchart representing a preferred embodiment of a Page Nurse Function in a preferred embodiment of a system according to the present invention.

FIG. 67 describes a preferred embodiment of process 6700, which starts at 6701, for implementing the Page Nurse function. When the Nurses' Station personnel or the person with a bidirectional Caregiver Communication Module performs some action (for example, pushing a "Page Nurse" button 6106, pressing a preselected key, or issuing a voice command) to initiate a page of the nurse, step 6710 performs a lookup (of previously entered staff information) to identify the nurse assigned to the room as well as any required telephone numbers or other information required to page the individual. Step 6720 extracts the telephone number or other paging codes required to send a paging request, and passes that information to an appropriate paging software interface. Step 6730 displays the special paging screen, which allows the user to either relay the text message sent by Patient Module 2, or alternatively to send previously stored or custom generated messages to the nurse's communication device. Process 6700 ends at 6740.

The following section describes the operation of

Figure 68A:
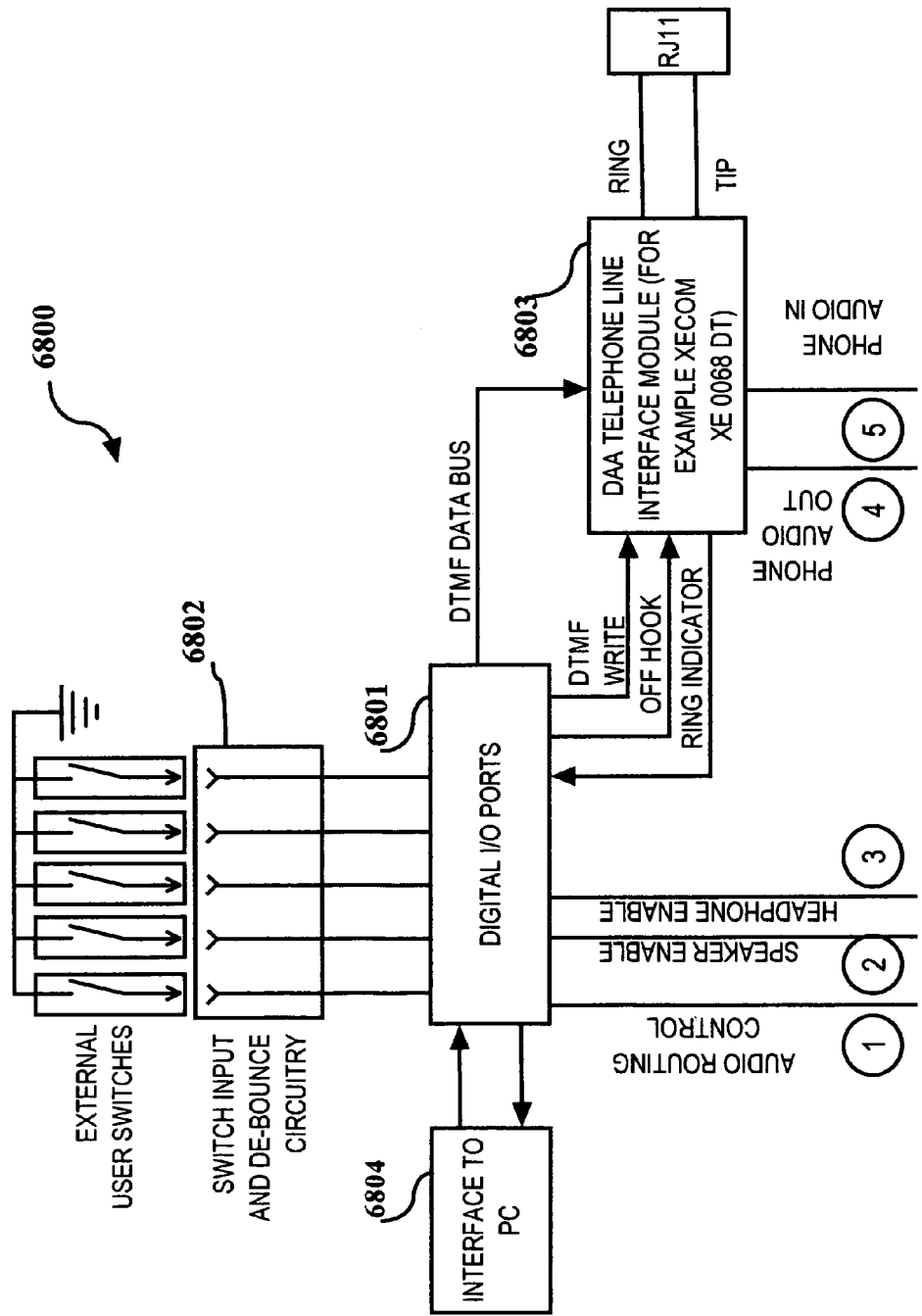
FIGS. 68A and 68B (hereafter collectively referred to as FIG. 68) are a Block diagram of External Interface Module in a preferred embodiment of a system according to the present invention.
Figure 68B:
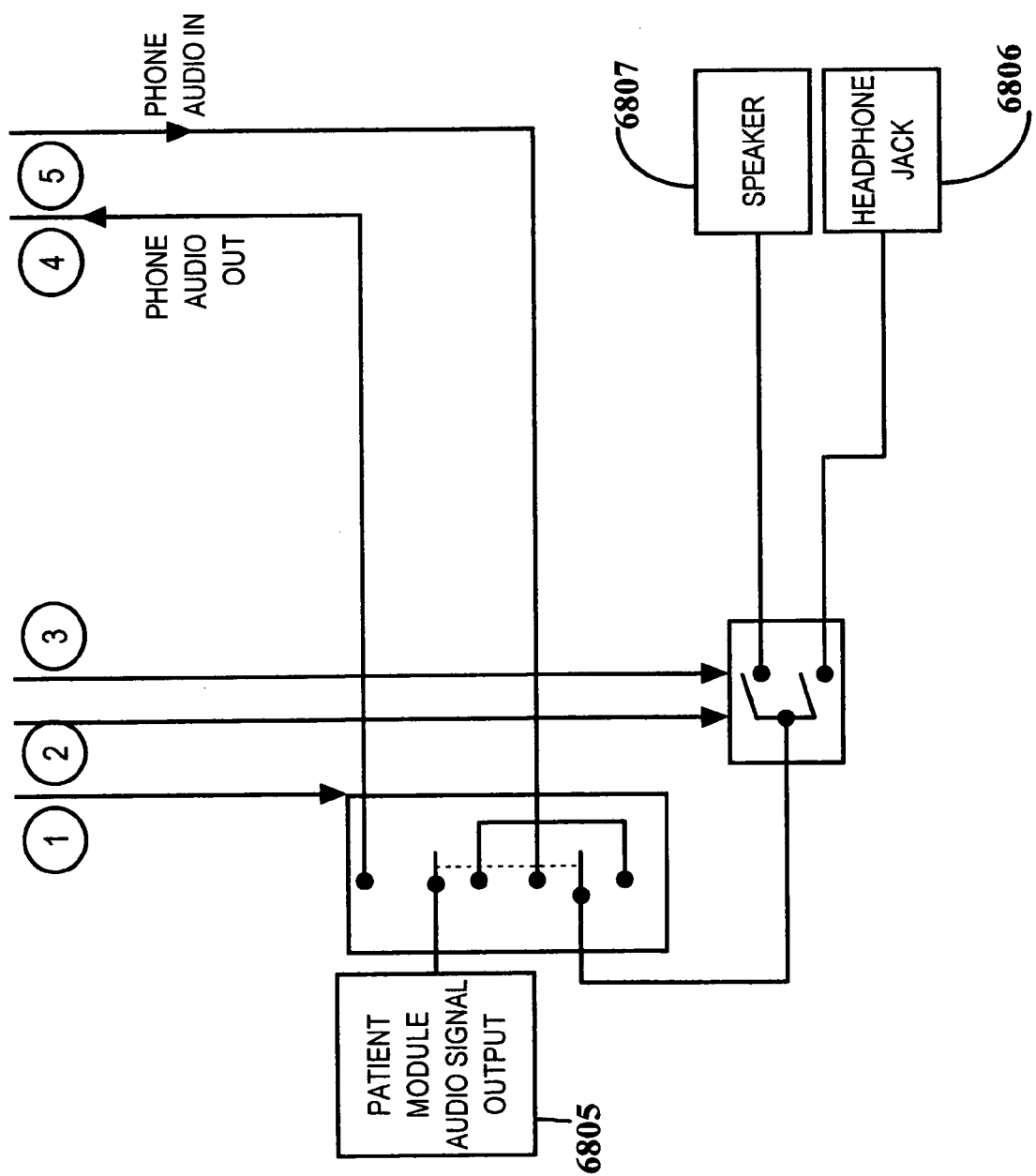

External Interface Module 1:

FIG. 68 is a functional block diagram which describes External Interface Module 1. External Interface Module 1 preferably includes a set of digital input/output ports 6801, switch input and associated de-bounce circuitry 6802, audio output circuitry, a telephone line interface DAA module 6803 (such as a model XE0068DT from Xecom, Inc., of Milpitas, Calif.), and an appropriate link between Patient Module computer 2 and digital I/O ports 6801.

A variety of commercially available assistive external devices (for example, sensitive push button switches and eye blink sensors), designed for use by individuals with disabilities, can generate or simulate mechanical switch closures. These devices, when connected to the digital inputs 6801 of External Interface Module 1, can be utilized to indicate which direction the user wishes to move the highlight (in Switch Advance Mode), or to indicate that the user wishes to perform the function associated with the currently highlighted panel (in Scan Mode or Switch Advance Mode).

A digital I/O monitoring routine preferably monitors de-bounced digital inputs in order to recognize changes of state of the user switch-inputs and similar changes of state of the telephone line interface ring indicator. When a change of state is observed, this routine determines the identity of the particular input(s) on which the state change(s) occurred, so that appropriate action can be taken.

The digital outputs on the digital I/O ports 6801 preferably control switches which allow an audio signal from the Patient Module 2 to be routed to headphones 6806 and/or speakers 6807 as required by Patient Module 2. Digital outputs are also used to place telephone interface 6803 "off-hook" or "on-hook," and to dial phone numbers via a DTMF tone generation interface.

Having now described the various components and functions of apparatus embodying the invention, the operation of the invention will now be described.

Self-Instruction Mode:

The most straight forward mechanism to implement the Self-Instruction mode described above is to simultaneously turn on Switch Advance Mode and Self-Instruction Mode (e.g., by setting appropriate flag variables). A simple two-switch configuration, with one switch given the Move Highlight (Advance) assignment, and the second switch given the Perform Action assignment (see FIG. 10) will result in a system in which each activation of the "Advance" switch will move the highlight from the currently highlighted panel to the panel whose index is associated with the "Advance" argument of the Action Object associated with the currently highlighted panel (see FIG. 14). After the new panel is highlighted, the Instruction function (FIG. 24) is called, which, based on the settings in the Action Object of the newly highlighted panel, preferably will either:

1. Explain to the user what action will occur if he or she activates the "Perform Action" switch; or 2. Preview what the new message would be if the user were to activate the "Perform Action" switch; or 3. Review the current message as it presently exists (primarily for the assistance of users who cannot see or understand text messages displayed on the screen); or 4. Review the current message as it presently exists and explain to the user what action will occur if he or she activates the "Perform Action" switch; or 5. If the user is in the process of spelling a word on the screen, explain what letters have been typed so far (again, for the assistance of visually impaired or other users who cannot read/understand text messages displayed on the screen).

Using the above methodology and a series of appropriately worded instructions keyed to the action associated with each panel, the user preferably can be guided through the process of using the system, substantially without the need for human instruction.

Functioning of a preferred embodiment of a system with Self-Instruction Mode enabled can be illustrated by the following example, in which it is assumed that the "Advance" function is assigned to the right button of a two-switch system, and the "Perform Action" function is assigned to the left button.

Figure 69:
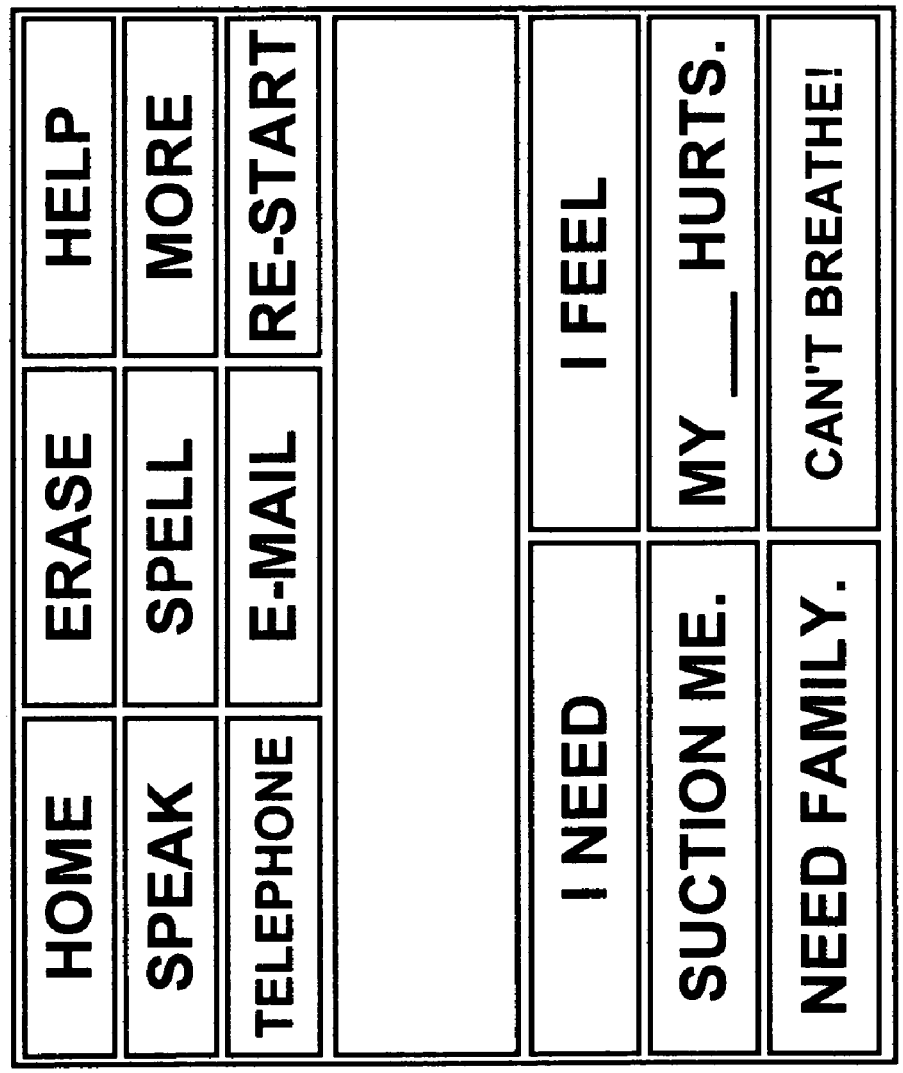
FIG. 69 is a representation of a preferred embodiment of an implementation of a Patient Module Main Screen in a preferred embodiment of a system according to the present invention.

FIG. 69 represents one potential implementation of a Patient Module screen in which Switch Advance Mode is enabled. Upon system startup, the user preferably is presented with an audible instruction (via the headphone 6806 or speaker 6807) which might say "Push the right button to hear the next option, and, if it is what you would like to do, indicate this by pushing the left button." If the user were using other kinds of sensors (for example, an eye blink sensor or a pillow switch), this prompt could be suitably modified. For example, it could say "Push the pillow switch to hear the next option, and, if it is what you would like to do, indicate this by blinking your eye." The instructions or prompts could be context-sensitive, changing depending on (a) the panel that is highlighted, (b) other system information such as user-specific settings, or (c) whether or not there is a partially or completely constructed message in the Message Display Window.

Referring to screen 6900 and assuming that the currently highlighted panel at system startup was the panel located in the upper left corner of the screen (which, for convenience is referred to as the "Home" position) and that: (1) Switch Advance Mode and Self-Instruction Mode were both enabled, (2) an appropriate instruction string was associated with the Action Code of the Action Objects of each of the Control Panels and WordGroup Panels on the screen, and (3) the user repetitively pushed the right button to advance the highlight through the Command Panels on the screen, a series of instructions similar to the following would be heard as the Switch Closure Event Handler (FIG. 10), the Move Highlight function (FIG. 13), and the Instruction function (FIG. 24), were called in response to the button presses:

1. "You would push the left button now if you wished to erase the last thing added to your displayed message."
2. "Push the left button now if you wish to send a message to the Nurses' Station or if you have an Emergency."
3. "Push the left button now if you wish to speak any message currently displayed in the Message Window."
4. "Push the left button now if you wish to add words by spelling them."
5. "Push the left button now if you wish to see more ways to begin a sentence."
6. "Push the left button now if you wish to use the telephone."
7. "Push the left button now if you wish to send an e-mail message or read new e-mail.
8. "Push the left button now if you wish to erase your entire message and start over."

Subsequent pushes of the right button would advance the highlight through the WordGroup Panels (such as those which contain the labels "I need," "feel," etc.) and, because the Action Object associated with each WordGroup Panel has the Sentence Preview Flag set and its Action Code set to ACT_APPEND, the Sentence Preview function (FIG. 25) would be called in addition to the Switch Closure Event Handler, Move Highlight and Instruction functions. This would result in the user hearing a series of instructions similar to the following:

1. "Push the left button now if you wish to begin your message with 'I need.'"
2. "Push the left button now if you wish to begin your message with 'I feel.'"
3. "Push the left button now if you wish to begin your message with 'Please suction me.'"
4. "Push the left button now if you wish to begin your message with 'This part of my body hurts:'".
5. "Push the left button now if you wish to begin your message with 'I need my family.'"
6. "Push the left button now if you wish to begin your message with 'I can't breathe.'"

Providing the user had been told that "Click now" means "Push the left button", the above prompts could be revised as desired, with no substantial change in system functionality. Thus, the instructional prompts could, equally well, say: "Click now to erase the last thing added to your message"; "Click now to call the nurse or if you have an emergency"; "Click now to speak your message"; "Click now to begin your message with 'I need,'" and so on.

Operation of Self-Instruction Mode when the user selects an option (in this case, by pushing the left button) can be illustrated by assuming that the patient pushed the left button when the panel containing "I need" was highlighted. One can easily see that the Switch Closure Event Handler (FIG. 10), coupled with DoAction (FIG. 11) and Append Word-Group (FIG. 16) functions, would result in the words "I need" being appended to the Message Display Window. Subsequent to the addition of these words to the Message Display Window, the LoadWordGroupList function (FIG. 23) would load the next WordGroup List (containing things the patient might need) into the WordGroup Panels, perhaps resulting in a Patient Module screen similar to FIG. 70. The Move Highlight Specific function (FIG. 15) would then be called to move the highlight to the next position (which, in this example, might be the "Home" position in the upper left corner of the screen).

The next push of the right button would move the highlight to the "Erase" panel, resulting in a call to the Instruction function which would first say "So far your message is 'I need,' and then say "Push the left button now if you wish to erase the last thing added to your displayed message".

Assuming that the patient did not opt to erase the last word group (i.e., "I need") added to the message, the next six pushes of the right button would advance the highlight through the remaining Control Panels, and present the same basic sequence of instruction prompts referred to in the paragraphs above. In another preferred embodiment, a simple conditional test could determine that a string was present in the Message Display Window and, based on this, modify the third and fifth prompts in the seven prompt sequence above for clarity, so that they said (respectively): "So far your message is 'I need'; push the left button now to speak your message" and "Push the left button now to see more ways to continue your message."

Examination of the flowcharts for the Instruction function (FIG. 24) and the Sentence Preview function (FIG. 25) illustrates that the sequence of instructions which the user would hear when the highlight moved through the Word-Group Panel area of the screen would be:

1. "Push the left button now if you want your message to be: I need pain medicine."
2. "Push the left button now if you want your message to be: I need my minister."
3. "Push the left button now if you want your message to be: I need to go to the bathroom."

4. "Push the left button now if you want your message to be: I need to sleep."

5. "Push the left button now if you want your message to be: I need some ice."

6. "Push the left button now if you want your message to be: I need a Bible."

The above example assumes that the Alternate Display String associated with the panel labeled "bathroom" contains the string "to go to the bathroom", and similarly that the Alternate Display String associated with the panel labeled "ice" contains the string "some ice".

One can see that if the user pushed the left button when the panel containing "bathroom" was highlighted, the Message Display Window would be changed to display "I need to go to the bathroom," and similarly that the user might hear the following instructions as subsequent right button presses moved the highlight through the Command Panels at the top of the screen:

1. "So far your message is 'I need to go to the bathroom.' Push the left button now if you wish to erase the last thing added to your message."

2. "Push the left button now if you wish to send a message to the Nurses' Station or if you have an Emergency."

3. "So far your message is 'I need to go to the bathroom.' Push the left button now to speak your message."

4. "Push the left button now if you wish to add words by spelling them."

5. "Push the left button now if you wish to see more ways to continue your message."

6. "Push the left button now if you wish to use the telephone."

7. "Push the left button now if you wish to send an e-mail message or read new e-mail."

8. "Push the left button now if you wish to erase your entire message and start over."

The operation of the spelling interface in Self-Instruction Mode can be illustrated by assuming that, after the user had selected the panel labeled "I need," he or she had pressed the left button upon hearing the prompt: "Push the left button now if you wish to add words by spelling them."

Figure 71:
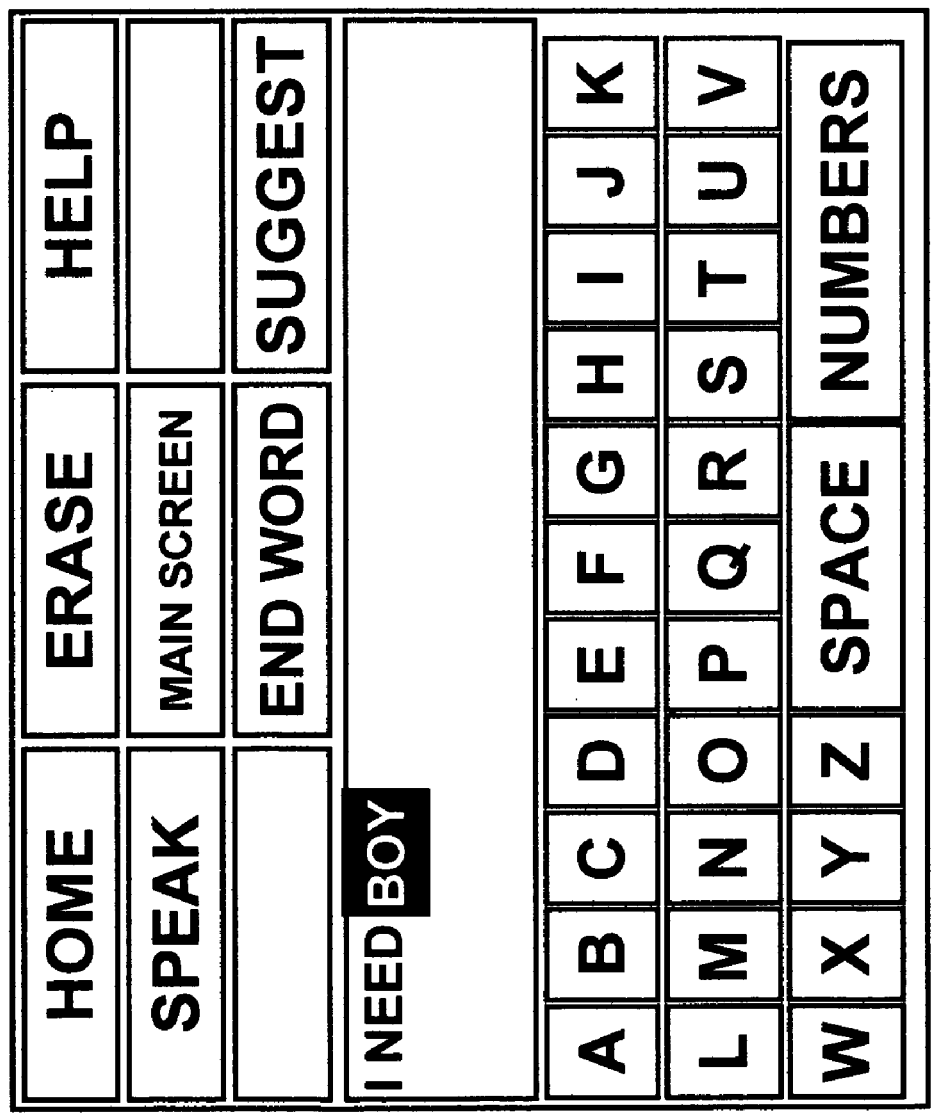
FIG. 71 is a representation of a preferred embodiment of an implementation of a Patient Module Spelling Interface screen in a preferred embodiment of a system according to the present invention after addition of letters "b," "o," and "y"

The Show Spelling Mode function (FIG. 29) (called by the DoAction function) would result in the display of a spelling interface screen which might have features similar to those shown on FIG. 71.

Subsequent to the display of the spelling interface screen, the highlight might be moved to the WordGroup panel labeled "A," at which point the user would hear the following instruction: "So far your message is 'I need'; push the left button if you wish to start your next word with 'a.'" Subsequent pushes of the right button would result in an obvious sequence of prompts such as, "Push the left button if you wish to start your next word with 'b'"; "Push the left button if you wish to start your next word with 'c'" etc.

Alternatively, if the record of the user's previous actions had indicated frequent calls for assistance or frequent errors, the conditional statements within step 1665 of FIG. 16 could initially highlight the "Home" panel on the spelling interface screen, because of its proximity to the "Erase" and "Help" panels. In this case, subsequent pushes of the right button would advance the highlight through the remaining Control Panels on the spelling interface screen, providing instructions for each item as it was highlighted. Eventually the highlight would be moved to the WordGroup panel labeled "A," at which point the user would hear the same sequence of instructions described in the previous paragraph.

If, for example, the user pushed the left button when the letter "B" was highlighted, the Add Letter to Spelled Word function (FIG. 30) would be called which would add the letter to the TypedLetters String in the Message Display Window, and move the highlight to a panel which, depending on, preferably, user-specific settings, the current context and the record of the user's previous actions, might be the panel labeled "End Word" or potentially could be the "Erase" panel or any other appropriate panel on the screen.

If the highlighted panel were the "End Word" panel, the Self-Instruction function (FIG. 24), when called by the Move Highlight Specific function, might immediately issue the following prompt: "So far your message is 'I need,' and for the next word, so far you have typed 'b.' Push the left button now if your word is complete or push the right button to select from a list of words which begin with 'b' or to continue spelling."

On the other hand, if user-specific settings, the current context or the record of the user's previous actions resulted in the next highlighted panel being the "Erase" panel, the Self-Instruction function (FIG. 24), might issue the following prompt: "So far your message is 'I need,' and for the next word, so far you have typed 'b.' Push the left button now to erase the last letter added to your sentence."

Assuming that the user had decided to continue spelling, an appropriate number of presses of the right button would eventually highlight the next letter for the user's desired word, at which time pressing the left button would add the selected letter to the TypedLetters String in the Message Display Window, and result in an instructional prompt similar to one of those described above.

Thus, after using the above procedure to add the letters "o" and "y" to the Message Display Window, the user (when the "End Word" panel was highlighted) would hear the prompt: "So far your message is 'I need,' and, for the next word, so far you have typed 'b' 'o' 'y.' Push the left button now if your word is complete or push the right button to select from a list of words which begin with 'b' 'o' 'y' or to continue spelling."

If, at that point, the user pushed the right button, the user would hear "Push the left button now to select from the list of words which begin with 'b' 'o' 'y' or push the right button to continue spelling.

If the user then pushed the left button, execution of the Generate Suggested Words List (FIG. 33) and Load Suggested Words Panel (FIG. 34) functions would result in a screen with features similar to those shown in FIG. 72. Because, in this example, Self-Instruction Mode has been enabled, the PreviewSuggestedWords function would then be called and might speak the list of "suggested" words on the screen. Assuming that the user-specific settings were such that the highlight was automatically placed on the "More" panel, the following instruction prompt might be output: "To select one of these words push the right button; to hear some more suggested words beginning with 'b' 'o' 'y', push the left button."

Given the hypothetical spelling interface screen shown in (FIG. 72), the following sequence of instruction prompts would be heard as the user repetitively pushed the right button:

1. "Push the left button now if you want your message to be: 'I need boy.'"

2. "Push the left button now if you want your message to be: 'I need boycott.'"

3. "Push the left button now if you want your message to be: 'I need boyfriend.'"

4. "Push the left button now if you want your message to be: 'I need boyhood.'"

5. "Push the left button now if you want your message to be: 'I need boyish.'"

6. "Push the left button now if you want your message to be: 'I need boys.'"

One can see that, by designing a series of appropriately worded instructions, keyed to the action associated with each panel, as well as a planned and dynamically optimized sequence of highlighted panels, one can implement a system in which, when Self-Instruction Mode is enabled, the user can be guided through the process of using the Patient Module substantially without the need for human instruction.

Although the above Self-Instruction example for simplicity assumed that the system was operating in Switch Advance Mode, one can see that the same basic "guided instruction functionality" can be accomplished when the system is operating in Scan Mode or TouchScreen Mode. In these latter two modes, some of the instructional strings would be slightly modified to make their wording more appropriate for the respective mode. For example, references to pushing the right button would be eliminated for Scan Mode, because in Scan Mode the Scan Timer Event replaces right button actuations as the mechanism for moving the highlight to the next specified panel.

Similarly, in TouchScreen Mode some of the strings might be modified to recommend what panel the user should touch next, after performing some operation. Thus, after the user selected the letter "b" on the spelling interface screen, the following instruction prompt might be issued: "So far your message is 'I need,' and for the next word, so far you have typed 'b'. Touch the panel labeled "Suggest" if you want to hear instructions for the suggested words option." Alternatively, the system could be configured so that, in certain cases, the highlight was automatically moved to the next recommended panel, thus guiding the user to the most likely "follow-up" operation, and automatically providing audible instructions for that operation.

Blind User Mode:

The Blind User Mode of the system according to the present invention is a special case of the Self-Instruction Mode, modified slightly to reflect the fact that fully or partially visually impaired, and some cognitively-impaired, users may not be able to read (or understand) the labels on the Control Panels and WordGroup Panels on the system screens. Because these types of users may need to rely entirely on the audible instructions to use the system in the absence of visual cues, the sequence of highlighted panels (and hence the sequence of instruction prompts) and, in some cases, the wording of instruction prompts may be slightly different than in the "normal" Self-Instruction Mode.

For example, referring to the previous discussion regarding the Self-Instruction Mode, one can see that, in "normal" Self-Instruction Mode, the user might be presented with the prompt: "Push the left button now if you wish to see more ways to begin a sentence," prior to being presented with the following options as he or she moves the highlight to the various WordGroup Panels:

1. "Push the left button now if you wish to begin your message with 'I need.'"

2. "Push the left button now if you wish to begin your message with 'I feel.'"

3. "Push the left button now if you wish to begin your message with 'Please suction me.'"

4. "Push the left button now if you wish to begin your message with 'This part of my body hurts:'".

5. "Push the left button now if you wish to begin your message with 'I need my family.'"

6. "Push the left button now if you wish to begin your message with 'I can't breathe.'"

Because the user who is not visually impaired is able to see and understand the words on the screen, and presumably has already reviewed the various ways in which he or she might begin a sentence, the prompt: "Push the left button now if you wish to see more ways to begin a sentence," could be presented before the system highlights and reads the instructions (1-6 above) for the WordGroup Panels.

In Blind User Mode, however, the sequence of prompts and the wording might be modified to reflect the fact that the user can only determine if he or she wishes to use the "More" option after the first set of options has been audibly reviewed. Thus, in Blind User Mode, the sequence of audible prompts presented to the user (upon successive presses of the right button) might, instead, be the following:

1. "Push the left button now if you wish to begin your message with 'I need.'"

2. "Push the left button now if you wish to begin your message with 'I feel.'"

3. "Push the left button now if you wish to begin your message with 'Please suction me.'"

4. "Push the left button now if you wish to begin your message with 'This part of my body hurts:'".

5. "Push the left button now if you wish to begin your message with 'I need my family.'"

6. "Push the left button now if you wish to begin your message with 'I can't breathe.'"

7. "Push the left button now if you wish to hear more ways to begin a sentence."

Revised prompt sequences during Blind User Mode preferably are a direct consequence of the highlight sequence, which itself preferably is a result of the directional indices assignment which occurs during the DoAction function (see, FIG. 11, step 1185), and preferably is based on the mode of operation, user-specific settings and the current context. Because the directional indices assignment which occurs in step 1185 of FIG. 11 preferably is based on user-specific settings (such as Blind User Mode) and current context (such as the presence or absence of text strings in the Message Display Window), the moving highlights during Blind User Mode preferably can bypass irrelevant panels to optimize the instructions given to the user. For example, when the Message Display Window is empty, and the system is in Blind User Mode, step 1185 of FIG. 11 can assign the index of the Help Panel to the Advance directional property of the Action Object associated with the Home Panel. By making this context-sensitive, conditional assignment, the system avoids providing the visually impaired user with an irrelevant, and perhaps confusing, prompt about erasing the message in the Message Display Window, when the Message Display Window is empty. Similarly, conditional assignment of directional indices to the Help Panel can insure that the visually impaired user is not provided with a similarly confusing prompt about speaking the current message, when none exists.

Certain audible review features might be disabled for certain users utilizing the "normal" Self-Instruction Mode. For example, for a sighted user who can read the suggested words, or can read the sentence composed so far, the audible review of suggested words, or the audible review of what the user's sentence says, might not be necessary. However, this "thorough" audible review functionality would always be enabled when the system was operating in Blind User Mode.

Questionnaire Mode:

Functioning of a preferred embodiment of a Questionnaire Mode can be illustrated by the following example. In this example, it is assumed that a family member or member of the hospital staff has previously selected a menu option which placed the system in Questionnaire Mode. In this example, it is also assumed that the system is operating in a simple two-button Switch Advance Mode, and that one button is assigned to "Advance" and the second button is assigned to "Perform Action" (see FIG. 10). Although the following discussion and associated screens are based on system use in Switch Advance Mode, the operation of Questionnaire Mode using Touch Screen or Scan mode is very similar.

Figure 73:
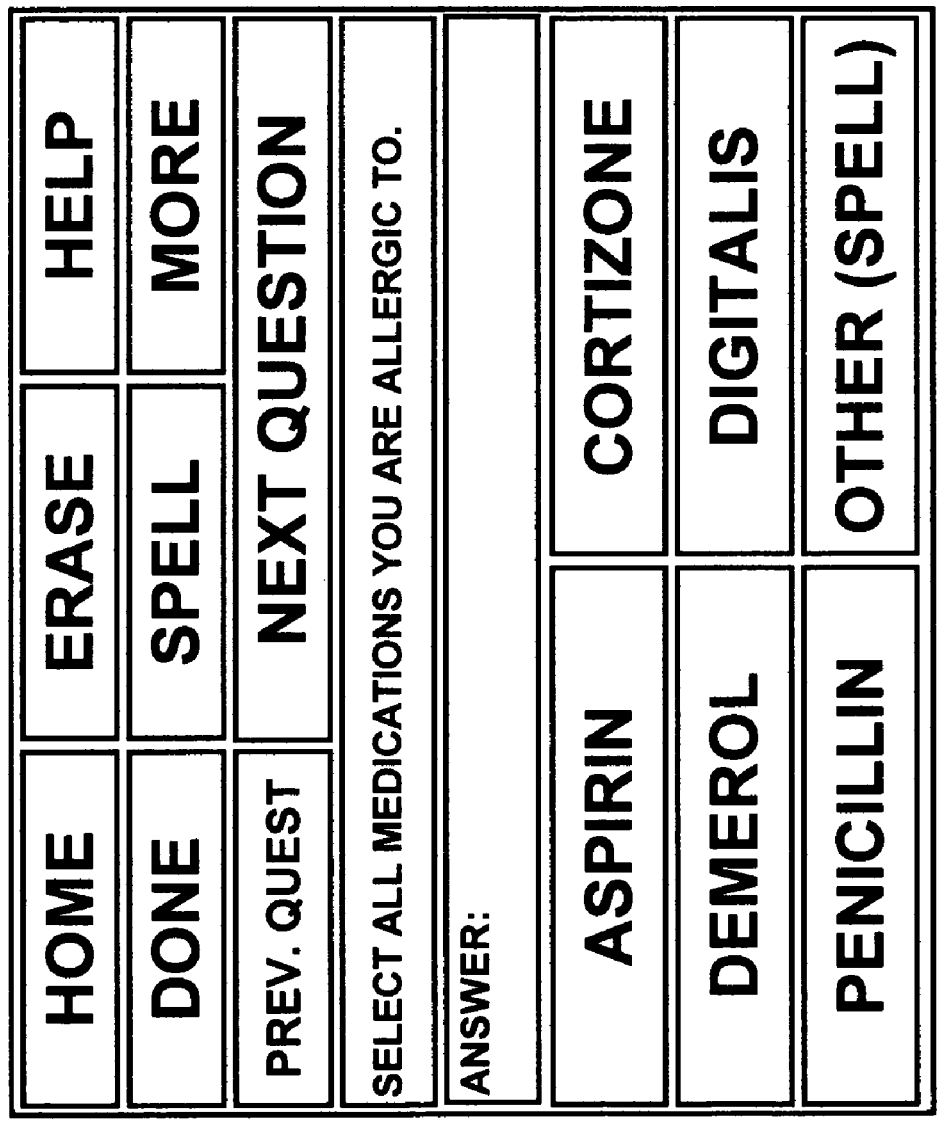

FIG. 73 represents one preferred embodiment of a Questionnaire Mode screen. Upon Questionnaire Mode startup, the first question (such as "Select all medications you are allergic to") and some potential answers would be loaded into appropriate areas of the screen by the Load Question function (FIG. 53).

If the patient were returning to a questionnaire which he or she previously started but did not complete, a "Return to Last Question" function could be used to place the system at the first unanswered question, allowing the patient to complete the questionnaire in several short sessions, rather than requiring the entire questionnaire to be completed at one time.

Figure 74:
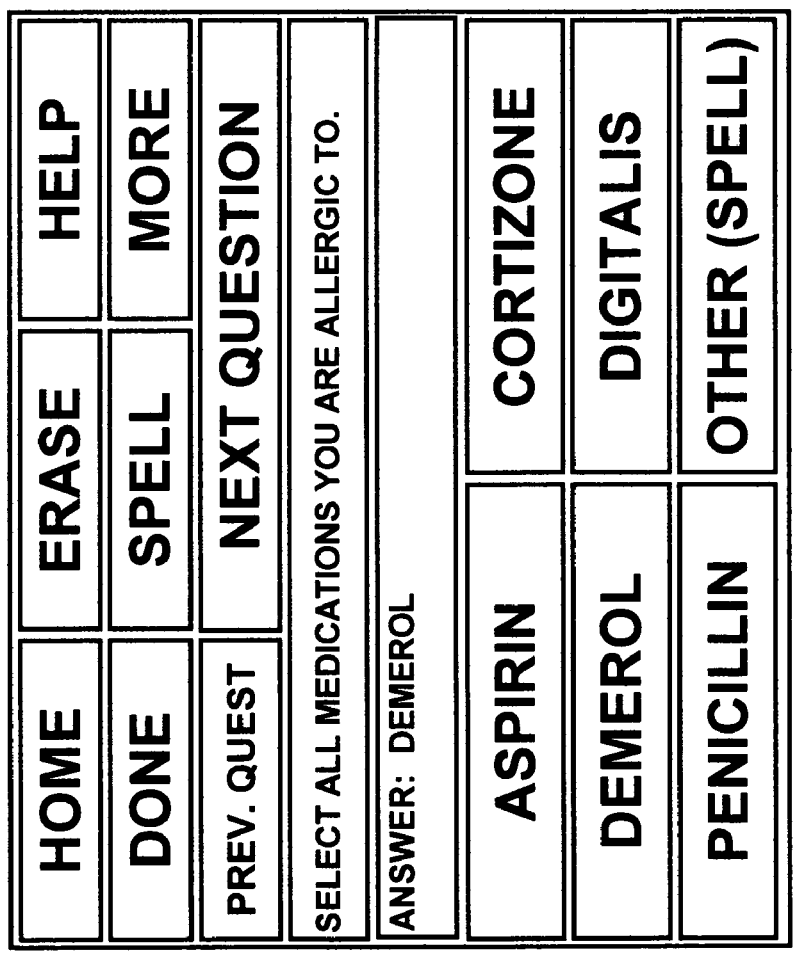
Figure 75:
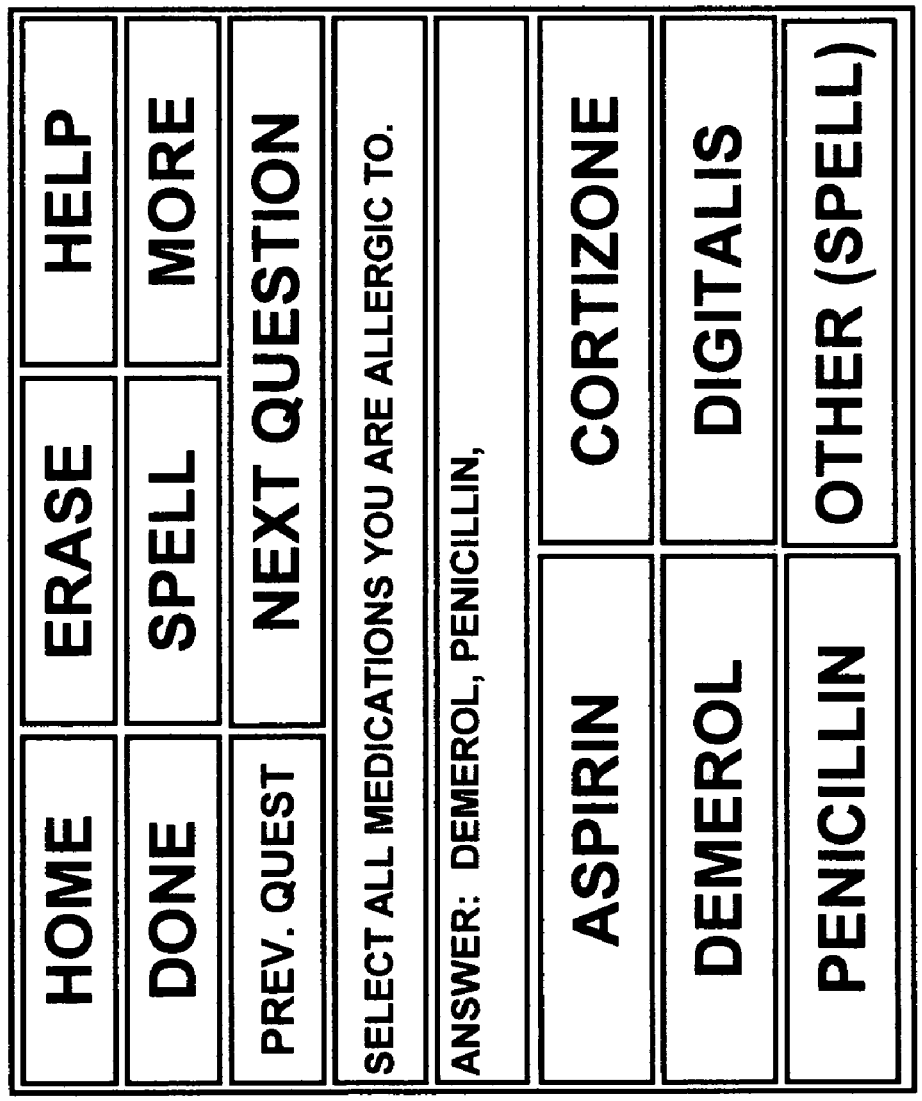

After the first question for the current session is displayed, the patient would move the highlight to the WordGroup Panel containing his or her desired answer, and then use the "Perform Action" switch to select that answer, which would be appended to the Message Display Window by the Append Answer function (FIG. 57), resulting in a display similar to that shown in FIG. 74.

Figure 76:
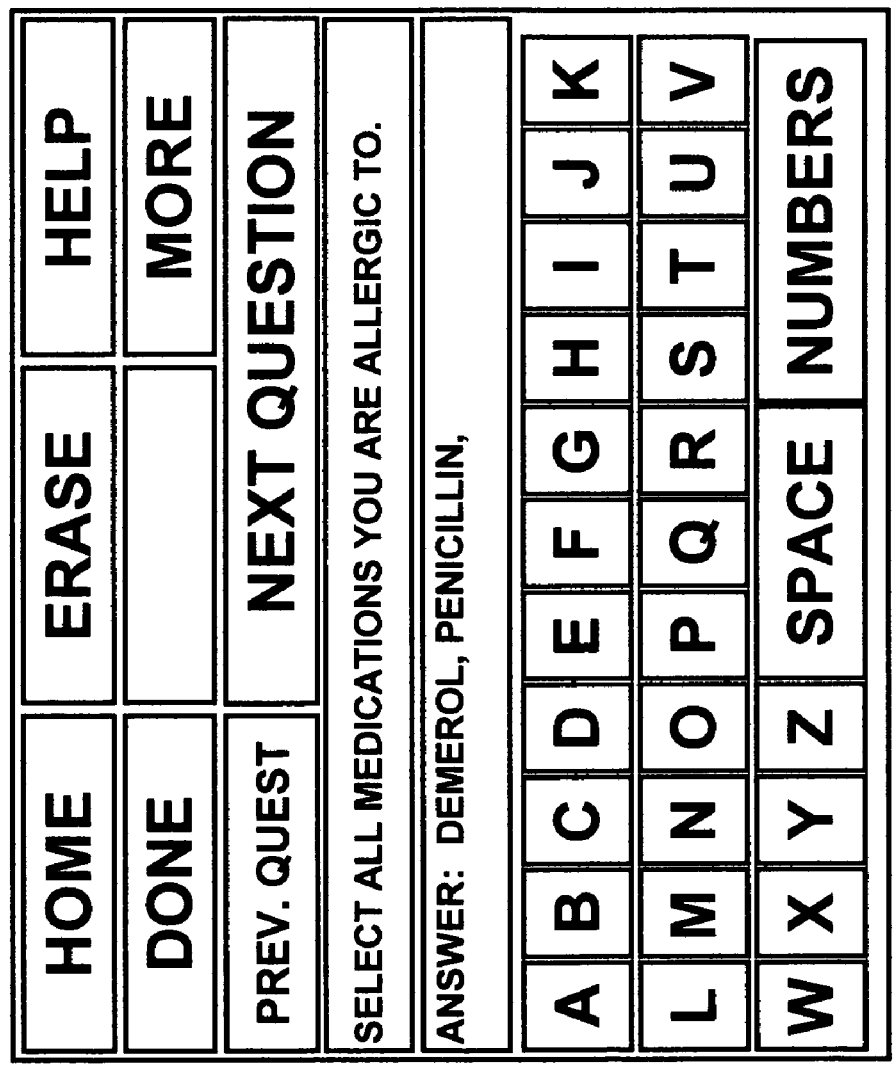
Figure 77:
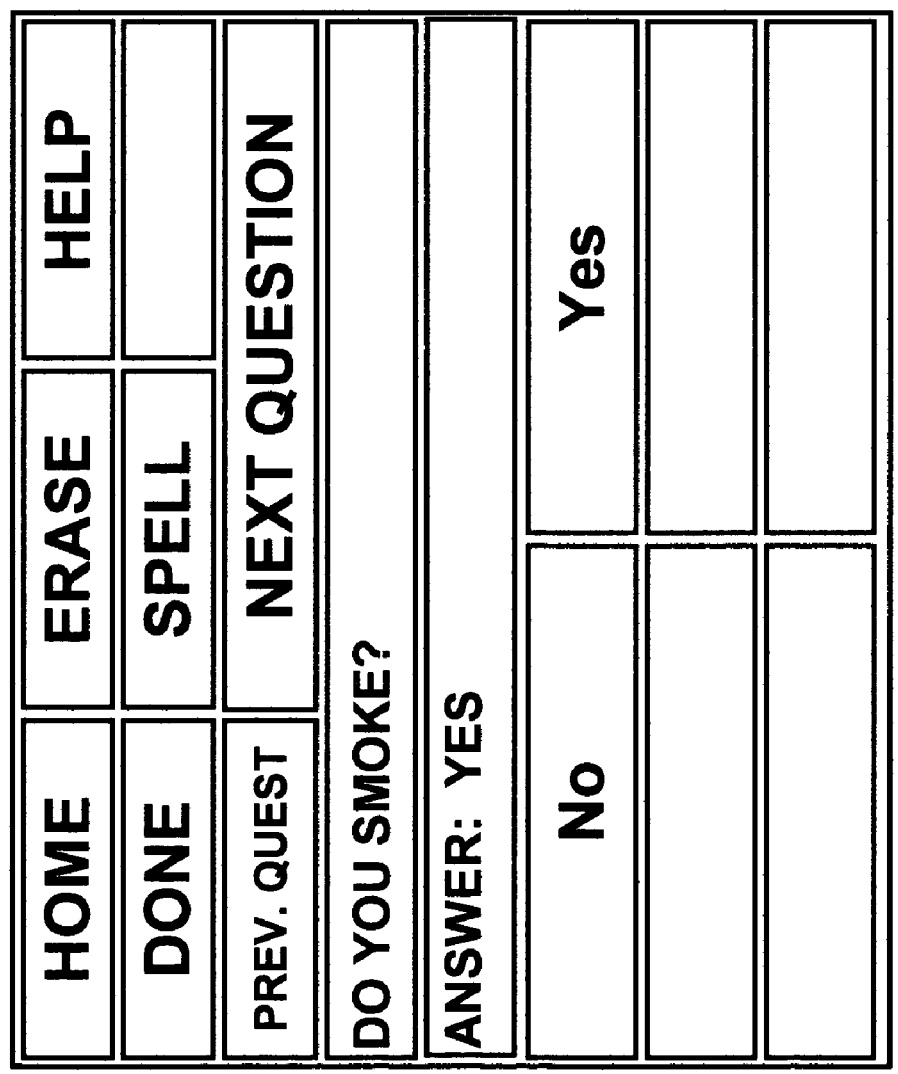
Figure 78:
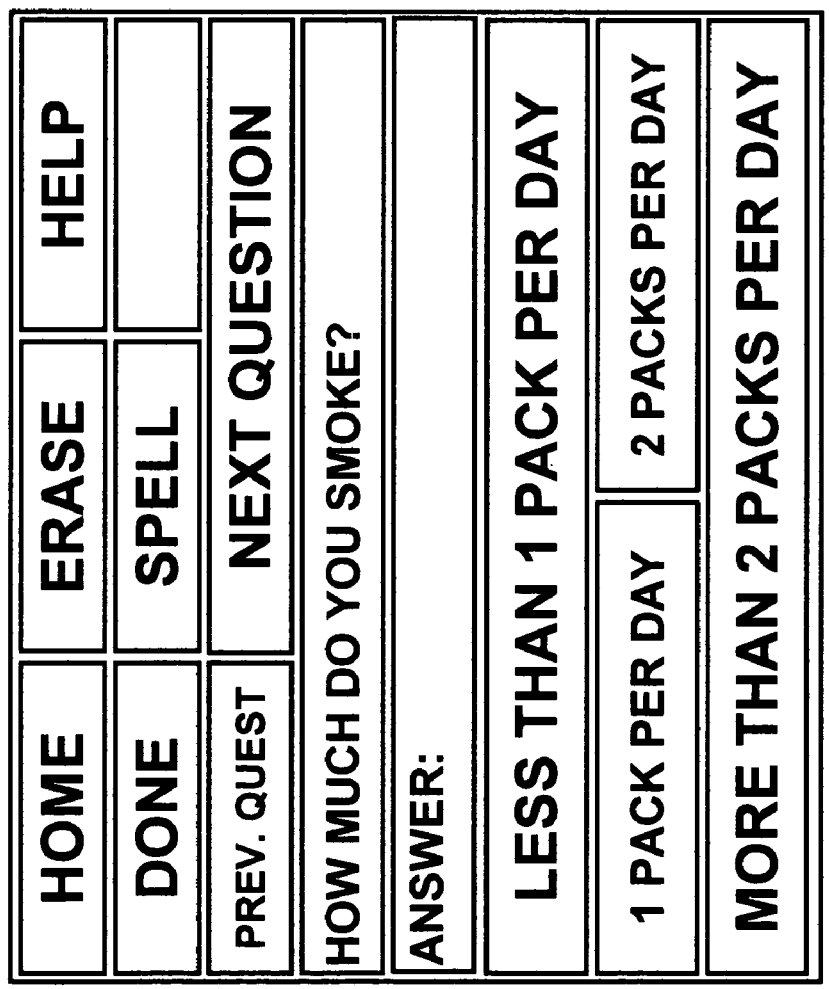

The user would continue to select additional answers to this question (see, e.g., FIG. 75), and, in cases in which the desired answer was not displayed, he or she could select an appropriately named option (such as "Other (Spell)") which, as discussed in FIG. 57, would display a spelling mode screen modified for use in Questionnaire Mode (see, e.g., FIG. 76).

Use of the spelling mode when answering questions is virtually identical to that described in the discussion for FIGS. 29-36, with the exception that, as described in the discussion related to FIG. 53, a special dictionary may be pre-appended to the standard dictionary so that, for example, any use of the "Suggest" option (FIG. 33) while the screen shown in FIG. 76 was displayed could result in an initial display of suggested words extracted from a "medicines" dictionary.

When the user was finished with the answer to the question, he or she preferably would highlight and preferably select "Next Question", at which time the Determine and Load Next Question function (FIG. 54) preferably would store the answer and determine the index of the next question. For some questions, the index of the next question (which is a configurable property of each answer) might be the same for all answers. However, for other questions (such as that shown in FIG. 77), the index of the next question might be different for one or more of the potential answers, allowing the user's answer to the question to determine appropriate follow-up questions (such as that shown in FIG. 78).

By referring to the previous discussions of the Move Highlight Directional (FIG. 14) and Move Highlight Specific (FIG. 15) functions and the Load Question function (FIG. 53), and recalling that Blind User Mode is a special case of Self-Instruction Mode, it is clear that all of the Questionnaire Mode functionality could be utilized by fully or partially visually impaired users.

Figure 79:
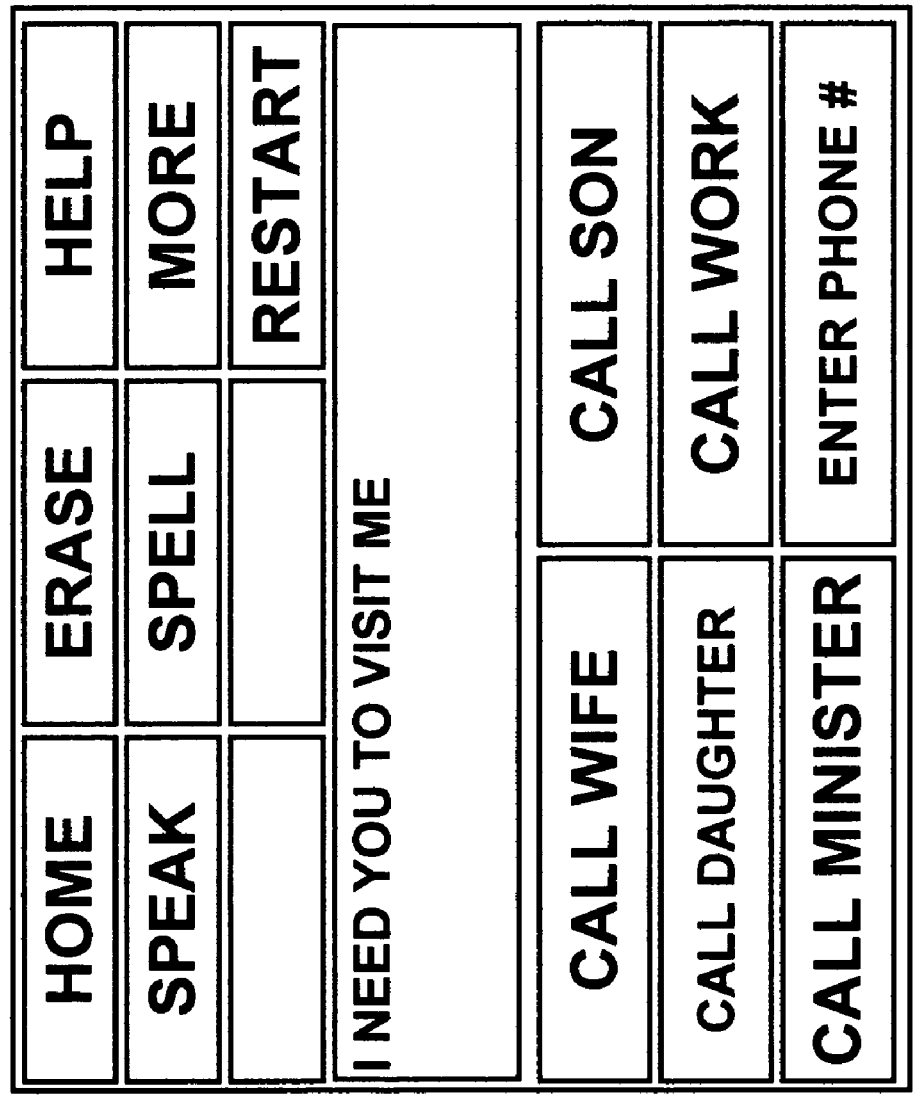
Figure 80:
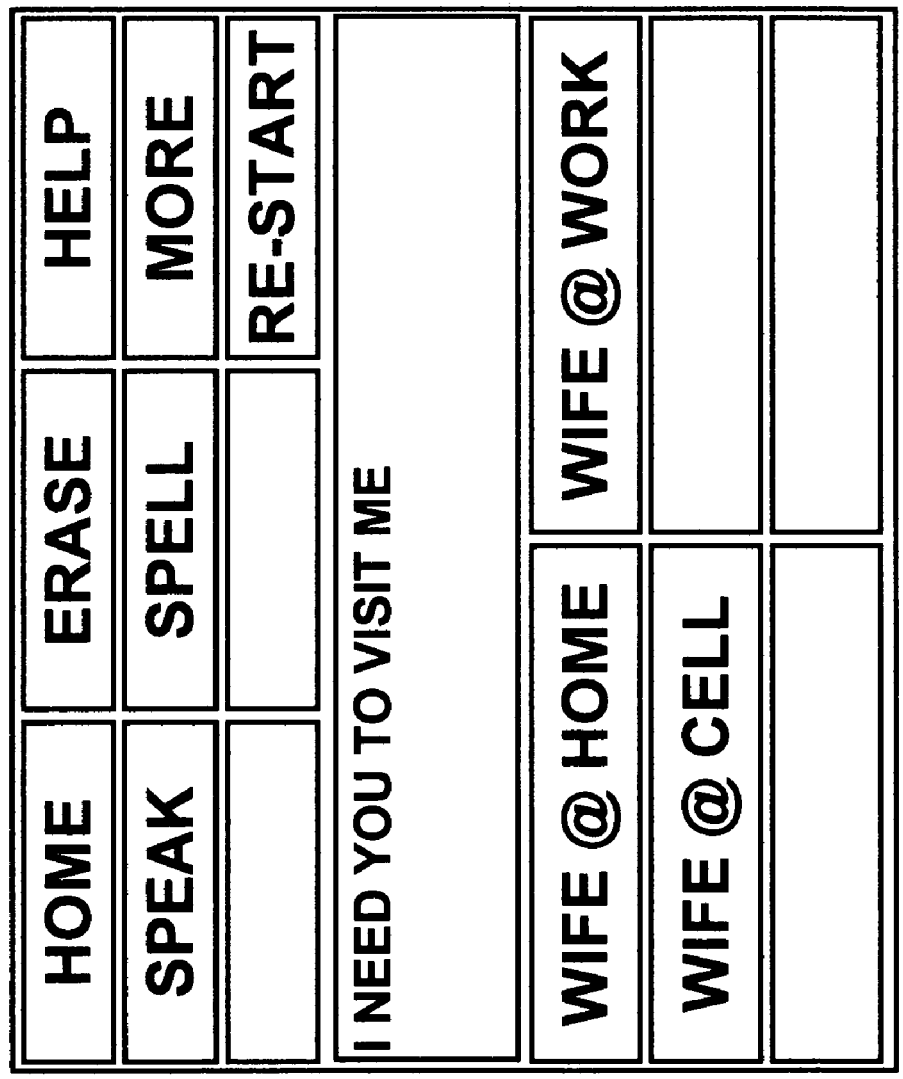
Figure 81:
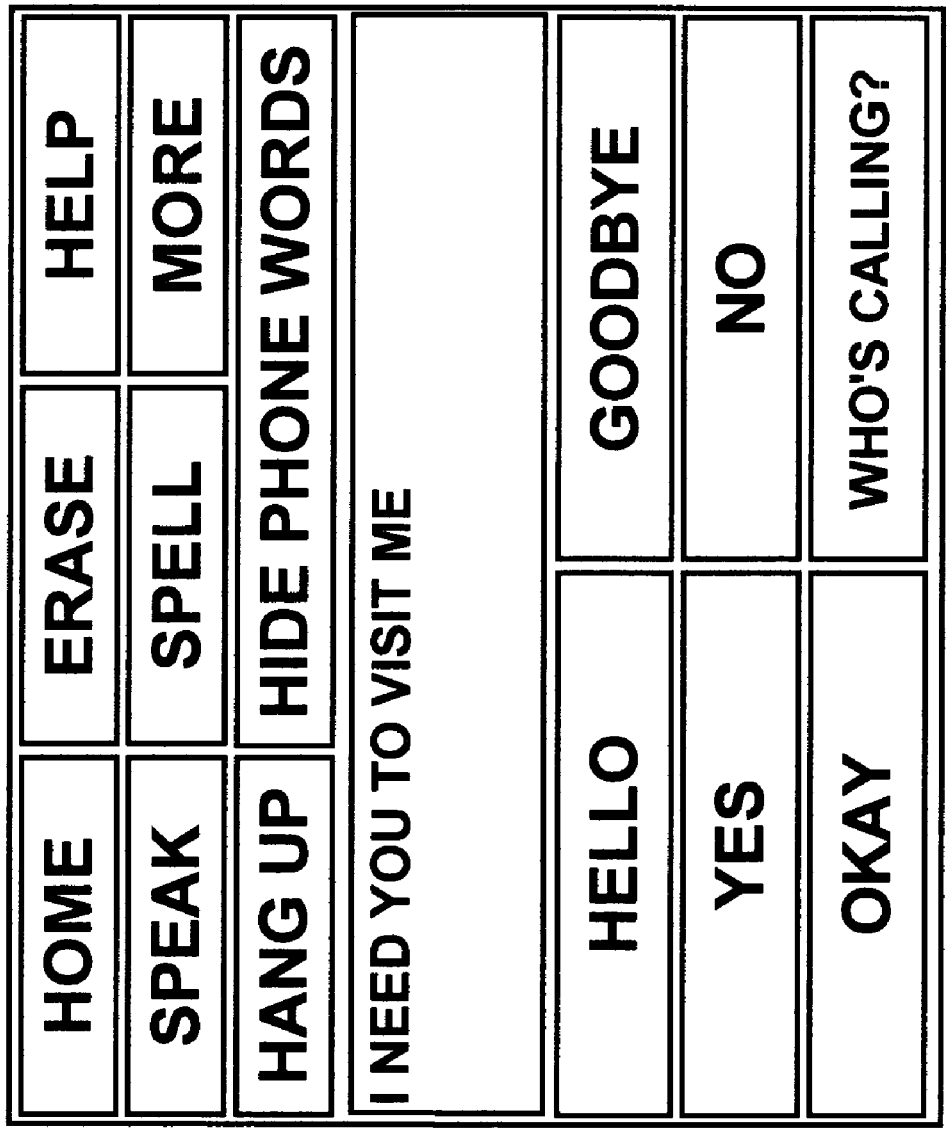
Figure 82:
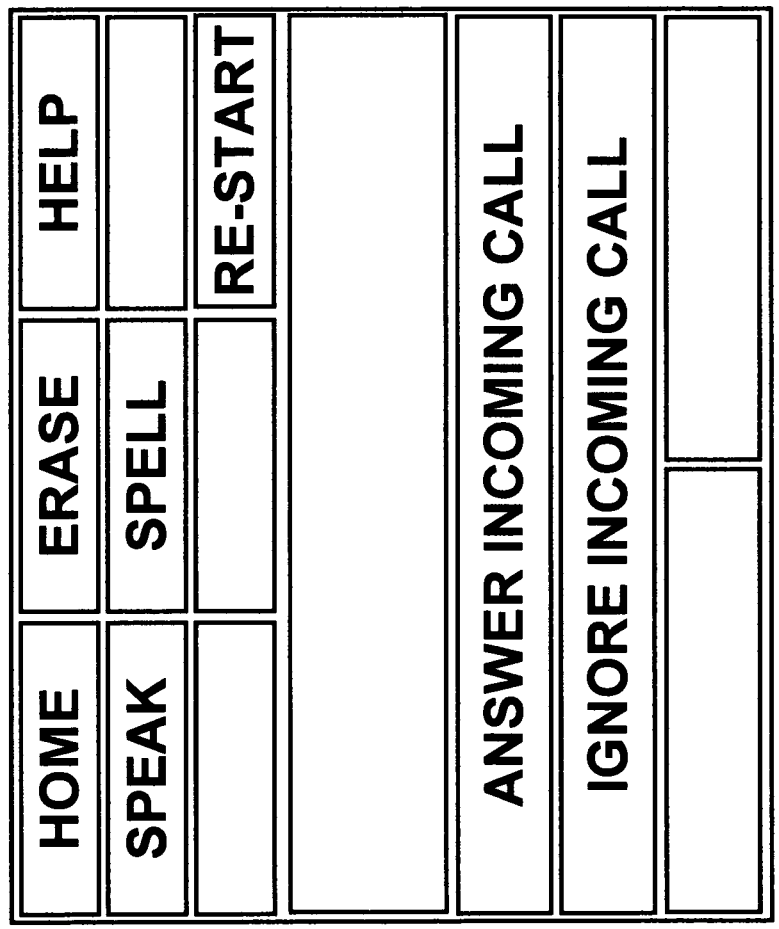

Telephone/Blind User Telephone Mode:

Assuming that the user had previously selected an appropriately labeled Control Panel (such as the "Telephone" Panel shown in FIG. 69), the sequence of screens shown in FIGS. 79-81 illustrates a preferred embodiment of the process of initiating a telephone call as well as some of the special conversational words which would be loaded into the WordGroup Panels by the Place Telephone Call function (FIG. 41).

It is clear in view of the foregoing that after the system executes the Place Telephone Call function (FIG. 41), and the receiving party answers the telephone, the standard system functionality described in FIGS. 1-81 would allow the patient to compose sentences which would be heard by the remote party, and that any conversation from the remote party would be heard by the patient. Optionally, process 4100 could be modified to play an outgoing message as soon as the called party answers, advising the called party that the caller is using an assistive communication device, and to be patient. One can see from the hypothetical screen shown in FIG. 82, and associated flowcharts (FIGS. 42 and 43) that the process of responding to an incoming telephone call is equally straightforward in view of the foregoing.

Similarly, it is clear in view of the foregoing that an appropriate set of instruction strings associated with the WordGroup and Control Panels containing the various telephone options would enable a fully or partially visually impaired, speech-disabled user to place or receive telephone calls and to participate in two-way telephone conversations.

Figure 83:
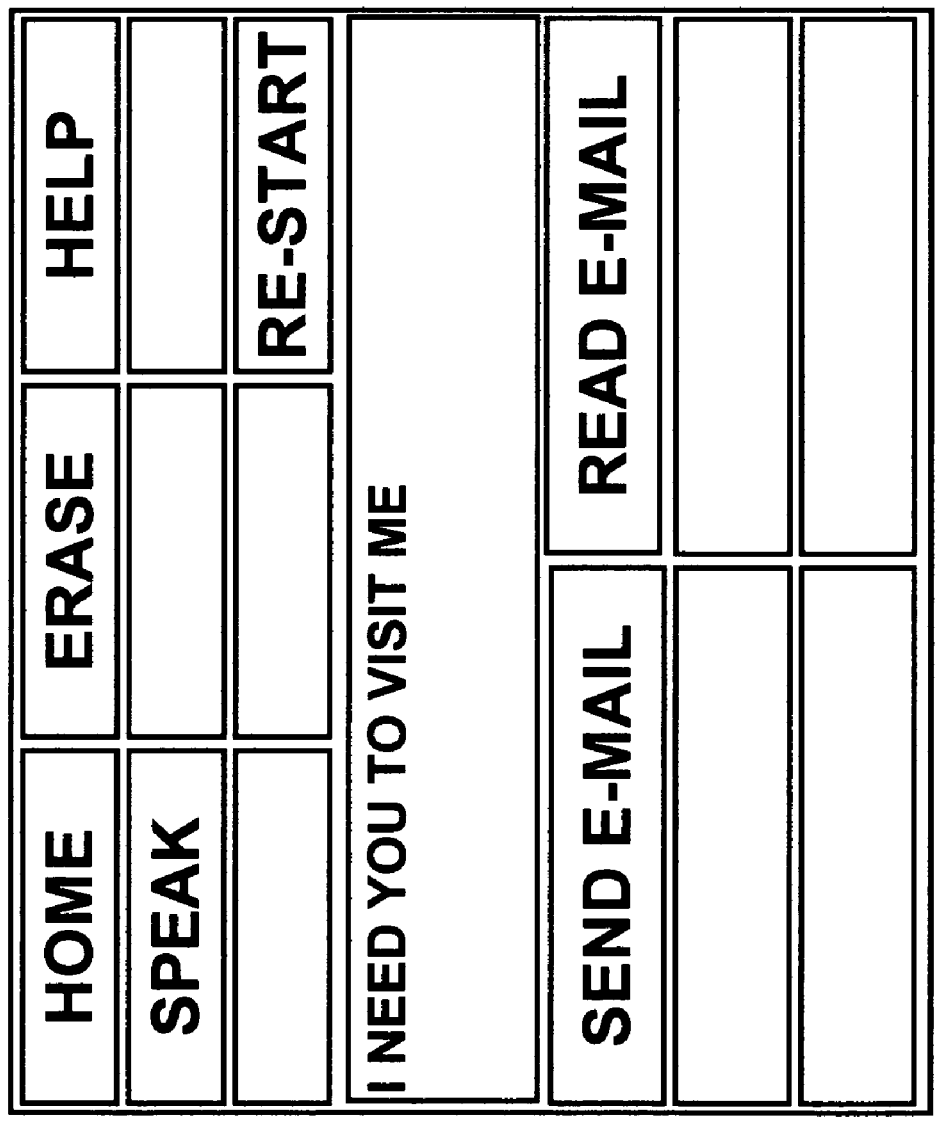
Figure 84:
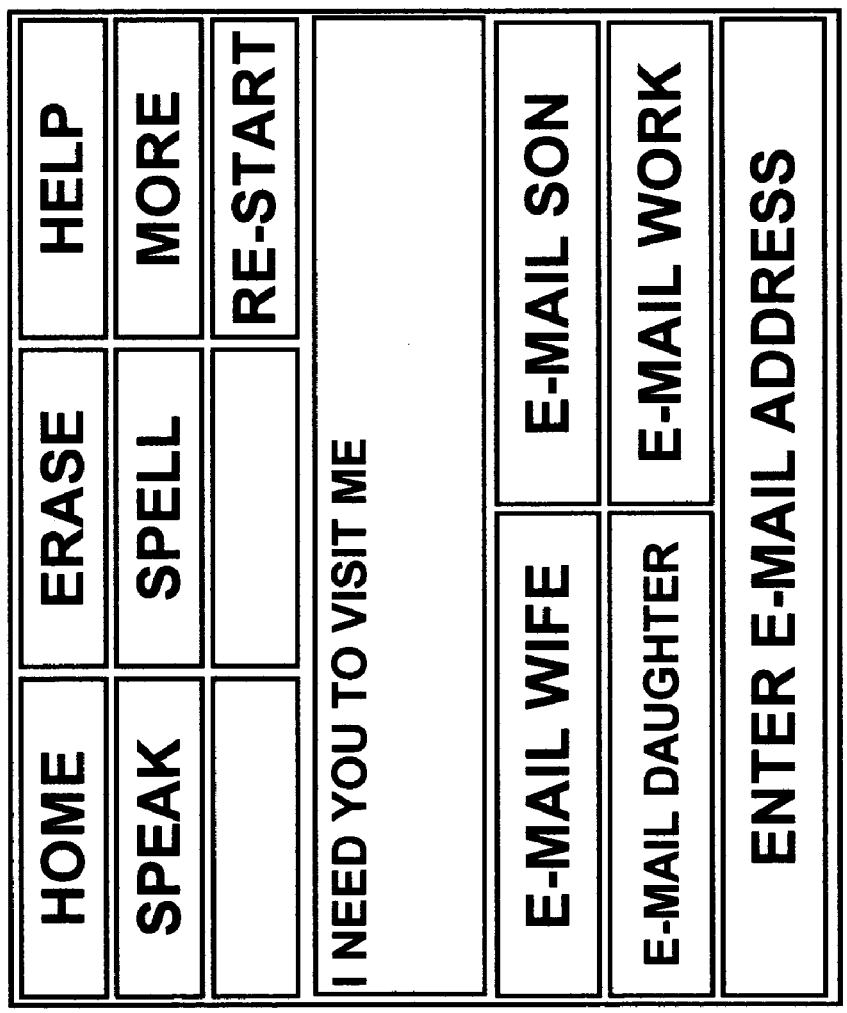
Figure 85:
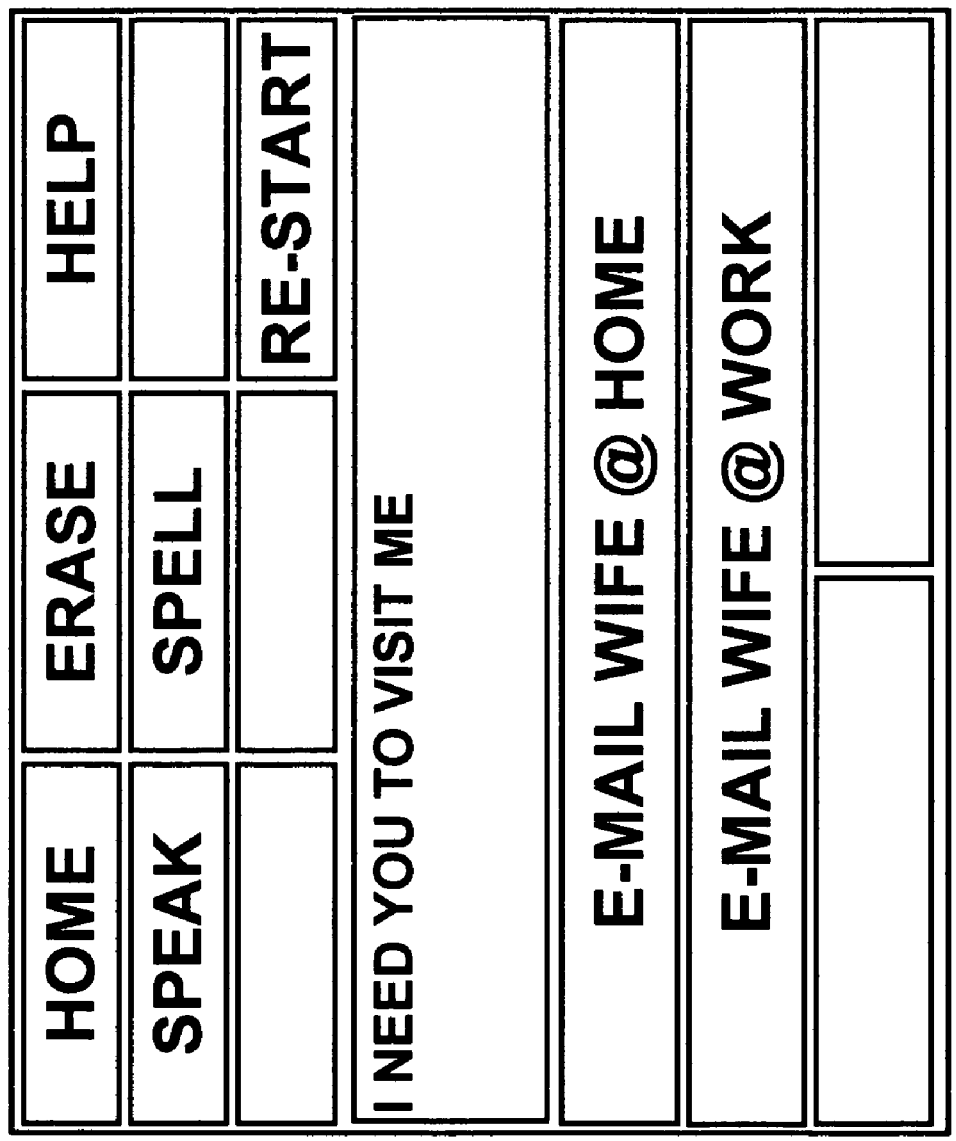

E-mail Interface for Disabled Users:

Assuming that the user had previously selected an appropriately labeled Control Panel (such as the "E-mail" Panel shown in FIG. 69), the sequence of screens shown in FIGS. 83-85 illustrates a preferred embodiment of the process of sending an outgoing e-mail message.

Figure 86:
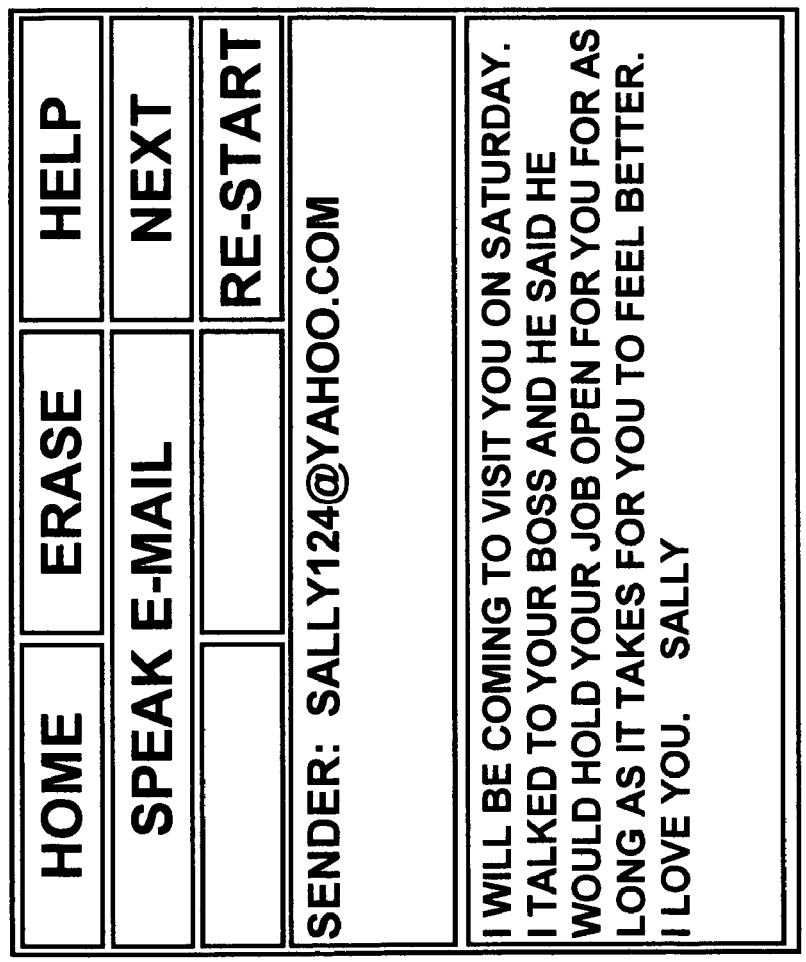

One can see from the preferred embodiment of a screen shown in FIG. 86 and the associated flowcharts (FIGS. 49 and 50), that the process of reviewing and reading incoming e-mail messages is equally straightforward in view of the foregoing.

Similarly, it is clear in view of the foregoing that an appropriate set of instruction strings associated with the WordGroup and Control Panels containing the various e-mail options would enable a fully or partially visually impaired user to send or read e-mail using the same basic system features as would a non-visually impaired user.

Intelligent, Self-Optimizing Conditional Scanning and Navigation Functionality:

Given the system's ability to assign the next panel to highlight based on user-specific settings, current context, mode of operation, and the record of the user's previous actions while using the system, optimized scan and switch advance sequences preferably can be provided to facilitate use of the system in any one or more of the operational modes described above. As one example, consider again the screen shown in FIG. 70. Assuming that the user was operating the system in Scan Mode and that he or she had just selected the Word Group Panel containing the word group "pain medicine," conditional statements within step 1665 of FIG. 16 could optimally select the next panel to highlight, as follows:

If the user's previous actions using the system indicated that he or she frequently used the Help panel to call for assistance, and/or frequently erased erroneous selections, conditional statements within step 1665 of FIG. 16 could determine that the next panel to highlight based on this context should be the Erase Panel, in order to facilitate either erasure or a call for assistance. If, on the other hand, the user's history using this system indicated very infrequent use of the Erase or Help Panels, step 1665 could determine the next panel to highlight, in the following way.

If the system were configured so that display of a list of pain medicines was linked to the selection of the "pain medicine" WordGroup, then step 1665 could determine that the next panel to highlight should be first Word Group Panel containing the first item in the list of pain medicines. However, if the system were configured so that a new WordGroup List was not loaded when "pain medicine" was selected, then step 1665 could determine that additions to the current message are unlikely, and therefore that the optimal panel to highlight should be the Speak panel, because of the likelihood that the next thing the user would wish to do is to speak the displayed message.

This example illustrates the fact that any selection in the system might generate or not generate further selections, and the system can conditionally highlight the next most likely panel based on that context. There may be some selections that always do one or the other; other selections may be configurable to do one or the other. In the foregoing "pain medicine" example, some caregivers may choose to have "pain medicine" as one of the "I need" sub-items, and some may not. Even if all caregivers were to choose to have "pain medicine" as one of the "I need" sub-items, some might choose to list types of pain medicines, and some might not. Some might choose to have the follow-up item (when "pain medicine" is selected) be a list of how severe the pain is. The system is preferably fully configurable to allow for these variations.

More specifically, known assistive communication devices for individuals with long term disabilities have fixed scanning patterns, when using what has been referred to above as Scan Mode or Switch Advance mode.

For example, when scanning across rows, a screen highlight might start at the top of the screen at the left end of the top row, and with each advance, move across the panels in the top row, then to the left side of the second row, scanning all items in that row, and repeating that pattern for all rows until the item at the right end of the last row has been scanned. Upon a selection which brings up a new "page" or new "screen," the highlight again starts at the top.

On the other hand, in accordance with the present invention, consider a visually impaired user, using the Blind User Mode:

If the device operated as known assistive communication device and started at the top of the screen and gave instructions for each item as the highlight passed over it, then the user would have to listen to instructions for the Erase function and Speak functions, even if no message had yet been generated which could be erased or spoken. In a device according to the present invention with intelligent scanning/navigation, depending on the mode of operation (e.g., Blind User Mode, Self-Instruction Mode, etc.), the scanning sequence is not fixed, but can skip over irrelevant items, depending on context (such as the presence or absence of items in the Message Display Window).

Similarly, the conditional scanning aspect can have a scanning sequence which is not fixed, but again is based on mode of operation or context. For example, in the Blind User Mode, it makes no sense to highlight and give instructions for the "More" panel in a fixed order sequence (i.e., after instructions for going to the spelling screen), because the purpose of the "More" panel is to give the user the option to review additional items in the Word Group Panels at the bottom of the screen. If the scanning sequence were fixed as in a known device, and started at the top of the screen, the user would be asked if he or she wished to hear more options (such as "I need," "I feel," etc.) before those options were highlighted and annunciated.

But with conditional scanning, and in Blind User Mode, the device according to the present invention preferably scans from the "Spell" panel directly to the first Word Group Panel (where the first option is explained), and then scans through all the other Word Group Panels before scanning to the "More" panel. In this manner, the user has heard all of the potential options, before he or she is asked whether he or she wishes to hear additional options.

The above examples illustrate how conditional scanning facilitates use of the invention in Self-Instruction Mode or Blind-User Mode. There are other situations, but all have intent of providing one or both of (a) clearer, more straightforward use of the system by visually impaired users, particularly "novice" visually impaired users, and (b) faster message generation, thus leading to more effective communication and less user frustration.

In this context, references to scanning and navigation, refer to the two modes in which potential user selections are highlighted in sequence, and when the desired item has been highlighted, the user pushes a button or performs some other operation to "select" that item. The word "scan" may be used to refer to the process in which the highlight automatically moves from one item to the other under timer control, while the word "navigation" may be used to refer to movement of the highlight under switch control.

Figure 70:
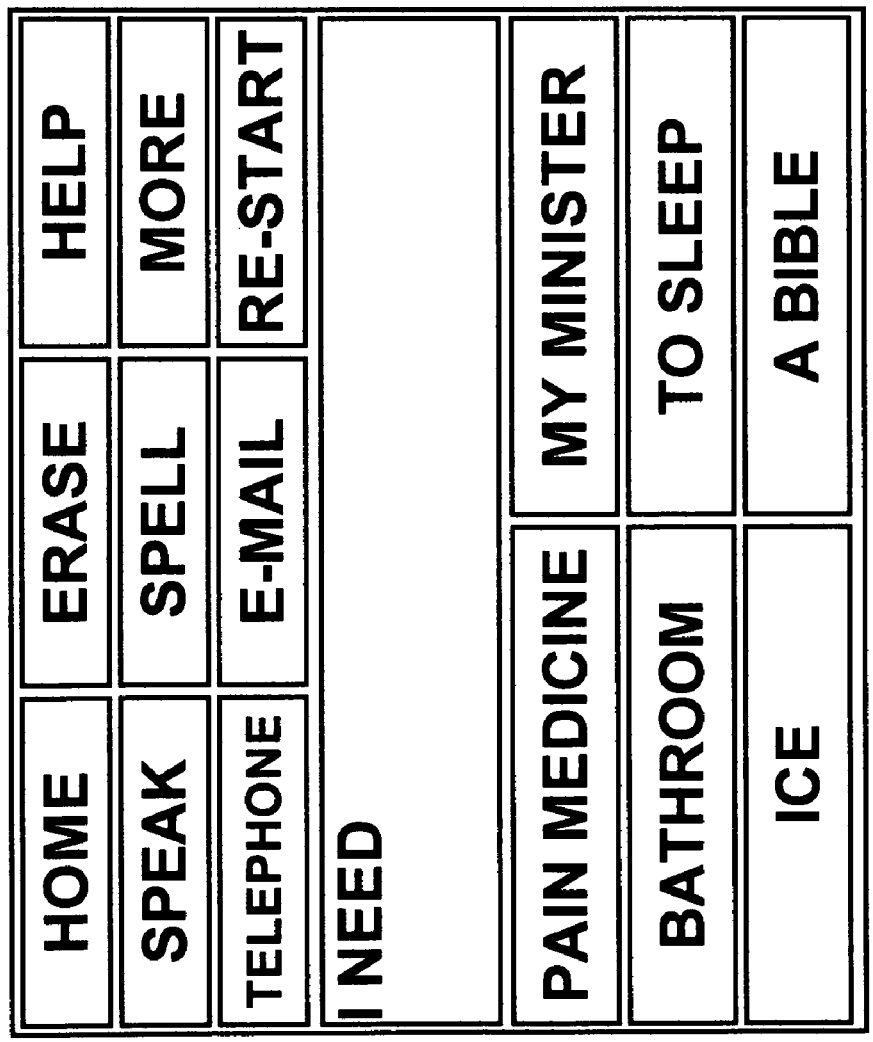
FIG. 70 is a representation of a preferred embodiment of an implementation of a Patient Module Main Screen in a preferred embodiment of a system according to the present invention after user selection of a WordGroup Panel labeled "I need"

The following example, by reference to FIG. 70, illustrates a situation in which self-optimizing conditional scanning and navigation can be used. In this example, the system determines optimally where the next highlight should appear after the user has selected an option.

In FIG. 70, after the user selects "pain medication" to add to the phrase "I need," there are a number of choices. First, if the user's recent system use has indicated frequent calls for assistance (via the Help panel in the upper right of the screen), and/or frequent erroneous selections (as indicated by frequent use of the Erase panel in the top row), the system can optimize itself for the current user by automatically highlighting the Erase Panel (which also gives quick access to the Help Panel, if required). On the other hand, if the previous activity by the user indicates infrequent calls for Help and relatively few uses of the Erase function, the system can optimize for speed of sentence generation/output in the following way:

If there are no sub-items under the chosen item (e.g., "pain medicine"), indicating that the desired sentence is most likely complete, the highlight can automatically move to the "Speak" panel, so that the user can cause the desired sentence "I need pain medicine" to be spoken with little delay. If, on the other hand, sub-items exist under the selected item (e.g., pain medications may include Demerol®, Imitrex®, aspirin, etc.), the system can minimize selection time by displaying the list of possible sub-items and placing the highlight on the first sub-item in the list.

There are a wide variety of other situations in which the system can use this "self-optimizing" conditional scanning function, to make the system either easier to use for a novice user, faster to use for an adept user, more suitable for use by a "panicky" user (one who frequently erases or uses Help, etc.).

By having the system adjust its configuration automatically based on the current or previous behavior of the user, setup/customization of the system by a caregiver is minimized, thus making it more appropriate for temporary users in a hospital/health-care environment. If desired, however, the self-optimization feature could be disabled, so that the decision about whether the user needs to have quick, immediate access to, e.g., the Help/Erase options in the upper row, could be left to the caregiver, or, for a competent user, to the user him- or herself.

It will be understood that the foregoing is only illustrative of the principles of the invention, and that various modifications can be made by those skilled in the art without departing from the scope and spirit of the invention, and the present invention is limited only by the claims that follow.

What is claimed is:

1. An assistive communication device for allowing a speech-impaired user to construct at least one of a statement, a query and a request, and to communicate said at least one of said statement, query and request to another person, said assistive communication device comprising:
    an input device that accepts inputs from said user;
    a plurality of output devices that communicate with said user and with said another person, said plurality of output devices comprising at least a display and a transducer for creating aural output; and
    a processor that operates on said inputs and interacts with said user via at least one of said plurality of output devices to construct said at least one of a statement, a query and a request; wherein:
    said processor operates in a first mode when said user is all of (a) familiar with use of said assistive communication device, (b) able to see, and (c) able to use full function of standard computer input devices, and in at least one other mode different from said first mode when said user is both (a) unfamiliar with use of the assistive communication device, and (b) at least one of (i) visually impaired, and (ii) unable to use full function of standard computer input devices, to allow said user who is both (a) unfamiliar with use of the assistive communication device, and (b) at least one of (i) visually impaired, and (ii) unable to use full function of standard computer input devices, to use said assistive communication device to communicate with said another person.

2. The assistive communication device of claim 1 wherein:
    said plurality of output devices comprises said display and said transducer comprises a speech generation unit and one of speaker and headphones;
    said input device allows said user to interact with said assistive communication device by selecting items displayed on said display and commanding said processor to perform an action;
    in said first mode, in response to said selecting and said commanding, said processor performs one or both of altering said display and issuing a spoken message through said speech generation unit; and
    in said at least one other mode, upon an action by said user, said processor performs at least one of:
    (1) highlighting on said display at least one potential as-yet-untaken action by said user,
    (2) causing said speech generation unit to announce a consequence of said as-yet-untaken action by said user; and
    (3) causing said speech generation unit to preview a message as thus far constructed by said user.

3. The assistive communication device of claim 2 wherein:
    when said user who is both (a) unfamiliar with use of the assistive communication device, and (b) at least one of (i) visually impaired, and (ii) unable to use full function of standard computer input devices, is unable to use full function of standard computer input devices, said at least one other mode is a self-instruction mode in which said at least one of said highlighting, said announcing and said previewing includes a first set of items in a first order; and
    when said user who is both (a) unfamiliar with use of the assistive communication device, and (b) at least one of (i) visually impaired, and (ii) unable to use full function of standard computer input devices, is visually impaired, said at least one other mode is a blind-user mode in which said at least one of said highlighting, said announcing and said previewing includes a second set of items in a second order.

4. The assistive communication device of claim 3 wherein said second set of items is different from said first set of items.

5. The assistive communication device of claim 3 wherein said second order is different from said first order.

6. The assistive communication device of claim 2 wherein said highlighting occurs in an order that is dependent on a record of user actions.

7. The assistive communication device of claim 2 wherein said highlighting occurs in an order that is dependent on context.

8. The assistive communication device of claim 2 wherein said highlighting occurs in an order that is dependent on user settings.

9. The assistive communication device of claim 2 wherein said at least one other mode is a questionnaire mode, such that said user who is both (a) unfamiliar with use of the assistive communication device, and (b) at least one of (i) visually impaired, and (ii) unable to use full function of standard computer input devices, is enabled to reply to a questionnaire.

10. The assistive communication device of claim 9 wherein:
    said questionnaire mode is a medical history mode; and
    said questionnaire comprises questions asked to ascertain said user's medical history.

11. The assistive communication device of claim 1 further comprising a remote communication connection.

12. The assistive communication device of claim 11 wherein:
    said remote communication connection is a telephone interface; and
    said processor speaks said constructed statement, query or request via said telephone interface; whereby:
    said user can place a telephone call and conduct a conversation during said telephone call using said assistive communication device.

13. The assistive communication device of claim 11 wherein:
    said remote communication connection is a data network interface; and
    said processor writes said constructed statement, query or request to said data network interface; whereby:

said user can send electronic mail using said assistive communication device.

14. The assistive communication device of claim 11 wherein said remote communication connection connects to a caregiver message device.

15. The assistive communication device of claim 14 wherein:
said caregiver message device comprises a caregiver display for displaying status of communication with any one of said plurality of assistive communication devices; wherein:
said caregiver display has a plurality of status indicators indicating when a message has arrived from a respective one of said assistive communication devices and at least one of (1) whether a caregiver has been notified of said message, (2) whether said caregiver has acknowledged said notification, and (3) whether said caregiver has responded to said message.

16. The assistive communication device of claim 15 wherein said status indicator further indicates degree of urgency of said message.

17. The assistive communication device of claim 15 wherein said caregiver message device is a caregivers' station console connected to a plurality of assistive communication devices used by a plurality of users.

18. The assistive communication device of claim 17 wherein:
said caregiver display comprises a plurality of caregiver displays corresponding to said plurality of assistive communication devices;
each of said plurality of caregiver displays has a plurality of status indicators indicating when a message has arrived from a respective one of said assistive communication devices and at least one of (1) whether a caregiver has been notified of said message, (2) whether said caregiver has acknowledged said notification, and (3) whether said caregiver has responded to said message.

19. The assistive communication device of claim 18 wherein:
each of said plurality of caregiver displays comprises a border; and
said plurality of status indicators comprises a plurality of conditions of said border.

20. The assistive communication device of claim 19 wherein said plurality of conditions comprises at least one of shading, color and flashing.

21. The assistive communication device of claim 15 wherein said caregiver message device is a portable device connected wirelessly to a plurality of assistive communication devices used by a plurality of users.

22. The assistive communication device of claim 21 wherein:
said caregiver display comprises a plurality of caregiver displays corresponding to said plurality of assistive communication devices.

23. The assistive communication device of claim 21 wherein:
said caregiver display comprises a border; and
said plurality of status indicators comprises a plurality of conditions of said border.

24. The assistive communication device of claim 23 wherein said plurality of conditions comprises at least one of shading, color and flashing.

25. The assistive communication device of claim 21 wherein said portable device comprises a pager.

26. An assistive communication device for allowing a speech-impaired user to construct at least one of a statement, a query and a request, and to communicate said at least one of said statement, query and request to another person, said assistive communication device comprising:
an input device that accepts inputs from said user;
at least one output device that communicates with said user and with said another person, said at least one output device comprising at least a transducer for creating aural output; and
a processor that operates on said inputs and interacts with said user via said at least one output device to construct said at least one of a statement, a query and a request; wherein:
when said user is both (a) unfamiliar with use of the assistive communication device, and (b) at least one of (i) visually impaired, and (ii) unable to use full function of standard computer input devices, said processor operates to allow said user who is both (a) unfamiliar with use of the assistive communication device, and (b) at least one of (i) visually impaired, and (ii) unable to use full function of standard computer input devices, to use said assistive communication device to communicate with said another person.

* * * * *